US008084448B2

(12) United States Patent
Neubert et al.

(10) Patent No.: US 8,084,448 B2
(45) Date of Patent: *Dec. 27, 2011

(54) ORGANIC COMPOUNDS

(75) Inventors: Alan Neubert, North Attleborough, MA (US); David Barnes, Waban, MA (US); Young-Shin Kwak, Lexington, MA (US); Katsumasa Nakajima, Winchester, MA (US); Gregory Raymond Bebernitz, Stow, MA (US); Gary Mark Coppola, Budd Lake, NJ (US); Louise Kirman, Swampscott, MA (US); Michael H. Serrano-Wu, Belmont, MA (US); Travis Stams, Stow, MA (US); Sidney Wolf Topiol, Fair Lawn, NJ (US); Thalaththani Ralalage Vedananda, Shrewsbury, MA (US); James Richard Wareing, Stow, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/295,545

(22) PCT Filed: Mar. 29, 2007

(86) PCT No.: PCT/US2007/065421
  § 371 (c)(1),
  (2), (4) Date: Sep. 30, 2008

(87) PCT Pub. No.: WO2007/115058
  PCT Pub. Date: Oct. 11, 2007

(65) Prior Publication Data
  US 2009/0181928 A1    Jul. 16, 2009

Related U.S. Application Data

(60) Provisional application No. 60/788,502, filed on Mar. 31, 2006.

(51) Int. Cl.
  A61K 31/55    (2006.01)
  A61K 31/445   (2006.01)
  A61K 31/41    (2006.01)
  C07D 487/00   (2006.01)
  C07D 401/00   (2006.01)
  C07D 285/10   (2006.01)

(52) U.S. Cl. .................... 514/212.07; 514/326; 514/362; 540/523; 546/209; 548/135

(58) Field of Classification Search ............. 514/212.07, 514/326, 362; 540/523; 546/209; 548/135
  See application file for complete search history.

(56) References Cited

U.S. PATENT DOCUMENTS

2004/0023974 A1*  2/2004  Coppola et al. .......... 514/252.05
2008/0293776 A1* 11/2008  Barnes et al. ................. 514/342
2008/0293782 A1* 11/2008  Barnes et al. ................. 514/362
2010/0035942 A1*  2/2010  Barnes et al. ................. 514/362

FOREIGN PATENT DOCUMENTS

| WO | 97/40017 A | 10/1997 | |
|---|---|---|---|
| WO | 03/082841 A | 10/2003 | |
| WO | 2004/041799 A | 5/2004 | |
| WO | WO 2004/041799 | * 5/2004 | ............. 548/200 |
| WO | 2004/050646 A | 6/2004 | |
| WO | 2007/067612 A | 6/2007 | |
| WO | 2007/067613 A | 6/2007 | |
| WO | 2007/067614 A | 6/2007 | |

OTHER PUBLICATIONS

Golub et al. Science (1999), vol. 286 531-537.*
Lala et al. Cancer and Metastasis Reviews (1998), 17(1), 91-106.*
Emma Black et al: "Structure-based design of protein tyrosine phosphatase-1B inhibitors" Bioorganic & Medicinal Chemistry Letters, Oxford, GB, vol. 15, No. 10, Apr. 16, 2005, pp. 2503-2507. p. 2503, left-hand column, paragraph 1; table 2; compound 9; p. 2505, right-hand column, last paragraph.
Bright S W et al: "Competitive particle concentration flourescence immunoassays for measuring antidiabetic drug levels in mouse plasma" Journal of Immunological Methods, Elsevier Science Publishers B.V. Amsterdam, NL, vol. 207, Apr. 25, 1997, pp. 23-31. Table 4; compound 12.

* cited by examiner

Primary Examiner — Rebecca Anderson
Assistant Examiner — Samantha Shterengarts
(74) Attorney, Agent, or Firm — John B. Alexander

(57) ABSTRACT

Compounds of the formula (I)

are inhibitors of protein tyrosine phosphatases (PTPases) and, thus, may be employed for the treatment of conditions mediated by PTPase activity. The compounds of the present invention may also be employed as inhibitors of other enzymes characterized with a phosphotyrosine binding region such as the SH2 domain. Accordingly, the compounds of formula (I) may be employed for prevention and/or treatment of insulin resistance associated with obesity, glucose intolerance, diabetes mellitus, hypertension and ischemic diseases of the large and small blood vessels, conditions that accompany type-2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat and/or prevent cancer, osteoporosis, musculoskeletal, neurodegenerative and infectious diseases, and diseases involving inflammation and the immune system.

11 Claims, No Drawings

ORGANIC COMPOUNDS

This application is the National Stage of Application No. PCT/US2007/065421, filed on Mar. 29, which claims benefit under 35 U.S.C. §119(e) of U.S. Provisional Application No. 60/788,502, filed Mar. 31, 2006, the contents of which are incorporated herein by reference in their entirety.

The present invention relates to thiadiazolidinone derivatives, pharmaceutical compositions containing such compounds, methods of making such and methods of treating conditions mediated by protein tyrosine phosphatases by employing such compounds.

Accordingly, the present invention provides compounds of the formula

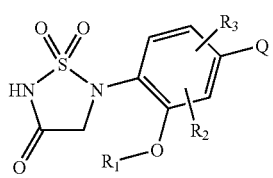

(I)

wherein
Q is:
i) —X, or
ii) —Y—(CH$_2$)$_n$—(CR$_8$R$_9$)$_p$—(CH$_2$)$_m$—Z—X in which
Y is oxygen or S(O)$_q$ in which q is zero or an integer of 1 or 2; or
Y is —C≡C— or —C=C—; or
Y is cyclopropyl or
Y is absent;
n and m are, independently from each other, zero or an integer from 1 to 8;
R$_8$ and R$_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or
R$_8$ and R$_9$ combined are alkylene which together with the carbon atom to which they are attached form a 3- to 7-membered ring;
p is zero or an integer selected from 1 or 2 Z is absent;
Z is —C(O)—O—; or
Z is —(O)—; or
Z is —(O)—NRα-alkylene- or —C(O)—NRα-alkylene-O—, wherein Rα is H or lower alkyl; or
Z is —CO—NRα-(CH$_2$)$_n'$—(CR$_{8'}$R$_{9'}$)$_{p'}$—(CH$_2$)$_{m'}$—, or —C(O)—NRα-(CH$_2$)$_{n'}$—(CR$_{8'}$R$_{9'}$)$_{p'}$—(CH$_2$)$_{m'}$—O—, wherein p' is zero or an integer of 1, n' and m' are, independently from each other, zero or an integer from 1 to 8, R$_{8'}$ and R$_{9'}$ are, independently from each other, hydrogen or lower alkyl, Rα is H or lower alkyl; or
Z is —NRα'-C(O)—, or —NRα'-C(O)—O—, wherein Rα' is H or lower alkyl, or Rα' and R$_9$ combined are alkylene which together with the carbon atom to which they are attached form a 3- to 7-membered ring; or
Z is —(O)—NH—NH—C(O)—O—; or
Z is S(O)$_2$—, or —S(O)—; or
Z is —NRβ-S(O)$_2$—, wherein Rβ is H, lower alkyl, or Rβ and R$_9$ combined are alkylene which together with the carbon atom to which they are attached form a 3- to 7-membered ring; or Z is —NH—S(O)$_2$—NH—C(O)—O—; or
Z is —NRγ-C(O)—NRγ'—; wherein Rγ' is H, alkyl, aryl, heterocyclyl or lower alkoxy and Rγ is H, lower alkyl, or Rγ and R$_9$ combined are alkylene which together with the carbon atom to which they are attached form a 3- to 7-membered ring; or Rγ' and X combined are alkylene which together with the carbon atom to which they are attached form a 3- to 7-membered ring or
Z is —NRτ-C(O)—NH—S(O)$_2$—, wherein Rτ is H or lower alkyl,
X is hydrogen, hydroxy, NH$_2$, halogen, substituted or unsubstituted alkoxy, substituted or unsubstituted alkylthio, substituted or unsubstituted alkyl, —S(O)—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio, wherein the alkyl, cycloalkyl, aryl, heteroaryl and heterocyclyl groups are unsubstituted or optionally substituted by 1, 2, 3, 4, or 5 substituents;
R$_1$ is hydrogen, —C(O)R$_4$, —C(O)NR$_5$R$_6$ or —C(O)OR$_7$ in which
R$_4$ and R$_5$ are, independently from each other, hydrogen, cycloalkyl, aryl, heterocyclyl, aralkyl, heteroaralkyl or alkyl, optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R$_6$ and R$_7$ are, independently from each other, cycloalkyl, aryl, heterocyclyl, aralkyl, heteroaralkyl or alkyl, optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R$_2$ and R$_3$ are, independently from each other, hydrogen, halogen, (C$_{1-3}$)alkyl or (C$_{1-3}$)alkoxy;
or a pharmaceutically acceptable salt thereof,
and wherein n+m+p is >1 or is 0, when X is aryl, and Y and Z are absent,
n+m+p is not 0 when X is —O-aryl, and Y and Z are absent, or
n+m+p is not 0 when X is —S-aryl, and Y and Z are absent, or
n+m+p is not 0 when X is —CH$_2$-aryl, and Y and Z are absent, or
n+m+p is not 0 when X is aryl, Z is absent and Y is —O— or Y is —S—, or
wherein Q cannot be —CH$_2$-aryl, —S-aryl or —O-aryl.

Preferably, the orientation of the Z function is with the X group on the right side of the listed function —Z→X e.g. Z is —NRα'-C(O)— means Z is —NRα'-C(O)—X.

The compounds of the present invention are inhibitors of protein tyrosine phosphatases (PTPases), in particular, the compounds of formula (I) inhibit PTPase-1B (PTP-1B) and T-cell PTPase (TC PTP) and, thus, may be employed for the treatment of conditions mediated by PTPase activity. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer, osteoporosis, musculoskeletal, neurodegenerative and infectious diseases, and diseases involving inflammation and the immune system.

Listed below are definitions of various terms used to describe the compounds of the instant invention. These definitions apply to the terms as they are used throughout the specification unless they are otherwise limited in specific instances either individually or as part of a larger group. In general, whenever an alkyl group is referred to as a part of the structure, an optionally substituted alkyl is also inended.

Accordingly, the term "optionally substituted alkyl" refers to unsubstituted or substituted straight or branched chain hydrocarbon groups having 1 to 20 carbon atoms, preferably 1 to 8 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halogen, hydroxy, cycloalkyl, cycloalkoxy, acyl, acyloxy, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy including indolyl, imidazolyl, furyl, thienyl, thiazolyl, pyrrolidyl, pyridyl, pyrimidyl, piperidyl, morpholinyl and the like.

The term "lower alkyl" refers to any of the above alkyl groups as described above having 1 to 8, preferably 1 to 4 carbon atoms.

The term "halogen" or "halo" refers to fluorine, chlorine, bromine and iodine.

The term "alkenyl" refers to any of the above alkyl groups having at least 2 carbon atoms and containing a carbon to carbon double bond at the point of attachment. Groups having 2 to 8 carbon atoms are preferred.

The term "alkynyl" refers to any of the above alkyl groups having at least two carbon atoms and containing a carbon to carbon triple bond at the point of attachment. Groups having 2 to 8 carbon atoms are preferred.

The term "alkylene" refers to a straight-chain bridge of 2-6 carbon atoms connected by single bonds, e.g., —$(CH_2)_x$—, wherein x is 2-6, which may be interrupted with one or more heteroatoms selected from O, S, S(O), $S(O)_2$ or NR", wherein R" may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl, heterocyclyloxy and the like.

The term "cycloalkyl" refers to optionally substituted monocyclic, bicyclic or tricyclic hydrocarbon groups of 3 to 12 carbon atoms, each of which may be substituted by one or more substituents such as alkyl, halo, oxo, hydroxy, alkoxy, alkanoyl, acylamino, carbamoyl, alkylamino, dialkylamino, thiol, alkylthio, nitro, cyano, carboxy, carboxyalkyl, alkoxycarbonylamino, alkoxycarbonyl, sulfonyl, sulfonamido, sulfamoyl, heterocyclyl and the like.

Exemplary monocyclic hydrocarbon groups include but are not limited to cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and $(alkyl)_2N$—, respectively.
The term "alkanoylamino" refers to alkyl-C(O)—NH—.
The term "alkylthio" refers to alkyl-S—.
The term "alkylaminothiocarbonyl" refers to alkyl-NHC(S)—.
The term "trialkylsilyl" refers to $(alkyl)_3Si$—.
The term "trialkylsilyloxy" refers to $(alkyl)_3SiO$—.
The term "alkylthiono" refers to alkyl-S(O)—.
The term "alkylsulfonyl" refers to alkyl-$S(O)_2$—.
The term "alkoxycarbonyl" refers to alkyl-O—C(O)—.
The term "alkoxycarbonylamino" refers to alkyl-O—C(O)—NH—.
The term "alkoxycarbonyloxy" refers to alkyl-O—C(O)O—.
The term "carboxycarbonyl" refers to HO—C(O)C(O)—.
The term "carbamoyl" refers to $H_2NC(O)$—, alkyl-NHC(O)—, $(alkyl)_2NC(O)$—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to $H_2NS(O)_2$—, alkyl-NHS$(O)_2$—, $(alkyl)_2NS(O)_2$—, aryl-NHS$(O)_2$—, alkyl(aryl)-NS$(O)_2$—, $(aryl)_2NS(O)_2$—, heteroaryl-NHS$(O)_2$—, aralkyl-NHS$(O)_2$—, heteroaralkyl-NHS$(O)_2$— and the like.
The term "sulfonamido" refers to alkyl-S$(O)_2$—NH—, aryl-S$(O)_2$—NH—, aralkyl-S$(O)_2$—NH—, heteroaryl-S$(O)_2$—NH—, heteroaralkyl-S$(O)_2$—NH—, alkyl-S$(O)_2$—N(alkyl)-, aryl-S$(O)_2$—N(alkyl)-, aralkyl-S$(O)_2$—N(alkyl)-, heteroaryl-S$(O)_2$—N(alkyl)-, heteroaralkyl-S$(O)_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "sulfonate" or "sulfonyloxy" refers to alkyl-S$(O)_2$—O—, aryl-S$(O)_2$—O—, aralkyl-S$(O)_2$—O—, heteroaryl-S$(O)_2$—O—, heteroaralkyl-S$(O)_2$—O— and the like.
The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carboxycarbonyl, carbamoyl, alkylaminothiocarbonyl, arylaminothiocarbonyl and the like.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to five substituents such as alkyl, trifluoromethyl, halo, hydroxy, alkoxy, phenoxy, acyl, alkanoyl, alkanoyloxy, optionally substituted amino, thiol, alkylthio, nitro, cyano, carboxy, carboxyalkyl, alkoxycarbonyl, carbamoyl, alkylthiono, sulfonyl, sulfonamido, sulfonate, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroylamino" refers to aryl-C(O)—NH—.

The term "aryloxycarbonyl" refers to aryl-O—C(O)—.

The term "heterocyclyl" or "heterocycle" refers to an optionally substituted, aromatic, or a partially or fully saturated nonaromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl (such as trioxothiadiazolidinyl; 1,1,4-trioxo-1,2,5-thiadiazolidin-2-yl), isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridyl, pyrazinyl, pyrimidinyl, pyridazinyl, tetrahydropyranyl, dioxotetrahydrothiophen, morpholinyl, thiamorpholinyl, thiamorpholinyl sulfoxide, thiamorpholinyl sulfone, 1,3-dioxolane, 1,1-dioxo-1,2,5-thiadiazolidin-3-one, 1,1-Dioxo-1,2-thiazinanyl (such as 1,1-Dioxo-1,2-thiazinan-3-yl), and tetrahydro-1,1-dioxothienyl, 1,1,4-trioxo-1,2,5-thiadiazolidin-2-yl and the like.

Exemplary bicyclic heterocyclic groups include indolyl, dihydroindolyl, benzothiazolyl, benzoxazinyl, benzoxazolyl, benzothienyl, benzothiazinyl, quinuclidinyl, quinazoline (such as 1H-quinazoline-2,4-dione), quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, chromenenyl (such as 2-Oxo-2H-chromenenyl), isoindole-1,3-dione, coumarinyl, benzopyranyl, benzodiazepinyl, cinnolinyl, quinoxalinyl, indazolyl, pyrrolopyridyl, furopyridinyl (such as furo[2,3-c]pyridinyl, furo[3,2-b]-pyridinyl] or furo[2,3-b] pyridinyl), dihydroisoindolyl, 1,3-dioxo-1,3-dihydroisoindol-2-yl, dihydroquinazolinyl (such as 3,4-dihydro-4-oxo-quinazolinyl), tetrahydroisoquinolinyl (such as 1,2,3,4-tetrahydroisoquinolin-3-yl), tetrahydro-benzo[b]azepine (such as tetrahydro-benzo[b]azepinone, 1,3,4,5-tetrahydro-benzo[b]azepin-2-one), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" or "heterocycle" also covers heterocyclyl groups comprising an amide (i.e. —NH—CO— or a Nitro ring member substituted by an acyl or an alkoxycarbonyl) or sulfonamide (e.g. —NH—S(O)$_2$— or a Nitro ring member substituted by sulfamoyl) function within at least one cycle and which is designated hereinafter as "amide" type heterocyclyl. Exemplary amide type heterocyclyl are oxopyrrolidinyl, pyridine-X-one (e.g. pyridine-2-one), piperidine-X-one (such as piperidine-2-one), azepan-2-one, acylpiperidinyl (such as 1-Acetylpiperidin-2-yl), oxothiadiazolidinyl (e.g. 1,1,4-trioxo-1,2,5-thiadiazolidin-2-yl), piperidine-1-carboxylic acid alkyl ester (piperidine-1-carboxylic acid tert-butyl ester), azepan-2-one, azepane-1-carboxylic acid alkyl ester (e.g. azepane-1-carboxylic acid tert-butyl ester), dihydro-2H-isoquinolinone (e.g. dihydro-2H-isoquinolin-1-one, or 3,4-dihydro-2H-isoquinolin-1-one), benzoazepinone (such as 2,3-dihydro-benzo[c]azepin-1-one, 1,2,4,5-tetrahydro-benzo[c]azepin-1-one, 1,2,4,5-tetrahydrobenzo[c]azepin-3-one 1,3,4,5-tetrahydrobenzo[d]azepin-2-one, 6,7-dihydro-dibenzo[c,e]azepin-5-one, 3,4-dihydro-2H-naphtol[1,8-c,d]azepin-1-one, 2,3,4,5-tetrahydrobenzo[c]azepin-1-one), isoindole-1,3-dione, 1-acetylpiperidin-2-yl, piperidine-1-carboxylic acid alkyl ester, 1-methanesulfonylpiperidin-2-yl.

The term "heterocyclyl" includes substituted heterocyclic groups. Substituted heterocyclic groups refer to heterocyclic groups that are substituted with 1, 2 or 3 substituents selected from the group consisting of the following:

(a) optionally substituted alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(o) alkylcarbonyloxy;
(p) arylcarbonyloxy;
(q) arylthio;
(r) aryloxy;
(s) alkylthio;
(t) formyl;
(u) carbamoyl;
(v) aralkyl;
(w) aryl optionally substituted with alkyl, cycloalkyl, alkoxy, hydroxy, amino, acylamino, alkylamino, dialkylamino or halo;
(x) sulphonyl; and
(y) alkanoyl.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl such as 1H-Benzoimidazol-2-yl, benzofuryl, and the like, optionally substituted by e.g. lower alkyl, lower alkoxy or halo.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O)NH—

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, aroyl, heteroaroyl, aralkanoyl, heteroaralkanoyl and the like.

The term "acyloxy" refers to alkanoyloxy, cycloalkanoyloxy, aroyloxy, heteroaroyloxy, aralkanoyloxy, heteroaralkanoyloxy and the like.

The term "acylamino" refers to alkanoylamino, cycloalkanoylamino, aroylamino, heteroaroylamino, aralkanoylamino, heteroaralkanoylamino and the like.

The term "alkoxycarbonylamino" refers to alkyl-O—C(O)—NH—.

The term "esterified carboxy" refers to optionally substituted alkoxycarbonyl, cycloalkoxycarbonyl, aryloxycarbonyl, aralkoxycarbonyl, heterocyclooxycarbonyl and the like.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids e.g. hydrochloric acid, maleic acid and methanesulfonic acid, are possible provided a basic group, such as pyridyl, constitutes part of the structure.

As described herein above, the present invention provides 1,1-dioxo-1,2,5-thiadiazolidin-3-one derivatives of formula (I), pharmaceutical compositions containing the same, methods for preparing such compounds and methods of treating and/or preventing conditions associated with PTPase activity, in particular, PTP-1B and TC PTP activity, by administration of a therapeutically effective amount of a compound of the present invention, or a pharmaceutical composition thereof.

Preferred are the compounds of formula (I), designated as the ALPHA group, wherein Q is: —Y—$(CH_2)_n$—$(CR_8R_9)_p$—$(CH_2)_m$—Z—X in which Y is oxygen or $S(O)_q$ in which q is zero or an integer of 1 or 2; or Y is —C≡C— or —C=C—; or Y is cyclopropyl or Y is absent;

n and m are, independently from each other, zero or an integer from 1 to 8;

$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or $R_8$ and $R_9$ combined are alkylene which together with the carbon atom to which they are attached form a 3- to 7-membered ring;

p is zero or an integer selected from 1 or 2

Z is absent;

Z is —(O)—O—; or

Z is —(O)—; or

Z is —C(O)—NRα-alkylene- or —(O)—NRα-alkylene-O—, wherein Rα is H or lower alkyl; or Z is —CO—NRα-$(CH_2)_{n'}$—$(CR_{8'}R_{9'})_{p'}$—$(CH_2)_{m'}$—, or —C(O)—NRα-$(CH_2)_{n'}$—$(CR_{8'}R_{9'})_{p'}$—$(CH_2)_{m'}$—O—, wherein p' is zero or an integer of 1, n' and m' are, independently from each other, zero or an integer from 1 to 8, $R_{8'}$ and $R_{9'}$ are, independently from each other, hydrogen or lower alkyl, Rα is H or lower alkyl; or Z is —NRα'-C(O)—, or —NRα'-C(O)—O—, wherein Rα' is H or lower alkyl, or Rα' and $R_9$ combined are alkylene which together with the carbon atom to which they are attached form a 3- to 7-membered ring; or Z is —C(O)—NH—NH—C(O)—O—; or Z is —$S(O)_2$, or —S(O)—; or Z is —NRβ-$S(O)_2$—, wherein Rβ is H, lower alkyl, or Rβ and $R_9$ combined are alkylene which together with the carbon atom to which they are attached form a 3- to 7-membered ring; or Z is —NH—$S(O)_2$—NH—C(O)—O—; or Z is —NRγ-C(O)—NRγ'—; wherein Rγ' is H, alkyl, aryl, heterocyclyl, or lower alkoxy and Rγ is H, lower alkyl, or Rγ and $R_9$ combined are alkylene which together with the carbon atom to which they are attached form a 3- to 7-membered ring; or Rγ' and X combined are alkylene which together with the carbon atom to which they are attached form a 3- to 7-membered ring or Z is —NRτ-C(O)—NH—$S(O)_2$—, wherein Rτ is H or lower alkyl, X is hydrogen, hydroxy, $NH_2$, halogen, substituted or unsubstituted alkoxy, substituted or unsubstituted alkylthio, substituted or unsubstituted alkyl, —S(O)—OH, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio, wherein the alkyl, cycloalkyl, aryl, heteroaryl and heterocyclyl groups are unsubstituted or optionally substituted by 1, 2, 3, 4, or 5 substituents;

$R_1$ is hydrogen, —$C(O)R_4$, —$C(O)NR_5R_6$ or —$C(O)OR_7$ in which $R_4$ and $R_5$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_6$ and $R_7$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$ and $R_3$ are, independently from each other, hydrogen, halogen, $(C_{1-3})$alkyl or $(C_{1-3})$alkoxy;

or a pharmaceutically acceptable salt thereof, and wherein n+m+p is >1 or is 0, when X is aryl, and Y and Z are absent, n+m+p is not 0 when X is —O-aryl, and Y and Z are absent, or n+m+p is not 0 when X is —S-aryl, and Y and Z are absent, or n+m+p is not 0 when X is $CH_2$-aryl, and Y and Z are absent, or n+m+p is not 0 when X is aryl, Z is absent and Y is —O— or Y is —S—, or wherein Q cannot be —$CH_2$-aryl, S-aryl or —O-aryl Preferably, the orientation of the Z function is with the X group on the right side of the listed function —Z→X e.g. Z is —NRα'-C(O)— means Z is —NRα'-C(O)—X.

Preferred are the compounds in the ALPHA group wherein;

Y is oxygen; or

Y is —C≡C— or —C═C—; or

Y is cyclopropyl or

Y is absent; and

X is, hydrogen, hydroxy, $NH_2$, halogen, substituted or unsubstituted alkoxy, substituted or unsubstituted alkylthio, substituted or unsubstituted alkyl, —S(O)—OH, substituted or unsubstituted alkyl, substituted or unsubstituted cycloalkyl, cyano, trifluoromethyl, carboxy, substituted or unsubstituted esterified carboxy, substituted or unsubstituted heterocyclyl, substituted or unsubstituted heteroaryl, substituted or unsubstituted heteroaralkyl, substituted or unsubstituted aryl, substituted or unsubstituted aralkyl, substituted or unsubstituted aryloxy, wherein the alkyl, cycloalkyl, aryl, heteroaryl and heterocyclyl groups are unsubstituted or optionally substituted by 1, 2, 3, 4, or 5 substituents;

Preferred are the compounds in the ALPHA group wherein $R_2$ and $R_3$ are hydrogen;

or a pharmaceutically acceptable salt thereof.

Preferred are the compounds in the ALPHA group wherein $R_1$ is hydrogen;

or a pharmaceutically acceptable salt thereof.

Further preferred are the compounds in the ALPHA group wherein n is zero or an integer from 1 to 4;

m is zero or an integer from 1 to 4;

p is zero or 1;

or a pharmaceutically acceptable salt thereof.

Especially preferred are the compounds in the ALPHA group, wherein m+n+p is between 0 and 7 or preferably between 0 and 5, or a pharmaceutically acceptable salt thereof.

Preferred are the compounds of formula (I), designated as the A group, wherein

Q is —Y—($CH_2$), —$(CR_8R_9)_p$—$(CH_2)_m$—Z—X, in which

Y is oxygen or $S(O)_q$ in which q is zero or an integer of 1 or 2; or

Y is —C≡C— or —C═C—; or

Y is cyclopropyl; or

Y is absent;

n and m are, independently from each other, zero or an integer from 1 to 8;

$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl;

p is zero or an integer selected from 1 or 2

Z is absent;

Z is —CO—O; or

Z is —CO—; or

X is hydrogen, hydroxy, $NH_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio, wherein the alkyl, cycloalkyl, aryl, heteroaryl and heterocyclyl groups are unsubstituted or optionally substituted by 1, 2, 3, 4, or 5 substituents;

or a pharmaceutically acceptable salt thereof.

Preferred are the compounds in the A group wherein

Y is oxygen; or

Y is cyclopropyl; or

Y is absent;

or a pharmaceutically acceptable salt thereof.

Preferred are the compounds in the A group wherein $R_8$ and $R_9$ are, independently from each other, hydrogen, alkoxy, alkanoyl, alkoxycarbonyl, aralkyl, aryl, or alkyl;

or a pharmaceutically acceptable salt thereof.

Preferred are the compounds in the A group wherein

X is hydrogen, hydroxy, substituted or unsubstituted alkyl, substituted or unsubstituted heterocyclyl, substituted or unsubstituted heteroaryl or substituted or unsubstituted aryl, wherein the alkyl, aryl, heteroaryl and heterocyclyl groups are unsubstituted or optionally substituted by 1, 2, 3, 4, or 5 substituents;

or a pharmaceutically acceptable salt thereof.

Preferred are the compounds in the A group wherein $R_2$ and $R_3$ are hydrogen;

or a pharmaceutically acceptable salt thereof.

Preferred are the compounds in the A group wherein $R_1$ is hydrogen;

or a pharmaceutically acceptable salt thereof.

Further preferred are the compounds in the A group wherein n is zero or an integer from 1 to 3;

m is zero or an integer from 1 to 3;

p is zero or 1;

or a pharmaceutically acceptable salt thereof.

Especially preferred are the compounds in the A group, wherein m+n+p is between 0 and 4, or a pharmaceutically acceptable salt thereof.

Other preferred compounds are the compounds in the A group, wherein m+n+p is between 1 and 3, and n is 1,
or a pharmaceutically acceptable salt thereof.

Other preferred compounds are the compounds in the A group, wherein
X is a substituted or unsubstituted phenyl.

Preferred are the compounds of formula (I), designated as B, wherein;
Q is —Y—$(CH_2)_n$—$(CR_8R_9)_p$—$(CH_2)_m$—Z—X, in which
  Y is oxygen or $S(O)_q$ in which q is zero or an integer of 1 or 2; or
  Y is —C≡C— or —C=C—; or
  Y is cyclopropyl; or
  Y is absent;
  n and m are, independently from each other, zero or an integer from 1 to 8;
  $R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or
  $R_8$ and $R_9$ combined are alkylene which together with the carbon atom to which they are attached form a 3- to 7-membered ring;
  p is zero or an integer selected from 1 or 2
  Z is absent;
  X is hydrogen, hydroxy, $NH_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio, wherein the alkyl, cycloalkyl, aryl, heteroaryl and heterocyclyl groups are unsubstituted or optionally substituted by 1, 2, 3, 4, or 5 substituents;
or a pharmaceutically acceptable salt thereof.

Preferred are the compounds in the B group wherein
$R_8$ and $R_9$ are, independently from each other, hydrogen, alkoxy, alkanoyl, alkoxycarbonyl, aralkyl, or alkyl, wherein the alkyl and aryl groups are unsubstituted or optionally substituted by 1, 2, 3, 4, or 5 substituents;
or a pharmaceutically acceptable salt thereof.

Preferred are the compounds in the B group wherein
X is hydrogen, $NH_2$, hydroxy, substituted or unsubstituted alkylthio, —SO—OH, substituted or carboxy, substituted or unsubstituted esterified carboxy, substituted or unsubstituted heterocyclyl, substituted or unsubstituted heteroaryl, substituted or unsubstituted aryl; wherein the alkyl and aryl groups are unsubstituted or optionally substituted by 1, 2, 3, 4, or 5 substituents;
or a pharmaceutically acceptable salt thereof.

Preferred are the compounds in the B group wherein
$R_2$ and $R_3$ are hydrogen;
or a pharmaceutically acceptable salt thereof.

Preferred are the compounds in the B group wherein
$R_1$ is hydrogen;
or a pharmaceutically acceptable salt thereof.

Further preferred are the compounds in the B group wherein
  n is zero or an integer from 1 to 3,
  m is zero or an integer from 1 to 3;
  p is zero or 1;
or a pharmaceutically acceptable salt thereof.

Especially preferred are the compounds in the B group, wherein
  m+n+p is between 0 and 6 or preferably 0 and 4,
or a pharmaceutically acceptable salt thereof.

Other preferred compounds are the compounds in the B group, wherein
  m+n is between 0 and 6 or preferably 0 and 4, and
  p is 0,
or a pharmaceutically acceptable salt thereof.

Other preferred compounds are the compounds in the B group, wherein
  X is selected from substituted or unsubstituted phenyl or substituted or unsubstituted heteroaryl, preferably unsubstituted or substituted by at least one substituent e.g. one or two, which is preferably a substituent selected from carboxy, carbamoyl, and lower alkyl,
or a pharmaceutically acceptable salt thereof.

Other preferred compounds are the compounds in the B group, wherein
  m+n is 1, 2 or 3, preferably 1 or 2,
  m+m+p is preferably 2 or 3,
  p is 1 or 0, and
  X is substituted or unsubstituted cycloalkyl, substituted or unsubstituted heterocyclyl, substituted or unsubstituted heteroaryl, or substituted or unsubstituted aryl, preferably unsubstituted or substituted by at least one substituent e.g. one or two, which is preferably a substituent selected from sulfonamido, carboxy, carbamoyl, and lower alkyl,
or a pharmaceutically acceptable salt thereof.

Other preferred compounds are the compounds in the B group, wherein
  m+n is 1, 2 or 3, preferably 1 or 2,
  m+n+p is 2, 3 or 4, preferably 2 or 3,
  p is 1 or 0, and
  X is substituted or unsubstituted aryl, preferably unsubstituted or substituted by at least one substituent e.g. one or two, which is preferably a substituent selected from sulfonamido, carboxy, carbamoyl, and lower alkyl,
or a pharmaceutically acceptable salt thereof.

Other preferred compounds are the compounds in the B group, wherein
  m+n is 1, 2 or 3, preferably 1 or 2,
  p is 1 or 0, and
  X is substituted or unsubstituted "amide" type heterocyclyl, substituted or unsubstituted cycloalkyl substituted by at least one substituent e.g. one or two, which is preferably sulfonamide, or aryl substituted by at least one substituent e.g. one or two, which is preferably sulfonamido
or a pharmaceutically acceptable salt thereof.

Preferred are the compounds of formula (I), designated as the C, wherein
Q is —Y—$(CH_2)_n$—$(CR_8R_9)_p$—$(CH_2)_m$—Z—X, in which
  Y is oxygen or $S(O)_q$ in which q is zero or an integer of 1 or 2; or
  Y is —C≡C— or —C=C—; or
  Y is absent;
  n and m are, independently from each other, zero or an integer from 1 to 8;

$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or $R_8$ and $R_9$ combined are alkylene which together with the carbon atom to which they are attached form a 3- to 7-membered ring;

p is zero or an integer selected from 1 or 2

Z is —CO—NRα-alkylene- or CO—NRα-alkylene-O, wherein Rα is H or lower alkyl; or

Z is —CO—NRα-$(CH_2)_{n'}$—$(CR_8R_9)_{p'}$—$(CH_2)_{m'}$—, or —CO—NRα-$(CH_2)_{n'}$—$(CR_8R_9)_{p'}$—$(CH_2)_{m'}$—O—, wherein p' is zero or an integer of 1, n' and m' are independently from each other, zero or an integer from 1 to 8, $R_{8'}$ and $R_{9'}$ are, independently from each other, hydrogen or lower alkyl, Rα is H or lower alkyl; or Z is —NRα'-CO—, or —NRα'-CO—O— wherein Rα' is, H or lower alkyl, or Rα' and $R_9$ combined are alkylene which together with the carbon atom to which they are attached form a 3- to 7-membered ring; or Z is CO—NH—NH—CO—O—; or X is hydrogen, hydroxy, $NH_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio;

or a pharmaceutically acceptable salt thereof.

Preferred are the compounds in the C group wherein Y is absent;

or a pharmaceutically acceptable salt thereof.

Preferred are the compounds in the C group wherein $R_8$ and $R_9$ are, independently from each other, hydrogen, alkanoylamino, aralkyl, aryl, or alkyl;

or a pharmaceutically acceptable salt thereof.

Preferred are the compounds in the C group wherein X is hydrogen, substituted or unsubstituted alkyl, substituted or unsubstituted cycloalkyl, carboxy, substituted or unsubstituted esterified carboxy, substituted or unsubstituted aryl, substituted or unsubstituted aralkyl, substituted or unsubstituted aryloxy;

or a pharmaceutically acceptable salt thereof.

Preferred are the compounds in the C group wherein $R_2$ and $R_3$ are hydrogen;

or a pharmaceutically acceptable salt thereof.

Preferred are the compounds in the C group wherein $R_1$ is hydrogen;

or a pharmaceutically acceptable salt thereof.

Further preferred are the compounds in the C group wherein n is zero or an integer from 1 to 3;
m is zero or an integer from 1 to 3;
p is zero or 1;

or a pharmaceutically acceptable salt thereof.

Especially preferred are the compounds in the C group, wherein m+n+p is between 0 and 6 or preferably between 0 and 4, or a pharmaceutically acceptable salt thereof.

Other preferred compounds are the compounds in the C group, wherein i) m+n+p is between 1 and 3 (i.e. 1, 2 or 3)
ii) m+n is between 1 and 3 (i.e. 1, 2 or 3) and p is 0
iii) m+n+p is between 1 and 3 (i.e. 1, 2 or 3) and p is 1
iv) m is 0, n is between 1 and 2 (i.e. 1, or 2) and p is 1 or a pharmaceutically acceptable salt thereof.

Especially preferred are the compounds in the C group, wherein n' and m' are independently from each other, zero or an integer from 1 to 6, and p' is zero or an integer of 1, or a pharmaceutically acceptable salt thereof.

Especially preferred are the compounds in the C group, wherein p'+n'+m' is comprised between zero and 5, or between 3 and 5 i.e. 3, 4 or 5, or a pharmaceutically acceptable salt thereof.

Especially preferred are the compounds in the C group, wherein n' and m' are independently from each other, zero or an integer from 1 to 6, preferably from 1 to 4, or a pharmaceutically acceptable salt thereof.

Other preferred compounds are the compounds in the C group, wherein n'+m' is between 0 and 5, or between 3 and 5, preferably 4, and p' is 0, or a pharmaceutically acceptable salt thereof.

Especially preferred are the compounds in the C group, wherein

X is substituted or unsubstituted phenyl, preferably unsubstituted or substituted preferably by at least one, e.g. one or two, of the substituents selected preferably from alkoxycarbonyl, carboxy, alkoxy, cyano, lower alkyl, (lower alkyl)-NHC(O)—, (lower alkyl)$_2$—NC(O)— and hydroxy.

Preferred are the compounds of formula (I), designated as the D group, wherein

Q is —Y—$(CH_2)_n$—$(CR_8R_9)_p$—$(CH_2)_m$—Z—X, in which

Y is absent;
n and m are, independently from each other, zero;
p is zero;
Z is absent;
X is hydrogen, hydroxy, $NH_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio;

or a pharmaceutically acceptable salt thereof.

Preferred are the compounds in the D group wherein
X is halogen, cyano, trifluoromethyl, substituted or unsubstituted heterocyclyl, substituted or unsubstituted heteroaryl, substituted or unsubstituted aryl,
or
X is halogen, cyano, trifluoromethyl, substituted or unsubstituted heterocyclyl, substituted or unsubstituted heteroaryl, substituted or unsubstituted aryl, substituted or unsubstituted lower alkyl,
or a pharmaceutically acceptable salt thereof.

Preferred are the compounds in the D group wherein
$R_2$ and $R_3$ are independently from each other, hydrogen, halogen, $C_{1-3}$ alkyl or $C_{1-3}$ alkoxy;
or a pharmaceutically acceptable salt thereof.

Preferred are the compounds in the D group wherein
$R_2$ and $R_3$ are hydrogen;
or a pharmaceutically acceptable salt thereof.

Preferred are the compounds in the D group wherein
$R_1$ is hydrogen;
or a pharmaceutically acceptable salt thereof.

Further preferred are the compounds in the D group wherein
X is substituted or unsubstituted aryl or substituted or unsubstituted heteroaryl, or a pharmaceutically acceptable salt thereof.

Especially preferred are the compounds in the D group, wherein
X is substituted or unsubstituted aryl substituted by an "amide" type heterocyclyl, or a pharmaceutically acceptable salt thereof.

Preferred are the compounds of formula (I), designated as the E group, wherein
Q is —Y—$(CH_2)$, —$(CR_8R_9)_p$—$(CH_2)_m$—Z—X, in which
Y is oxygen or $S(O)_q$ in which q is zero or an integer of 1 or 2; or
Y is —C≡C— or —C=C—; or
Y is absent;
n and m are, independently from each other, zero or an integer from 1 to 8;
$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or
$R_8$ and $R_9$ combined are alkylene which together with the carbon atom to which they are attached form a 3- to 7-membered ring;
p is zero or an integer selected from 1 or 2
Z is —$SO_2$—, or —SO—; or
Z is —NRβ-$SO_2$—, wherein Rβ is H, lower alkyl, or Rβ and $R_9$ combined are alkylene which together with the carbon atom to which they are attached form a 3- to 7-membered ring preferably 5-, 6- or 7-membered ring; or
Z is —NH—$SO_2$—NH—CO—O—; or
X is hydrogen, hydroxy, $NH_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio;
or a pharmaceutically acceptable salt thereof.

Preferred are the compounds in the E group wherein
Y is absent; or a pharmaceutically acceptable salt thereof.

Preferred are the compounds in the E group wherein
$R_8$ and $R_9$ are, independently from each other, hydrogen, aralkyl, heteroaryl, heterocyclyl, heterocyclyl, carbamoyl; or
$R_8$ and $R_9$ combined are alkylene which together with the carbon atom to which they are attached form a 3- to 7-membered ring;
or a pharmaceutically acceptable salt thereof.

Preferred are the compounds in the E group wherein
X is hydrogen, substituted or unsubstituted alkyl, substituted or unsubstituted cycloalkyl, substituted or unsubstituted heteroaryl, substituted or unsubstituted aryl, substituted or unsubstituted aralkyl;
or a pharmaceutically acceptable salt thereof.

Preferred are the compounds in the E group wherein
$R_2$ and $R_3$ are hydrogen;
or a pharmaceutically acceptable salt thereof.

Preferred are the compounds in the E group wherein
$R_1$ is hydrogen;
or a pharmaceutically acceptable salt thereof.

Further preferred are the compounds in the E group wherein
n is zero or an integer from 1 to 4;
m is zero or an integer from 1 to 4;
p is zero or 1;
or a pharmaceutically acceptable salt thereof.

Especially preferred are the compounds in the E group, wherein
m+n+p is between 0 and 7 or preferably between 0 and 5,
or a pharmaceutically acceptable salt thereof.

Other preferred compounds are the compounds in the E group, wherein
i) m+n+p is 2 or 3, or
ii) $_m$+n is 2 or 3, and p is 0, or
iii) n is 1 or 2, m is 0 or 1, and p is 1 when Rβ and $R_9$ combined are alkylene which together with the carbon atom to which they are attached form a 5-, 6- or 7-membered ring or a pharmaceutically acceptable salt thereof.

Other preferred compounds are the compounds in the E group, wherein
i) m+n is 1 or 2, m is 0 or 1, and p is 1, or
ii) n is 1 or 2, m is 0 or 1, and p is 1 when $R_8$ is hydrogen and $R_9$ is selected from aralkyl, heteroaryl, heterocyclyl, heterocyclyl, or carbamoyl;
or a pharmaceutically acceptable salt thereof.

Other preferred compounds are the compounds in the E group, wherein
X is selected from substituted or unsubstituted phenyl, substituted or unsubstituted biphenyl, substituted or unsubstituted benzyl, substituted or unsubstituted lower alkyl, methyl substituted by on or two phenyl, ethyl substituted by on or two phenyl, or methyl substituted by cycloalkyl Preferred are the compounds of formula (I), designated as the F group, wherein
Q is —Y—$(CH_2)_n$—$(CR_8R_9)_p$—$(CH_2)_m$—Z—X, in which
Y is oxygen or $S(O)_q$ in which q is zero or an integer of 1 or 2; or
Y is —C≡C— or —C=C—; or Y is absent;

n and m are, independently from each other, zero or an integer from 1 to 8;

$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or $R_8$ and $R_9$ combined are alkylene which together with the carbon atom to which they are attached form a 3- to 7-membered ring;

p is zero or an integer selected from 1 or 2 Z is —NRγ-CO—NRγ'—; wherein Rγ' is H, alkyl, aryl, heterocyclyl, or lower alkoxy and Rγ is H, lower alkyl, or Rγ and $R_9$ combined are alkylene which together with the carbon atom to which they are attached form a 3- to 7-membered ring; or Rγ' and X combined are alkylene which together with the carbon atom to which they are attached form a 3- to 7-membered ring; or Z is —NRτ-CO—NH—SO$_2$—, wherein Rτ is H or lower alkyl, X is hydrogen, hydroxy, NH$_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio;

or a pharmaceutically acceptable salt thereof.

Preferred are the compounds in the F group wherein Y is absent; or a pharmaceutically acceptable salt thereof.

Preferred are the compounds in the F group wherein $R_8$ and $R_9$ are, independently from each other, hydrogen; or a pharmaceutically acceptable salt thereof.

Preferred are the compounds in the F group wherein X is hydrogen, substituted or unsubstituted alkyl, substituted or unsubstituted cycloalkyl, substituted or unsubstituted heterocyclyl, substituted or unsubstituted aryl, substituted or unsubstituted aralkyl;

or a pharmaceutically acceptable salt thereof.

Preferred are the compounds in the F group wherein $R_2$ and $R_3$ are hydrogen;

or a pharmaceutically acceptable salt thereof.

Preferred are the compounds in the F group wherein Rγ' is H or lower alkyl, or a pharmaceutically acceptable salt thereof.

Preferred are the compounds in the F group wherein $R_1$ is hydrogen;

or a pharmaceutically acceptable salt thereof.

Especially preferred are the compounds in the F group, wherein m+n+p is between 0 and 7 or preferably between 0 and 5 or between 2 and 3, or a pharmaceutically acceptable salt thereof.

Further preferred are the compounds in the F group wherein n is zero or an integer from 1 to 4;

m is zero or an integer from 1 to 4;

p is zero or 1;

or a pharmaceutically acceptable salt thereof.

Especially preferred are the compounds in the F group, wherein m+n+p is 2 or 3, and X is substituted or unsubstituted lower alkyl, substituted or unsubstituted phenyl, substituted or unsubstituted benzyl, or substituted or unsubstituted cyclohexyl, or a pharmaceutically acceptable salt thereof.

Compound according to any of the above described groups wherein;

the term alkyl preferably refers to a lower alkyl, aryl is preferably a phenyl, and/or when $R_8$ and $R_9$ are present, at least one of $R_8$ or $R_9$ is hydrogen.

Compounds according to any of the hereinabove described formula, or compounds according to any of the hereinabove described groups, in which $R_8$ or $R_9$ are unsubstituted or optionally substituted by 1, 2, 3, 4, or 5 substituents as described hereinabove for the different groups.

Compounds according to any of the hereinabove described formula, or compounds according to any of the hereinabove described groups, in which X is selected from hydrogen, hydroxy, NH$_2$, halogen, substituted or unsubstituted alkoxy, substituted or unsubstituted alkylthio, substituted or unsubstituted alkyl, —S(O)—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio, wherein the alkyl, cycloalkyl, aryl, heteroaryl and heterocyclyl groups are unsubstituted or optionally substituted by 1, 2, 3, 4, or 5 substituents as described hereinabove for the different groups.

In one embodiment, the substituents are, independently from each other, selected from halogen, cyano, amino, hydroxy, sulfonamido, carboxy, carbamoyl, sulfonyl, —SO—$C_{1-6}$ alkyl, —SO$_2$—OH, alkoxycarbonyl, alkanoyl, alkyl, trifluoromethyl, alkoxy, aryl, trifluoromethyl, aryloxy, heterocyclyl (e.g. "amide" type heterocyclyl) and cycloalkyl, wherein the alkyl groups are optionally substituted by 1, 2, 3 or 4 substituents selected independently from each other from; carboxy, amino, hydroxy or halogen, and wherein the aryl groups are optionally substituted by 1, 2, 3 or 4 substituents selected independently from each other from; e.g. halogen, amino, $C_{1-6}$ alkoxy or $C_{1-6}$ alkyl.

In a further embodiment, the substituents are, independently from each other, selected from; halogen, cyano, oxo, amino, hydroxy, —NH—SO$_2$—$C_{1-6}$ alkyl, —NH—SO$_2$-phenyl, carboxy, (lower alkyl)-NHC(O)—, (lower alkyl)$_2$—NC(O)—, —C(O)—O—$C_{1-6}$alkyl, —C(O)—$C_{1-6}$-alkyl, $C_{1-6}$ alkyl, —C(O)—$C_{1-6}$ alkyl, trifluoromethyl, —SO$_2$—OH, —SO$_2$-phenyl, —SO$_2$—$C_1$—alkyl, —SO—$C_1$—alkyl, $C_{1-6}$ alkoxy, phenyl, trifluoromethyl phenyl-O—, heterocyclyl (e.g. "amide" type heterocyclyl) and cycloalkyl, wherein the alkyl groups are optionally substituted by 1, 2, 3 or 4 substituents selected independently from each other from; carboxy, amino, hydroxy or halogen, and wherein the phenyl groups are optionally substituted by 1, 2, 3 or 4 substituents selected independently from each other from; e.g. halogen, amino, $C_{1-6}$ alkoxy or $C_{1-6}$ alkyl.

Particular embodiments of the invention are: the below specific exemplified compounds, 3-{2-[3-Hydroxy-4-(1,1,4-trioxo-1,2,5-thiadiazolidin-2-yl)-phenyl]-ethyl}-benzamide
3-{2-[3-Hydroxy-4-(1,1,4-trioxo-1,2,5-thiadiazolidin-2-yl)-phenyl]-ethyl}-N-methyl benzamide
3-{2-[3-Hydroxy-4-(1,1,4-trioxo-1,2,5-thiadiazolidin-2-yl)-phenyl]-ethyl}-N,N-dimethylbenzamide
4-{2-[3-Hydroxy-4-(1,1,4-trioxo-1,2,5-thiadiazolidin-2-yl)-phenyl]-ethyl}-N,N-dimethylbenzamide
4-{2-[3-Hydroxy-4-(1,1,4-trioxo-1,2,5-thiadiazolidin-2-yl)-phenyl]-ethyl}-benzamide
4-{2-[3-Hydroxy-4-(1,1,4-trioxo-1,2,5-thiadiazolidin-2-yl)-phenyl]-ethyl}-N-methylbenzamide
3-{2-[3-Hydroxy-4-(1,1,4-trioxo-1,2,5-thiadiazolidin-2-yl)-phenyl]-ethyl}-benzoic acid
4-{2-[3-Hydroxy-4-(1,1,4-trioxo-1,2,5-thiadiazolidin-2-yl)-phenyl]-ethyl}-benzoic acid
4-{2-[3-Hydroxy-4-(1,1,4-trioxo-1,2,5-thiadiazolidin-2-yl)-phenyl]-ethyl}-benzonitrile
2-{2-[3-Hydroxy-4-(1,1,4-trioxo-1,2,5-thiadiazolidin-2-yl)-phenyl]-ethyl}-benzonitrile
5-(2-Hydroxy-4-phenethylphenyl)-1,1-dioxo-1,2,5-thiadiazolidin-3-one
5-{2-Hydroxy-4-[2-(3-methoxyphenyl)-ethyl]-phenyl}-1,1-dioxo-1,2,5-thiadiazolidin-3-one
5-{4-[2-(3-Fluorophenyl)-ethyl]-2-hydroxyphenyl}-1,1-dioxo-1,2,5-thiadiazolidin-3-one
5-{4-[2-(2-Fluorophenyl)-ethyl]-2-hydroxyphenyl}-1,1-dioxo-1,2,5-thiadiazolidin-3-one
5-[2-Hydroxy-4-(2-pentafluorophenylethyl)-phenyl]-1,1-dioxo-1,2,5-thiadiazolidin-3-one
5-[2-Hydroxy-4-(2-p-tolylethyl)-phenyl]-1,1-dioxo-1,2,5-thiadiazolidin-3-one
5-{2-Hydroxy-4-[2-(4-octylphenyl)-ethyl]-phenyl}-1,1-dioxo-1,2,5-thiadiazolidin-3-one
5-[4-(2-Biphenyl-4-yl-ethyl)-2-hydroxyphenyl]-1,1-dioxo-1,2,5-thiadiazolidin-3-one
5-{4-[2-(4-tert-Butylphenyl)-ethyl]-2-hydroxyphenyl}-1,1-dioxo-1,2,5-thiadiazolidin-3-one
5-{4-[2-(2,5-Dimethylphenyl)-ethyl]-2-hydroxyphenyl}-1,1-dioxo-1,2,5-thiadiazolidin-3-one
5-{4-[2-(2,4-Dimethylphenyl)-ethyl]-2-hydroxyphenyl}-1,1-dioxo-1,2,5-thiadiazolidin-3-one
5-{2-Hydroxy-4-[2-(4-trifluoromethylphenyl)-ethyl]-phenyl}-1,1-dioxo-1,2,5-thiadiazolidin-3-one
Acetic acid 4-{2-[3-hydroxy-4-(1,1,4-trioxo-1,2,5-thiadiazolidin-2-yl)-phenyl]ethyl}-phenyl ester
5-{2-Hydroxy-4-[2-(4-phenoxyphenyl)-ethyl]-phenyl}-1,1-dioxo-1,2,5-thiadiazolidin-3-one
5-[2-Hydroxy-4-(2-pyridin-4-ylethyl)-phenyl]-1,1-dioxo-1,2,5-thiadiazolidin-3-one
5-[2-Hydroxy-4-(2-pyridin-3-yl-ethyl)-phenyl]-1,1-dioxo-1,2,5-thiadiazolidin-3-one
5-[2-Hydroxy-4-(2-naphthalenethyl)-phenyl]-1,1-dioxo-1,2,5-thiadiazolidin-3-one
5-[2-Hydroxy-4-(2-quinolin-3-yl-ethyl)-phenyl]-1,1-dioxo-1,2,5-thiadiazolidin-3-one
5-{4-[2-(4,6-Diamino-[1,3,5]triazin-2-yl)-ethyl]-2-hydroxy-phenyl}-1,1-dioxo-1,2,5-thiadiazolidin-3-one
5-[2-Hydroxy-4-(2-phenylpropyl)-phenyl]-1,1-dioxo-1,2,5-thiadiazolidin-3-one
5-{4-[2-(2-Aminophenyl)-propyl]-2-hydroxyphenyl}-1,1-dioxo-1,2,5-thiadiazolidin-3-one
3-[3-Hydroxy-4-(1,1,4-trioxo-1,2,5-thiadiazolidin-2-yl)-phenyl]-2-phenylpropionic acid ethyl ester
5-[2-Hydroxy-4-(1-methyl-2-phenylethyl)-phenyl]-1,1-dioxo-1,2,5-thiadiazolidin-3-one
5-{2-Hydroxy-4-[2-(6-methoxypyridin-2-yl)-ethyl]-phenyl}-1,1-dioxo-1,2,5-thiadiazolidin-3-one
5-[2-Hydroxy-4-((E)-2-pyridin-3-yl-vinyl)-phenyl]-1,1-dioxo-1,2,5-thiadiazolidin-3-one
5-[2-Hydroxy-4-(1-methoxy-2-phenylethyl)-phenyl]-1,1-dioxo-1,2,5-thiadiazolidin-3-one
5-[2-Hydroxy-4-(3-oxo-2-phenylbutyl)-phenyl]-1,1-dioxo-1,2,5-thiadiazolidin-3-one
5-{2-Hydroxy-4-[2-(2H-pyrazol-3-yl)-ethyl]-phenyl}-1,1-dioxo-1,2,5-thiadiazolidin-3-one
5-{2-Hydroxy-4-[2-(1H-pyrazol-4-yl)-ethyl]-phenyl}-1,1-dioxo-1,2,5-thiadiazolidin-3-one
5-{2-Hydroxy-4-[2-(1-methyl-1H-pyrazol-4-yl)-ethyl]-phenyl}-1,1-dioxo-1,2,5-thiadiazolidin-3-one
5-[2-Hydroxy-4-(2-thiazol-5-yl-ethyl)-phenyl]-1,1-dioxo-1,2,5-thiadiazolidin-3-one
5-{4-[2-(2,4-Dimethyl-thiazol-5-yl)-ethyl]-2-hydroxyphenyl}-1,1-dioxo-1,2,5-thiadiazolidin-3-one
5-[2-Hydroxy-4-(2-[1,2,4]triazol-yl-ethyl)-phenyl]-1,1-dioxo-1,2,5-thiadiazolidin-3-one
5-[2-Hydroxy-4-(2-imidazol-1-yl-ethyl)-phenyl]-1,1-dioxo-1,2,5-thiadiazolidin-3-one
5-{2-Hydroxy-4-[2-(2-methyl-thiazol-5-yl)-ethyl]-phenyl}-1,1-dioxo-1,2,5-thiadiazolidin-3-one
5-{2-Hydroxy-4-[2-(2-propyl-thiazol-5-yl)-ethyl]-phenyl}-1,1-dioxo-1,2,5-thiadiazolidin-3-one
5-(2-Hydroxy-4-{2-[4-methyl-2-(4-trifluoromethyl-phenyl)-thiazol-5-yl]-ethyl}-phenyl)-1,1-dioxo-1,2,5-thiadiazolidin-3-one
5-{2-Hydroxy-4-[2-(2-methyl-4-trifluoromethyl-thiazol-5-yl)-ethyl]-phenyl}-1,1-dioxo-1,2,5-thiadiazolidin-3-one
5-{4-[2-(1H-Benzoimidazol-2-yl)-ethyl]-2-hydroxyphenyl}-1,1-dioxo-1,2,5-thiadiazolidin-3-one
5-[2-Hydroxy-4-(3-phenylpropyl)-phenyl]-1,1-dioxo-1,2,5-thiadiazolidin-3-one
5-{4-[3-(3,4-Dimethoxyphenyl)-propyl]-2-hydroxyphenyl}-1,1-dioxo-1,2,5-thiadiazolidin-3-one
5-[2-Hydroxy-4-(2-methyl-3-phenylpropyl)-phenyl]-1,1-dioxo-1,2,5-thiadiazolidin-3-one
5-[2-Hydroxy-4-(3-hydroxy-3-phenylpropyl)-phenyl]-1,1-dioxo-1,2,5-thiadiazolidin-3-one
5-(2-Hydroxy-4-(4-phenethyloxyphenyl)-1,1-dioxo-1,2,5-thiadiazolidin-3-one
5-[2-Hydroxy-4-(4-phenylbutyl)-phenyl]-1,1-dioxo-1,2,5-thiadiazolidin-3-one
{3-[3-Hydroxy-4-(1,1,4-trioxo-1,2,5-thiadiazolidin-2-yl)-phenyl]-propyl}-carbamic acid tert-butyl ester
5-[4-(3-Aminopropyl)-2-hydroxyphenyl]-1,1-dioxo-1,2,5-thiadiazolidin-3-one
{2-[3-Hydroxy-4-(1,1,4-trioxo-1,2,5-thiadiazolidin-2-yl)-phenyl]-ethyl}carbamic acid tert-butyl ester
{(S)-1-Benzyl-2-[3-hydroxy-4-(1,1,4-trioxo-1,2,5-thiadiazolidin-2-yl)-phenyl]-ethyl}-carbamic acid tert-butyl ester
{3-[3-Hydroxy-4-(1,1,4-trioxo-1,2,5-thiadiazolidin-2-yl)-phenyl]-1,1-dimethylpropyl}-carbamic acid tert-butyl ester
2-{2-[3-Hydroxy-4-(1,1,4-trioxo-1,2,5-thiadiazolidin-2-yl)-phenyl]-ethyl}-piperidine-1-carboxylic acid tert-butyl ester
2-{2-[3-Hydroxy-4-(1,1,4-trioxo-1,2,5-thiadiazolidin-2-yl)-phenyl]-ethyl}-azepane-1-carboxylic acid tert-butyl ester
3-[3-Hydroxy-4-(1,1,4-trioxo-1,2,5-thiadiazolidin-2-yl)-benzyl]-piperidine-1-carboxylic acid tert-butyl ester 5-(2-Hydroxy-4-piperidin-3-ylmethylphenyl)-1,1-dioxo-1, 2,5-thiadiazolidin-3-one
{(1R*,2S*)-2-[3-Hydroxy-4-(1,1,4-trioxo-1,2,5-thiadiazolidin-2-yl)-benzyl]-cyclohexyl}-carbamic acid tert-butyl ester
N-{2-[3-Hydroxy-4-(1,1,4-trioxo-1,2,5-thiadiazolidin-2-yl)-phenyl]-ethyl}-benzamide
4-Fluoro-N-{2-[3-hydroxy-4-(1,1,4-trioxo-1,2,5-thiadiazolidin-2-yl)-phenyl]-ethyl}-benzamide
N-{2-[3-Hydroxy-4-(1,1,4-trioxo-1,2,5-thiadiazolidin-2-yl)-phenyl]-ethyl}-acetamide
N-{2-[3-Hydroxy-4-(1,1,4-trioxo-1,2,5-thiadiazolidin-2-yl)-phenyl]-ethyl}-propionamide
N-{2-[3-Hydroxy-4-(1,1,4-trioxo-1,2,5-thiadiazolidin-2-yl)-phenyl]-ethyl}-isobutyramide
N-{2-[3-Hydroxy-4-(1,1,4-trioxo-1,2,5-thiadiazolidin-2-yl)-phenyl]-ethyl}-2,2-dimethyl-propionamide
Adamantane-1-carboxylic acid {2-[3-hydroxy-4-(1,1,4-trioxo-1,2,5-thiadiazolidin-2-yl)-phenyl]-ethyl}-amide
N-{3-[3-Hydroxy-4-(1,1,4-trioxo-1,2,5-thiadiazolidin-2-yl)-phenyl]-propyl}-acetamide
4-Fluoro-N-{3-[3-hydroxy-4-(1,1,4-trioxo-1,2,5-thiadiazolidin-2-yl)-phenyl]-propyl}-benzamide
-{3-[3-Hydroxy-4-(1,1,4-trioxo-1,2,5-thiadiazolidin-2-yl)-phenyl]-propyl}-propionamide
N-{3-[3-Hydroxy-4-(1,1,4-trioxo-1,2,5-thiadiazolidin-2-yl)-phenyl]-propyl}-isobutyramide
N-{3-[3-Hydroxy-4-(1,1,4-trioxo-1,2,5-thiadiazolidin-2-yl)-phenyl]-propyl}-2,2-dimethyl-propionamide
Adamantane-1-carboxylic acid {3-[3-hydroxy-4-(1,1,4-trioxo-1,2,5-thiadiazolidin-2-yl)-phenyl]-propyl}-amide
5-[2-Hydroxy-4-((S)-5-oxopyrrolidin-2-ylmethyl)-phenyl]-1,1-dioxo-1,2,5-thiadiazolidin-3-one
6-[3-Hydroxy-4-(1,1,4-trioxo-1,2,5-thiadiazolidin-2-yl)-benzyl]-1H-pyridin-2-one
6-[3-Hydroxy-4-(1,1,4-trioxo-1,2,5-thiadiazolidin-2-yl)-benzyl]-piperidin-2-one
7-[3-Hydroxy-4-(1,1,4-trioxo-1,2,5-thiadiazolidin-2-yl)-benzyl]-azepan-2-one
(R)-3-[3-Hydroxy-4-(1,1,4-trioxo-1,2,5-thiadiazolidin-2-yl)-benzyl]-3,4-dihydro-2H-isoquinolin-1-one
(S)-3-[3-Hydroxy-4-(1,1,4-trioxo-1,2,5-thiadiazolidin-2-yl)-benzyl]-2,3-dihydro-benzo[c]azepin-1-one
(R)-3-[3-Hydroxy-4-(1,1,4-trioxo-1,2,5-thiadiazolidin-2-yl)-benzyl]-2,3,4,5-tetrahydrobenzo[c]azepin-1-one
1-[3-Hydroxy-4-(1,1,4-trioxo-1,2,5-thiadiazolidin-2-yl)-benzyl]-1,2,4,5-tetrahydrobenzo[c]azepin-3-one
1-[3-Hydroxy-4-(1,1,4-trioxo-1,2,5-thiadiazolidin-2-yl)-benzyl]-1,3,4,5-tetrahydrobenzo[d]azepin-2-one
7-[3-Hydroxy-4-(1,1,4-trioxo-1,2,5-thiadiazolidin-2-yl)-benzyl]-6,7-dihydro-dibenzo[c,e]azepin-5-one
(S)-7-[3-Hydroxy-4-(1,1,4-trioxo-1,2,5-thiadiazolidin-2-yl)-benzyl]-6,7-dihydro-dibenzo[c,e]azepin-5-one
3-[3-Hydroxy-4-(1,1,4-trioxo-1,2,5-thiadiazolidin-2-yl)-benzyl]-3,4-dihydro-2H-naphtho[1,8-cd]azepin-1-one
5-{4-[2-(1-Acetylpiperidin-2-yl)-ethyl]-2-hydroxyphenyl}-1,1-dioxo-1,2,5-thiadiazolidin-3-one
N-{(1R*,2S*)-2-[3-Hydroxy-4-(1,1,4-trioxo-1,2,5-thiadiazolidin-2-yl)-benzyl]-cyclohexyl}-acetamide
N-{(S)-1-Benzyl-2-[3-hydroxy-4-(1,1,4-trioxo-1,2,5-thiadiazolidin-2-yl)-phenyl]-ethyl}-2,2,2-trifluoroacetamide
N-{4-[3-Hydroxy-4-(1,1,4-trioxo-1,2,5-thiadiazolidin-2-yl)-phenyl]-butyl}-phthalamic acid
2-{4-[3-Hydroxy-4-(1,1,4-trioxo-1,2,5-thiadiazolidin-2-yl)-phenyl]-butyl}-isoindole-1,3-dione
3-[3-Hydroxy-4-(1,1,4-trioxo-1,2,5-thiadiazolidin-2-yl)-phenyl]-N-isopropyl-N-methylpropionamide
5-{4-[3-(3,4-Dihydro-1H-isoquinolin-2-yl)-3-oxopropyl]-2-hydroxyphenyl}-1,1-dioxo-1,2,5-thiadiazolidin-3-one
N'-{3-[3-Hydroxy-4-(1,1,4-trioxo-1,2,5-thiadiazolidin-2-yl)-phenyl]-propionyl}-hydrazinecarboxylic acid tert-butyl ester
N-Butyl-3-[3-hydroxy-4-(1,1,4-trioxo-1,2,5-thiadiazolidin-2-yl)-phenyl]-propionamide
3-[3-Hydroxy-4-(1,1,4-trioxo-1,2,5-thiadiazolidin-2-yl)-phenyl]-N-pentylpropionamide
N-Hexyl-3-[3-hydroxy-4-(1,1,4-trioxo-1,2,5-thiadiazolidin-2-yl)-phenyl]-propionamide
3-[3-Hydroxy-4-(1,1,4-trioxo-1,2,5-thiadiazolidin-2-yl)-phenyl]-N-(4-phenylbutyl)-propionamide
3-[3-Hydroxy-4-(1,1,4-trioxo-1,2,5-thiadiazolidin-2-yl)-phenyl]-N-(5-phenylpentyl)-propionamide
N-(2-Hydroxyphenyl)-3-[3-hydroxy-4-(1,1,4-trioxo-1,2,5-thiadiazolidin-2-yl)-phenyl]-propionamide
3-[3-Hydroxy-4-(1,1,4-trioxo-1,2,5-thiadiazolidin-2-yl)-phenyl]-N-phenylpropionamide
3-[3-Hydroxy-4-(1,1,4-trioxo-1,2,5-thiadiazolidin-2-yl)-phenyl]-N-o-tolyl-propionamide
3-[3-Hydroxy-4-(1,1,4-trioxo-1,2,5-thiadiazolidin-2-yl)-phenyl]-N-isopropyl-propionamide
2-{3-[3-Hydroxy-4-(1,1,4-trioxo-1,2,5-thiadiazolidin-2-yl)-phenyl]-propionylamino}-2-methylpropionic acid
2-Hydroxy-6-(4-{3-[3-hydroxy-4-(1,1,4-trioxo-1,2,5-thiadiazolidin-2-yl)-phenyl]-propionylamino}-butoxy)-benzoic acid methyl ester
2-(4-{3-[3-Hydroxy-4-(1,1,4-trioxo-1,2,5-thiadiazolidin-2-yl)-phenyl]-propionylamino}-butoxy)-benzoic acid methyl ester
2-(4-{3-[3-Hydroxy-4-(1,1,4-trioxo-1,2,5-thiadiazolidin-2-yl)-phenyl]-propionylamino}-butoxy)-benzoic acid
3-[3-Hydroxy-4-(1,1,4-trioxo-1,2,5-thiadiazolidin-2-yl)-phenyl]-N-(4-phenoxybutyl)-propionamide
3-[3-Hydroxy-4-(1,1,4-trioxo-1,2,5-thiadiazolidin-2-yl)-phenyl]-N-[4-(2-trifluoromethylphenoxy)-butyl]-propionamide
3-[3-Hydroxy-4-(1,1,4-trioxo-1,2,5-thiadiazolidin-2-yl)-phenyl]-N-[4-(2-methanesulfonylphenoxy)-butyl]-propionamide
3-[3-Hydroxy-4-(1,1,4-trioxo-1,2,5-thiadiazolidin-2-yl)-phenyl]-N-[4-(3-methoxyphenoxy)-butyl]-propionamide.
N-[4-(2,3-Dimethoxyphenoxy)-butyl]-3-[3-hydroxy-4-(1,1,4-trioxo-1,2,5-thiadiazolidin-2-yl)-phenyl]-propionamide
N-[4-(3-Hydroxyphenoxy)-butyl]-3-[3-hydroxy-4-(1,1,4-trioxo-1,2,5-thiadiazolidin-2-yl)-phenyl]-propionamide
N-[4-(2-Hydroxyphenoxy)-butyl]-3-[3-hydroxy-4-(1,1,4-trioxo-1,2,5-thiadiazolidin-2-yl)-phenyl]-propionamide
N-[4-(3-Hydroxy-2-methoxyphenoxy)-butyl]-3-[3-hydroxy-4-(1,1,4-trioxo-1,2,5-thiadiazolidin-2-yl)-phenyl]-propionamide
N-[4-(3-Hydroxy-2-methylphenoxy)-butyl]-3-[3-hydroxy-4-(1,1,4-trioxo-1,2,5-thiadiazolidin-2-yl)-phenyl]-propionamide
N-[4-(2-Acetyl-3-methoxyphenoxy)-butyl]-3-[3-hydroxy-4-(1,1,4-trioxo-1,2,5-thiadiazolidin-2-yl)-phenyl]-propionamide
2-Hydroxy-6-(4-{3-[3-hydroxy-4-(1,1,4-trioxo-1,2,5-thiadiazolidin-2-yl)-phenyl]-propionylamino}-butoxy)-N,N-dimethylbenzamide2-(4-{3-[3-Hydroxy-4-(1,1,4-trioxo-1,2,5-thiadiazolidin-2-yl)-phenyl]-propionylamino}-butoxy)-6,N,N-trimethylbenzamide
2-Fluoro-6-(4-{3-[3-hydroxy-4-(1,1,4-trioxo-1,2,5-thiadiazolidin-2-yl)-phenyl]-propionylamino}-butoxy)-N,N-dimethylbenzamide 2-Hydroxy-6-(4-{3-[3-hydroxy-4-(1,1,4-trioxo-1,2,5-thiadiazolidin-2-yl)-phenyl]-propionylamino}-butoxy)-benzoic acid
N-[4-(2-Acetyl-3-hydroxyphenoxy)-butyl]-3-[3-hydroxy-4-(1,1,4-trioxo-1,2,5-thiadiazolidin-2-yl)-phenyl]-propionamide
N-[4-(2-Cyano-3-hydroxyphenoxy)-butyl]-3-[3-hydroxy-4-(1,1,4-trioxo-1,2,5-thiadiazolidin-2-yl)-phenyl]-propionamide
N-[4-(3-Hydroxy-2-methanesulfinylphenoxy)-butyl]-3-[3-hydroxy-4-(1,1,4-trioxo-1,2,5-thiadiazolidin-2-yl)-phenyl]-propionamide
N-[4-(3-Hydroxy-2-methanesulfonylphenoxy)-butyl]-3-[3-hydroxy-4-(1,1,4-trioxo-1,2,5-thiadiazolidin-2-yl)-phenyl]-propionamide
2-(4-{2-Acetylamino-3-[3-hydroxy-4-(1,1,4-trioxo-1,2,5-thiadiazolidin-2-yl)-phenyl]-propionylamino}-butoxy)-6-hydroxybenzoic acid methyl ester
2-(4-{(S)-2-Acetylamino-3-[3-hydroxy-4-(1,1,4-trioxo-1,2,5-thiadiazolidin-2-yl)-phenyl]-propionylamino}-butoxy)-6-hydroxybenzoic acid methyl ester
3-[3-Hydroxy-4-(1,1,4-trioxo-1,2,5-thiadiazolidin-2-yl)-phenyl]-propionic acid methyl ester
3-[3-Hydroxy-4-(1,1,4-trioxo-1,2,5-thiadiazolidin-2-yl)-phenyl]-2-methylpropionic acid methyl ester
3-[3-Hydroxy-4-(1,1,4-trioxo-1,2,5-thiadiazolidin-2-yl)-phenyl]-2-methylpropionic acid tert-butyl ester
(1R*,2R*)-2-[3-Hydroxy-4-(1,1,4-trioxo-1,2,5-thiadiazolidin-2-yl)-phenyl]-cyclopropanecarboxylic acid ethyl ester
(1R*,2S*)-2-[3-Hydroxy-4-(1,1,4-trioxo-1,2,5-thiadiazolidin-2-yl)-phenyl]-cyclopropanecarboxylic acid ethyl ester
N-[3-Hydroxy-4-(1,1,4-trioxo-1,2,5-thiadiazolidin-2-yl)-benzyl]-N-methylbenzenesulfonamide
N-[3-Hydroxy-4-(1,1,4-trioxo-1,2,5-thiadiazolidin-2-yl)-benzyl]-N-methylmethanesulfonamide
C-Cyclohexyl-N-{2-[3-hydroxy-4-(1,1,4-trioxo-1,2,5-thiadiazolidin-2-yl)-phenyl]-ethyl}-methanesulfonamide
N-{2-[3-Hydroxy-4-(1,1,4-trioxo-1,2,5-thiadiazolidin-2-yl)-phenyl]ethyl}-methanesulfonamide
Ethanesulfonic acid {2-[3-hydroxy-4-(1,1,4-trioxo-1,2,5-thiadiazolidin-2-yl)-phenyl]-ethyl}-amide
Butane-1-sulfonic acid {2-[3-hydroxy-4-(1,1,4-trioxo-1,2,5-thiadiazolidin-2-yl)-phenyl]-ethyl}-amide
Propane-2-sulfonic acid {2-[3-hydroxy-4-(1,1,4-trioxo-1,2,5-thiadiazolidin-2-yl)-phenyl]-ethyl}-amide
Octane-1-sulfonic acid {2-[3-hydroxy-4-(1,1,4-trioxo-1,2,5-thiadiazolidin-2-yl)-phenyl]-ethyl}-amide
N-{2-[3-Hydroxy-4-(1,1,4-trioxo-1,2,5-thiadiazolidin-2-yl)-phenyl]-ethyl}-benzenesulfonamide
N-{2-[3-Hydroxy-4-(1,1,4-trioxo-1,2,5-thiadiazolidin-2-yl)-phenyl]-ethyl}-C-phenyl-methanesulfonamide
4-Fluoro-N-{2-[3-hydroxy-4-(1,1,4-trioxo-1,2,5-thiadiazolidin-2-yl)-phenyl]-ethyl}-benzenesulfonamide
3,4-Dichloro-N-{2-[3-hydroxy-4-(1,1,4-trioxo-1,2,5-thiadiazolidin-2-yl)-phenyl]-ethyl}-benzenesulfonamide
3-(4-{2-[3-Hydroxy-4-(1,1,4-trioxo-1,2,5-thiadiazolidin-2-yl)-phenyl]-ethylsulfamoyl}-phenyl)-propionic acid
2-Hydroxy-5-{2-[3-hydroxy-4-(1,1,4-trioxo-1,2,5-thiadiazolidin-2-yl)-phenyl]ethylsulfamoyl}-benzoic acid
Naphthalene-1-sulfonic acid {2-[3-hydroxy-4-(1,1,4-trioxo-1,2,5-thiadiazolidin-2-yl)-phenyl]-ethyl}-amide
2-Naphthalen-1-yl-ethanesulfonic acid {2-[3-hydroxy-4-(1,1,4-trioxo-1,2,5-thiadiazolidin-2-yl)-phenyl]-ethyl}-amide
N-{3-[3-Hydroxy-4-(1,1,4-trioxo-1,2,5-thiadiazolidin-2-yl)-phenyl]-propyl}-methanesulfonamide
N-{3-[3-Hydroxy-4-(1,1,4-trioxo-1,2,5-thiadiazolidin-2-yl)-phenyl]-propyl}-benzenesulfonamide
N-{3-[3-Hydroxy-4-(1,1,4-trioxo-1,2,5-thiadiazolidin-2-yl)-phenyl]-propyl}-C-phenylmethanesulfonamide
C-(4-Fluorophenyl)-N-{3-[3-hydroxy-4-(1,1,4-trioxo-1,2,5-thiadiazolidin-2-yl)-phenyl]-propyl}-methanesulfonamide
N-{3-[3-Hydroxy-4-(1,1,4-trioxo-1,2,5-thiadiazolidin-2-yl)-phenyl]-propyl}-4-isopropylbenzenesulfonamide
N-{3-[3-Hydroxy-4-(1,1,4)-trioxo-1,2,5-thiadiazolidin-2-yl)-phenyl]-propyl}-4-trifluoromethylbenzenesulfonamide
N-{3-[3-Hydroxy-4-(1,1,4-trioxo-1,2,5-thiadiazolidin-2-yl)-phenyl]-propyl}-4-trifluoromethoxybenzenesulfonamide
C-(3-Aminophenyl)-N-{3-[3-hydroxy-4-(1,1,4-trioxo-1,2,5-thiadiazolidin-2-yl)-phenyl]-propyl}-methanesulfonamide
N-{3-[3-Hydroxy-4-(1,1,4-trioxo-1,2,5-thiadiazolidin-2-yl)-phenyl]-propyl}-2,4,6-triisopropylbenzenesulfonamide
2-Hydroxy-5-{3-[3-hydroxy-4-(1,1,4-trioxo-1,2,5-thiadiazolidin-2-yl)-phenyl]-propylsulfamoyl}-benzoic acid
3-Amino-N-{3-[3-hydroxy-4-(1,1,4-trioxo-1,2,5-thiadiazolidin-2-yl)-phenyl]-propyl}-benzenesulfonamide
4-Amino-N-{3-[3-hydroxy-4-(1,1,4-trioxo-1,2,5-thiadiazolidin-2-yl)-phenyl]-propyl}-benzenesulfonamide
N-{3-[3-Hydroxy-4-(1,1,4-trioxo-1,2,5-thiadiazolidin-2-yl)-phenyl]-propyl}-3,5-dimethylbenzenesulfonamide
N-{3-[3-Hydroxy-4-(1,1,4-trioxo-1,2,5-thiadiazolidin-2-yl)-phenyl]-propyl}-2,5-dimethylbenzenesulfonamide
N-{3-[3-Hydroxy-4-(1,1,4-trioxo-1,2,5-thiadiazolidin-2-yl)-phenyl]-propyl}-2,4,6-trimethylbenzenesulfonamide
4-tert-Butyl-N-{3-[3-hydroxy-4-(1,1,4-trioxo-1,2,5-thiadiazolidin-2-yl)-phenyl]-propyl}-benzenesulfonamide
4-(1,1-Dimethylpropyl)-N-{3-[3-hydroxy-4-(1,1,4-trioxo-1,2,5-thiadiazolidin-2-yl)-phenyl]-propyl}benzenesulfonamide
N-{3-[3-Hydroxy-4-(1,1,4-trioxo-1,2,5-thiadiazolidin-2-yl)-phenyl]-propyl}-3,4-dimethoxybenzenesulfonamide
N-{3-[3-Hydroxy-4-(1,1,4-trioxo-1,2,5-thiadiazolidin-2-yl)-phenyl]-propyl}-2,5-bis-(2,2,2-trifluoroethoxy)-benzenesulfonamide
Biphenyl-4-sulfonic acid {3-[3-hydroxy-4-(1,1,4-trioxo-1,2,5-thiadiazolidin-2-yl)-phenyl]-propyl}-amide
N-{3-[3-Hydroxy-4-(1,1,4-trioxo-1,2,5-thiadiazolidin-2-yl-phenyl]-propyl}-2-phenoxybenzenesulfonamide
N-{3-[3-Hydroxy-4-(1,1,4-trioxo-1,2,5-thiadiazolidin-2-yl)-phenyl]-propyl}-3-phenoxybenzenesulfonamide
N-{3-[3-Hydroxy-4-(1,1,4-trioxo-1,2,5-thiadiazolidin-2-yl)-phenyl]-propyl}-2,5-bis-(2,2,2-trifluoroethoxy)-benzenesulfonamide
2,2-Diphenylethanesulfonic acid {3-[3-hydroxy-4-(1,1,4-trioxo-1,2,5-thiadiazolidin-2-yl)-phenyl]-propyl}-amide
C-(2-Aminophenyl)-N{3-[3-hydroxy-4-(1,1,4-trioxo-1,2,5-thiadiazolidin-2-yl)-phenyl]-propyl}-methanesulfonamide
Naphthalene-1-sulfonic acid {3-[3-hydroxy-4-(1,1,4-trioxo-1,2,5-thiadiazolidin-2-yl)-phenyl]-propyl}-amide
C-Cyclohexyl-N-{3-[3-hydroxy-4-(1,1,4-trioxo-1,2,5-thiadiazolidin-2-yl)-phenyl]-propyl}-methanesulfonamide
2-Naphthalen-1-yl-ethanesulfonic acid {3-[3-hydroxy-4-(1,1,4-trioxo-1,2,5-thiadiazolidin-2-yl)-phenyl]-propyl}-amide
2-Phenyl-2-(2-trifluoromethylphenyl)-ethanesulfonic acid {3-[3-hydroxy-4-(1,1,4-trioxo-1,2,5-thiadiazolidin-2-yl)-phenyl]-propyl}-amide 2-Oxo-2H-chromene-6-sulfonic acid {3-[3-hydroxy-4-(1,1,4-trioxo-1,2,5-thiadiazolidin-2-yl)-phenyl]-propyl}-amide N-{3-[3-Hydroxy-4-(1,1,4-trioxo-1,2,5-thiadiazolidin-2-yl)-phenylpropyl]-N-isopropylbenzenesulfonamide N-(1-{2-[3-Hydroxy-4-(1,1,4-trioxo-1,2,5-thiadiazolidin-2-yl)-phenyl]-ethyl}-cyclopropyl)-benzenesulfonamide N—{(S)-1-Benzyl-2-[3-hydroxy-4-(1,1,4-trioxo-1,2,5-thiadiazolidin-2-yl)-phenyl]-ethyl}-methanesulfonamide Ethanesulfonic acid {(S)-1-benzyl-2-[3-hydroxy-4-(1,1,4-trioxo-1,2,5-thiadiazolidin-2-yl)-phenyl]-ethyl}-amide N-{(S)-1-Benzyl-2-[3-hydroxy-4-(1,1,4-trioxo-1,2,5-thiadiazolidin-2-yl)-phenyl]-ethyl}-C-phenyl-methanesulfonamide N-{(R)-1-Benzyl-2-[3-hydroxy-4-(1,1,4-trioxo-1,2,5-thiadiazolidin-2-yl)-phenyl]-ethyl}-C-phenylmethanesulfonamide N-{4-[3-Hydroxy-4-(1,1,4-trioxo-1,2,5-thiadiazolidin-2-yl)-phenyl]-butyl}-methanesulfonamide N-{5-[3-Hydroxy-4-(1,1,4-trioxo-1,2,5-thiadiazolidin-2-yl)-phenyl]-pentyl}-methanesulfonamide 5-[2-Hydroxy-4-(1-methanesulfonylpiperidin-3-ylmethyl)-phenyl]-1,1-dioxo-1,2,5-thiadiazolidin-3-one 5-{2-Hydroxy-4-[2-(1-methanesulfonylpiperidin-2-yl)-ethyl]-phenyl}1,1-dioxo-1,2,5-thiadiazolidin-3-one 5-{4-[2-(1-Benzenesulfonylpiperidin-2-yl)-ethyl]-2-hydroxyphenyl}-1,1-dioxo-1,2,5-thiadiazolidin-3-one 5-{4-[2-((S)-1-Benzenesulfonylpiperidin-2-yl)-ethyl]-2-hydroxyphenyl}-1,1-dioxo-1,2,5-thiadiazolidin-3-one 5-{4-[2-((R)-1-Benzenesulfonylpiperidin-2-yl)-ethyl]-2-hydroxyphenyl}-1,1-dioxo-1,2,5-thiadiazolidin-3-one 5-{4-[2-(1-Benzenesulfonylpyrrolidin-2-yl)-ethyl]-2-hydroxyphenyl}-1,1-dioxo-1,2,5-thiadiazolidin-3-one 5-{4-[2-(1-Benzenesulfonyl-1H-pyrrol-2-yl)-ethyl]-2-hydroxyphenyl}-1,1-dioxo-1,2,5-thiadiazolidin-3-one 5-{4-[2-(1-Benzenesulfonylpyrrolidin-3-yl)-ethyl]-2-hydroxyphenyl}-1,1-dioxo-1,2,5-thiadiazolidin-3-one 5-{4-[2-(1-Benzenesulfonylazepan-2-yl)-ethyl]-2-hydroxyphenyl}-1,1-dioxo-1,2,5-thiadiazolidin-3-one 5-{2-Hydroxy-4-[2-((R)-2-methanesulfonyl-1,2,3,4-tetrahydroisoquinolin-3-yl)-ethyl]-phenyl}-1,1-dioxo-1,2,5-thiadiazolidin-3-one 5-{4-[2-((R)-2-Benzenesulfonyl-1,2,3,4-tetrahydroisoquinolin-3-yl)-ethyl]-2-hydroxyphenyl}-1,1-dioxo-1,2,5-thiadiazolidin-3-one 5-(2-Hydroxy-4-{2-[2-(4-trifluoromethylbenzenesulfonyl)-1,2,3,4-tetrahydroisoquinolin-3-yl]-ethyl}-phenyl)-1,1-dioxo-1,2,5-thiadiazolidin-3-one 5-{2-Hydroxy-4-[2-(2-phenylmethanesulfonyl-1,2,3,4-tetrahydroisoquinolin-3-yl)-ethyl]-phenyl}-1,1-dioxo-1,2,5-thiadiazolidin-3-one 5-{4-[2-(1,1-Dioxo-1,2-thiazinan-3-yl)-ethyl]-2-hydroxyphenyl}-1,1-dioxo-1,2,5-thiadiazolidin-3-one N-{(1R*,2S*)-2-[3-Hydroxy-4-(1,1,4-trioxo-1,2,5-thiadiazolidin-2-yl)-benzyl]-cyclohexyl}-methanesulfonamide N-{(1R,2S)-2-[3-Hydroxy-4-(1,1,4-trioxo-1,2,5-thiadiazolidin-2-yl)-benzyl]-cyclohexyl}-methanesulfonamide N-{(1S,2R)-2-[3-Hydroxy-4-(1,1,4-trioxo-1,2,5-thiadiazolidin-2-yl)-benzyl]cyclohexyl}-methanesulfonamide Ethanesulfonic acid {(1R*,2S*)-2-[3-hydroxy-4-(1,1,4-trioxo-1,2,5-thiadiazolidin-2-yl)-benzyl]-cyclohexyl}-amide N-{(1R*,2S*)-2-[3-Hydroxy-4-(1,1,4-trioxo-1,2,5-thiadiazolidin-2-yl)-benzyl]-cyclohexyl}-benzenesulfonamide (S)-2-Benzenesulfonylamino-3-[3-hydroxy-4-(1,1,4-trioxo-1,2,5-thiadiazolidin-2-yl)-phenyl]-N-pentylpropionamide (S)-2-Benzenesulfonylamino-3-[3-hydroxy-4-(1,1,4-trioxo-1,2,5-thiadiazolidin-2-yl)-phenyl]-N-(4-phenylbutyl)-propionamide N-{(S)-1-(1H-Benzoimidazol-2-yl)-2-[3-hydroxy-4-(1,1,4-trioxo-1,2,5-thiadiazolidin-2-yl)-phenyl]-ethyl}-benzenesulfonamide tert-Butyl [({2-[4-(1,1-dioxido-4-oxo-1,2,5-thiadiazolidin-2-yl)-3-hydroxyphenyl]ethyl}amino)sulfonyl]carbamate 1-Cyclohexyl-3-{2-[3-hydroxy-4-(1,1,4-trioxo-1,2,5-thiadiazolidin-2-yl)-phenyl]-ethyl}-urea 1-{2-[3-Hydroxy-4-(1,1,4-trioxo-1,2,5-thiadiazolidin-2-yl)-phenyl]-ethyl}-3-phenyl-urea 1-Ethyl-3-{2-[3-hydroxy-4-(1,1,4-trioxo-1,2,5-thiadiazolidin-2-yl)-phenyl]-ethyl}-urea 1-Adamantan-1-yl-3-{2-[3-hydroxy-4-(1,1,4-trioxo-1,2,5-thiadiazolidin-2-yl)-phenyl]-ethyl}-urea Benzenesulfonyl-N-{2-[3-hydroxy-4-(1,1,4-trioxo-1,2,5-thiadiazolidin-2-yl)-phenyl]-ethyl}-urea 1-(2,4-Dimethoxybenzyl)-3-{2-[3-hydroxy-4-(1,1,4-trioxo-1,2,5-thiadiazolidin-2-yl)-phenyl]-ethyl}-urea 1-(2-Hydroxyethyl)-3-{2-[3-hydroxy-4-(1,1,4-trioxo-1,2,5-thiadiazolidin-2-yl)-phenyl]ethyl}-urea 3-{2-[3-Hydroxy-4-(1,1,4-trioxo-1,2,5-thiadiazolidin-2-yl)-phenyl]-ethyl}-1,1-bis-(2-methoxyethyl)-urea Morpholine-4-carboxylic acid {2-[3-hydroxy-4-(1,1,4-trioxo-1,2,5-thiadiazolidin-2-yl)-phenyl]-ethyl}-amide 4-(3-{2-[3-Hydroxy-4-(1,1,4-trioxo-1,2,5-thiadiazolidin-2-yl)-phenyl]-ethyl}-ureido)-piperidine-1-carboxylic acid tert-butyl ester 1-{2-[3-Hydroxy-4-(1,1,4-trioxo-1,2,5-thiadiazolidin-2-yl)-phenyl]-ethyl}-3-piperidin-4-yl-urea 1-{3-[3-Hydroxy-4-(1,1,4-trioxo-1,2,5-thiadiazolidin-2-yl)-phenyl]-propyl}-3-phenyl-urea 1-Cyclohexyl-3-{3-[3-hydroxy-4-(1,1,4-trioxo-1,2,5-thiadiazolidin-2-yl)-phenyl]-propyl}-urea 1-Adamantan-1-yl-3-{3-[3-hydroxy-4-(1,1,4-trioxo-1,2,5-thiadiazolidin-2-yl)-phenyl]-propyl}-urea 3-{3-[3-Hydroxy-4-(1,1,4-trioxo-1,2,5-thiadiazolidin-2-yl)-phenyl]-propyl}-1H-quinazoline-2,4-dione 3-[3-Hydroxy-4-(1,1,4-trioxo-1,2,5-thiadiazolidin-2-yl)-benzyl]-piperidine-1-carboxylic acid ethylamide 5-(2-Hydroxy-4-methanesulfonylmethylphenyl)-1,1-dioxo-1,2,5-thiadiazolidin-3-one 5-(4-Ethanesulfonylmethyl-2-hydroxy-phenyl)-1,1-dioxo-1,2,5-thiadiazolidin-3-one 5-[2-Hydroxy-4-(propane-2-sulfonylmethyl)-phenyl]-1,1-dioxo-1,2,5-thiadiazolidin-3-one 5-(4-Benzenesulfonylmethyl-2-hydroxyphenyl)-1,1-dioxo-1,2,5-thiadiazolidin-3-one 5-(2-Hydroxy-4-methanesulfinylmethylphenyl)-1,1-dioxo-1,2,5-thiadiazolidin-3-one 5-(4-Ethanesulfinylmethyl-2-hydroxy-phenyl)-1,1-dioxo-1,2,5-thiadiazolidin-3-one 5-[2-Hydroxy-4-(propane-2-sulfinylmethyl)-phenyl]-1,1-dioxo-1,2,5-thiadiazolidin-3-one 5-(2-Hydroxy-4-methylsulfanylmethylphenyl)-1,1-dioxo-1,2,5-thiadiazolidin-3-one 5-(4-Ethylsulfanylmethyl-2-hydroxyphenyl)-1,1-dioxo-1,2,5-thiadiazolidin-3-one 5-(2-Hydroxy-4-isopropylsulfanylmethylphenyl)-1,1-dioxo-1,2,5-thiadiazolidin-3-one 5-[4-(2-Benzenesulfonylethyl)-2-hydroxyphenyl]-1,1-dioxo-1,2,5-thiadiazolidin-3-one 5-[4-(4-Benzenesulfonylbutyl)-2-hydroxyphenyl]-1,1-dioxo-1,2,5-thiadiazolidin-3-one 5-{4-[3-(1,1-Dioxotetrahydrothiophen-2-yl)-prop-1-ynyl]-2-hydroxyphenyl}-1,1-dioxo-1,2,5-thiadiazolidin-3-one 5-{4-[3-(1,1-Dioxotetrahydrothiophen-2-yl)-propyl]-2-hydroxyphenyl}-1,1-dioxo-1,2,5-thiadiazolidin-3-one
5-[2-Hydroxy-4-(3-oxopentyl)-phenyl]-1,1-dioxo-1,2,5-thiadiazolidin-3-one
5-[2-Hydroxy-4-(2-methyl-3-oxopentyl)-phenyl]-, 1,1-dioxo-1,2,5-thiadiazolidin-3-one
5-[2-Hydroxy-4-(2-methyl-3-oxo-3-phenylpropyl)-phenyl]-1,1-dioxo-1,2,5-thiadiazolidin-3-one
5-[4-(2-Benzoylbutyl)-2-hydroxyphenyl]-1,1-dioxo-1,2,5-thiadiazolidin-3-one
5-[4-(2-Benzoylpentyl)-2-hydroxyphenyl]-1,1-dioxo-1,2,5-thiadiazolidin-3-one
5-[2-Hydroxy-4-(3-oxo-2,3-diphenylpropyl)-phenyl]-1,1-dioxo-1,2,5-thiadiazolidin-3-one
5-[4-(2-Benzyl-3-oxo-3-phenylpropyl)-2-hydroxyphenyl]-1,1-dioxo-1,2,5-thiadiazolidin-3-one
5-[4-(2,2-Dimethyl-3-oxo-3-phenylpropyl)-2-hydroxyphenyl]-1,1-dioxo-1,2,5-thiadiazolidin-3-one
5-[2-Hydroxy-4-(1-oxo-indan-2-ylmethyl)-phenyl]-1,1-dioxo-1,2,5-thiadiazolidin-3-one
5-[2-Hydroxy-4-(6-oxo-6,7,8,9-tetrahydro-5H-benzocyclohepten-5-ylmethyl)-phenyl]-1,1-dioxo-1,2,5-thiadiazolidin-3-one
5-[2-Hydroxy-4-(2-methoxy-3-oxo-3-phenylpropyl)-phenyl]-1,1-dioxo-1,2,5-thiadiazolidin-3-one
5-[2-Hydroxy-4-(3-hydroxy-2-methyl-3-phenylpropyl)-phenyl]-1,1-dioxo-1,2,5-thiadiazolidin-3-one
5-{2-Hydroxy-4-[2-(hydroxylphenylmethyl)-butyl]-phenyl}-1,1-dioxo-1,2,5-thiadiazolidin-3-one
5-{2-Hydroxy-4-[2-(hydroxyphenylmethyl)-pentyl]-phenyl}-1,1-dioxo-1,2,5-thiadiazolidin-3-one
5-[4-(2-Benzyl-3-hydroxy-3-phenylpropyl)-2-hydroxyphenyl]-1,1-dioxo-1,2,5-thiadiazolidin-3-one
5-[2-Hydroxy-4-(3-hydroxy-2,2-dimethyl-3-phenylpropyl)-phenyl]-1,1-dioxo-1,2,5-thiadiazolidin-3-one
5-[2-Hydroxy-4-(1-hydroxyindan-2-ylmethyl)-phenyl]-1,1-dioxo-1,2,5-thiadiazolidin-3-one
5-[2-Hydroxy-4-(3-hydroxy-2-methoxy-3-phenyl-propyl)-phenyl]-1,1-dioxo-1,2,5-thiadiazolidin-3-one
5-(2-Hydroxy-4-vinylphenyl)-1,1-dioxo-1,2,5-thiadiazolidin-3-one
5-[2-Hydroxy-4-(1-hydroxyethyl)-phenyl]-1,1-dioxo-1,2,5-thiadiazolidin-3-one
5-[2-Hydroxy-4-(2-hydroxyhexyl)-phenyl]-1,1-dioxo-1,2,55-thiadiazolidin-3-one
5-[2-Hydroxy-4-(3-hydroxybutyl)-phenyl]-1,1-dioxo-1,2,5-thiadiazolidin-3-one
5-{2-Hydroxy-4-[2-(1-hydroxycyclohexyl)-ethyl]-phenyl}-1,1-dioxo-1,2,5-thiadiazolidin-3-one
5-[2-Hydroxy-4-(4,4,4-trifluoro-3-hydroxy-3-phenylbutyl)-phenyl]-1,1-dioxo-1,2,5-thiadiazolidin-3-one
5-(3-Hydroxybiphenyl-4-yl)-1,1-dioxo-1,2,5-thiadiazolidin-3-one
5-(3,3'-Dihydroxybiphenyl-4-yl)-1,1-dioxo-1,2,5-thiadiazolidin-3-one
[3'-Hydroxy-4'-(1,1,4-trioxo-1,2,5-thiadiazolidin-2-yl)-biphenyl-4-yl]-acetic acid
5,5'-(3,3'-Dihydroxybiphenyl-4-yl)-1,1,1',1'-tetraoxo-1,1',2,2',5,5'-dithiadiazolidin-3,3'-one
5-(4-Furan-3-yl-2-hydroxyphenyl)-1,1-dioxo-1,2,5-thiadiazolidin-3-one
5-(2-Hydroxy-4-thiophen-3-yl-phenyl)-1,1-dioxo-1,2,5-thiadiazolidin-3-one
5-(4-Benzofuran-3-yl-2-hydroxyphenyl)-1,1-dioxo-1,2,5-thiadiazolidin-3-one
5-[2-Hydroxy-4-(6-methoxybenzofuran-3-yl)-phenyl]-1,1-dioxo-1,2,5-thiadiazolidin-3-one
5-(2-Hydroxy-4-thiazol-5-yl-phenyl)-1,1-dioxo-1,2,5-thiadiazolidin-3-one
5-(2-Hydroxy-4-thiazol-2-yl-phenyl)-1,1-dioxo-1,2,5-thiadiazolidin-3-one
5-[2-Hydroxy-4-(1H-pyrrol-3-yl)-phenyl]-1,1-dioxo-1,2,5-thiadiazolidin-3-one
5-[2-Hydroxy-4-(1H-pyrazol-3-yl)-phenyl]-1,1-dioxo-1,2,5-thiadiazolidin-3-one
5-[2-Hydroxy-4-(1H-pyrazol-4-yl)-phenyl]-1,1-dioxo-1,2,5-thiadiazolidin-3-one
5-[2-Hydroxy-4-(1-propyl-1H-pyrazol-4-yl)-phenyl]-1,1-dioxo-1,2,5-thiadiazolidin-3-one
5-[2-Hydroxy-4-(1-isobutyl-1H-pyrazol-4-yl)-phenyl]-1,1-dioxo-1,2,5-thiadiazolidin-3-one
5-{2-Hydroxy-4-[1-(3-methylbutyl)-1H-pyrazol-4-yl]-phenyl}-1,1-dioxo-1,2,5-thiadiazolidin-3-one
5-[2-Hydroxy-4-(tetrahydrofuran-3-yl)-phenyl]-1,1-dioxo-1,2,5-thiadiazolidin-3-one
5-[4-(2,3-Dihydrobenzofuran-3-yl)-2-hydroxyphenyl]-1,1-dioxo-1,2,5-thiadiazolidin-3-one
5-(2-Hydroxy-4-thiazol-2-ylmethylphenyl)-1,1-dioxo-1,2,5-thiadiazolidin-3-one
5-[2-Hydroxy-4-(2H-pyrazol-3-ylmethyl)-phenyl]-1,1-dioxo-1,2,5-thiadiazolidin-3-one
5-(2-Hydroxy-4-pyrazol-1-ylmethyl-phenyl)-1,1-dioxo-1,2,5-thiadiazolidin-3-one
5-[2-Hydroxy-4-(3-trifluoromethylpyrazole-1-ylmethyl)-phenyl]-1,1-dioxo-1,2,5-thiadiazolidin-3-one
5-[3-Hydroxy-4-(1,1,4-trioxo-1,2,5-thiadiazolidin-2-yl)-phenyl]-pentanoic acid
4-[3-Hydroxy-4-(1,1,4-trioxo-1,2,5-thiadiazolidin-2-yl)-phenyl]-butane-1-sulfinic acid
4-[3-Hydroxy-4-(1,1,4-trioxo-1,2,5-thiadiazolidin-2-yl)-phenyl]-butyronitrile
4-[3-Hydroxy-4-(1,1,4-trioxo-1,2,5-thiadiazolidin-2-yl)-phenyl]-2-methyl-butyronitrile
4-[3-Hydroxy-4-(1,1,4-trioxo-1,2,5-thiadiazolidin-2-yl)-phenyl]-3,3-dimethylbutyronitrile
[3-Hydroxy-4-(1,1,4-trioxo-1,2,5-thiadiazolidin-2-yl)-phenoxy]-acetic acid 2-trimethylsilanylethyl ester
[3-Hydroxy-4-(1,1,4-trioxo-1,2,5-thiadiazolidin-2-yl)-phenoxy]-acetic acid
3-[3-Hydroxy-4-(1,1,4-trioxo-1,2,5-thiadiazolidin-2-yl)-phenoxy]-1,3,4,5-tetrahydro-benzo[b]azepin-2-one
5-(4-Ethyl-2-hydroxyphenyl)-1,1-dioxo-1,2,5-thiadiazolidin-3-one
5-(4-Hexyl-2-hydroxyphenyl)-1,1-dioxo-1,2,5-thiadiazolidin-3-one
5-(2-Hydroxy-4-isobutylphenyl)-1,1-dioxo-1,2,5-thiadiazolidin-3-one
5-[4-(3,3-Dimethylbutyl)-2-hydroxyphenyl]-1,1-dioxo-1,2,5-thiadiazolidin-3-one
5-[2-Hydroxy-4-(3,3,3-trifluoropropyl)-phenyl]-1,1-dioxo-1,2,5-thiadiazolidin-3-one
5-(4-Cyclopentylmethyl-2-hydroxyphenyl)-1,1-dioxo-1,2,5-thiadiazolidin-3-one
5-(4-Cyclohexylmethyl-2-hydroxyphenyl)-1,1-dioxo-1,2,5-thiadiazolidin-3-one
5-{2-Hydroxy-4-[1-(2,4,6-trimethylphenyl)-ethyl]-phenyl}-1,1-dioxo-1,2,5-thiadiazolidin-3-one
5-[4-(2-Aminobenzyl)-2-hydroxyphenyl]-1,1-dioxo-1,2,5-thiadiazolidin-3-one
5-[2-Hydroxy-4-(2-hydroxybenzyl)-phenyl]-1,1-dioxo-1,2,5-thiadiazolidin-3-one
5-[2-Hydroxy-4-(2-hydroxy-5-methylbenzyl)-phenyl]-1,1-dioxo-1,2,5-thiadiazolidin-3-one 5-[4-(2-Aminomethylbenzyl)-2-hydroxyphenyl]-1,1-dioxo-1,2,5-thiadiazolidin-3-one 5-[2-Hydroxy-4-(2-methoxymethylbenzyl)-phenyl]-1,1-dioxo-1,2,5-thiadiazolidin-3-one {2-[3-Hydroxy-4-(1,1,4-trioxo-1,2,5-thiadiazolidin-2-yl)-benzyl]-phenyl}-acetonitrile {2-[3-Hydroxy-4-(1,1,4-trioxo-1,2,5-thiadiazolidin-2-yl)-benzyl]-phenyl}-acetic acid methyl ester {2-[3-Hydroxy-4-(1,1,4-trioxo-1,2,5-thiadiazolidin-2-yl)-benzyl]-phenyl}-acetic acid N-Ethyl-2-{2-[3-hydroxy-4-(1,1,4-trioxo-1,2,5-thiadiazolidin-2-yl)-benzyl]-phenyl}-acetamide 5-(2-Hydroxy-4-{2-[2-(4-methylpiperidin-1-yl)-2-oxo-ethyl]-benzyl}-phenyl)-1,1-dioxo-1,2,5-thiadiazolidin-3-one 5-{2-Hydroxy-4-[2-(2-hydroxyethyl)-benzyl]-phenyl}-1,1-dioxo-1,2,5-thiadiazolidin-3-one 5-[2-Hydroxy-4-(pyridine-2-carbonyl)-phenyl]-1,1-dioxo-1,2,5-thiadiazolidin-3-one 5-(4-Benzenesulfonyl-2-hydroxyphenyl)-1,1-dioxo-1,2,5-thiadiazolidin-3-one 5-(2-Hydroxy-4-trifluoromethylphenyl)-1,1-dioxo-1,2,5-thiadiazolidin-3-one 5-(2-Hydroxy-4-methoxyphenyl)-1,1-dioxo-1,2,5-thiadiazolidin-3-one 3-Hydroxy-4-(1,1,4-trioxo-1,2,5-thiadiazolidin-2-yl)-benzonitrile, 5-(4-Chloro-2-hydroxyphenyl)-1,1-dioxo-1,2,5-thiadiazolidin-3-one, 5-(4-Fluoro-2-hydroxyphenyl)-1,1-dioxo-1-[1,2,5]thiadiazolidin-3-one, 5-(2-Hydroxy-4-methylphenyl)-1,1-dioxo-[1,2,5]thiadiazolidin-3-one, 5-(2-Hydroxy-4,6-dimethylphenyl)-1,1-dioxo-[1,2,5]thiadiazolidin-3-one, 5-(4,5-Difluoro-2-hydroxyphenyl)-1,1-dioxo-[1,2,5]thiadiazolidin-3-one, and 5-(3,5-Difluoro-2-hydroxy-4-methylphenyl)-1,1-dioxo-1,2,5-thiadiazolidin-3-one, or a pharmaceutically acceptable salt thereof.

The compounds of the invention depending on the nature of the substituents, may possess one or more asymmetric centers. The resulting diastereoisomers, enantiomers and geometric isomers are encompassed by the instant invention.

Compounds of formula (I) may be prepared according to the below described synthesis schemes;

Scheme 1

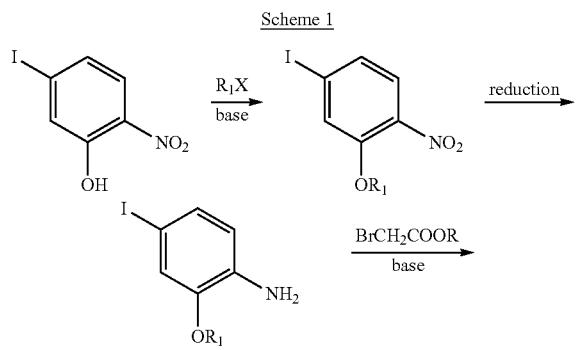

-continued

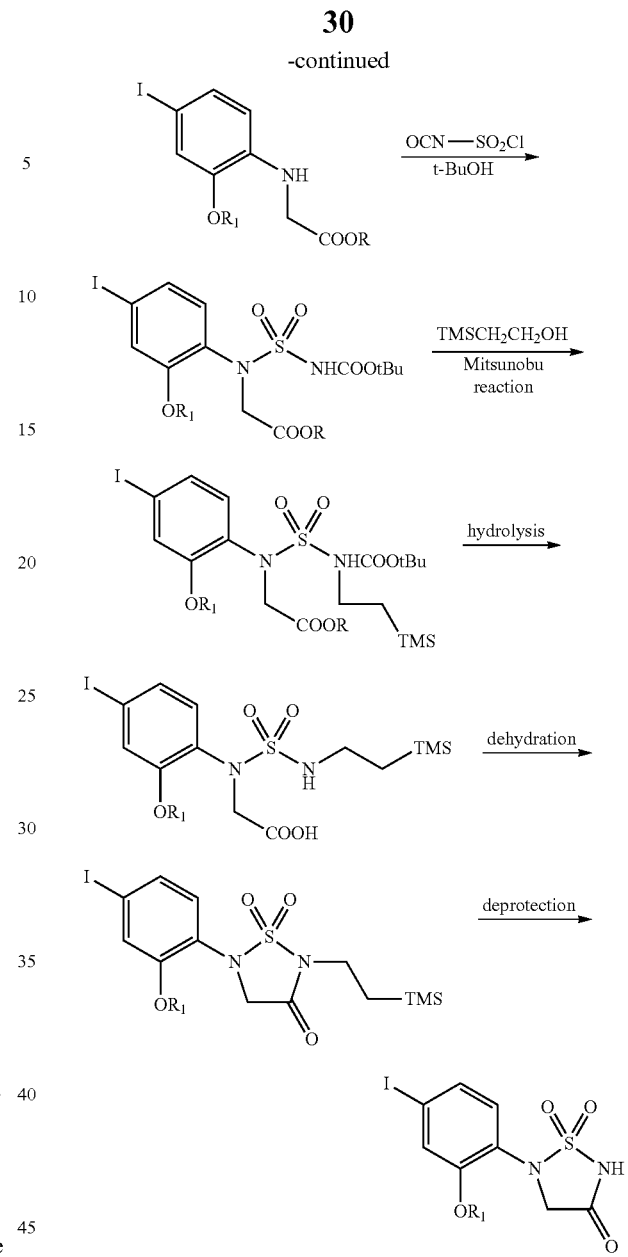

Scheme 2

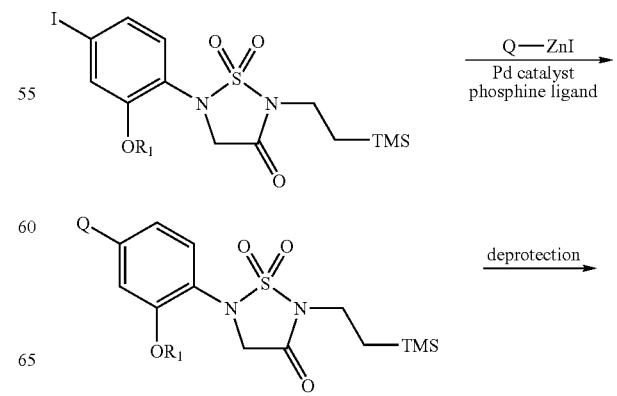

-continued
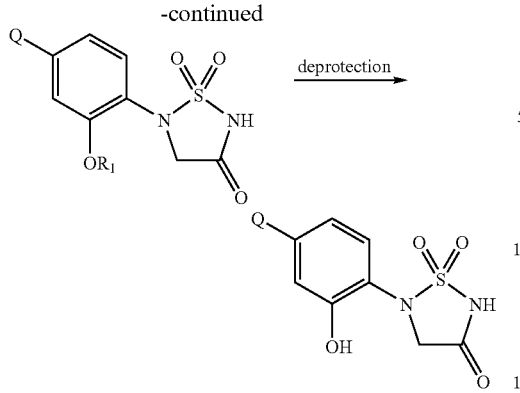
In Scheme 1, R can be an alkyl and $R_1$ is as defined hereinabove.
In Scheme 3, R can be X as defined hereinabove or is preferably aryl, heterocyclyl, alkyl, esterified carboxy.
Scheme 5
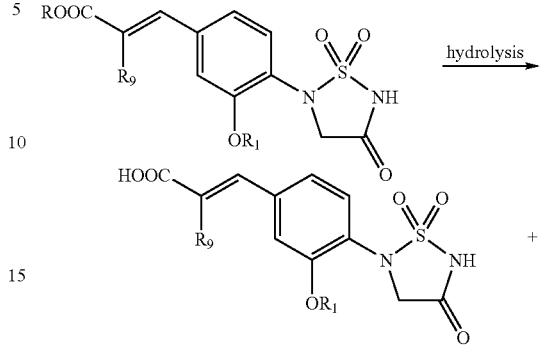
Scheme 3
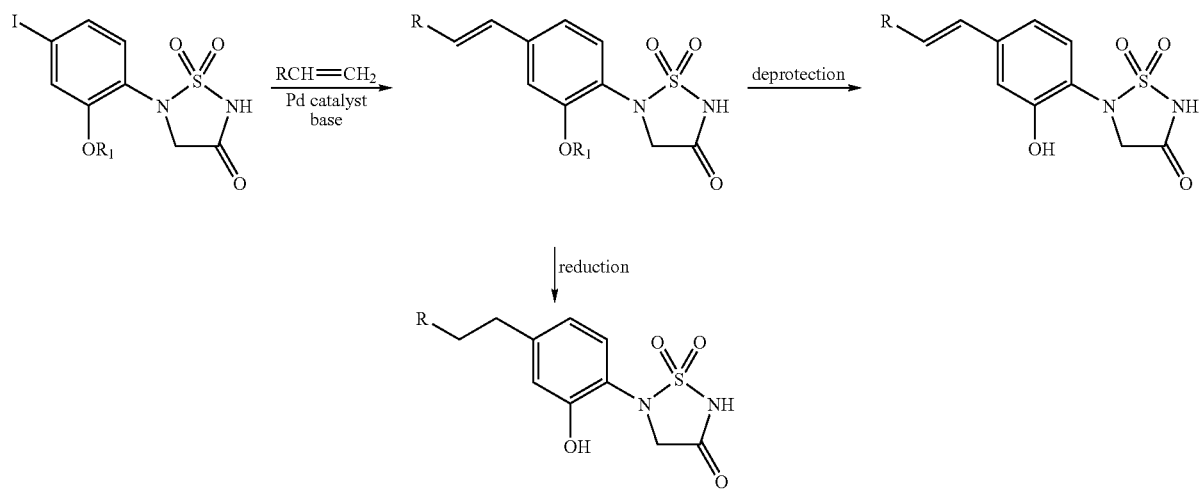
Scheme 4
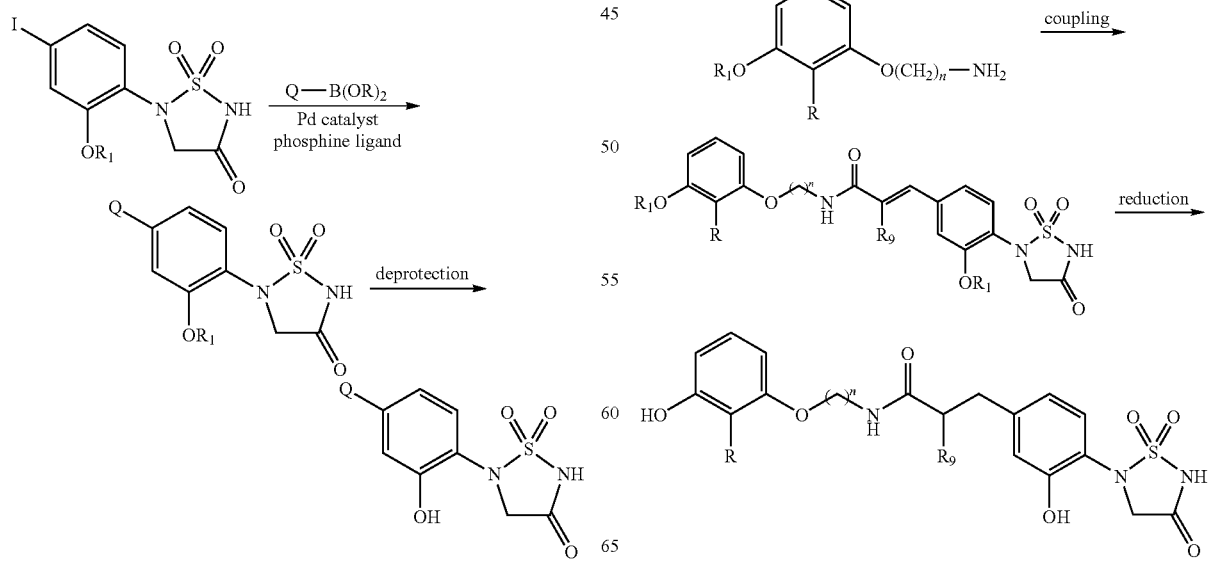

In scheme 5, $R_9$ is the same as defined above herein. R is any of the hereinabove substituents listed as possible aryl substituent. OH can be present or replaced by another substituent.
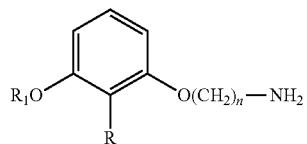
is an example to show how to couple an arly. The same approach can be used for other aryls or for an alkyl, or heterocyclyl.
Scheme 6
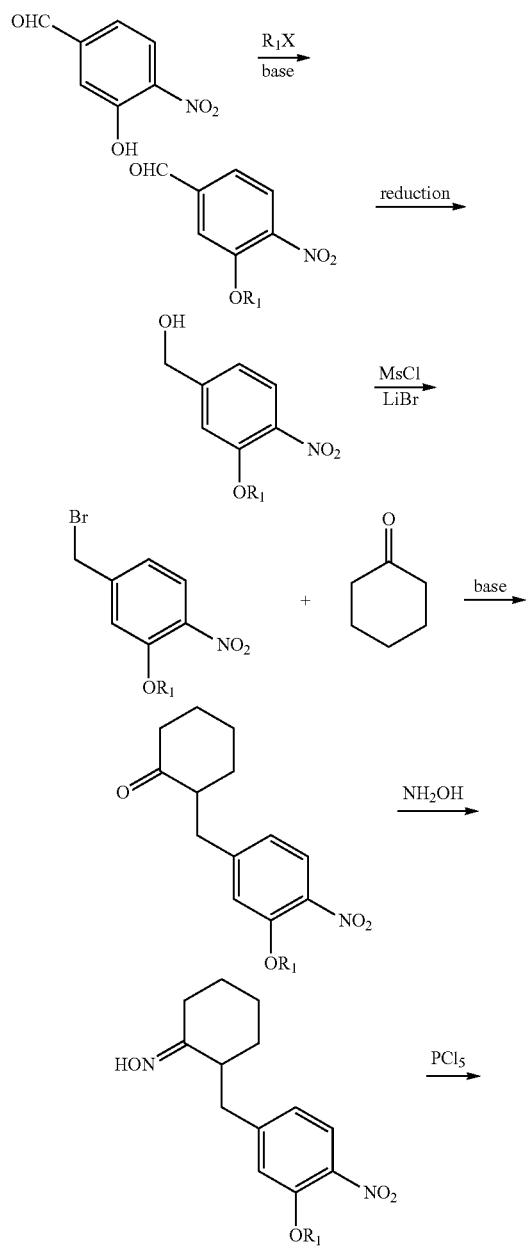
-continued
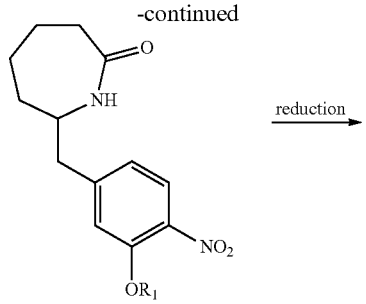
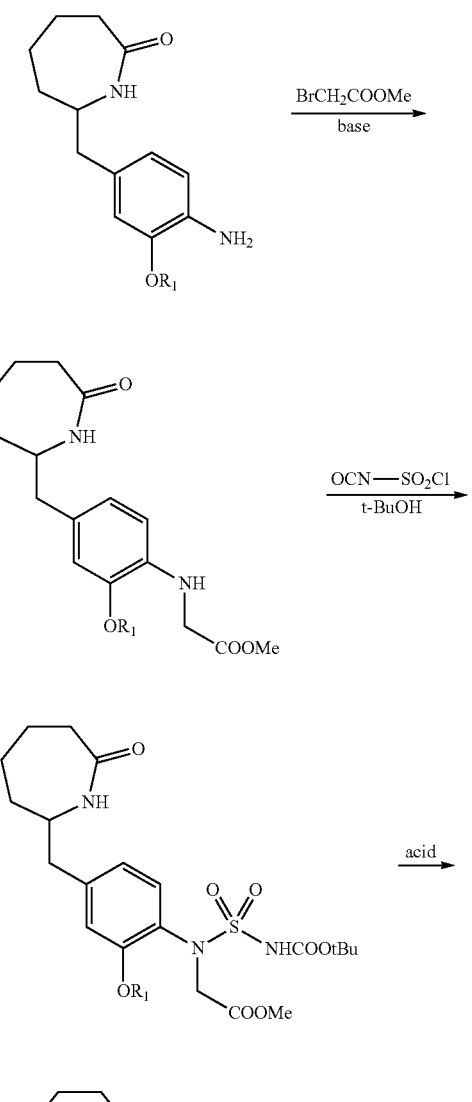
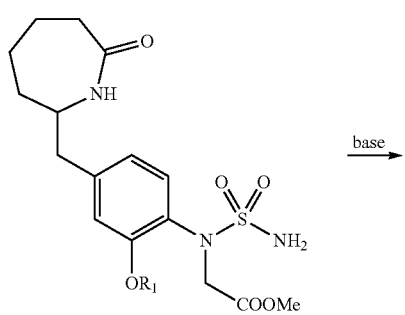

35
-continued
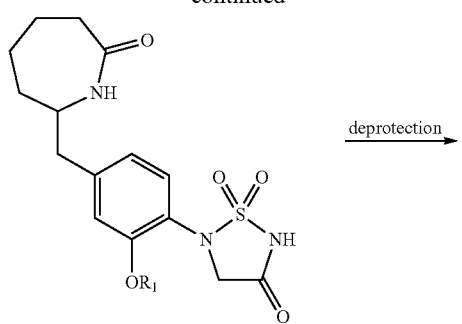
deprotection →
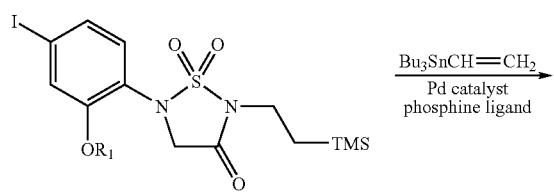
Scheme 7
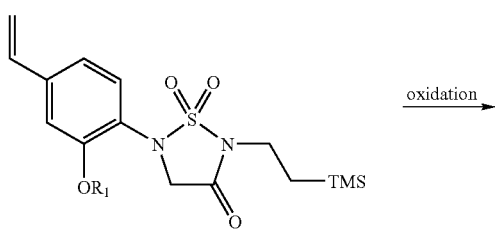
Bu₃SnCH=CH₂
Pd catalyst
phosphine ligand →
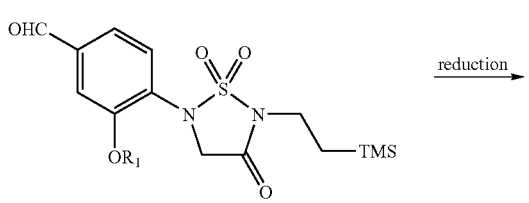
oxidation →
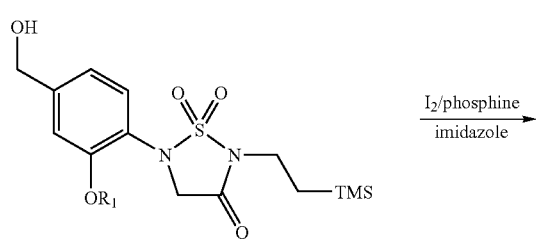
reduction →
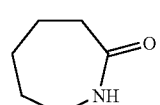
I₂/phosphine
imidazole →
36
-continued
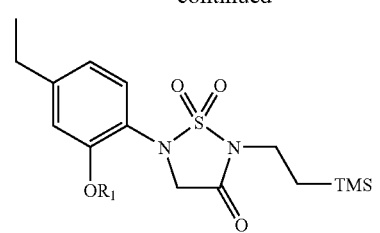
+
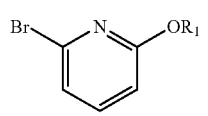
Zn
Pd catalyst
phosphine ligand →
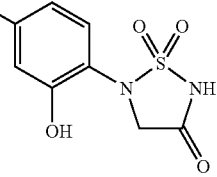
deprotection →
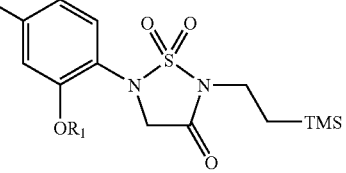
hydrogenation →
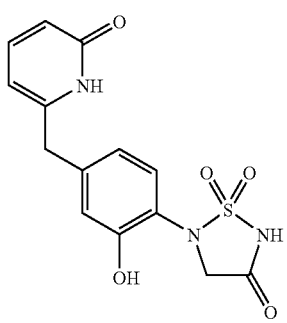

37
Scheme 8
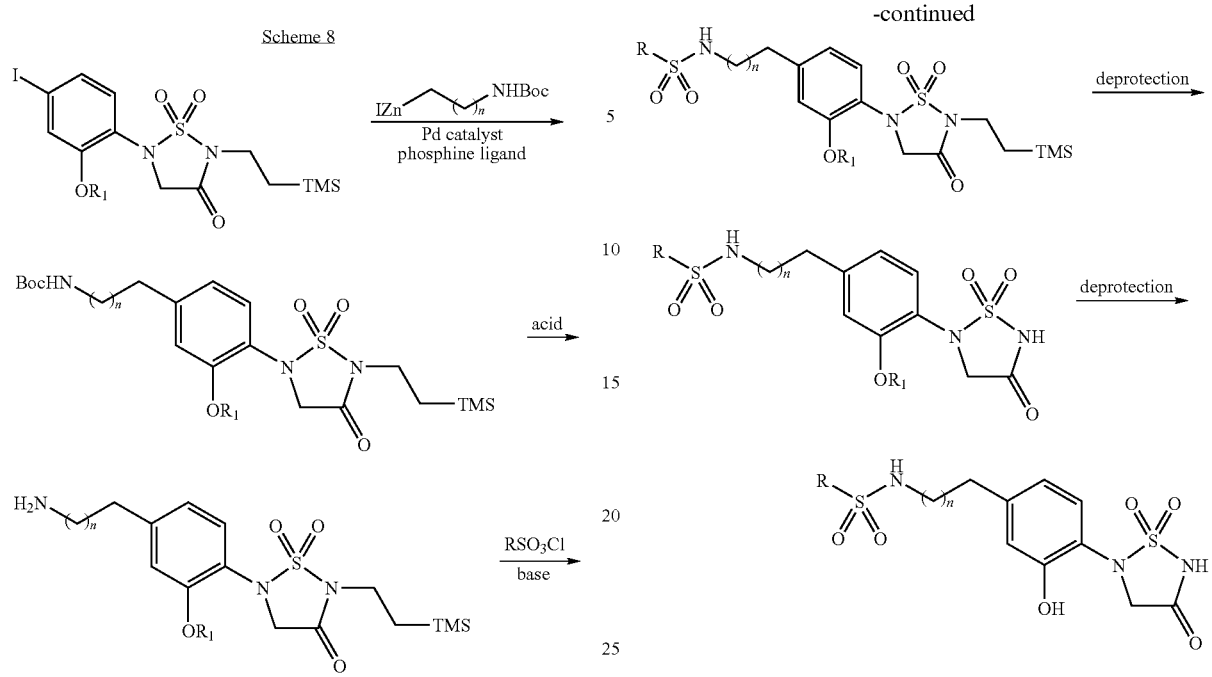
38
Scheme 9
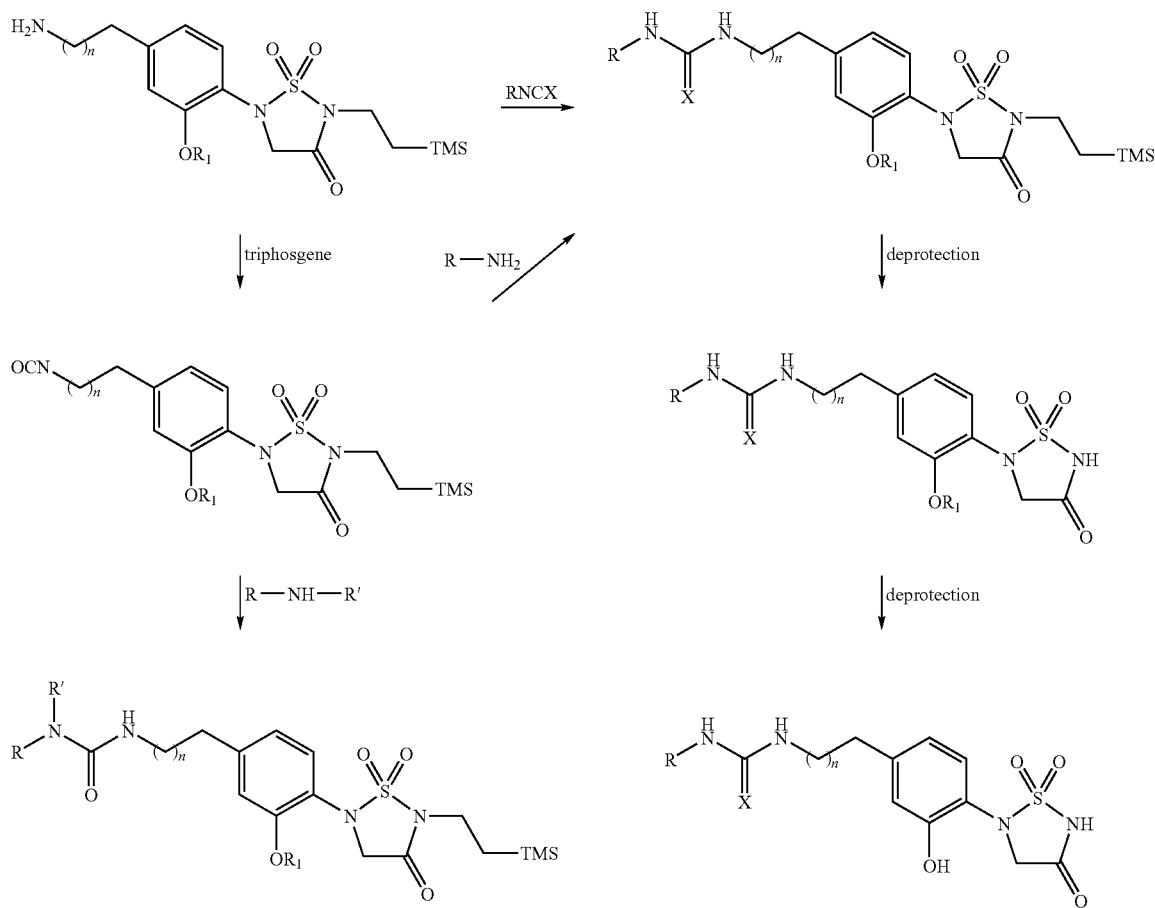

In Scheme 8, R can be X as defined hereinabove or is preferably aryl, heterocyclyl, or alkyl.
In Scheme 9, R can be X as defined hereinabove or is preferably aryl, heterocyclyl, or alkyl. R' can be Rγ' as defined hereinabove. X is O or S.
Scheme 10
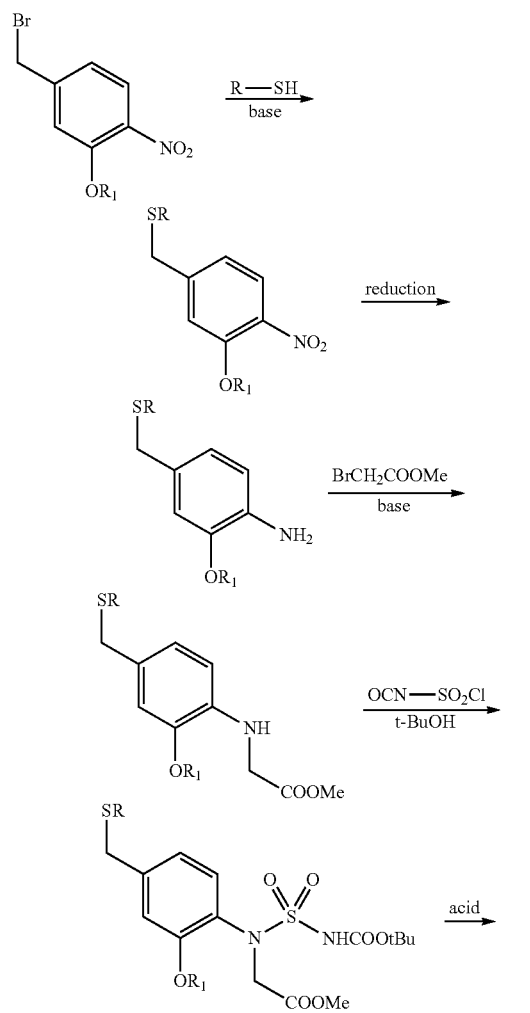
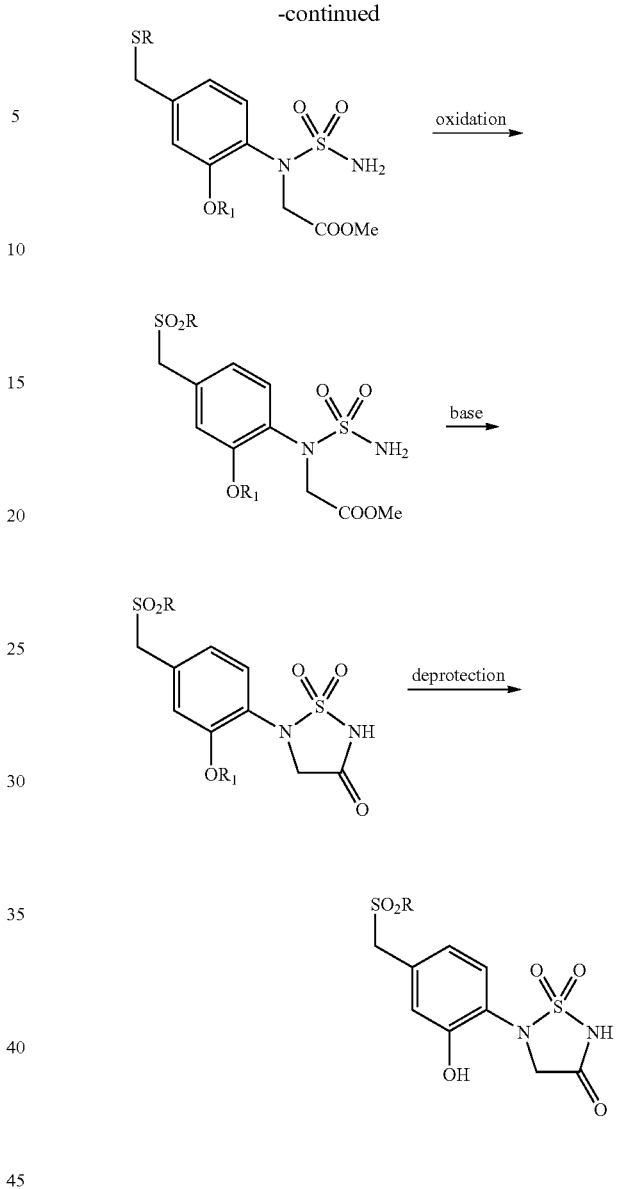
In Scheme 10, R can be X as defined hereinabove or is preferably aryl, heterocyclyl, or alkyl.
Scheme 11
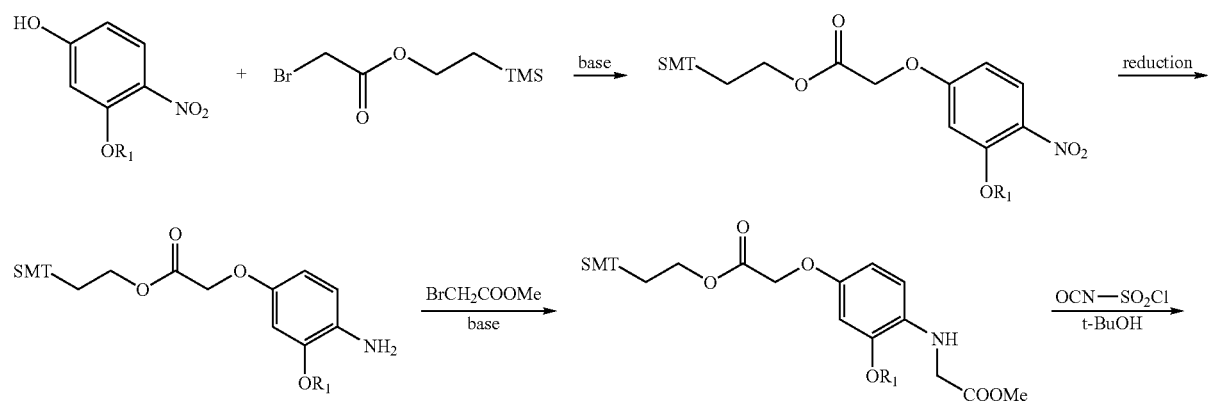

41 42
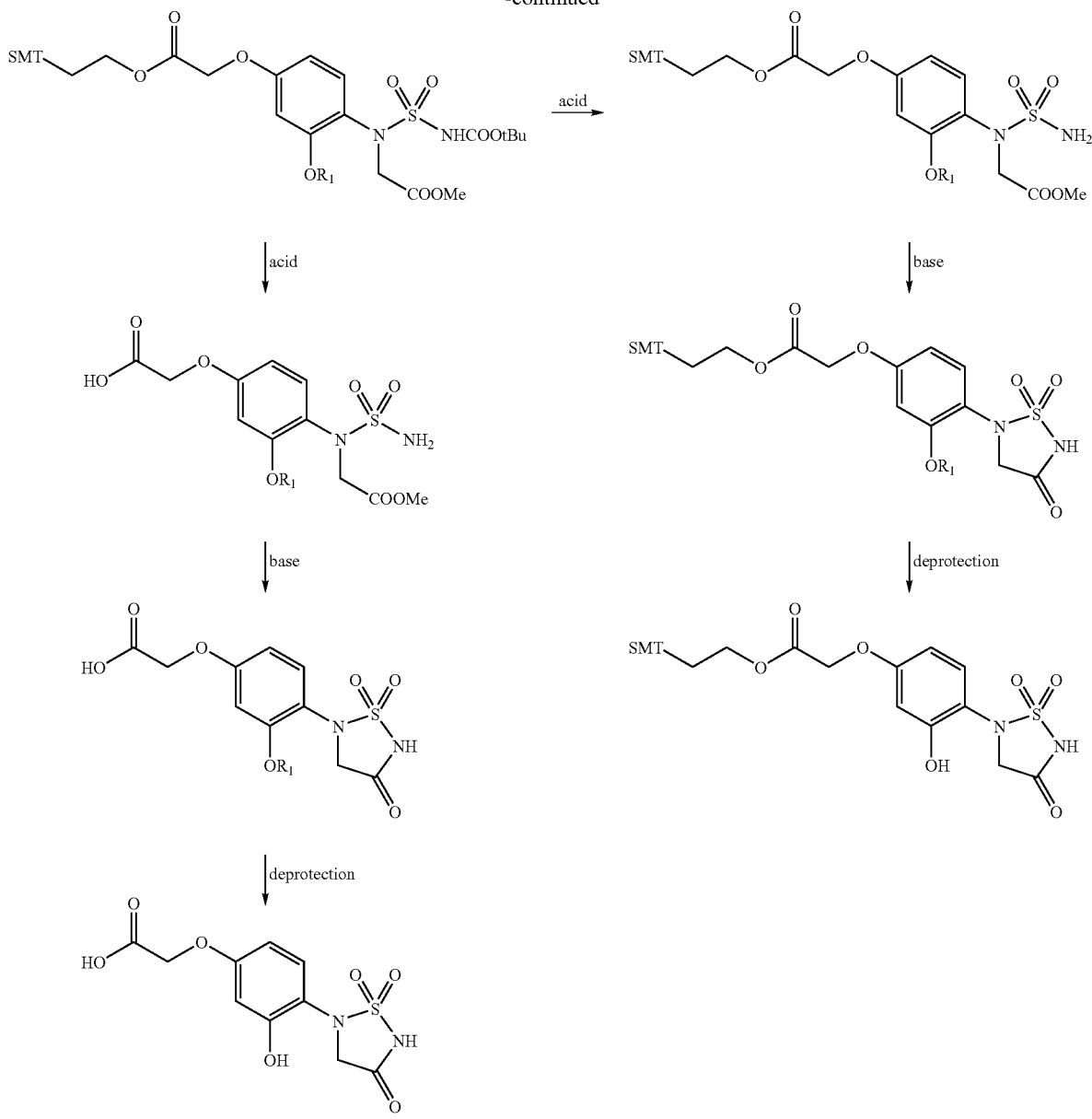
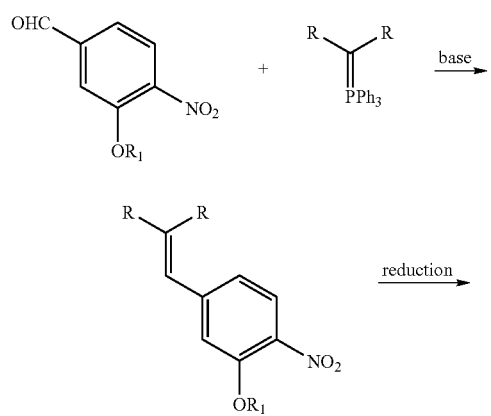
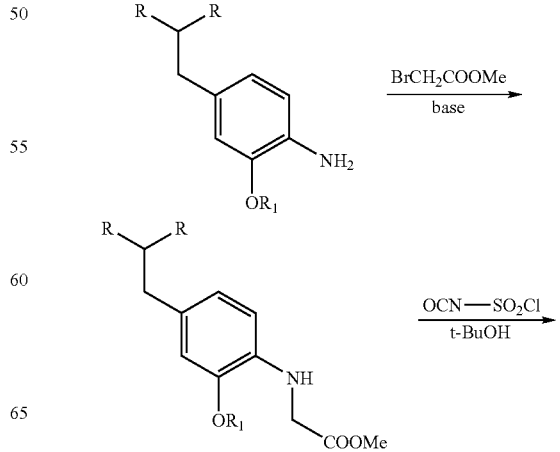

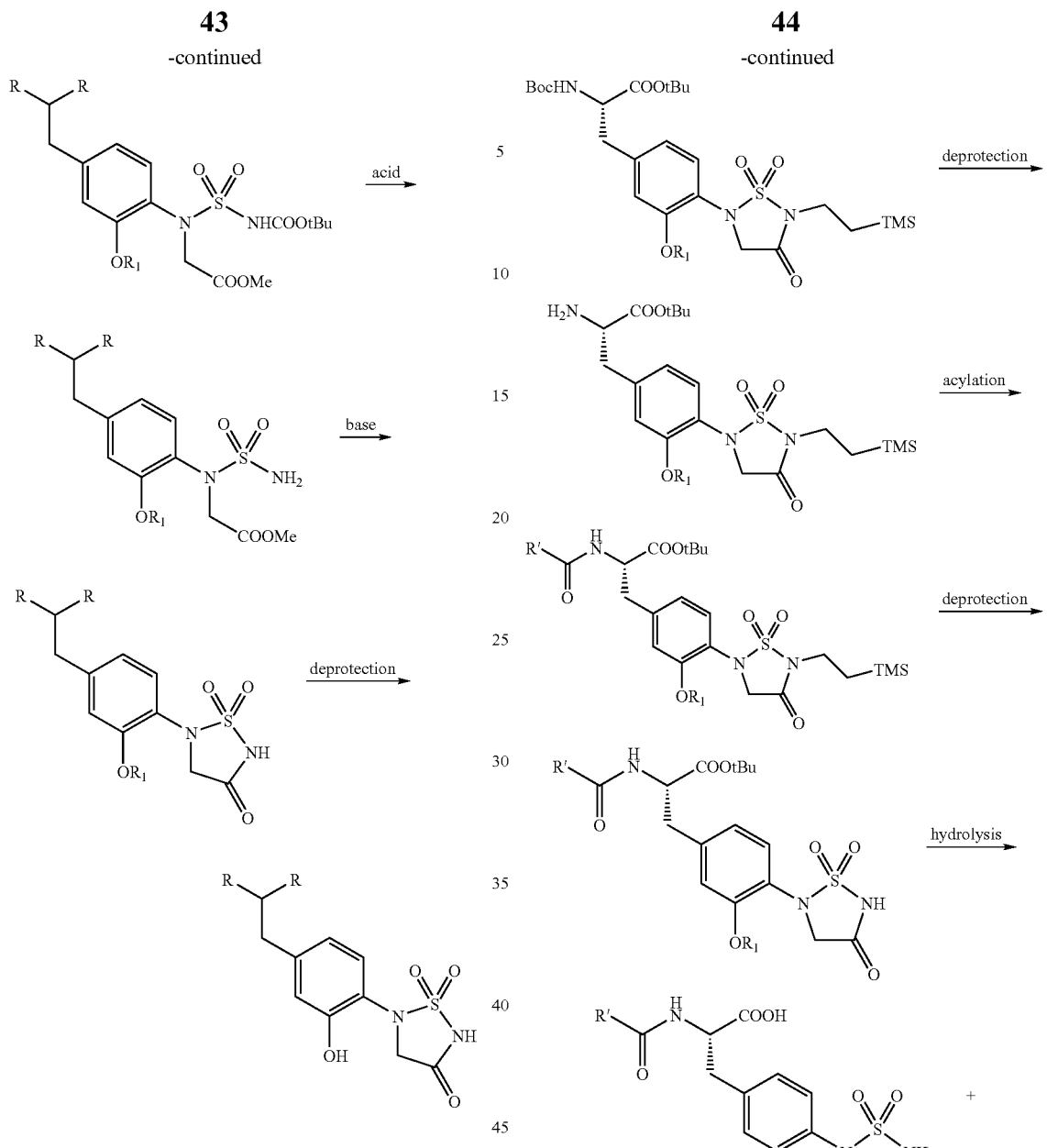
In Scheme 12, R can be X as defined hereinabove or is preferably aryl, heterocyclyl, alkyl, or —O—X such as —C(O)-aryl, —C(O)-alkyl.
Scheme 13
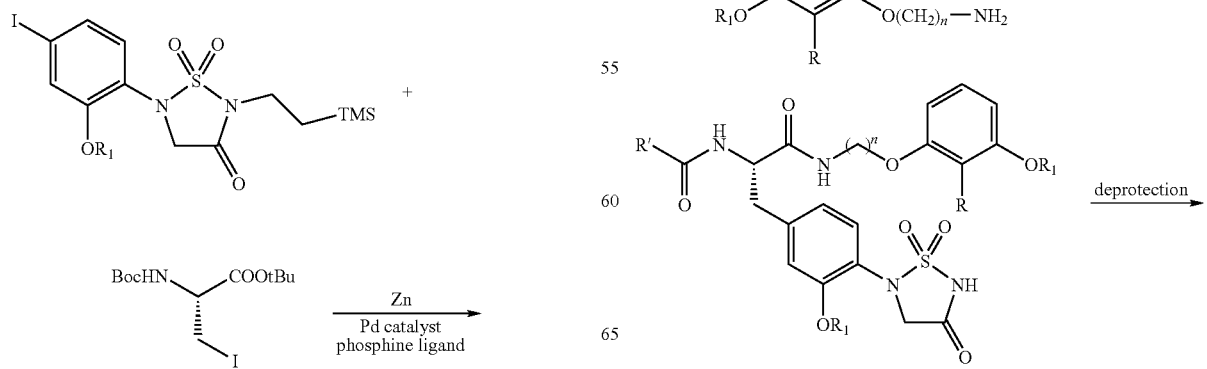

-continued

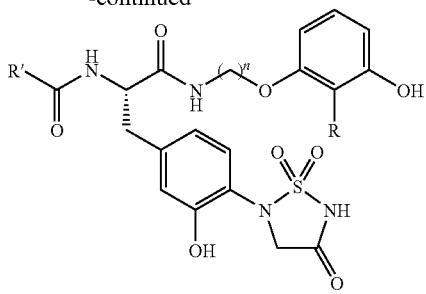

In Scheme 13, R is any of the hereinabove substituents listed as possible aryl substituent.

R' can be as defined hereinabove for the term "acylamino" and is preferably aryl, heterocyclyl, or alkyl. Preferably used is N-acetyl.

In all the above described schemes, $R_1$ has the same definition as hereinabove described.

Compounds of formula (I) may be prepared starting, e.g., by cyclizing compounds of the formula

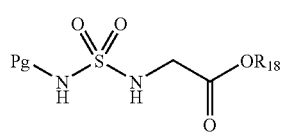
(II)

wherein Pg is an appropriate N-protecting group such as 4-methoxybenzyl, 2,4-dimethoxybenzyl or 2-trimethylsilyl-ethyl, and $R_{18}$ is hydrogen to afford compounds of the formula

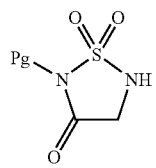
(III)

wherein Pg has a meaning as defined herein above, by treatment with a coupling agent such as diisopropyl carbodiimide (DIC) or 1-ethyl-3-(3-dimethylaminopropyl)carbodiimide hydrochloride (EDCl) in the presence a base such as triethylamine (TEA) or N-methyl-morpholine (NMM) in an organic solvent such as tetrahydrofuran (THF), N,N-dimethyl-formamide (DMF) or dichloromethane (DCM). The reaction may be carried out in the presence of an additive such as of hydroxybenzotriazole (HOBt).

Compounds of formula (II) wherein $R_{18}$ is hydrogen may be obtained from compounds of formula (II) wherein $R_{18}$ is an alkyl group according to methods well known in the art, e.g. compounds of formula (II) in which $R_{18}$ is methyl or ethyl can be treated with an aqueous base such as sodium or potassium hydroxide in an organic solvent such as THF, 1,4-dioxane, methanol (MeOH) or ethanol (EtOH) to afford compounds of formula (II) wherein $R_{18}$ is hydrogen, or compounds of formula (II) in which $R_{18}$ is t-butyl may be treated with an acid such as hydrochloric acid (HCl) or trifluoroacetic acid (TFA) in an organic solvent such as DCM or ethyl acetate (EtOAc) to afford compounds of formula (II) wherein $R_{18}$ is hydrogen.

Compounds of formula (II) wherein $R_{18}$ is an alkyl group such as methyl, ethyl or t-butyl, and the like, may be obtained analogously to a literature procedure described by Ducry et al. in *Helvetica Chimica Acta*, 1999, 82, 2432.

Resulting compounds of formula (II) wherein Pg has a meaning as defined herein can then be coupled with a variety of boronic acid derivatives of the formula

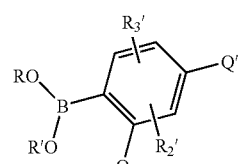
(IV)

wherein $R_1'$, $R_2'$, $R_3'$ and Q' have meanings as defined herein for $R_1$, $R_2$, $R_3$ and Q, or $R_1'$, $R_2'$, $R_3'$ and Q' are groups convertible to $R_1$, $R_2$, $R_3$ and Q, respectively, and R and R' are hydrogen or lower alkyl, or R and R' combined are alkylene which together with the boron and the oxygen atoms form a 5- or 6-membered ring, in the presence of a copper catalyst such as copper(II) acetate and a base such as cesium(II) carbonate ($Cs_2CO_3$) or TEA in an organic solvent such as THF, 1,4-dioxane or DCM to form compounds of the formula

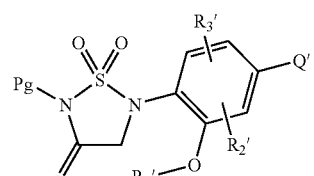
(V)

wherein Pg, $R_1'$, $R_2'$, $R_3'$ and Q' have meanings as defined herein for $R_1$, $R_2$, $R_3$ and Q, or $R_1'$, $R_2'$, $R_3'$ and Q' are groups convertible to $R_1$, $R_2$, $R_3$ and Q, respectively. Alternatively, compounds of formula (III) may be coupled with a boroxine derivative corresponding to a boronic acid derivative of formula (IV) as described, e.g., by Chan et al. in *Tet Lett.* 2003, 44, 3863.

Compounds of formula (IV) are known, or if they are novel, they may be prepared using methods well known in the art, or as illustrated herein in the Examples, or modifications thereof.

Alternatively, compounds of formula (V) wherein $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, may be obtained by reacting a compound of formula (III) wherein Pg has a meaning as defined herein with compounds of the formula

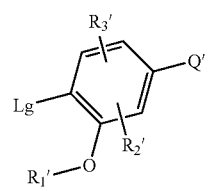
(VI)

wherein Lg represents a leaving group such as halide or trifluoromethanesulfonate, preferably fluoride or chloride, and $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and $Q$, respectively, using conditions well know in the art or using methods described herein or modifications thereof, e.g., a compound of formula (III) may be first treated with a base such as $Cs_2CO_3$, or sodium, lithium or potassium bis(trimethylsilyl) amide in an inert organic solvent such as THF or 1,4-dioxane followed by reaction with a compound of formula (VI) at a temperature ranging from room temperature (RT) to 110° C.

Compounds of formula (VI) are known, or if they are novel, they may be prepared using methods well known in the art, or as illustrated herein in the Examples, or modifications thereof.

Compounds of formula (V) wherein Pg, $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and $Q$, respectively, can be converted to compounds of the formula

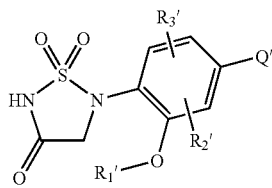

(I')

by removal of the N-protecting group according to methods well known in the art, e.g. in particular when Pg is 4-methoxybenzyl or 2,4-dimethoxybenzyl group using hydrogen in the presence of a catalyst such as palladium on carbon in a polar organic solvent such as MeOH or EtOAc, or by treatment with an acid such as TFA in an organic solvent such as DCM, preferably in the presence of an additive such as t-butyldimethylsilane or triethylsilane, or in particular when Pg is trimethylsilylethyl group using a fluoride reagent such as tetra-n-butylammoniumfluoride in an organic solvent such as THF or 1,4-dioxane.

In addition, compounds of formula (I') wherein $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and $Q$, respectively, may be prepared by condensing compounds of the formula

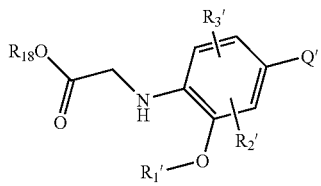

(VII)

wherein $R_{18}$ has a meaning as defined herein above, with sulfamoyl chloride analogs of the formula

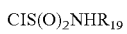 (VIII)

wherein $R_{19}$ is hydrogen or alkoxycarbonyl such as t-butoxycarbonyl or 2-trimethylsilyl-ethoxycarbonyl in the presence of a base such as TEA or NMM in an organic solvent such as acetonitrile (MeCN), DCM or THF to form compounds of the formula

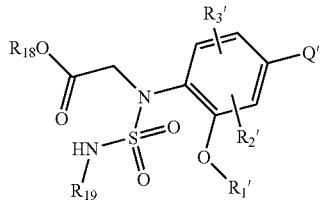

(IX)

wherein $R_{18}$ and $R_{19}$ have meanings as defined herein, and $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and $Q$, respectively.

Compounds of formula (VIII) wherein $R_{19}$ is alkoxycarbonyl may be obtained by reacting chlorosulfonyl isocyanate with the appropriate alcohol in an organic solvent such as MeCN, DCM or THF.

Compounds of formula (VII) may be prepared using methods well known in the art or according to methods described herein or modifications thereof, e.g., under conditions of reductive amination, or according to the method described by Tohru Fukuyama et al. in *Tet. Lett.*, 1997, 38 (33), 5831; or by reacting amines of the formula

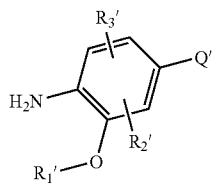

(X)

wherein $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and $Q$, respectively, with an acetate of the formula

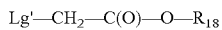 (XI)

wherein Lg' and $R_{18}$ have meanings as defined herein, in the presence of a base such as TEA or NMM in an inert solvent such as THF or 1,4-dioxane.

Amines of formula (X) are known, or if they are novel, they may be obtained according to methods well known in the art, or as described herein in the illustrative Examples, or using modifications thereof.

Compounds of formula (IX) wherein $R_{18}$ has a meaning as defined herein, and $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and $Q$, respectively, and $R_{19}$ is alkoxycarbonyl may be converted to compounds of formula (IX) wherein $R_{19}$ is hydrogen according to methods known in the art or using methods described herein or modifications thereof, e.g., compounds of formula (IX) wherein $R_{19}$ is t-butoxycarbonyl may be treated with an acid such as TFA, neat or in an extrinsic organic solvent such as DCM, or compounds of formula (IX) wherein $R_{19}$ is 2-trimethylsilylethoxycarbonyl may be treated with a fluoride reagent such as tetra-n-butylammoniumfluoride in an organic solvent such as THF or 1,4-dioxane to afford compounds of formula (IX) wherein $R_{19}$ is hydrogen.

Compounds of formula (IX) wherein $R_{18}$ has a meaning as defined herein, and $R_1'$, $R_2'$, $R_3'$ and $Q'$ have meanings as defined herein for $R_1$, $R_2$, $R_3$ and $Q$, or $R_1'$, $R_2'$, $R_3'$ and $Q'$ are groups convertible to $R_1$, $R_2$, $R_3$ and Q, respectively, and $R_{19}$ is hydrogen can be cyclized to form compounds of formula (I') using methods and conditions well known in the art or as illustrated with Examples herein or modifications thereof.

Alternatively, compounds of formula (IX) wherein $R_{18}$ has a meaning as defined herein; $R_1'$, $R_2'$, $R_3'$ and Q' have meanings as defined herein for $R_1$, $R_2$, $R_3$ and Q, or $R_1'$, $R_2'$, $R_3'$ and Q' are groups convertible to $R_1$, $R_2$, $R_3$ and Q, respectively; and $R_{19}$ is hydrogen, may be obtained by first condensing amines of formula (X) with sulfamide in an aqueous solution and in the presence of a base such as sodium bicarbonate ($NaHCO_3$) at an elevated temperature, preferably at the boiling point of the solution, to afford compounds of the

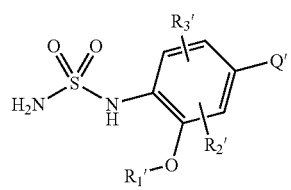

(XII)

wherein $R_1'$, $R_2'$, $R_3'$ and Q' have meanings as defined herein for $R_1$, $R_2$, $R_3$ and Q, or $R_1'$, $R_2'$, $R_3'$ and Q are groups convertible to $R_1$, $R_2$, $R_3$ and Q, respectively. Compound of formula (XII) may then be converted to compound of formula (IX) in which $R_{19}$ is hydrogen by the reaction with acetates of formula (XI) in the presence of a base such as sodium hydride in an inert solvent such as THF or DMF.

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well known protecting groups that meet these conditions and their introduction and removal are described, for example, in McOmie, "Protective Groups in Organic Chemistry", Plenum Press, London, New York (1973); and Greene and Wuts, "Protective Groups in Organic Synthesis", John Wiley and Sons, Inc, New York (1999).

The above mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, optical isomers (enantiomers, antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof obtained with an optically active acid or base, and liberating the optically active acidic or basic compound. The carboxylic acid intermediates can thus be resolved into their optical antipodes e.g. by fractional crystallization of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, as a salt thereof if salt forming groups are present or as prodrug derivatives thereof.

In particular, the NH-group of the 1,1-dioxo-1,2,5-thiadiazolidin-3-one moiety, may be converted into salts with pharmaceutically acceptable bases. Salts may be formed using conventional methods, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_{1-4}$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxy-carboxylic acids, for example glycolic, lactic, malic, tartaric or citric acid, such as amino acids, for example aspartic or glutamic acid, or with organic sulfonic acids, such as ($C_{1-4}$)alkyl-sulfonic acids (for example methanesulfonic acid) or arylsulfonic acids which are unsubstituted or substituted (for example by halogen). Preferred are salts formed with hydrochloric acid, methanesulfonic acid and maleic acid.

Prodrug derivatives of any compound of the present invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention are inhibitors of PTPases and, thus, may be employed for the treatment of conditions mediated by the PTPases. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer, osteoporosis, musculoskeletal, neurodegenerative and infectious diseases, and diseases involving inflammation and the immune system.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by PTPase activity, in particular, PTP-1B and TC PTP activity. Such conditions include insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer, osteoporosis, musculoskeletal, neurodegenerative and infectious diseases, and diseases involving inflammation and the immune system.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbents, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, welting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by PTPases, preferably, insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer, osteoporosis, musculoskeletal, neurodegenerative and infectious diseases, and diseases involving inflammation and the immune system.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) anti-diabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; thiazolidone derivatives such as glitazones, e.g., pioglitazone and rosiglitazone; glucokinase activators; GSK3 (glycogen synthase kinase-3) inhibitors such as SB-517955, SB4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; modulators of PPARs (peroxisome proliferator-activated receptors), e.g., non-glitazone type PPARγ agonists such as N-(2-benzoylphenyl)-L-tyrosine analogues, e.g. GI-262570, and JTT501; DPPIV (dipeptidyl peptidase IV) inhibitors such as LAF237, MK-0431, saxagliptin and GSK23A; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products);

b) anti-dyslipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; HDL increasing compounds such as cholesterol ester transfer protein (CETP) inhibitors, e.g., JTT705; Apo-A1 analogs and mimetics; squalene synthase inhibitors; FXR (farnesoid X receptor) and LXR (liver X receptor) ligands; cholestyramine; fibrates; nicotinic acid; and aspirin;

c) anti-obesity agents such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine, ecopipam, ephedrine, and pseudoephedrine; cholesterol absorption modulators such as ZETIA® and KT6-971; and cannabinoid receptor antagonists such as rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists such as eplerenone; and aldosterone synthase inhibitors such as anastrazole and fadrazole.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or anti-obesity agents as described above.

The present invention further relates to pharmaceutical compositions as described above for use as a medicament.

The present invention further relates to use of pharmaceutical compositions or combinations as described above for the preparation of a medicament for the treatment of conditions mediated by PTPase activity, in particular, PTP-1B and TC PTP activity. Such conditions include insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer, osteoporosis, musculoskeletal, neurodegenerative and infectious diseases, and diseases involving inflammation and the immune system.

Thus, the present invention also relates to a compound of formula (I) for use as a medicament, to the use of a compound of formula (I) for the preparation of a pharmaceutical composition for treatment of conditions mediated by PTPase activity, in particular, PTP-1B and TC PTP activity, and to a pharmaceutical composition for use in conditions mediated by PTPase activity, in particular, PTP-1B and TC PTP activity, comprising a compound of formula (I), or a pharmaceutically acceptable salt thereof, in association with a pharmaceutically acceptable diluent or carrier therefore.

The present invention further provides a method for the treatment of conditions mediated by PTPase activity, in particular, PTP-1B and TC PTP activity, which method comprises administering a therapeutically effective amount of a compound of the present invention.

A unit dosage for a mammal of about 50 to 70 kg may contain between about 1 mg and 1000 mg, advantageously between about 5 mg to 500 mg of the active ingredient. The therapeutically effective dosage of a compound of formula I is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of PTPase activity, in particular, PTP-1B and TC PTP activity.

Preferably, the condition associated with PTPase activity, in particular, PTP-1B and TC PTP activity, is selected from insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer, osteoporosis, musculoskeletal, neurodegenerative and infectious diseases, and diseases involving inflammation and the immune system.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-3}$ molar and $10^{-10}$ molar concentrations. A therapeutically effective amount in vivo may range depending on the route of administration, between about 1 and 500 mg/kg, preferably between about 5 and 100 mg/kg.

The activity of a compound according to the invention may be assessed by the following methods or by following methods well described in the art (e.g. Peters G. et al. *J. Biol. Chem.*, 2000, 275, 18201-09).

For example, the PTP-1B inhibitory activity in vitro may be determined as follows:

Assessment of human PTP-1B (hPTP-1B) activity in the presence of various agents is determined by measuring the amount of inorganic phosphate released from a phosphopeptide substrate using a 96-well microtiter plate format. The assay (100 µL) is performed in an assay buffer comprised of 50 mM TRIS (pH 7.5), 50 mM NaCl, 3 mM DTT at ambient temperature. The assay is typically performed in the presence of 0.4% dimethyl sulfoxide (DMSO). However, concentrations as high as 10% are used with certain poorly soluble compounds. A typical reaction is initiated by the addition of 0.4 pmoles of hPTP-1B (amino acids 1-411) to wells containing assay buffer, 3 nmoles of the synthetic phosphopeptide substrate (GNGDpYMPMSPKS), and the test compound. After 10 min, 180 µL malachite green reagent (0.88 mM malachite green, 8.2 mM ammonium molybdate, aqueous 1 N HCl, and 0.01% Triton X-100) is added to terminate the reaction. Inorganic phosphate, a product of the enzyme reaction, is quantitated after 15 min as the green color resulting from complexing with the Malichite reagent and is determined as an $A_{620}$ using a Molecular Devices (Sunnyvale, Calif.) SpectraMAX Plus spectrophotometer. Test compounds are solubilized in 100% DMSO (Sigma, D-8779) and diluted in DMSO. Activity is defined as the net change in absorbance resulting from the activity of the uninhibited hPTP-1B$_{[1-411]}$ minus that of a tube with acid-inactivated hPTP-1B$_{[1-411]}$.

The hPTP-1B$_{[1-114]}$ is cloned by PCR from a human hippocampal cDNA library (Clonetech) and inserted into a pET 19-b vector (Novagen) at the NcoI restriction site. *E. coli* strain BL21 (DE3) is transformed with this clone and stored as a stock culture in 20% glycerol at −80° C. For enzyme production, a stock culture is inoculated into Lb/Amp and grown at 37° C. Expression of PTP-1B is initiated by induction with 1 mM IPTG after the culture had reached an $OD_{600}$=0.6. After 4 h, the bacterial pellet is collected by centrifugation. Cells are resuspended in 70 mL lysis buffer (50 mM Tris, 100 mM NaCl, 5 mM DTT, 0.1% Triton X-100, pH7.6), incubated on ice for 30 min then sonicated (4×10 sec bursts at full power). The lysate is centrifuged at 100,000×g for 60 min and the supernatant is buffer exchanged and purified on a cation exchange POROS 20SP column followed by an anion exchange Source 30Q (Pharmacia) column, using linear NaCl gradient elutions. Enzyme is pooled, adjusted to 1 mg/mL and frozen at 80° C.

Alternatively, the assessment of human PTP-1B activity in the presence of various agents may be determined by measuring the hydrolysis products of known competing substrates. For example, cleavage of substrate para-nitrophenylphosphate (pap) results in the release of the yellow-colored para-nitrophenol (pNP) which can be monitored in real time using a spectrophotometer. Likewise, the hydrolysis of the fluorogenic substrate 6,8-difluoro-4-methylumbelliferyl phosphate ammonium salt (DiFMUP) results in the release of the fluorescent DiFMU which can be readily followed in a continuous mode with a fluorescence reader (Anal. Biochem. 273, 41, 1999; Anal. Biochem. 338, 32, 2005):

pNPP Assay

Compounds were incubated with 1 nM recombinant human PTP-1B$_{[1-298]}$, or PTP-1B$_{[1-322]}$ in buffer (50 mM Hepes, pH 7.0, 50 mM KCl, 1 mM EDTA, 3 mM DTT, 0.05% NP-40 for 5 min at room temperature. The reaction is initiated by the addition of pNPP (2 mM final concentration) and run for 120 min at room temperature. Reactions are quenched with 5 N NaOH. Absorbance at 405 nm is measured using any standard 384 well plate reader.

DiFMUP Assay

Compounds are incubated with 1 nM recombinant human PTP-1B$_{[1-298]}$ or PTP-1B$_{[1-322]}$ in buffer (50 mM Hepes, pH 7.0, 50 mM KCl, 1 mM EDTA, 3 mM DTT, 0.05% NP-40 (or 0.001% BSA) for 5 min at room temperature. The reaction is initiated by the addition of DiFMUP (6 µM final concentration) and run kinetically on fluorescence plate reader at 355 nm excitation and 460 nm emission wavelengths. Reaction rates over 15 min are used to calculate inhibition.

PTP-1B$_{[1-298]}$ is expressed in *E. coli* BL21 (DE3) containing plasmids constructed using pET19b vectors (Novagen).

The bacteria is grown in minimal media using an "On Demand" Fed-batch strategy. Typically, a 5.5 liter fermentation is initiated in Fed-batch mode and grown overnight unattended at 37° C. Optical densities varied between 20-24 $OD_{600}$ and the cultures are induced at 30° C. with IPTG to a final concentration of 0.5 mM. The bacterial cells are harvested 8 hours later and yield 200-350 gm (wet weight). The cells are frozen as pellets and stored at −80° C. until use. All steps are performed at 4° C. unless noted. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 µM PMSF and 100 µg/mL DNase I. The cells are lysed by sonication (4×10 second burst, full power) using a Virsonic 60 (Virtus). The pellet is collected at 35,000×g, resuspended in 25 mL of lysis buffer using a Polytron and collected as before. The two supernatants are combined and centrifuged for 30 min at 100,000×g. The soluble lysate could be stored at this stage at −80° C. or used for further purification. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. An analytical column (4.6×100 mm) is run in a similar fashion except the flow rate was reduced to 10 mL/min. Protein is eluted from the column using a linear salt gradient (75-500 mM NaCl in 25 CV). Fractions containing PTP-1B$_{[1\text{-}298]}$ are identified and pooled according to SDS-PAGE analyses. Final purification is performed using Sephacryl S-100 HR (Pharmacia). The column (2.6×35 cm) is equilibrated with 50 mM HEPES, 100 mM NaCl, 3 mM DTT, pH 7.5 and run at a flow rate of 2 mL/min. The final protein is pooled and concentrated to ~5 mg/mL using an Ultrafree-15 concentrator (Millipore) with a MWCO 10,000. The concentrated protein is stored at −80° C. until use.

Competitive binding to the active site of the enzyme may be determined as follows:

Ligand binding is detected by acquiring $^1$H-$^{15}$N HSQC spectra on 250 µL of 0.15 mM PTP-1B$_{[1\text{-}298]}$ in the presence and absence of added compound (1-2 mM). The binding is determined by the observation of $^{15}$N- or $^1$H-amide chemical shift changes in two dimensional HSQC spectra upon the addition of a compound to $^{15}$N-label protein. Because of the $^{15}$N spectral editing, no signal from the ligand is observed, only protein signals. Thus, binding can be detected at high compound concentrations. Compounds which caused a pattern of chemical shift changes similar to the changes seen with known active site binders are considered positive.

All proteins are expressed in *E. coli* BL21 (DE3) containing plasmids constructed using pET19b vectors (Novagen). Uniformly $^{15}$N-labeled PTP-1B$_{1\text{-}298}$ is produced by growth of bacteria on minimal media containing $^{15}$N-labeled ammonium chloride. All purification steps are performed at 4° C. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 µM PMSF and 100 µg/mL DNase I. The cells are lysed by sonication. The pellet is collected at 35,000×g, resuspended in 25 mL of lysis buffer using a Polytron and collected as before. The two supernatants are combined and centrifuged for 30 min at 100,000×g. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. Protein is eluted from the column using a linear salt gradient (75-500 mM NaCl in 25 CV). Fractions containing PTP-1B's are identified and pooled according to SDS-PAGE analyses. PTP-1B$_{1\text{-}298}$ is further purified by anion exchange chromatography using a POROS 20 HQ column (1×10 cm). The pool from cation exchange chromatography is concentrated and buffer exchanged in 50 mM Tris-HCl, pH 7.5 containing 75 mM NaCl and 5 mM DTT. Protein is loaded onto column at 20 mL/min and eluted using a linear NaCl gradient (75-500 mM in 25 CV). Final purification is performed using Sephacryl S-100 HR (Pharmacia) (50 mM HEPES, 100 mM NaCl, 3 mM DTT, pH 7.5). The NMR samples are composed of uniformly $^{15}$N-labeled PTP-1B$_{1\text{-}298}$ (0.15 mM) and inhibitor (1-2 mM) in a 10% $D_2O$/90% $H_2O$ Bis-Tris-d$_{19}$ buffer (50 mM, pH=6.5) solution containing NaCl (50 mM), DL-1,4-Dithiothreitol-d$_{10}$ (5 mM) and Sodium azide (0.02%).

The $^1$H-$^{15}$N HSQC NMR spectra are recorded at 20° C., on Bruker DRX500 or DMX600 NMR spectrometers. In all NMR experiments, pulsed field gradients are applied to afford the suppression of solvent signal. Quadrature detection in the indirectly detected dimensions is accomplished by using the States-TPPI method. The data are processed using Bruker software and analyzed using NMRCompass software (MSI) on Silicon Graphics computers.

The glucose and insulin lowering activity in vivo may be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1 tail blood samples are taken at 8:00 am and plasma glucose levels are determined. The animals are randomly assigned to the control and compound groups. The means of plasma glucose values of the groups are matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4 basal blood samples are taken. The plasma samples are analyzed for glucose concentrations using a YSI2700 Dual Channel Biochemistry Analyzer (Yellow Springs Instrument Co., Yellow Springs, Ohio) and insulin concentrations using an ELISA assay.

The following Examples are intended to illustrate the invention and are not to be construed as being limitations thereon. The IC$_{50}$ (affinity) of the following examples toward the PTP-1B protein is comprised between around 15 micro Molar and 0.0001 micro Molar or between around 13.5 micro Molar and 0.0002 micro Molar or between around 1 micro Molar and 0.0002 micro Molar.

Temperatures are given in degrees Centigrade (° C.). If not mentioned otherwise, all evaporations are performed under reduced pressure, preferably between about 15 and 100 mmHg (=20–133 mbar). The structure of final products, intermediates and starting materials is confirmed by standard analytical methods, e.g. microanalysis, melting point (mp) and spectroscopic characteristics (e.g. MS, IR, NMR). In general, abbreviations used are those conventional in the art.

HPLC Methods

Method A: 4.6 mm×5 cm C-8 reverse phase column, 3 µM particle size running a gradient of 10-90% MeCN/water (5 mM ammonium formate) over a period of 2 min at a flow rate of 4 mL/min at 50° C. (3 µL injection). DAD-UV detection, 220-600 nm.

Method B: Inertsil ODS-3 4.6 mm×5 cm C-8 reverse phase column, 3 µM particle size running a gradient of 0-90% MeCN/water (5 mM ammonium formate) over a period of 2 min at a flow rate of 4 mL/min at 50° C. (3 µL injection). DAD-UV detection, 220400 nm.

Method C: 4.6 mm×5 cm C-8 reverse phase column, 3 µM particle size running a gradient of 40-90% MeCN/water (5 mM ammonium formate) over a period of 1.2 min at a flow rate of 4 mL/min at 50° C. (3 µL injection). DAD-UV detection, 220-600 nm.

EXAMPLE 1

5-(2-Benzyloxy-4-iodophenyl)-1,1-dioxo-1,2,5-thiadiazolidin-3-one

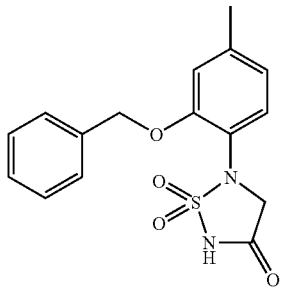

A. 2-Benzyloxy-4-iodo-1-nitrobenzene

To a solution of 5-iodo-2-nitrophenol (2.65 g, 10 mmol) (*J. Org. Chem.* 1998, 63, 4199-4208) in DMF (10 mL) is added benzyl bromide (1.71 g, 10 mmol) and K$_2$CO$_3$ (2.07 g, 15 mmol) and the mixture is heated at 65° C. for 30 min. Then water is added (400 mL) and it is extracted by EtOAc (2×200 mL). The water layer is then acidified and extracted with EtOAc (100 mL). The combined EtOAc layer is then washed with 1N HCl and brine, dried with NaSO$_4$ and concentrated to give the title compound as a yellow solid.

B. 2-Benzyloxy-4-iodophenylamine

To a mixture of 2-benzyloxy-4-iodo-1-nitrobenzene (2.35 g, 6.62 mmol) and Fe (1.85 g, 33.1 mmol) is added AcOH (24 mL) and EtOH (12 mL) and it is refluxed at 100° C. for 1.5 h. The mixture is then cooled and filtered through Celite. EtOAc (300 mL) is added and it is then washed with sat. NaHCO$_3$ (2×), brine (1×) and dried with NaSO$_4$. It is then concentrated and the residue is purified by column chromatography to give the title compound.

C. (2-Benzyloxy-4-iodophenylamino)-acetic Acid Tert-butyl Ester

To a solution of 2-benzyloxy-4-iodophenylamine (2.35 g, 7.23 mmol) in DMF (15 mL) is added bromoacetic acid tert-butyl ester (1.76 g, 9.04 mmol) and K$_2$CO$_3$ (5.0 g, 36.2 mmol) and the mixture is heated at 50° C. for 4 h. 2N HCl solution (200 mL) is added with cooling and it is then extracted with EtOAc. The organic layer is then washed with brine, dried and concentrated. The residue is then purified by column chromatography to give the title compound as a white solid.

D. N-(t-Butoxycarbonylsulfamoyl)-N-(2-benzyloxy-4-iodophenyl)glycine Tert-butyl Ester To an ice cooled solution of chlorosulfonyl isocyanate (0.788 mL, 8.94 mmol) in methylene chloride (40 mL) is added dropwise t-butanol (0.855 mL, 8.94 mmol). Then at 0° C., (2-benzyloxy-4-iodophenylamino)-acetic acid tert-butyl ester (2.62 g, 5.96 mmol) and triethylamine (2.08 mL, 14.9 mmol) in methylene chloride (40 mL) is added dropwise. After stirring for 30 min, methylene chloride (300 mL) is added and the organic layer is washed with 2N HCl solution. It is then dried with NaSO$_4$, and concentrated. The residue is purified by column chromatography to give the title compound as an off-white foam.

E. Tert-butyl N-[2-(benzyloxy)-4-iodophenyl]-N-({(tert-butoxycarbonyl)[2-(trimethylsilyl)ethyl]amino}sulfonyl)glycinate To a solution of N-(t-butoxycarbonylsulfamoyl)-N-(2-benzyloxy-4-iodophenyl)glycine tert-butyl ester (3.49 g, 5.6 mmol) in toluene (224 mL) is added triphenylphosphine (2.22 g, 8.47 mmol) and 2-trimethylsilanylethanol (992 mg, 8.38 mmol). DIAD (1.6 mL, 8.13 mmol) is then added dropwise over 10 min. The mixture is stirred for 50 min then the toluene is remove under reduced pressure. After 18 h, 20% EtOAc/hexane is added (50 ml in 4 increments) to form a precipitate. The solid is filtered and the filtrate is then concentrated. The residue is then purified by column chromatography to give the title compound as a white foam.

F. N-[2-(benzyloxy)-4-iodophenyl]-N-({[2-(trimethylsilyl)ethyl]amino}sulfonyl)glycine To a solution of above compound (3.11 g, 4.33 mmol) in DCM (20 mL) is added TFA (10 ml). The mixture is stirred at RT for 2 h and volatiles are evaporated to dryness. The residue is dissolved in toluene and re-evaporated. The residue is recrystallized from ether/hexane to give the title compound as a white solid, (M−H)$^-$=561.

G. 5-(2-Benzyloxy-4-iodophenyl)-1,1-dioxo-2-(2-trimethylsilanylethyl)-1,2,5-thiadiazolidin-3-one To a solution of above compound (2.05 g, 3.64 mmol) in THF (20 ml) is added EDCl (1.05 g, 4.0 mmol) followed by HOBT (0.54 g, 4.0 mmol) and TEA (1.01 mL, 7.28 mmol). The mixture is stirred at RT for 3 h and the solvent is then evaporated. The residue is partitioned between EtOAc and 1 N HCl solution and the organic layer is washed with saturated NaHCO$_3$, dried with MgSO$_4$, and concentrated. The residue is purified by column chromatography to give the title compound as a solid.

H. 5-(2-Benzyloxy-4-iodophenyl)-1,1-dioxo-1,2,5-thiadiazolidin-3-one

Tetrabutylammonium fluoride (1.0M in THF, 15 mL) is added to a solution of PS-isocyanate resin (3.5 g) in THF. The mixture is stirred at RT for 2 h. The resin is filtered off and the filtrate is added to a solution of 5-(2-benzyloxy-4-iodophenyl)-1,1-dioxo-2-(2-trimethylsilanylethyl)-1,2,5-thiadiazolidin-3-one (5.0 g, 9.18 mmol) in THF. The reaction is stirred at 50° C. for 18 h. The mixture is cooled and concentrated. The residue is partitioned between EtOAc and water and the organic layer is washed with 1N HCl (5×50 mL) and brine. The organic layer is dried over $Na_2SO_4$ and concentrated. The residue is purified by reverse phase chromatography using a 10-60% gradient of EtOH/water as eluent to afford the title compound as a light yellow solid: $(M-1)^- = 442$.

EXAMPLE 2

3-{2-[3-Hydroxy-4-(1,1,4-trioxo-1,2,5-thiadiazolidin-2-yl)-phenyl]-ethyl}-benzamide

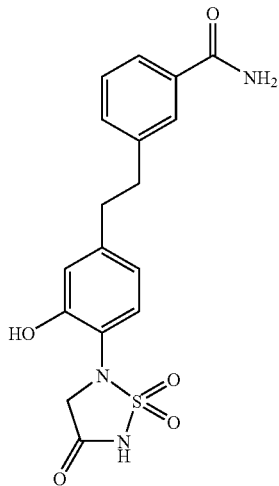

A. 3-Vinylbenzoyl Chloride

To a mixture of 3-vinylbenzoic acid (1.0 g, 6.75 mmol) in $CH_2Cl_2$ (20 mL) is added oxalyl chloride (2.35 mL, 3.42 g, 26.9 mmol) and 1 drop of DMF. After 2 h the solvent is removed under reduced pressure and the residue is redissolved in $CH_2Cl_2$ and concentrated again (4×) to afford the title compound which is used without further purification.

B. 3-Vinylbenzamide

3-Vinylbenzoyl chloride is saturated with ammonia gas to afford an immediate precipitate. This mixture is poured into EtOAc and extracted with water and brine. The EtOAc is dried, filtered, and concentrated to afford the title compound: mp=128-130° C.; $^1H$ NMR (CDCl$_3$) δ 7.86 (d, J=1.3 Hz, 1H), 7.66 (dd, J=8.6, 1.0 Hz, 1H), 7.57 (d, 7.8 Hz, 1H), 7.41 (t, 7.8 Hz, 1H), 6.75 (dd, J=17.4, 10.9 Hz, 1H), 6.05 (br s, 1H), 5.83 (d, J=17.9 Hz, 1H), 5.61 (br s, 1H), 5.34 (d, J=10.9 Hz, 1H).

C. 3-{2-[3-Benzyloxy-4-(1,1,4-trioxo-1,2,5-thiadiazolidin-2-yl)-phenyl]-vinyl}-benzamide A mixture of 3-vinylbenzamide (32 mg, 0.22 mmol), 5-(2-benzyloxy-4-iodophenyl)-1,1-dioxo-1,2,5-thiadiazolidin-3-one (80 mg, 0.18 mmol), Pd(OAc)$_2$ (20 mg, 0.09 mmol) and triethylamine (0.256 mL, 1.84 mmol) in MeCN (2 mL) is heated in a microwave apparatus at 120° C. for 25 min. The mixture is filtered over Celite and washed with MeCN. The filtrate is evaporated to give the title compound which is used directly in the next step.

D. 3-{2-[3-Hydroxy-4-(1,1,4-trioxo-1,2,5-thiadiazolidin-2-yl)-phenyl]-ethyl}-benzamide To a solution of 3-{2-[3-benzyloxy-4-(1,1,4-trioxo-1,2,5-thiadiazolidin-2-yl)-phenyl]-vinyl}-benzamide in ethanol (2 mL) is added two equivalents of KHCO$_3$. The mixture is diluted with 5 mL water and hydrogenated at 1 atm over 50 mg of 10% Pd/C for 18 h. The catalyst is filtered and the filtrate lyophilized. The resulting solid is purified by HPLC to give the title compound as an amorphous powder: m/z $(M-1)^- = 374$; $^1H$ NMR (DMSO-d$_6$) δ 7.95 (m, 1H), 7.81 (s, 1H), 7.72 (m, 1H), 7.35 (m, 4H), 6.75 (d, J=1.5 Hz 1H), 6.70 (m, 1H), 4.04 (s, 2H), 2.86 (m, 4H).

EXAMPLES 3 TO 34

The following compounds are prepared using the appropriate starting materials analogous to the procedures outlined in Example 2. For Examples 34, 31 and 29, 5-(2-benzyloxy-4-iodophenyl)-1,1-dioxo-2-(2-trimethylsilanylethyl)-1,2,5-thiadiazolidin-3-one is used and TMS-ethyl deprotection is performed after the Heck reaction.

| Example | Chemical Name | MS (m/z) | Retention time (min) Method |
|---|---|---|---|
| 3 | 3-{2-[3-Hydroxy-4-(1,1,4-trioxo-1,2,5-thiadiazolidin-2-yl)-phenyl]-ethyl}-N-methyl benzamide | $(M - 1)^- = 388$ | 0.83 A |
| 4 | 3-{2-[3-Hydroxy-4-(1,1,4-trioxo-1,2,5-thiadiazolidin-2-yl)-phenyl]-ethyl}-N,N-dimethylbenzamide | $(M - 1)^- = 402$ | 1.06 A |
| 5 | 4-{2-[3-Hydroxy-4-(1,1,4-trioxo-1,2,5-thiadiazolidin-2-yl)-phenyl]-ethyl}-N,N-dimethylbenzamide | $(M - 1)^- = 402$ | 0.99 A |
| 6 | 4-{2-[3-Hydroxy-4-(1,1,4-trioxo-1,2,5-thiadiazolidin-2-yl)-phenyl]-ethyl}-benzamide | $(M - 1)^- = 374$ | 0.84 A |
| 7 | 4-{2-[3-Hydroxy-4-(1,1,4-trioxo-1,2,5-thiadiazolidin-2-yl)-phenyl]-ethyl}-N-methylbenzamide | $(M - 1)^- = 388$ | 0.90 A |
| 8 | 3-{2-[3-Hydroxy-4-(1,1,4-trioxo-1,2,5-thiadiazolidin-2-yl)-phenyl]-ethyl}-benzoic acid | $(M - 1)^- = 375$ | 0.77 A |
| 9 | 4-{2-[3-Hydroxy-4-(1,1,4-trioxo-1,2,5-thiadiazolidin-2-yl)-phenyl]-ethyl}-benzoic acid | $(M - 1)^- = 375$ | 0.73 A |

-continued

| Example | Chemical Name | MS (m/z) | Retention time (min) Method |
|---|---|---|---|
| 10 | 4-{2-[3-Hydroxy-4-(1,1,4-trioxo-1,2,5-thiadiazolidin-2-yl)-phenyl]-ethyl}-benzonitrile | $(M-1)^- = 356$ | 1.07 A |
| 11 | 2-{2-[3-Hydroxy-4-(1,1,4-trioxo-1,2,5-thiadiazolidin-2-yl)-phenyl]-ethyl}-benzonitrile | $(M-1)^- = 356$ | |
| 12 | 5-(2-Hydroxy-4-phenethylphenyl)-1,1-dioxo-1,2,5-thiadiazolidin-3-one | $(M-1)^- = 331$ | |
| 13 | 5-{2-Hydroxy-4-[2-(3-methoxyphenyl)-ethyl]-phenyl}-1,1-dioxo-1,2,5-thiadiazolidin-3-one | $(M-1)^- = 361$ | 1.15 A |
| 14 | 5-{4-[2-(3-Fluorophenyl)-ethyl]-2-hydroxyphenyl}-1,1-dioxo-1,2,5-thiadiazolidin-3-one | $(M-1)^- = 349$ | 1.23 A |
| 15 | 5-{4-[2-(2-Fluorophenyl)-ethyl]-2-hydroxyphenyl}-1,1-dioxo-1,2,5-thiadiazolidin-3-one | $(M-1)^- = 349$ | 1.18 A |
| 16 | 5-[2-Hydroxy-4-(2-pentafluorophenylethyl)-phenyl]-1,1-dioxo-1,2,5-thiadiazolidin-3-one | $(M-1)^- = 421$ | 1.36 A |
| 17 | 5-[2-Hydroxy-4-(2-p-tolylethyl)-phenyl]-1,1-dioxo-1,2,5-thiadiazolidin-3-one | $(M-1)^- = 345$ | 1.05 A |
| 18 | 5-{2-Hydroxy-4-[2-(4-octylphenyl)-ethyl]-phenyl}-1,1-dioxo-1,2,5-thiadiazolidin-3-one | $(M-1)^- = 443$ | 1.93 A |
| 19 | 5-[4-(2-Biphenyl-4-yl-ethyl)-2-hydroxyphenyl]-1,1-dioxo-1,2,5-thiadiazolidin-3-one | $(M-1)^- = 407$ | |
| 20 | 5-{4-[2-(4-tert-Butylphenyl)-ethyl]-2-hydroxyphenyl}-1,1-dioxo-1,2,5-thiadiazolidin-3-one | $(M-1)^- = 387$ | 1.46 A |
| 21 | 5-{4-[2-(2,5-Dimethylphenyl)-ethyl]-2-hydroxyphenyl}-1,1-dioxo-1,2,5-thiadiazolidin-3-one | $(M-1)^- = 359$ | 1.12 A |
| 22 | 5-{4-[2-(2,4-Dimethylphenyl)-ethyl]-2-hydroxyphenyl}-1,1-dioxo-1,2,5-thiadiazolidin-3-one | $(M-1)^- = 359$ | 1.11 A |
| 23 | 5-{2-Hydroxy-4-[2-(4-trifluoromethylphenyl)-ethyl]-phenyl}-1,1-dioxo-1,2,5-thiadiazolidin-3-one | $(M-1)^- = 399$ | 1.51 A |
| 24 | Acetic acid 4-{2-[3-hydroxy-4-(1,1,4-trioxo-1,2,5-thiadiazolidin-2-yl)-phenyl]-ethyl}-phenyl ester | $(M-1)^- = 389$ | 1.11 A |
| 25 | 5-{2-Hydroxy-4-[2-(4-phenoxyphenyl)-ethyl]-phenyl}-1,1-dioxo-1,2,5-thiadiazolidin-3-one | $(M-1)^- = 423$ | 1.54 A |
| 26 | 5-[2-Hydroxy-4-(2-pyridin-4-ylethyl)-phenyl]-1,1-dioxo-1,2,5-thiadiazolidin-3-one | $(M-1)^- = 332$ | 0.73 A |
| 27 | 5-[2-Hydroxy-4-(2-pyridin-3-yl-ethyl)-phenyl]-1,1-dioxo-1,2,5-thiadiazolidin-3-one | $(M-1)^- = 332$ | 0.71 A |
| 28 | 5-[2-Hydroxy-4-(2-naphthalenethyl)-phenyl]-1,1-dioxo-1,2,5-thiadiazolidin-3-one | $(M-1)^- = 381$ | 1.40 A |
| 29 | 5-[2-Hydroxy-4-(2-quinolin-3-yl-ethyl)-phenyl]-1,1-dioxo-1,2,5-thiadiazolidin-3-one | $(M-1)^- = 382$ | |
| 30 | 5-{4-[2-(4,6-Diamino-[1,3,5]triazin-2-yl)-ethyl]-2-hydroxy-phenyl}-1,1-dioxo-1,2,5-thiadiazolidin-3-one | $(M-1)^- = 364$ | 0.90 B |
| 31 | 5-[2-Hydroxy-4-(2-phenylpropyl)-phenyl]-1,1-dioxo-1,2,5-thiadiazolidin-3-one | $(M-1)^- = 345$ | 1.24 A |
| 32 | 5-{4-[2-(2-Aminophenyl)-propyl]-2-hydroxyphenyl}-1,1-dioxo-1,2,5-thiadiazolidin-3-one | $(M-1)^- = 360$ | 1.11 A |
| 33 | 3-[3-Hydroxy-4-(1,1,4-trioxo-1,2,5-thiadiazolidin-2-yl)-phenyl]-2-phenylpropionic acid ethyl ester | $(M-1)^- = 403$ | 1.30 A |
| 34 | 5-[2-Hydroxy-4-(1-methyl-2-phenylethyl)-phenyl]-1,1-dioxo-1,2,5-thiadiazolidin-3-one | $(M-1)^- = 345$ | 1.22 A |

| Example | NMR |
|---------|-----|
| 12 | $^1$H NMR (400 MHz, DMSO-D6) δ ppm 2.72-2.79 (m, 2H) 2.80-2.86 (m, 2H) 4.03 (s, 2H) 6.58 (d, J = 7.83 Hz, 1H) 6.68 (d, J = 1.52 Hz, 1H) 7.14-7.22 (m, 1H) 7.23-7.29 (m, 5H) |

EXAMPLE 35

5-{2-Hydroxy-4-[2-(6-methoxypyridin-2-yl)-ethyl]-phenyl}-1,1-dioxo-1,2,5-thiadiazolidin-3-one

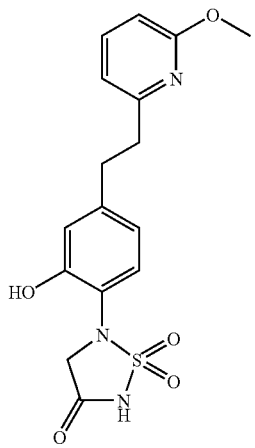

A. 5-{2-Benzyloxy-4-[(E)-2-(6-methoxypyridin-2-yl)-vinyl]-phenyl}-1,1-dioxo-2-(2-trimethylsilanyl-ethyl)-1,2,5-thiadiazolidin-3-one To a solution of 5-(2-benzyloxy-4-vinylphenyl)-1,1-dioxo-2-(2-trimethylsilanylethyl)-1,2,5-thiadiazolidin-3-one (Example 81, step A) (75 mg, 0.17 mmol) in acetonitrile (2 mL), in a pressure vessel, is added 2-bromo-6-methoxypyridine (32 mg, 0.17 mmol), NEt$_3$ (0.05 mL, 0.34 mmol), Pd(OAc)$_2$ (8 mg, 0.034 mmol), and 2-(di-t-butylphosphino) biphenyl (20 mg, 0.068 mmol). The vessel is sealed and stirred at 100° C. for 18 h. The reaction is cooled to RT and filtered through Celite. The solvent is removed under reduced pressure and the crude material purified by column chromatography using a gradient of 0-35% EtOAc/hexanes as eluent to afford the title compound as a yellow oil: (M+H)$^+$=552.

B. 5-{2-Hydroxy-4-[2-(6-methoxypyridin-2-yl)-ethyl]-phenyl}-1,1-dioxo-1,2,5-thiadiazolidin-3-one The title compound is prepared from 5-{2-benzyloxy-4-[(E)-2-(6-methoxypyridin-2-yl)-vinyl]-phenyl}-1,1-dioxo-2-(2-trimethylsilanylethyl)-1,2,5-thiadiazolidin-3-one analogous to Example 57, steps C and D: LC rt 1.13 (Method A); (M−1)$^-$=362.1.

EXAMPLE 36

5-[2-Hydroxy-4-((E)-2-pyridin-3-yl-vinyl)-phenyl]-1,1-dioxo-1,2,5-thiadiazolidin-3-one

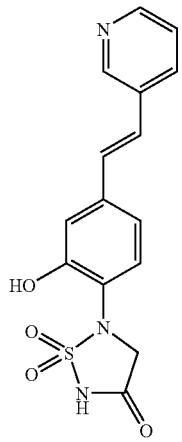

A. 5-[2-Benzyloxy-4-((E)-2-pyridin-3-yl-vinyl)-phenyl]1,1-dioxo-1,2,5-thiadiazolidin-3-one The title compound is prepared using 5-(2-benzyloxy-4-iodophenyl)-1,1-dioxo-1,2,5-thiadiazolidin-3-one and 3-vinylpyridine analogous to Example 2, step C.

B. 5-[2-Hydroxy-4-((E)-2-pyridin-3-yl-vinyl)-phenyl]-1,1-dioxo-1,2,5-thiadiazolidin-3-one To a solution of 5-[2-benzyloxy-4-((E)-2-pyridin-3-yl-vinyl)-phenyl]-1,1-dioxo-1,2,5-thiadiazolidin-3-one (52 mg, 0.123 mmol) in methylene chloride (2 mL) at 0° C. is added BBr$_3$ (0.247 mL, 1M in methylene chloride, 0.247 mmol) slowly and the mixture is stirred for 30 min. The mixture is quenched with 1N HCl and extracted with EtOAc. A yellow precipitate forms in the aqueous layer and is filtered and dried under reduced pressure to give the title compound: (M−1)$^-$=330; HPLC retention time=0.77 min (method A).

EXAMPLE 37

5-[2-Hydroxy-4-(1-methoxy-2-phenylethyl)-phenyl]-1,1-dioxo-1,2,5-thiadiazolidin-3-one

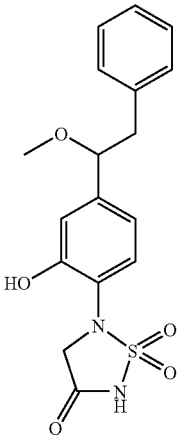

A. 5-[2-Benzyloxy-4-(1,2-dibromo-2-phenylethyl)-phenyl]-1,1-dioxo-1,2,5-thiadiazolidin-3-one To a stirred solution of 5-[2-benzyloxy-4-(E)-styryl)-phenyl]-1,1-dioxo-1,2,5-thiadiazolidin-3-one (intermediate from Example 12) (150 mg, 0.36 mmol) in CCl$_4$ (1.5 mL) is added a solution of Br$_2$ (115 mg, 0.72 mmol) in methylene chloride (4 mL). The solution is stirred at RT for 18 h and the solvent is removed under reduced pressure and the residue is dissolved in methylene chloride. The suspension is filtered and the solid washed with methylene chloride and dried under reduced pressure to afford the title compound as a yellow solid: mp=173-175° C.

B. 5-[2-Benzyloxy-4-(2-bromo-1-methoxy-2-phenylethyl)-phenyl]-1,1-dioxo-1,2,5-thiadiazolidin-3-one To a stirred solution of 5-[2-benzyloxy-4-(1,2-dibromo-2-phenylethyl)-phenyl]-1,1-dioxo-1,2,5-thiadiazolidin-3-one (25 mg, 0.043 mmol) in MeOH/methylene chloride (1:1, 4 mL) is added NaOMe (0.17 mL, 0.086 mmol, 0.5M in THF). The solution is stirred at RT for 2 h and the solvent is removed under reduced pressure to give the title compound as a yellow solid.

C. 5-[2-Hydroxy-4-(1-methoxy-2-phenylethyl)-phenyl]-1,1-dioxo-1,2,5-thiadiazolidin-3-one The title compound is prepared from 5-[2-benzyloxy-4-(2-bromo-1-methoxy-2-phenylethyl)-phenyl]-1,1-dioxo-1,2,5-thiadiazolidin-3-one analogous to Example 62, step D: (M−1)$^-$=361. HPLC retention time: 1.10 min (Method A).

EXAMPLE 38

5-[2-Hydroxy-4-(3-oxo-2-phenylbutyl)-phenyl]-1,1-dioxo-1,2,5-thiadiazolidin-3-one

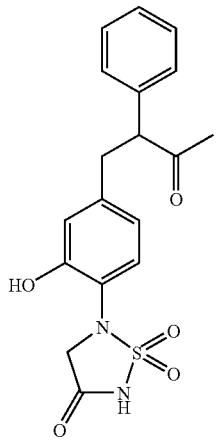

A. 1-Phenylpropane-2-one

To a stirred solution of 1-phenyl-2-propanol (2.18 g, 16.0 mmol) in CH$_2$Cl$_2$ (100 mL) is added Dess-Martin periodinane (50 mL, 15 wt % solution in methylene chloride) at 0° C. After stirring at 0° C. for 1 h, the mixture is warmed to RT and stirred for 1.5 h. To the reaction mixture is added saturated NaHCO$_3$ (200 mL) and stirred at RT for 20 min. The mixture is filtered through Celite and the organic phase is washed with water and brine then dried over MgSO$_4$. The solvent is removed under reduced pressure and the crude material is purified by flash chromatography to afford the title compound as a colorless oil: (M+1)$^+$=135.

B. (Z)-4-(3-Benzyloxy-4-nitrophenyl)-3-phenyl-but-3-en-2-one

To a mixture of 3-benzyloxy-4-nitrobenzaldehyde (83, step A) (1.16 g, 4.5 mmol) and 1-phenylpropane-2-one (0.726 g, 5.4 mmol) in toluene (50 mL) is added a catalytic amount of piperidine/glacial acetic acid and the mixture is refluxed for 3 h using a Dean-Stark apparatus. The mixture is cooled to room temperature and concentrated under reduced pressure. The crude material is purified by flash chromatography using a gradient of 15-50% EtOAc/hexane as eluent to give the title compound as an oil.

C. (Z)-4-(4-Amino-3-benzyloxyphenyl)-3-phenyl-but-3-en-2-one

A mixture of (Z)-4-(3-benzyloxy-4-nitrophenyl)-3-phenyl-but-3-en-2-one (760 mg, 2.03 mmol), 5% platinum on carbon (114 mg) in EtOAc (10 mL) is hydrogenated at 1 atm for 18 h. The mixture is filtered through Celite, washed with EtOAc and the filtrate is concentrated. The residue is purified by flash chromatography using methylene chloride/MeOH (100:1) as eluent to give the title compound as a yellow solid.

D. 5-[2-Hydroxy-4-(3-oxo-2-phenylbutyl)-phenyl]-1,1-dioxo-1,2,5-thiadiazolidin-3-one Starting with (Z)-4-(4-amino-3-benzyloxyphenyl)-3-phenyl-but-3-en-2-one, the 1,1-dioxo-1,2,5-thiadiazolidin-3-one ring is constructed analogous to Example 83, steps H-L to afford the title compound: (M−1)$^-$=373. HPLC retention time=1.13 min (Method A).

EXAMPLE 39

5-{2-Hydroxy-4-[2-(2H-pyrazol-3-yl)-ethyl]-phenyl}-1,1-dioxo-1,2,5-thiadiazolidin-3-one

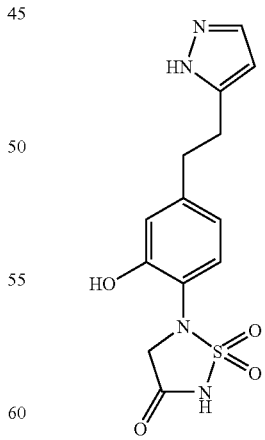

A. 1-Benzyloxymethyl-1H-pyrazole

To a solution of pyrazole (2.0 g, 29 mmol) in DMF (20 mL) is added potassium carbonate (12.4 g, 90 mmol) and benzyloxymethylchloride (4 mL, 32.3 mmol). The reaction is stirred for four days, then poured into water and extracted with EtOAc. The organic layer is washed with 1 N NaOH, dried over MgSO$_4$ and concentrated. The residue is purified by column chromatography using EtOAc as eluent to afford the title compound as a light yellow oil: (M+1)$^+$=189.

B. 2-Benzyloxymethyl-2H-pyrazole-3-carbaldehyde

A solution of 1-benzyloxymethyl-1H-pyrazole (4.6 g, 24 mmol) in THF (40 mL) is cooled to −78° C. n-Butyllithium (12 mL, 2.5 M in hexanes, 30 mmol) is added dropwise. After stirring at −78° C. for 30 min, DMF (1.0 mL) is added. The reaction mixture is warmed to RT over 1 h. The mixture is partitioned between aqueous NH$_4$Cl and EtOAc. The organic layer is concentrated to afford the title compound as a yellow oil, which is used directly in the next step: (M+1)$^+$=217.

C. 1-Benzyloxymethyl-5-vinyl-1H-pyrazole

A solution of methyltriphenylphosphoniumbromide (7.85 g, 22.0 mmol) in THF (40 mL) is cooled to 0° C. then MeLi (12.2 mL, 1.6 M in ether) is added dropwise. The mixture is stirred for 1 h then a solution of 2-benzyloxymethyl-2H-pyrazole-3-carbaldehyde (3.4 g, 15.7 mmol) in THF (15 mL) is added dropwise. The reaction is stirred for an hour at 0° C., then warmed to RT over 1 h. The mixture is partitioned between aqueous NH$_4$Cl and EtOAc and the organic layer is concentrated. Chromatography (10-15% EtOAc/hexane) affords the title compound as a yellow oil: (M+1)$^+$=215.

D. 5-{2-Benzyloxy-4-[(E)-2-(2-benzyloxymethyl-2H-pyrazol-3-yl)-vinyl]-phenyl}-1,1-dioxo-2-(2-trimethylsilanylethyl)-1,2,5-thiadiazolidin-3-one A mixture of 1-benzyloxymethyl-5-vinyl-1H-pyrazole (385 mg, 1.80 mmol), 5-(2-benzyloxy-4-iodophenyl)-1,1-dioxo-2-(2-trimethylsilanylethyl)-1,2,5-thiadiazolidin-3-one (500 mg, 0.90 mmol), Pd(OAc)$_2$ (13 mg, 0.06 mmol), P(o-tolyl)$_3$ (43 mg, 0.14 mmol) and triethylamine (0.21 mL, 1.5 mmol) in MeCN is heated at 110° C. for 30 min in a microwave apparatus. The reaction mixture is concentrated and chromatographed using a gradient of 15-30% EtOAc/hexanes to afford the title compound as a yellow oil: (M+1)$^+$=631.

E. 5-{2-Benzyloxy-4-[(E)-2-(2-benzyloxymethyl-2H-pyrazol-3-yl)-vinyl]-phenyl}-1,1-dioxo-1,2,5-thiadiazolidin-3-one A mixture of 5-{2-benzyloxy-4-[(E)-2-(2-benzyloxymethyl-2H-pyrazol-3-yl)-vinyl]-phenyl}-1,1-dioxo-2-(2-trimethylsilanylethyl)-1,2,5-thiadiazolidin-3-one (330 mg, 0.50 mmol)) and CsF (400 mg, 2.6 mmol) in DMF (5 mL) is heated at 60° C. for 18 h. The mixture is partitioned between aqueous NH$_4$Cl and EtOAc and the organic layer is concentrated to afford the title compound which is used directly in the next step: (M+1)$^+$=531.

F. 5-{2-Hydroxy-4-[2-(2H-pyrazol-3-yl)-ethyl]-phenyl}-1,1-dioxo-1,2,5-thiadiazolidin-3-one 5-{2-Benzyloxy-4-[(E)-2-(2-benzyloxymethyl-2H-pyrazol-3-yl)-vinyl]-phenyl} 1,1-dioxo-1,2,5-thiadiazolidin-3-one (240 mg, 0.40 mmol) is dissolved in methanol (5 mL). 10% Pd/C is added periodically (7×50 mg) at intervals over 4 days. The mixture is stirred under an atmosphere of hydrogen at balloon pressure. The catalyst is removed by filtering the mixture through Celite and the filtrate is concentrated. The residue is chromatographed (reverse phase, 0-25% EtOH/water) to afford the title compound as a grey solid: $^1$H NMR (CD$_3$OD) δ 7.46 (s, 1H), 7.31 (d, J=8.0 Hz, 1H), 6.75 (s, 1H), 6.71 (d, J=8.0 Hz, 1H) 6.10 (s, 1H) 4.29 (s, 2H), 2.89 (m, 4H); (M+1)$^+$=323.

EXAMPLE 40

5-{2-Hydroxy-4-[2-(1H-pyrazol-4-yl)-ethyl]-phenyl}-1,1-dioxo-1,2,5-thiadiazolidin-3-one

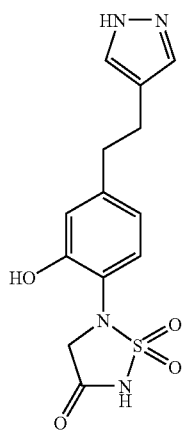

A. 4-Iodopyrazole-1-carboxylic Acid Benzyl Ester

CbzCl (95% grade, 2.9 mL, 20 mmol) is added to a solution of 4-iodo-1H-pyrazole (2.97 g, 15.3 mmol) and Et$_3$N (3.2 mL, 23 mmol) in toluene (30 mL) at 0° C. The mixture is stirred at 0° C. for 1 h and partitioned between EtOAc and aq. NaHCO$_3$. The organic layer is dried over MgSO$_4$, concentrated and chromatographed to afford the title compound as a white solid: $^1$H NMR (CDCl$_3$) δ 8.20 (s, 1H), 7.72 (s, 1H), 7.50-7.31 (m, 5H), 5.46 (s, 2H).

B. 4-Vinylpyrazole-1-carboxylic Acid Benzyl Ester

A mixture of 4-iodopyrazole-1-carboxylic acid benzyl ester (2.03 g, 6.20 mmol), Pd$_2$(dba)$_3$ (120 mg, 0.131 mmol), P(o-tolyl)$_3$ (283 mg, 0.929 mmol) and tributylvinyltin (2.71 mL, 9.28 mmol) in CH$_3$CN (15 ml) is heated at 80° C. for 3 h. The mixture is cooled to RT, stirred with aq. KF for 15 min and filtered through Celite. The filtrate is partitioned between EtOAc and brine. The organic layer is dried over MgSO$_4$, concentrated and chromatographed to afford the title compound as a light yellow solid: $^1$H NMR (CDCl$_3$) δ 8.06 (s, 1H), 7.84 (s, 1H), 7.50-7.32 (m, 5H), 6.51 (dd, J=16.0, 12.0 Hz, 1H), 5.60 (d, J=16.0 Hz, 1H), 5.46 (s, 2H), 5.26 (d, J=12.0 Hz, 1H).

C. 4-(2-{3-Benzyloxy-4-[1,1,4-trioxo-5-(2-trimethylsilanylethyl)-1,2,5-thiadiazolidin-2-yl]-phenyl}-vinyl)-pyrazole-1-carboxylic Acid Benzyl Ester The title compound is prepared from 4-vinylpyrazole-1-carboxylic acid benzyl ester and 5-(2-benzyloxy-4-iodophenyl)-1,1-dioxo-2-(2-trimethylsilanylethyl)-1,2,5-thiadiazolidin-3-one analogous to Example 39, step D. The deprotected pyrazole, 5-{2-benzyloxy-4-[2-(1H-pyrazol-4-yl)-vinyl]-phenyl}-1,1-dioxo-2-(2-trimethylsilanylethyl)-1,2,5-thiadiazolidin-3-one, is also isolated.

D. 5-{2-Hydroxy-4-[2-(1H-pyrazol-4-yl)-ethyl]-phenyl}-1,1-dioxo-1,2,5-thiadiazolidin-3-one The title compound is prepared from 4-(2-{3-benzyloxy-4-[1,1,4-trioxo-5-(2-trimethylsilanylethyl)-1,2,5-thiadiazolidin-2-yl]-phenyl}-vinyl)-pyrazole-1-carboxylic acid benzyl ester according to the general procedures outlined in Example 39, steps E and F: $^1$H NMR (CD$_3$OD) δ 7.36 (s, 2H), 7.31 (d, J=8.0 Hz, 1H), 6.74 (s, 1H), 6.69 (d, J=8.0 Hz, 1H), 4.31 (s, 2H), 2.79 (s, 4H); (M+1)$^+$=323, (M−1)$^-$=321.

EXAMPLE 41

5-{2-Hydroxy-4-[2-(1-methyl-1H-pyrazol-4-yl)-ethyl]-phenyl}-1,1-dioxo-1,2,5-thiadiazolidin-3-one

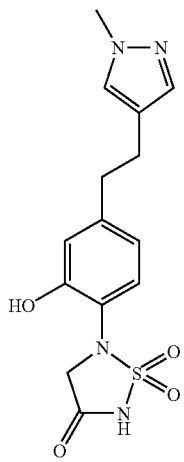

A. 5-{2-Benzyloxy-4-[2-(1-methyl-1H-pyrazol-4-yl)-vinyl]-phenyl}-1,1-dioxo-2-(2-trimethylsilanylethyl)-1,2,5-thiadiazolidin-3-one A mixture of 5-{2-benzyloxy-4-[2-(1H-pyrazol-4-yl)-vinyl]-phenyl}-1,1-dioxo-2-(2-trimethylsilanylethyl)-1,2,5-thiadiazolidin-3-one (example 40, step C) (114 mg, 0.224 mmol), MeI (0.05 mL, 0.80 mmol) and K$_2$CO$_3$ (60 mg, 0.43 mmol) in CH$_3$CN (3 mL) is stirred at RT for 2 days. The mixture is partitioned between EtOAc and aq. NaHCO$_3$. The organic phase is dried over MgSO$_4$ and concentrated to afford the crude product.

B. 5-{2-Hydroxy-4-[2-(1-methyl-1H-pyrazol-4-yl)-ethyl]-phenyl}-1,1-dioxo-1,2,5-thiadiazolidin-3-one The title compound is prepared from 5-{2-benzyloxy-4-[2-(1-methyl-1H-pyrazol-4-yl)-vinyl]-phenyl}-1,1-dioxo-2-(2-trimethylsilanylethyl)-1,2,5-thiadiazolidin-3-one analogous to Example 39, steps E and F: (M+1)$^+$=337, (M−1)$^-$=335; $^1$H NMR (DMSO-d$_6$) δ 7.46 (s, 1H), 7.23 (s, 1H), 7.23 (d, J=8.0 Hz, 1H), 6.76 (s, 1H), 6.70 (d, J=8.0 Hz, 1H), 6.39 (s, 2H), 3.75 (s, 3H), 2.72 (m, 2H), 2.68 (m, 2H).

EXAMPLE 42

5-[2-Hydroxy-4-(2-thiazol-5-yl-ethyl)-phenyl]-1,1-dioxo-1,2,5-thiadiazolidin-3-one

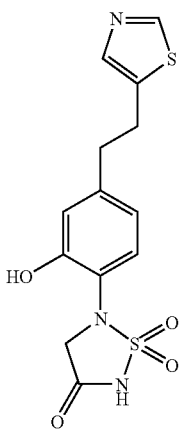

A. 5-Vinyl Thiazole

To a suspension of methyltriphenylphosphonium bromide (1.89 g, 5.30 mmol) in THF (20 mL) at 0° C. is added methyllithium (3.0M, 1.6M in ether) and the yellow mixture is stirred at 0° C. for 1 h. Thiazole-5-carbaldehyde (500 mg, 4.42 mmol), prepared by the procedure described by A. Dondoni, G. Fantin, M. Fogagnolo, A. Medici and P. Pedrini, *Synthesis*, 1987, 998-1001, in THF (5 mL) is added dropwise and the reaction mixture is stirred for 30 min. The mixture is quenched with water and extracted with ether. The organic layer is dried over MgSO$_4$ and concentrated. The residue is purified by column chromatography to afford the product as a light yellow oil: $^1$H NMR (CDCl$_3$) δ 5.31 (d, J=12 Hz, 1H), 6.57 (d, J=16 Hz, 1H), 6.84 (dd, J=12, 16 Hz, 1H), 7.76 (s, 1H), 8.65 (s, 1H).

B. 5-[2-Benzyloxy-4-(2-thiazol-5-yl-vinyl)-phenyl]-1,1-dioxo-2-(2-trimethylsilanylethyl)-1,2,5-thiadiazolidin-3-one A pressure vessel is charged with 5-(2-benzyloxy-4-iodophenyl)-1,1-dioxo-2-(2-trimethylsilanylethyl)-1,2,5-thiadiazolidin-3-one (828 mg, 1.52 mmol), 5-vinyl thiazole (186 mg, 1.68 mmol), triethylamine (0.32 mL, 2.28 mmol) and tri-o-tolylphosphine (37 mg, 0.12 mmol) in CH$_3$CN (1.5 mL). The vessel is degassed and palladium(II) acetate (6.80 mg, 0.03 mmol) is added. The vessel is sealed and heated at 80° C. for 20 h. The reaction mixture is concentrated and dissolved in EtOAc, washed with 1N HCl, dried over MgSO$_4$ and concentrated. The residue is purified by column chromatography to afford the title compound as a yellow solid; (M+H)$^+$=528.

C. 5-[2-Benzyloxy-4-(2-thiazol-5-yl-vinyl)-phenyl]-1,1-dioxo-1,2,5-thiadiazolidin-3-one The title compound is prepared analogous to Example 39, step E: (M+H)$^+$=428.

D. 5-[2-Hydroxy-4-(2-thiazol-5-yl-ethyl)-phenyl]-1,1-dioxo-1,2,5-thiadiazolidin-3-one The title compound is prepared analogous to Example 2, step D: $^1$H NMR (DMSO)__δ2.89 (t, J=8 Hz, 2H), 3.17 (t, J=8 Hz, 2H), 4.26 (s, 2H), 6.68 (d, J=8 Hz, 1H), 6.72 (s, 1H), 7.31 (d, J=8 Hz, 1H), 7.57 (s, 1H), 8.77 (s, 1H); $(M-1)^-=338$.

EXAMPLE 43

5-{4-[2-(2,4-Dimethyl-thiazol-5-yl)-ethyl]-2-hydroxyphenyl}-1,1-dioxo-1,2,5-thiadiazolidin-3-one

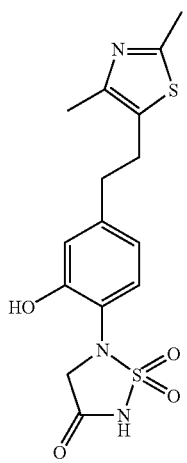

A. 2,4-Dimethyl-5-vinylthiazole

The title compound is prepared analogous to Example 42 step A, using 2,4-dimethyl-1,3-thiazole-5-carbaldehyde as the starting material.

B. 5-{2-Benzyloxy-4-[2-(2,4-dimethyl-thiazol-5-yl)-vinyl]-phenyl}-1,1-dioxo-2-(2-trimethylsilanyl-ethyl)-1,2,5-thiadiazolidin-3-one The title compound is prepared analogous to Example 42, step B, with the exception that microwave conditions (110° C. for 30 min) are used in place of conventional heating; $(M+1)^+=556$.

C. 5-{4-[2-(2,4-Dimethyl-thiazol-5-yl)-ethyl]-2-hydroxyphenyl}-1,1-dioxo-1,2,5-thiadiazolidin-3-one The title compound is prepared analogous to Example 42, steps C and D: $^1$H NMR (MeOD) δ 2.13 (s, 3H), 2.58 (s, 3H), 2.81 (t, J=8 Hz, 2H), 3.00 (t, J=8 Hz, 2H), 4.29 (s, 2H), 6.65 (d, J=8 Hz, 1H), 6.69 (s, 1H), 7.31 (d, J=8 Hz, 1H); $(M+1)^+=368$.

EXAMPLE 44

5-[2-Hydroxy-4-(2-[1,2,4]triazol-yl-ethyl)-phenyl]-1,1-dioxo-1,2,5-thiadiazolidin-3-one

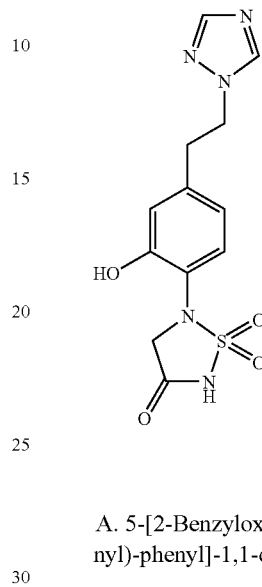

A. 5-[2-Benzyloxy-4-((E)-2-1,2,4-triazol-1-yl-vinyl)-phenyl]-1,1-dioxo-1,2,5-thiadiazolidin-3-one A mixture of 1-vinyl-1,2,4-triazole (0.100 g, 1.06 mmol), 5-(2-benzyloxy-4-iodophenyl)-1,1-dioxo-1,2,5-thiadiazolidin-3-one (0.236 g, 0.531 mmol), palladium acetate (0.024 g, 0.107 mmol), triethylamine (0.295 mL, 2.09 mmol) in acetonitrile is heated in a microwave apparatus at 110° C. for 30 min. The mixture is filtered over Celite, washed with acetonitrile, and concentrated. The residue is purified by column chromatography using a gradient of 10-60% EtOH/water as eluent to afford the title compound: $(M-1)^-=410$.

B. 5-[2-Hydroxy-4-(2-1,2,4-triazol-1-yl-ethyl)-phenyl]-1,1-dioxo-1,2,5-thiadiazolidin-3-one A solution of 5-[2-benzyloxy-4-((E)-1,2,4-triazol-1yl-ethyl)-phenyl]-1,1-dioxo-1,2,5-thiadiazolidin-3-one compound (0.120 g, 0.292 mmol) in EtOH and water is treated with 10% Pd/C (0.012 g) and stirred under an atmosphere of H$_2$ for 2.5 h. The mixture is filtered through Celite and washed with EtOH and concentrated. The resulting orange oil is dissolved in MeOH and EtOAc, and concentrated again to afford the title compound as a light yellow solid: $^1$H NMR (CD$_3$OD) δ 8.22 (s, 1H), 7.97 (s, 1H), 7.31 (d, J=8.0 Hz, 1H), 6.64 (d, J=1.77 Hz, 1H), 6.57 (dd, J=2.02, 8.08 Hz, 1H), 4.43 (t, J=7.07 Hz, 2H), 4.28 (s, 2H), 3.09 (t, J=7.07 Hz, 2H); $(M-1)^-=322$; HPLC retention time=0.84 min (method A)

EXAMPLES 45 TO 49

The following compounds are prepared using appropriate starting materials and general methods described in Examples 44 or 42.

| Example | Chemical Name | MS (m/z) | Retention time (min) Method |
|---|---|---|---|
| 45 | 5-[2-Hydroxy-4-(2-imidazol-1-yl-ethyl)-phenyl]-1,1-dioxo-1,2,5-thiadiazolidin-3-one | (M − 1)⁻ = 321 | 0.86 B |
| 46 | 5-{2-Hydroxy-4-[2-(2-methyl-thiazol-5-yl)-ethyl]-phenyl}-1,1-dioxo-1,2,5-thiadiazolidin-3-one | (M − 1)⁻ = 352 | 0.89 A |
| 47 | 5-{2-Hydroxy-4-[2-(2-propyl-thiazol-5-yl)-ethyl]-phenyl}-1,1-dioxo-1,2,5-thiadiazolidin-3-one | (M − 1)⁻ = 380 | 1.05 A |
| 48 | 5-(2-Hydroxy-4-{2-[4-methyl-2-(4-trifluoromethyl-phenyl)-thiazol-5-yl]-ethyl}-phenyl)-1,1-dioxo-1,2,5-thiadiazolidin-3-one | (M − 1)⁻ = 496 | 1.37 A |
| 49 | 5-{2-Hydroxy-4-[2-(2-methyl-4-trifluoromethyl-thiazol-5-yl)-ethyl]-phenyl}-1,1-dioxo-1,2,5-thiadiazolidin-3-one | (M − 1)⁻ = 420 | 1.16 A |

EXAMPLE 50

5-{4-[2-(1H-Benzoimidazol-2-yl)-ethyl]-2-hydroxyphenyl}-1,1-dioxo-1,2,5-thiadiazolidin-3-one

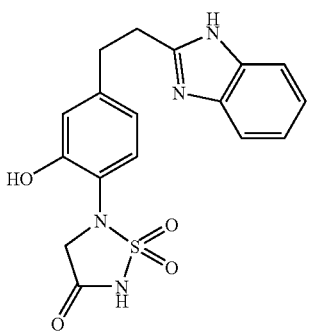

A. (E)-N-(2-Aminophenyl)-3-[3-benzyloxy-4-(1,1,4-trioxo-1,2,5-thiadiazolidin-2-yl)-phenyl]-acrylamide The title compound is prepared from (E)-3-[3-benzyloxy-4-(1,1,4-trioxo-1,2,5-thiadiazolidin-2-yl)-phenyl]-acrylic acid (Example 100, step B) and 1,2-diaminobenzene analogous to Example 131, step C.

B. 5-{4-[(E)-2-(1H-Benzoimidazol-2-yl)-vinyl]-2-benzyloxyphenyl}-1,1-dioxo-1,2,5-thiadiazolidin-3-one A solution of (E)-N-(2-aminophenyl)-3-[3-benzyloxy-4-(1,1,4-trioxo-1,2,5-thiadiazolidin-2-yl)-phenyl]-acrylamide in acetic acid is stirred at 60° C. for 18 h. The solvent is removed under reduced pressure to give the title compound.

C. 5-{4-[2-(1H-Benzoimidazol-2-yl)-ethyl]-2-hydroxyphenyl}-1,1-dioxo-1,2,5-thiadiazolidin-3-one The title compound is prepared from 5-{4-[(E)-2-(1H-benzoimidazol-2-yl)-vinyl]-2-benzyloxyphenyl}-1,1-dioxo-1,2,5-thiadiazolidin-3-one analogous to Example 57, step D: (M−1)⁻=371. HPLC retention time: 0.80 min. (Method A).

EXAMPLE 51

5-[2-Hydroxy-4-(3-phenylpropyl)-phenyl]-1,1-dioxo-1,2,5-thiadiazolidin-3-one

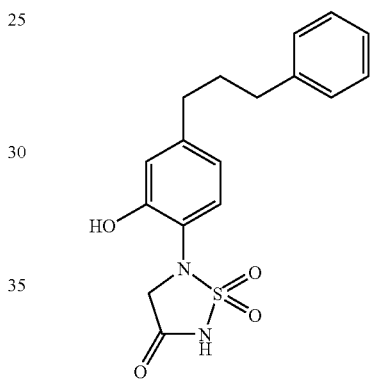

A. 5-[2-Benzyloxy-4-((E)-3-phenylpropenyl)-phenyl]-1,1-dioxo-2-(2-trimethylsilanylethyl)-1,2,5-thiadiazolidin-3-one To a solution of 5-(2-benzyloxy-4-iodophenyl)-1,1-dioxo-2-(2-trimethylsilanylethyl)-1,2,5-thiadiazolidin-3-one (100 mg, 0.184 mmol) in MeCN (5 mL) in a pressure vessel is added allylbenzene (22 mg, 0.184 mmol), Pd(OAc)₂ (3 mg) and triethylamine (186 mg, 1.84 mmol) and the mixture is heated at 100° C. for 10 h. The solvent is evaporated and the residue is purified by flash chromatography using a gradient of 10% to 40% EtOAc/hexane as eluent to give the title compound as a yellow foam.

B. 5-[2-Benzyloxy-4-((E)-3-phenylpropenyl)-phenyl]-1,1-dioxo-1,2,5-thiadiazolidin-3-one Tetrabutylammonium fluoride (1.0M in THF, 2 mL) is added to a solution of PS-isocyanate resin (0.5 g) in THF (2 mL) and the mixture is stirred at RT for 2 h. The resin is filtered off and the filtrate is added to a solution of 5-[2-benzyloxy-4-((E)-3-phenylpropenyl)-phenyl]-1,1-dioxo-2-(2-trimethylsilanylethyl)-1,2,5-thiadiazolidin-3-one (89 mg, 0.163 mmol) in THF (1 mL). The reaction is stirred at 75° C. for 1 h then the mixture is cooled and concentrated. The residue is partitioned between EtOAc and water and the organic layer is washed with 2N HCl (3×) and brine. The organic layer is dried over sodium sulfate and the solvent removed under reduced pressure to afford the title compound as a light yellow foam: (M−1)⁻=433.

C. 5-[2-Hydroxy-4-(3-phenylpropyl)-phenyl]-1,1-dioxo-1,2,5-thiadiazolidin-3-one A solution of 5-[2-benzyloxy-4-((E)-3-phenylpropenyl)-phenyl]-1,1-dioxo-1,2,5-thiadiazolidin-3-one (74 mg, 0.17 mmol) in 6 mL of EtOH/HOAc (4:2) is hydrogenated at 50 psi over 10% Pd/C (70 mg) for 18 h. The catalyst is filtered, the solvent is removed under reduced pressure and the residual oil purified by preparative HPLC to give the title compound as a solid: (M−1)⁻=345.

EXAMPLE 52

5-{4-[3-(3,4-Dimethoxyphenyl)-propyl]-2-hydroxyphenyl}-1,1-dioxo-1,2,5-thiadiazolidin-3-one

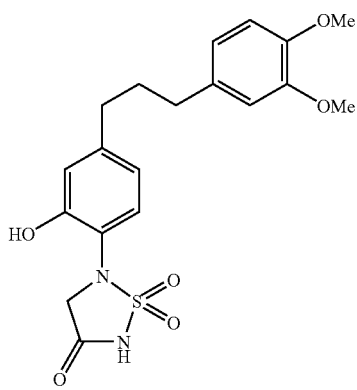

The title compound is prepared from 5-(2-benzyloxy-4-iodophenyl)-1,1-dioxo-2-(2-trimethylsilanylethyl)-1,2,5-thiadiazolidin-3-one and 4-allyl-1,2-dimethoxybenzene analogous to Example 51: (M−1)⁻=405.

EXAMPLE 53

5-[2-Hydroxy-4-(2-methyl-3-phenylpropyl)-phenyl]-1,1-dioxo-1,2,5-thiadiazolidin-3-one

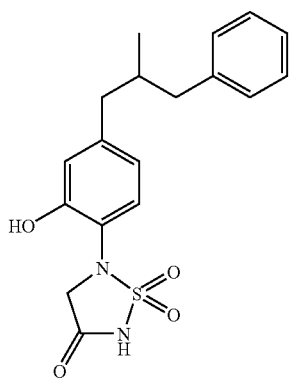

The title compound is prepared from 5-(2-benzyloxy-4-iodophenyl)-1,1-dioxo-2-(2-trimethylsilanylethyl)-1,2,5-thiadiazolidin-3-one and (2-methylallyl)-benzene analogous to Example 51: (M−1)⁻=359. HPLC retention time=1.65 min (Method A).

EXAMPLE 54

5-[2-Hydroxy-4-(3-hydroxy-3-phenylpropyl)-phenyl]-1,1-dioxo-1,2,5-thiadiazolidin-3-one

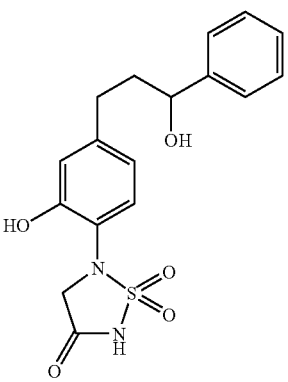

A. 5-[2-Benzyloxy-4-((E)-3-oxo-3-phenylpropenyl)-phenyl]-1,1-dioxo-2-(2-trimethylsilanylethyl)-1,2,5-thiadiazolidin-3-one 1-Phenylpropenone (58 mg, 0.44 mmol), 5-(2-benzyloxy-4-iodophenyl)-1,1-dioxo-2-(2-trimethylsilanylethyl)-1,2,5-thiadiazolidin-3-one (200 mg, 0.37 mmol), Pd(OAc)₂ (4 mg), triethylamine (372 mg, 0.367 mmol), and acetonitrile (3 mL) are placed in a microwave vial and heated at 120° C. for 15 min. The mixture is filtered over Celite and washed with acetonitrile. The filtrate is evaporated to give the title compound which is used directly in the next step.

B. 5-[2-Benzyloxy-4-((E)-3-oxo-3-phenylpropenyl)-phenyl]-1,1-dioxo-1,2,5-thiadiazolidin-3-one The title compound is prepared from 5-[2-benzyloxy-4-((E)-3-oxo-3-phenylpropenyl)-phenyl]-1,1-dioxo-2-(2-trimethylsilanylethyl)-1,2,5-thiadiazolidin-3-one analogous to Example 51, step B.

C. 5-[2-Hydroxy-4-(3-hydroxy-3-phenylpropyl)-phenyl]-1,1-dioxo-1,2,5-thiadiazolidin-3-one The title compound is prepared from 5-[2-benzyloxy-4-((E)-3-oxo-3-phenylpropenyl)-phenyl]-1,1-dioxo-1,2,5-thiadiazolidin-3-one analogous to Example 83, step L: (M−1)⁻=361; HPLC retention time=0.92 min. (Method A)

EXAMPLE 55

5-(2-Hydroxy-4-phenethyloxyphenyl)-1,1-dioxo-1,2,5-thiadiazolidin-3-one

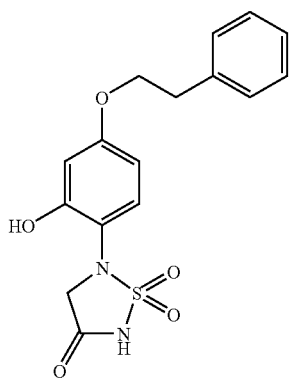

A. (3-Benzyloxy-4-nitrophenoxy)-tert-butyldimethylsilane

A solution of 3-benzyloxy-4-nitrophenol (EP application 095121) (6.3 g, 25.7 mmol), t-butyldimethychlorosilane (5.81 g, 38.6 mmol), imidazole (3.5 g, 51.4 mmol), and dimethylaminopyridine (2-3 mg) in DMF (20 mL) is stirred 18 h. The solution is poured into EtOAc and extracted once with water and five times with brine. The organic phase is dried, filtered, and concentrated to afford the title compound: $^1$H NMR (CDCl$_3$ δ 7.73 (d, J=9.1 Hz, 1H), 7.21 (m, 5H), 6.31 (d, J=2.5 Hz, 1H), 6.26 (dd, J=8.8, 2.5 Hz, 1H), 5.02 (s, 2H), 0.78 (s, 9H), 0.00 (s, 6H).

B. 2-Benzyloxy-4-(tert-butyldimethylsilanyloxy)-phenylamine

A solution of (3-benzyloxy-4-nitrophenoxy)-tert-butyldimethylsilane in EtOAc (50 mL) is hydrogenated over 5% Pt/C (630 mg) at 1 atm for 18 h. The catalyst is filtered off through Celite and the solvent removed under reduced pressure to afford the title compound as an oil: $^1$H NMR (CDCl$_3$δ7.26 (m, 5H), 6.48 (d, J=8.3 Hz, 1H), 6.29 (d, J=2.5 Hz, 1H), 6.19 (dd, J=8.3, 2.5 Hz, 1H), 4.93 (s, 2H), 0.83 (s, 9H), 0.00 (s, 6H); (M+1)$^+$=330.

C. [2-Benzyloxy-4-(tert-butyldimethylsilanyloxy)-phenylamino]-acetic Acid Tert-butyl Ester A mixture of 2-benzyloxy-4-(tert-butyldimethylsilanyloxy)-phenylamine, t-butyl bromoacetate (3.8 mL, 25.7 mmol), and potassium carbonate (7.1 g, 51.4 mmol) in DMF (20 mL) is heated at 60° C. for 18 h. Additional t-butyl bromoacetate (1 mL) is added and the mixture is stirred and heated for an additional 5 h. The mixture is poured into EtOAc and extracted once with water and four times with brine. The organic phase is dried over magnesium sulfate and the solvent removed under reduced pressure to furnish an oil consisting of product and desilylated product. A solution of this material, t-butyldimethychlorosilane (3.87 g, 25.7 mmol), imidazole (2.33 g, 34.2 mmol), and dimethylaminopyridine (3 mg) in DMF (15 mL) is stirred at RT for 18 h. This solution is poured into EtOAc and extracted with water (1×) and brine (5×). The organic phase is dried over magnesium sulfate and the solvent removed under reduced pressure to afford crude product, which is chromatographed on silica gel to afford the title compound: $^1$H NMR (CDCl$_3$δ 7.27 (m, 5H), 6.26 (m, 3H), 4.96 (s, 2H), 4.45 (br s, 1H), 3.91 (s, 2H), 1.35 (s, 9H), 0.84 (s, 9H), 0.00 (s, 6H); (M+1)$^+$=444.

D. N-{[2-Benzyloxy-4-(tert-butyldimethylsilanyloxy)phenyl]-N-[tert-butoxycarbonylsulfamoyl]} Acetic Acid Tert-butyl Ester To a solution of chlorosulfonyl isocyanate (3.8 g, 26.9 mmol) in CH$_2$Cl$_2$ (10 mL) at 0° C. is added dropwise a solution of t-butanol (2.0 g, 27 mmol) in CH$_2$Cl$_2$ (10 mL). The solution is stirred at RT for 15 min, then a solution of [2-benzyloxy-4-(tert-butyldimethylsilanyloxy)-phenylamino]-acetic acid tert-butyl ester (5.97 g, 18 mmol) and triethylamine (3.95 g, 30.6 mmol) in CH$_2$Cl$_2$ (10 mL) is added dropwise. The mixture is stirred at RT for 18 h, then washed with water. The organic phase is dried over Na$_2$SO$_4$ and the solvent is removed under reduced pressure. The residual oil is purified by flash chromatography using hexane/EtOAc (8:2) as eluent to give the title compound as an oil: $^1$H NMR (CDCl$_3$δ7.99 (m, 6H), 6.80 (m, 2H), 5.03 (s, 2H), 4.29 (br s, 2H), 1.33 (s, 18H), 0.82 (s, 9H), 0.00 (s, 6H); (M-1)$^-$=621.

E. N-{[2-Benzyloxy-4-(tert-butyldimethylsilanyloxy)phenyl]-[N'-tert-butoxycarbonyl-N'-trimethylsilylethyl]sulfamoyl} Acetic Acid Tert-butyl Ester To a solution of 2-trimethylsilylethanol (6.25 g, 5.28 mmol) and triphenylphosphine (5.54 g, 21.1 mmol) in THF (20 mL), is added dropwise N-{[2-benzyloxy-4-(tert-butyldimethylsilanyloxy)phenyl]-N-[tert-butoxycarbonylsulfamoyl]} acetic acid tert-butyl ester (3.29 g, 5.28 mmol) and DIAD (1.07 g, 5.28 mmol) in THF (15 mL) and the mixture is stirred at RT for 18 h. Additional 2-trimethylsilylethanol (3 eq) and DIAD are added to drive the reaction to completion. The solvent is removed under reduced pressure and the residue chromatographed on silica gel using hexane/EtOAc (9:1) as eluent to afford the title compound as an oil: $^1$H NMR (CDCl$_3$δ 7.61 (d, J=8.8 Hz, 1H), 7.43 (m, 5H), 6.48 (dd, J=8.8, 2.5 Hz, 1H), 6.89 (d, J=2.5 Hz, 1H), 5.19 (s, 2H), 4.66 (br s, 2H), 3.57 (m, 2H), 1.54 (s, 9H), 1.51 (s, 9H), 0.99 (s, 9H), 0.15 (s, 6H).

F. N-{[2-Benzyloxy-4-(tert-butyldimethylsilanyloxy)phenyl]-N'-(2-trimethylsilylethylsulfamoyl)} Acetic Acid A solution of N-{[2-benzyloxy-4-(tert-butyldimethylsilanyloxy)phenyl]-[N'-tert-butoxycarbonyl-N'-trimethylsilylethyl]sulfamoyl} acetic acid tert-butyl ester (3.29 g, 4.55 mmol) in 50 mL of TFA/CH$_2$Cl$_2$ (1:1) is stirred at RT for 30 min. The solution is concentrated, then four times redissolved in CH$_2$Cl$_2$ and reconcentrated. This material is stirred 18 h with t-butyldimethylsilyl chloride (1.03 g, 6.83 mmol), imidazole (620 mg, 9.10 mmol), and dimethylaminopyridine (2 mg) in DMF (5 mL). The solution is poured into EtOAc and extracted once with water, five times with brine, and twice with 1N HCl to afford the title compound: (M-1)$^-$=565.

G. 5-[2-Benzyloxy-4-(tert-butyl-dimethylsilanyloxy)-phenyl]-1,1-dioxo-2-(2-trimethylsilanylethyl)-1,2,5-thiadiazolidin-3-one A solution of N-{[2-benzyloxy-4-(tert-butyldimethylsilanyloxy)phenyl]-N'-(2-trimethylsilylethylsulfamoyl)} acetic acid (2.63 g, 4.64 mmol) and carbonyldiimidazole (941 mg, 5.80 mmol) in THF (20 mL) is stirred at RT for 18 h. The solvent is removed under reduced pressure and the residue chromatographed on an Isco Companion 40 g column using a gradient of 85:15 to 50:50 hexane/EtOAc to afford the title compound: $^1$H NMR (CDCl$_3$δ7.31 (m, 5H), 7.23 (d, J=8.6 Hz, 1H), 6.42 (d, J=2.5 Hz, 1H), 6.37 (dd, J=8.3, 2.5 Hz, 1H), 5.00 (s, 2H), 4.26 (s, 2H), 3.53 (m, 2H), 1.01 (m, 2H), 0.90 (s, 9H), 0.10 (s, 6H).

H. 5-(2-Benzyloxy-4-hydroxyphenyl)-1,1-dioxo-2-(2-trimethylsilanylethyl)-1,2,5-thiadiazolidin-3-one To a solution of 5-[2-benzyloxy-4-(tert-butyldimethylsilanyloxy)phenyl]-1,1-dioxo-2-(2-trimethylsilanylethyl)-1,2,5-thiadiazolidin-3-one (100 mg, 0.18 mmol) in THF (4.5 mL) is added 0.5 mL of 4N HCl in dioxane and the mixture is stirred at RT for 5 days. The solution is concentrated, dissolved in EtOAc and the aqueous phase separated. The organic phase is dried over magnesium sulfate and the solvent removed under reduced pressure to afford the title compound: $^1$H NMR (CDCl$_3$δ7.29 (m, 5H), 7.16 (d, J=8.3 Hz, 1H), 6.42 (d, J=2.5 Hz, 1H), 6.27 (dd, J=8.3, 2.5 Hz, 1H), 4.92 (s, 2H), 4.24 (s, 2H), 3.52 (m, 2H), 0.99 (m. 2H), 0.00 (s, 9H): (M+1)$^+$=435.

I. 5-(2-Benzyloxy-4-phenethyloxyphenyl)-1,1-dioxo-2-(2-trimethylsilanylethyl)-1,2,5-thiadiazolidin-3-one A solution of 5-(2-benzyloxy-4-hydroxyphenyl)-1,1-dioxo-2-(2-trimethylsilanylethyl)-1,2,5-thiadiazolidin-3-one (90 mg, 0.21 mmol), phenethyl alcohol (37.9 mg, 0.31 mmol), DIAD (0.0612 mL, 0.31 mmol), and triphenylphosphine (81.5 mg, 0.31 mmol) in (THF 5 mL) is stirred at RT for 18 h. The solvent is removed under reduced pressure and the residue chromatographed on a Biotage 40S column using a gradient of 80:20 to 60:40 hexane/EtOAc as eluent to afford the title compound: $^1$H NMR (CDCl$_3$δ7.30 (m, 11H), 6.62 (d, J=2.8 Hz, 1H), 6.43 (dd, J=8.6, 2.8 Hz, 1H), 5.00 (s, 2H), 4.25 (s, 2H), 4.11 (t, J=7.1 Hz, 2H), 3.51 (m, 2H), 3.03 (t, J=7.1 Hz, 2H), 0.99 (m, 2H), 0.00 (s, 9H).

J. 5-(2-Benzyloxy-4-phenethyloxyphenyl)-1,1-dioxo-1,2,5-thiadiazolidin-3-one

A solution of 5-(2-benzyloxy-4-phenethyloxyphenyl)-1,1-dioxo-2-(2-trimethylsilanylethyl)-1,2,5-thiadiazolidin-3-one (47 mg, 0.087 mmol) and tetrabutylammonium fluoride (0.5M in THF, 0.35 mL, 0.175 mmol) in THF (5 mL) is refluxed for 1 h. The mixture is cooled to RT, concentrated, and extracted with EtOAc. The organic phase is washed with 1N HCl and is dried over magnesium sulfate. The solvent is removed under reduced pressure to afford the title compound: (M–1)$^-$=437.

K. S-(2-Hydroxy-4-phenethyloxyphenyl)-1,1-dioxo-1,2,5-thiadiazolidin-3-one

To a solution of 5-(2-benzyloxy-4-phenethyloxyphenyl)-1,1-dioxo-1,2,5-thiadiazolidin-3-one (37.5 mg, 0.085 mmol) in EtOH (1 mL) is added 0.5236M potassium bicarbonate (0.163 mL, 0.085 mmol) and the mixture is stirred at RT for 10 min. This mixture is diluted with 4 mL of water and 10% palladium on carbon (19 mg) is added. The mixture is hydrogenated at 1 atm for 18 h. The resulting mixture is filtered first through Celite, then through a filter disk. The filtrate is lyophilized and purified by preparative HPLC. The product is lyophilized to afford the title compound as a solid: mp=65-70° C.: $^1$H NMR (DMSO-d$_6$δ7.81 (m, 4H), 7.23 (m, 1H), 7.21 (d, J=8.6 Hz, 1H), 6.46 (d, J=2.5 Hz, 1H), 6.42 (dd, J=8.6, 2.8 Hz, 1H), 4.33 (s, 2H), 4.14 (t, J=6.8 Hz, 2H), 3.01 (t, J=6.8 Hz, 2H); (M–1)$^-$=347.

EXAMPLE 56

5-[2-Hydroxy-4-(4-phenylbutyl)-phenyl]-1,1-dioxo-1,2,5-thiadiazolidin-3-one

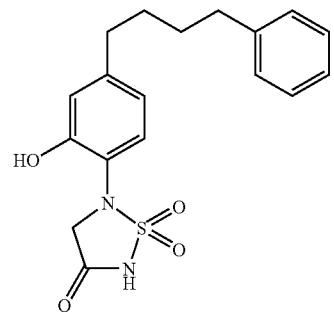

The title compound is prepared from 5-(2-benzyloxy-4-iodophenyl)-1,1-dioxo-2-(2-trimethylsilanylethyl)-1,2,5-thiadiazolidin-3-one and but-3-enyl-benzene analogous to Example 51: (M–1)$^-$=359.

EXAMPLE 57

{3-[3-Hydroxy-4-(1,1,4-trioxo-1,2,5-thiadiazolidin-2-yl)-phenyl]-propyl}-carbamic Acid Tert-butyl Ester

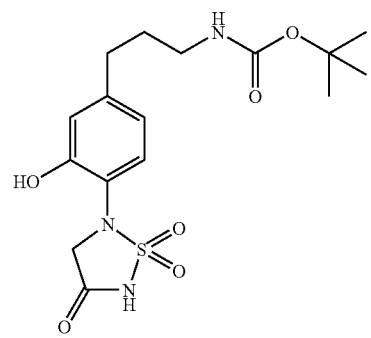

A. (3-Iodopropyl)-carbamic Acid Tert-butyl Ester

To a solution of triphenylphosphine (28.5 g, 108.6 mmol) and imidazole (7.39 g, 108.6 mmol) in CH$_2$Cl$_2$ (400 mL) at RT, is added iodine (28.92 g, 113.95 mmol) portionwise. To this solution is added a solution of (3-hydroxypropyl)-carbamic acid tert-butyl ester (18.66 g, 106.49 mmol) (Synthesis 1990, 366) in CH$_2$Cl$_2$ (75 mL) dropwise and the mixture allowed to stir at RT for 14 h. The mixture is then filtered and the filtrate concentrated to a crude red oil, which is partitioned between ether and sat. sodium thiosulfate. The aqueous phase is extracted with ether. The combined organic layers are

83 reduced to 200 mL and then filtered through a plug of silica, eluting with ether. Evaporation of solvent affords the title compound.

B. (3-{3-Benzyloxy-4-[1,1,4-trioxo-5-(2-trimethylsilanylethyl)-1,2,5-thiadiazolidin-2-yl]-phenyl}-propyl)-carbamic Acid Tert-butyl Ester Zinc dust (3.6 g, 55 mmol) is placed in a flask and heated under vacuum to remove traces of water. DMF (30 mL) is then added under nitrogen atmosphere. Dibromoethane (cat. 0.5 mL) is added and the mixture heated until effervescence occurs. The reaction is allowed to cool to RT over 30 min and chlorotrimethylsilane (cat 0.5 mL) is added, followed after 30 min with (3-iodopropyl)-carbamic acid tert-butyl ester (4.0 g, 14 mmol) dissolved in 10 mL of DMF. After 30 min, TLC indicates the iodide has been consumed and $Pd_2(dba)_3$ (0.6 g) and tri-o-tolylphosphine (0.5 g) are added, followed by the dropwise addition of 5-(2-benzyloxy-4-iodophenyl)-1,1-dioxo-2-(2-trimethylsilanylethyl)-1,2,5-thiadiazolidin-3-one (5 g, 9.2 mmol) dissolved in 25 mL of DMF. The reaction mixture is stirred for 14 h and then diluted with EtOAc and filtered through Celite. The filtrate is washed with 1M HCl, brine and water, dried over $MgSO_4$, filtered through a short plug of silica and concentrated to afford the title compound as a light yellow oil.

C. {3-[3-Benzyloxy-4-(1,1,4-trioxo-1,2,5-thiadiazolidin-2-yl)-phenyl]-propyl}-carbamic Acid Tert-butyl Ester To a solution of (2-{3-benzyloxy-4-[1,1,4-trioxo-5-(2-trimethylsilanylethyl)-1,2,5-thiadiazolidin-2-yl]-phenyl}-ethyl)-carbamic acid tert-butyl ester (0.35 g, 0.609 mmol) in 5 mL THF is added 1.0 mL of a 1.0M solution of TBAF in THF. The mixture is stirred at 50° C. for 2 h then is allowed to cool to RT. The solvent is removed under reduced pressure and aqueous $KHCO_3$ (10 mL of an 0.3M solution) is added. The aqueous phase is decanted from the insoluble material which coats the flask. The material is washed with water (2×) and MTBE (2×) then EtOAc and 1N HCl is added. The organic phase is separated, washed with brine and dried over magnesium sulfate. The solvent is removed under reduced pressure to give the title compound as a brown oil.

D. {3-[3-Hydroxy-4-(1,1,4-trioxo-1,2,5-thiadiazolidin-2-yl)-phenyl]-propyl}-carbamic Acid Tert-butyl Ester Potassium Salt To a mixture of {3-[3-benzyloxy-4-(1,1,4-trioxo-1,2,5-thiadiazolidin-2-yl)-phenyl]-propyl}-carbamic acid tert-butyl ester (0.27 g, 0.568 mmol) in 5 mL ethanol/water (1:3) is added 0.75 mL of a 0.75M aqueous $KHCO_3$ solution. The resulting solution is hydrogenated at 1 atm over 0.2 g of 10% Pd/C for 24 h. The catalyst is filtered through Celite and the filtrate is washed with ether. The aqueous phase is lyophilized to give the title compound as a white powder. $^1$H NMR (400 MHz, DMSO-D6) δ ppm 1.35-1.39 (m, 9 H) 1.57-1.67 (m, J=7.39, 7.39, 7.39, 7.39 Hz, 2 H) 2.39-2.47 (m, 2 H) 2.92 (q, J=6.65 Hz, 2 H) 4.02 (s, 2 H) 6.51 (d, J=8.08 Hz, 1 H) 6.61 (s, 1 H) 6.80 (s, 1 H) 7.22 (d, J=7.83 Hz, 1 H)

84

EXAMPLE 58

5-[4-(3-Aminopropyl)-2-hydroxyphenyl]-1,1-dioxo-1,2,5-thiadiazolidin-3-one

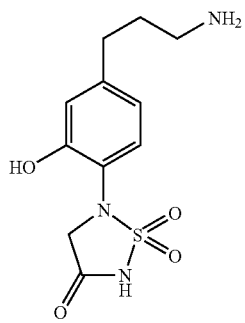

To HCl/dioxane (5 mL, 4.0 M) is added {3-[3-hydroxy-4-(1,1,4-trioxo-1,2,5-thiadiazolidin-2-yl)-phenyl]-propyl}-carbamic acid tert-butyl ester potassium salt (0.7 g, 1.65 mmol) and the mixture is stirred at RT for 4 h. The solvent is removed under reduced pressure and water is added. The solution is washed with ether and the aqueous phase lyophilized to give the hydrochloride salt of the title compound as a yellow powder: (M−1)⁻=284. $^1$H NMR (400 MHz, DMSO-D6) δ ppm 1.77-1.88 (m, 2 H) 2.58 (t, J=7.71 Hz, 2 H) 2.72-2.81 (m, 2 H) 4.40 (s, 2 H) 6.68 (d, J=8.34 Hz, 1 H) 6.81 (s, 1 H) 7.26 (d, J=8.08 Hz, 1 H)

EXAMPLE 59

{2-[3-Hydroxy-4-(1,1,4-trioxo-1,2,5-thiadiazolidin-2-yl)-phenyl]-ethyl}-carbamic Acid Tert-butyl Ester

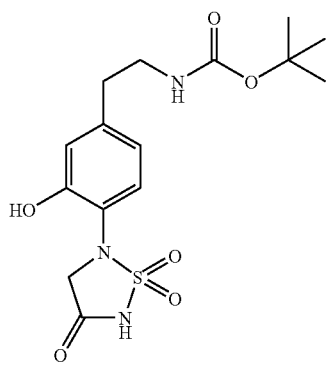

A. (2-Iodoethyl)-carbamic Acid Tert-butyl Ester

To a solution of triphenylphosphine (40 g, 153 mmol) and imidazole (10.4 g, 153 mmol) in $CH_2Cl_2$ (375 mL) at RT, is added iodine (40.8 g, 160.6 mmol) portionwise. To this solution is added (2-hydroxyethyl)-carbamic acid tert-butyl ester (24.2 g, 150 mmol) in $CH_2Cl_2$ (75 mL) dropwise and the mixture allowed to stir at RT for 14 h. The mixture is then filtered and the filtrate concentrated to a crude red oil, which is partitioned between ether and sat. sodium thiosulfate. The aqueous phase is extracted with ether. The combined organic layers are reduced to 500 mL and then filtered through a plug of silica, eluting with hexane. Evaporation of solvent affords the title compound.

B. (2-{3-Benzyloxy-4-[1,1,4-trioxo-5-(2-trimethylsilanylethyl)-1,2,5-thiadiazolidin-2-yl]-phenyl}-ethyl)-carbamic Acid Tert-butyl Ester Zinc dust (3 g, 46 mmol) is placed in a flask and heated under vacuum to remove traces of water. DMF (25 mL) is then added under nitrogen atmosphere. Dibromoethane (cat. 0.25 mL) is added and the mixture heated until effervescence occurs. The reaction is allowed to cool to RT over 30 min and chlorotrimethylsilane (cat 0.3 mL) is added, followed after 30 min with (2-iodoethyl)-carbamic acid tert-butyl ester (4.5 g, 16.5 mmol) dissolved in 10 mL of DMF. After 30 min, TLC indicates the iodide has been consumed and $Pd_2(dba)_3$ (0.20 g) and tri-o-tolylphosphine (0.30 g) are added, followed by the dropwise addition of 5-(2-benzyloxy-4-iodophenyl)-1,1-dioxo-2-(2-trimethylsilanylethyl)-1,2,5-thiadiazolidin-3-one (5 g, 9.2 mmol) dissolved in 25 mL of DMF. The reaction mixture is stirred for 14 h and then diluted with EtOAc and filtered through Celite. The filtrate is washed with 1M HCl, brine and water, dried over $MgSO_4$, filtered through a short plug of silica and concentrated to afford the title compound as a light yellow oil.

{2-[3-Hydroxy-4-(1,1,4-trioxo-1,2,5-thiadiazolidin-2-yl)-phenyl]-ethyl}-carbamic Acid Tert-butyl Ester The title compound is prepared from (2-{3-benzyloxy-4-[1,1,4-trioxo-5-(2-trimethylsilanylethyl)-1,2,5-thiadiazolidin-2-yl]-phenyl}-ethyl)-carbamic acid tert-butyl ester analogous to Example 57, steps C and D.

EXAMPLE 60

{(S)-1-Benzyl-2-[3-hydroxy-4-(1,1,4-trioxo-1,2,5-thiadiazolidin-2-yl)-phenyl]-ethyl}-carbamic Acid Tert-butyl Ester

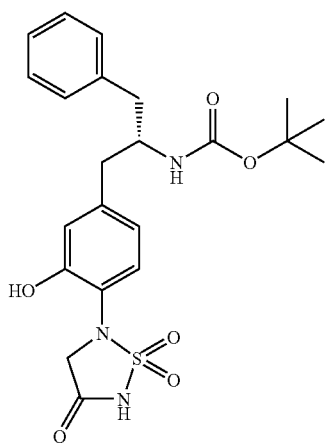

The title compound is prepared from Boc-(S)-2-amino-3-phenylpropan-1-ol [J. Org. Chem. 65, 5037 (2000)] using the steps described for Example 57.

EXAMPLE 61

{3-[3-Hydroxy-4-(1,1,4-trioxo-1,2,5-thiadiazolidin-2-yl)-phenyl]-1,1-dimethylpropyl}-carbamic Acid Tert-butyl Ester

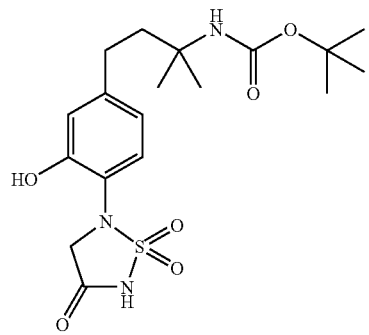

A. [1-(Methoxymethyl-carbamoyl)-1-methyl-ethyl]-carbamic Acid Tert-butyl Ester To a solution of 2-tert-butoxycarbonylamino-2-methyl-propionic acid (8.0 g, 39 mmol) and N,O-dimethylhydroxylamine hydrochloride (4.6 g, 47 mmol) in methylene chloride (80 mL) is added N-methylmorpholine (5.2 mL, 47 mmol), HOBT (6.4 g, 47 mmol) and EDCl (9.1 g, 47 mmol). The mixture is stirred at RT for 18 h then is washed sequentially with 10% citric acid (2×), sat. $NaHCO_3$ (2×) and brine. The organic solution is dried over magnesium sulfate and the solvent removed under reduced pressure. The resulting oil is purified by flash chromatography to give the title compound.

B. (1,1-Dimethyl-2-oxo-ethyl)-carbamic Acid Tert-butyl Ester

To a solution of [1-(methoxymethyl-carbamoyl)-1-methyl-ethyl]-carbamic acid tert-butyl ester (1.6 g, 7 mmol) in ether (30 mL) at −78° C. is added lithium aluminum hydride (9.8 mL of 1.0M in ether) dropwise. The mixture is warmed to 0° C. and stirred for 40 min. Aqueous $KHSO_4$ (20 mL of 0.5M solution) is added and the mixture is extracted with ether. The organic solution is washed sequentially with 10% citric acid (2×), 5% $NaHCO_3$ (2×) and brine. The solution is dried over magnesium sulfate and the solvent is removed under reduced pressure to afford the title compound.

C. (1,1-Dimethylallyl)-carbamic Acid Tert-butyl Ester

To a suspension of methyl triphenylphosphonium bromide (1.9 g, 5 mmol) in THF (25 mL) at −78° C. is added dropwise KHMDS (5 mmol, 11 mL of 0.5M solution). The mixture is stirred at 0° C. for 30 min then is recooled to −78° C. To this is added dropwise a solution of (1,1-dimethyl-2-oxo-ethyl)-carbamic acid tert-butyl ester (1.0 g, 5 mmol) in THF (5 mL). The mixture is stirred at −78° C. for 10 min then is allowed to warm to RT overnight. Water is added and the mixture is extracted with EtOAc. The organic phase is dried over magnesium sulfate and the solvent removed under reduced pressure. The resulting oil is purified by flash chromatography to give the title compound.

D. ((E)-3-{3-Benzyloxy-4-[1,1,4-trioxo-5-(2-trimethylsilanylethyl)-1,2,5-thiadiazolidin-2-yl]-phenyl}-1,1-dimethylallyl)-carbamic Acid Tert-butyl Ester To a solution of 5-(2-benzyloxy-4-iodophenyl)-1,1-dioxo-2-(2-trimethylsilanylethyl)-1,2,5-thiadiazolidin-3-one (1.4 g, 3 mmol) in DMF (20 mL) is added (1,1-dimethylallyl)-carbamic acid tert-butyl ester (560 mg, 3 mmol), triethylamine (0.7 mL, 5 mmol) and tert-di(mu-acetato) bis[o-(di-o-tolylphosphino)benzyl]dipalladium (II) (25 mg). The mixture is stirred at 80° C. for 18 h. The solvent is removed under reduced pressure and the residue is purified by flash chromatography to give the title compound

E. {(E)-3-[3-Benzyloxy-4-(1,1,4-trioxo-1,2,5-thiadiazolidin-2-yl)-phenyl]-1,1-dimethylallyl}-carbamic Acid Tert-butyl Ester To a solution of ((E)-3-{3-benzyloxy-4-[1,1,4-trioxo-5-(2-trimethylsilanylethyl)-1,2,5-thiadiazolidin-2-yl]-phenyl}-1,1-dimethylallyl)-carbamic acid tert-butyl ester (150 mg, 0.2 mmol) in DMF (3 mL) is added CsF (83 mg, 0.53 mmol) and the mixture is stirred at 60° C. for 3 h. The solvent is removed under reduced pressure and the residue is purified by flash chromatography using 10-20% MeOH/EtOAc as eluent to give the title compound as a solid.

F. {3-[3-Hydroxy-4-(1,1,4-trioxo-1,2,5-thiadiazolidin-2-yl)-phenyl]-1,1-dimethylpropyl}-carbamic Acid Tert-butyl Ester A solution of {(E)-3-[3-benzyloxy-4-(1,1,4-trioxo-1,2,5-thiadiazolidin-2-yl)-phenyl]-1,1-dimethylallyl}-carbamic acid tert-butyl ester (105 mg, 0.2 mmol) in ethanol (5 mL) is hydrogenated over 10% Pd/C at 1 atm for 18 h. The catalyst is removed by filtration through Celite and the solvent is removed under reduced pressure to give the title compound. It is converted to a potassium salt by addition of 1 equivalent of $KHCO_3$. 1H NMR (400 MHz, MeOD) δ ppm 1.17 (s, 6 H) 1.34 (s, 9 H) 1.77-1.87 (m, 2 H) 2.35-2.44 (m, 2 H) 4.20 (s, 2 H) 6.59 (dd, J=8.08, 1.77 Hz, 1 H) 6.65 (d, J=1.77 Hz, 1 H) 7.20 (d, J=8.08 Hz, 1 H) LCMS (method A) retention time=1.32 min, $(M-H)^-=142$

EXAMPLE 62

2-{2-[3-Hydroxy-4-(1,1,4-trioxo-1,2,5-thiadiazolidin-2-yl)-phenyl]-ethyl}-piperidine-1-carboxylic Acid Tert-butyl Ester

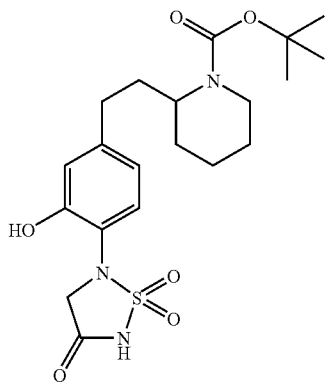

A. 2-Vinylpiperidine-1-carboxylic Acid Tert-butyl Ester

The title compound is prepared from 2-formylpiperidine-1-carboxylic acid tert-butyl ester and methyl triphenylphosphonium bromide analogous to Example 61, step C.

B. 2-((E)-2-{3-Benzyloxy-4-[1,1,4-trioxo-5-(2-trimethylsilanylethyl)-1,2,5-thiadiazolidin-2-yl]-phenyl}-vinyl)-piperidine-1-carboxylic Acid Tert-butyl Ester To a solution of 5-(2-benzyloxy-4-iodophenyl)-1,1-dioxo-2-(2-trimethylsilanylethyl)-1,2,5-thiadiazolidin-3-one (120 mg, 0.22 mmol) in MeCN (2 mL) is added 2-vinylpiperidine-1-carboxylic acid tert-butyl ester (51 mg, 0.242 mmol), triethylamine (33 mg, 0.33 mmol), 2,2'-bis(di-t-butylphosphino)biphenyl (2.6 mg) and $Pd(OAc)_2$ (1.0 mg). The vessel is flushed with nitrogen and the mixture is stirred at 100° C. for 4 h. The mixture is partitioned between EtOAc/water and the organic phase is washed with water, brine and dried over sodium sulfate. The solvent is removed under reduced pressure and the residue is purified by flash chromatography using a gradient of EtOAc/hexane (5 to 25%) as eluent to give the title compound.

C. 2-{2-[3-Benzyloxy-4-(1,1,4-trioxo-1,2,5-thiadiazolidin-2-yl)-phenyl]-ethyl}-piperidine-1-carboxylic Acid Tert-butyl Ester The title compound is prepared from 2-((E)-2-{3-benzyloxy-4-[1,1,4-trioxo-5-(2-trimethylsilanylethyl)-1,2,5-thiadiazolidin-2-yl]-phenyl}-vinyl)-piperidine-1-carboxylic acid tert-butyl ester analogous to Example 67, step C.

D. 2-{2-[3-Hydroxy-4-(1,1,4-trioxo-1,2,5-thiadiazolidin-2-yl)-phenyl]-ethyl}-piperidine-1-carboxylic Acid Tert-butyl Ester A solution of 2-{2-[3-benzyloxy-4-(1,1,4-trioxo-1,2,5-thiadiazolidin-2-yl)-phenyl]-ethyl}-piperidine-1-carboxylic acid tert-butyl ester in 2 mL of ethanol/water (1:1) is hydrogenated over 10% Pd/C at 1 atm for 2 h. The catalyst is removed by filtration through Celite and the solvent is removed under reduced pressure to give the title compound: LC rt 1.52 (method A); $(M-1)^-=438$.

EXAMPLE 63

2-{2-[3-Hydroxy-4-(1,1,4-trioxo-1,2,5-thiadiazolidin-2-yl)-phenyl]-ethyl}-azepane-1-carboxylic Acid Tert-butyl Ester

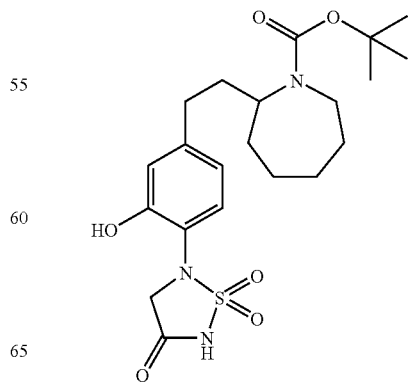

The title compound is prepared using azepane-1,2-dicarboxylic acid 1-tert-butyl ester analogous to the procedure described for the synthesis of Example 61.

EXAMPLE 64

3-[3-Hydroxy-4-(1,1,4-trioxo-1,2,5-thiadiazolidin-2-yl)-benzyl]-piperidine-1-carboxylic Acid Tert-butyl Ester

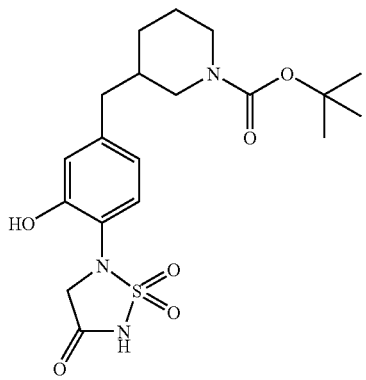

A. 3-Iodomethylpiperidine-1-carboxylic Acid Tert-butyl Ester

To a solution of NaI (0.593 g, 3.95 mmol) in acetone (20 mL) is added 3-bromomethylpiperidine-1-carboxylic acid tert-butyl ester (1.0 g, 3.59 mmol) and the mixture is heated at 80° C. for 2 h. The solvent is decanted from any insoluble material and is removed under reduced pressure. The residue is filtered through a pad of silica gel using MTBE as eluent to give the title compound as an oil.

B. 3-{3-Benzyloxy-4-[1,1,4-trioxo-5-(2-trimethylsilanylethyl)-1,2,5-thiadiazolidin-2-yl]-benzyl}-piperidine-1-carboxylic Acid Tert-butyl Ester The title compound is prepared from 3-iodomethylpiperidine-1-carboxylic acid tert-butyl ester and 5-(2-benzyloxy-4-iodophenyl)-1,1-dioxo-2-(2-trimethylsilanylethyl)-1,2,5-thiadiazolidin-3-one analogous to the method used in Example 57, step B.

C. 3-[3-Benzyloxy-4-(1,1,4-trioxo-1,2,5-thiadiazolidin-2-yl)-benzyl]-piperidine-1-carboxylic Acid Tert-butyl Ester The TMS-ethyl group is removed analogous to the method described for Example 57, step C to give the title compound.

D. 3-[3-Hydroxy-4-(1,1,4-trioxo-1,2,5-thiadiazolidin-2-yl)-benzyl]-piperidine-1-carboxylic Acid Tert-butyl Ester The benzyl protecting group is removed analogous to the method for Example 57, step D to give the title compound: (M−1)⁻=424. $^1$H NMR (400 MHz, DMSO-d$_6$) δ ppm 1.10 (br. s., 1 H) 1.28 (d, J=5.81 Hz, 1 H) 1.39 (br. s., 1 H) 1.35 (s, 9 H) 1.58 (br. s., 1 H) 1.54 (d, J=14.15 Hz, 2 H) 1.68 (br. s., 1 H) 2.34 (br. s., 1 H) 2.33 (d, J=1.77 Hz, 2 H) 2.70-2.80 (m, 1 H) 3.75 (br. s., 2 H) 4.02 (s, 2 H) 6.49 (br. s., 1 H) 6.59 (br. s., 1 H) 7.24 (d, J=7.83 Hz, 1 H)

EXAMPLE 65

5-(2-Hydroxy-4-piperidin-3-ylmethylphenyl)-1,1-dioxo-1,2,5-thiadiazolidin-3-one

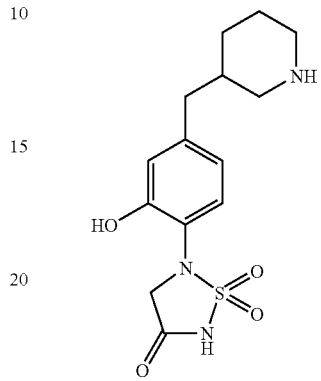

To a suspension of 3-[3-hydroxy-4-(1,1,4-trioxo-1,2,5-thiadiazolidin-2-yl)-benzyl]-piperidine-1-carboxylic acid tert-butyl ester (24 mg, 0.052 mmol) in ether (1.5 mL) is added 2 mL of HCl in dioxane (4 M) and the mixture is stirred at RT for 18 h. The solvent is removed under reduced pressure to give the hydrochloride salt of the title compound: (M−1)⁻=324.

EXAMPLE 66

{(1R*,2S*)-2-[3-Hydroxy-4-(1,1,4-trioxo-1,2,5-thiadiazolidin-2-yl)-benzyl]-cyclohexyl}-carbamic Acid Tert-butyl Ester

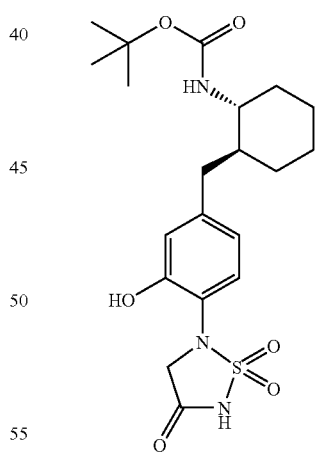

A. ((1R*,2R*)-2-Hydroxymethylcyclohexyl)-carbamic Acid Tert-butyl Ester

To a solution of trans-2-amino-cyclohexylmethanol (0.99 g, 5.97 mmol) and triethylamine (0.907 g, 8.97 mmol) in methylene chloride (30 mL) at 0-5° C. is added Boc-anhydride (1.3 g, 5.96 mmol). The mixture is allowed to warm to RT and is stirred for 18 h. The solution is washed sequentially with 1N HCl, 5% NaHCO$_3$ and brine then is dried over magnesium sulfate. The solvent is removed under reduced pressure to give the title compound as a solid.

B. ((1R*,2R*)-2-Iodomethylcyclohexyl)-carbamic Acid Tert-butyl Ester

To a solution of triphenylphosphine (1.49 g, 5.68 mmol) and imidazole (0.388 g, 5.7 mmol) in methylene chloride (75 mL) is added iodine (1.52 g, 5.99 mmol). The mixture is stirred at RT until a solution forms then ((1R*,2R*)-2-hydroxymethylcyclohexyl)-arbamic acid tert-butyl ester (1.28 g, 5.98 mmol) is added. After stirring the mixture at RT for 18 h the mixture is filtered and the filtrate evaporated. The residue is dissolved in EtOAc and is washed with sodium bisulfite solution and brine. The organic phase is dried over sodium sulfate and the solvent is removed under reduced pressure. The residue is purified by flash chromatography using a gradient of EtOAc/hexane (0 to 30%) as eluent to give the title compound.

C. ((1R*,2S*)-2-{3-Benzyloxy-4-[1,1,4-trioxo-5-(2-trimethylsilanylethyl)-1,2,5-thiadiazolidin-2-yl]-benzyl}-cyclohexyl)-carbamic Acid Tert-butyl Ester The title compound is prepared from ((1R*,2R*)-2-iodomethylcyclohexyl)-carbamic acid tert-butyl ester and 5-(2-benzyloxy-4-iodophenyl)-1,1-dioxo-2-(2-trimethylsilanylethyl)-1,2,5-thiadiazolidin-3-one analogous to the method used in Example 57, step B.

D. {(1R*,2S*)-2-[3-Benzyloxy-4-(1,1,4-trioxo-1,2,5-thiadiazolidin-2-yl)-benzyl]-cyclohexyl}-carbamic Acid Tert-butyl Ester The TMS-ethyl group is removed analogous to the method described for Example 61, step E to give the title compound.

E. {(1R*,2S*)-2-[3-Hydroxy-4-(1,1,4-trioxo-1,2,5-thiadiazolidin-2-yl)-benzyl]-cyclohexyl}-carbamic Acid Tert-butyl Ester The benzyl protecting group is removed analogous to the method for Example 57, step D to give the title compound as a white solid: $(M-1)^-=438$; HPLC retention time=1.20 min., Method A.

EXAMPLE 67

N-{2-[3-Hydroxy-4-(1,1,4-trioxo-1,2,5-thiadiazolidin-2-yl)-phenyl]-ethyl}-benzamide

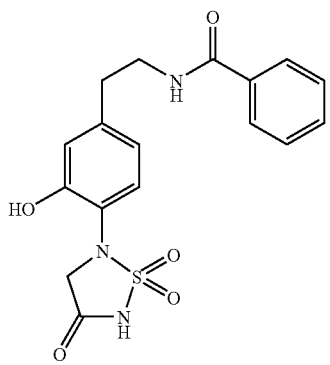

A. 5-[4-(2-Aminoethyl)-2-benzyloxyphenyl]-1,1-dioxo-2-(2-trimethylsilanylethyl)-1,2,5-thiadiazolidin-3-one TFA Salt To a solution of (2-{3-benzyloxy-4-[1,1,4-trioxo-5-(2-trimethylsilanylethyl)-1,2,5-thiadiazolidin-2-yl]-phenyl}-ethyl)-carbamic acid tert-butyl ester (1.5 g, 2.67 mmol) (from Example 59, step B) in 10 mL of $CH_2Cl_2$ is added TFA (4.0 mL). The mixture stirred for 30 min and then evaporated and azeotroped with toluene to afford the title compound as an orange foam.

B. N-(2-{3-Benzyloxy-4-[1,1,4-trioxo-5-(2-trimethylsilanylethyl)-1,2,5-thiadiazolidin-2-yl]-phenyl}-ethyl)-benzamide To a solution of 5-[4-(2-aminoethyl)-2-benzyloxyphenyl]-1,1-dioxo-2-(2-trimethylsilanylethyl)-1,2,5-thiadiazolidin-3-one TFA salt (235 mg, 0.356 mmol) in methylene chloride (2 mL) is added triethylamine (0.1 mL) then benzoyl chloride (56 mg, 0.4 mmol) and the mixture is stirred at RT for 2 h. The solvent is removed under reduced pressure and 1 N HCl is added. The mixture is extracted with ether and the organic phase is dried over magnesium sulfate. The solvent is removed under reduced pressure and the residue is purified by flash chromatography using hexane/EtOAc (7:3) as eluent to give the title compound.

C. N-{2-[3-Benzyloxy-4-(1,1,4-trioxo-1,2,5-thiadiazolidin-2-yl)-phenyl]-ethyl}-benzamide To a solution of N-(2-{3-benzyloxy-4-[1,1,4-trioxo-5-(2-trimethylsilanylethyl)-1,2,5-thiadiazolidin-2-yl]-phenyl}ethyl)-benzamide (0.13 g, 0.23 mmol) in 3 mL THF is added 0.7 mL of a 0.5M solution of TBAF in THF. The mixture is stirred at 50° C. for 2 h then is allowed to cool to RT. The mixture is poured into 1N HCl (20 mL) and extracted with EtOAc. The organic phase is washed with 1N HCl and brine and is dried over magnesium sulfate. The solvent is removed under reduced pressure and the resulting solid is triturated with ether/hexane to furnish the title compound.

D. N-{2-[3-Hydroxy-4-(1,1,4-trioxo-1,2,5-thiadiazolidin-2-yl)-phenyl]-ethyl}-benzamide The title compound is prepared from N-{2-[3-benzyloxy-4-(1,1,4-trioxo-1,2,5-thiadiazolidin-2-yl)-phenyl]-ethyl}-benzamide analogous to Example 57, step D: $(M-1)^-=374$.

EXAMPLES 68 TO 73

The following compounds are prepared using appropriate starting materials analogous to Example 67.

| Example | Chemical Name | MS (m/z) | Retention time (min) Method |
|---|---|---|---|
| 68 | 4-Fluoro-N-{2-[3-hydroxy-4-(1,1,4-trioxo-1,2,5-thiadiazolidin-2-yl)-phenyl]-ethyl}-benzamide | (M − 1)⁻ = 392 | |
| 69 | N-{2-[3-Hydroxy-4-(1,1,4-trioxo-1,2,5-thiadiazolidin-2-yl)-phenyl]-ethyl}-acetamide | (M − 1)⁻ = 312 | 0.28 A |
| 70 | N-{2-[3-Hydroxy-4-(1,1,4-trioxo-1,2,5-thiadiazolidin-2-yl)-phenyl]-ethyl}-propionamide | (M − 1)⁻ = 326 | 0.41 A |
| 71 | N-{2-[3-Hydroxy-4-(1,1,4-trioxo-1,2,5-thiadiazolidin-2-yl)-phenyl]-ethyl}-isobutyramide | (M − 1)⁻ = 340 | 0.52 A |
| 72 | N-{2-[3-Hydroxy-4-(1,1,4-trioxo-1,2,5-thiadiazolidin-2-yl)-phenyl]-ethyl}-2,2-dimethyl-propionamide | (M − 1)⁻ = 354 | 0.65 A |
| 73 | Adamantane-1-carboxylic acid {2-[3-hydroxy-4-(1,1,4-trioxo-1,2,5-thiadiazolidin-2-yl)-phenyl]-ethyl}-amide | (M − 1)⁻ = 432 | |

| Example | NMR |
|---|---|
| 68 | $^1$H NMR (400 MHz, DMSO-$d_6$) δ ppm 2.72 (t, J = 7.33 Hz, 2H) 3.40-3.47 (m, 1H) 3.42 (d, J = 8.08 Hz, 1H) 4.03 (s, 2H) 6.59 (d, J = 7.58 Hz, 1H) 6.69 (d, J = 1.52 Hz, 1H) 7.25-7.31 (m, 3H) 7.90 (dd, J = 8.84, 5.56 Hz, 2H) 8.59 (t, J = 5.68 Hz, 1H) |
| 73 | $^1$H NMR (400 MHz, DMSO-D6) δ ppm 1.60-1.70 (m, 7H) 1.75 (d, J = 2.78 Hz, 6H) 1.95 (s, 3H) 2.52-2.58 (m, 2H) 3.15-3.22 (m, 2H) 4.03 (s, 2H) 6.48 (s, 1H) 6.60 (s, 1H) 7.24 (d, J = 7.83 Hz, 1H) 7.41 (t, J = 5.68 Hz, 1H) |

EXAMPLE 74

N-{3-[3-Hydroxy-4-(1,1,4-trioxo-1,2,5-thiadiazolidin-2-yl)-phenyl]-propyl}-acetamide

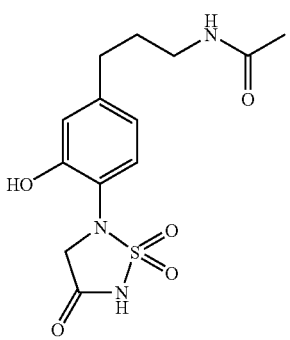

A. 5-[4-(3-Aminopropyl)-2-benzyloxyphenyl]-1,1-dioxo-2-(2-trimethylsilanylethyl)-1,2,5-thiadiazolidin-3-one TFA Salt To a solution of (3-{3-benzyloxy-4-[1,1,4-trioxo-5-(2-trimethylsilanylethyl)-1,2,5-thiadiazolidin-2-yl]-phenyl}-propyl)-carbamic acid tert-butyl ester (6.0 g, 10.4 mmol) (from Example 57, step B) in 20 mL of $CH_2Cl_2$ is added trifluoroacetic acid (5.0 mL). The mixture stirred for 1 h and then the solvent is removed under reduced pressure to afford the title compound as an orange oil.

B. N-(3-{3-Benzyloxy-4-[1,1,4-trioxo-5-(2-trimethylsilanylethyl)-1,2,5-thiadiazolidin-2-yl]-phenyl}-propyl)-acetamide To a solution of 5-[4-(3-aminopropyl)-2-benzyloxyphenyl]-1,1-dioxo-2-(2-trimethylsilanylethyl)-1,2,5-thiadiazolidin-3-one TFA salt (124 mg, 0.26 mmol) in methylene chloride (5 mL) is added diisopropylethylamine (0.1 mg, 0.781 mmol) then acetyl chloride (21 mg, 0.267 mmol) and the mixture is stirred at RT for 18 h. The solvent is removed under reduced pressure and 1 N HCl is added. The mixture is extracted with ether and the organic phase is dried over magnesium sulfate. The solvent is removed under reduced pressure and the residue is purified by flash chromatography using a gradient of 10-50% EtOAc/hexane as eluent to give the title compound.

C. N-{3-[3-Benzyloxy-4-(1,1,4-trioxo-1,2,5-thiadiazolidin-2-yl)-phenyl]-propyl}-acetamide The title compound is prepared from N-(3-{3-benzyloxy-4-[1,1,4-trioxo-5-(2-trimethylsilanylethyl)-1,2,5-thiadiazolidin-2-yl]-phenyl}-propyl)-acetamide analogous to Example 61, step E.

D. N-{3-[3-Hydroxy-4-(1,1,4-trioxo-1,2,5-thiadiazolidin-2-yl)-phenyl]-propyl}-acetamide The title compound is prepared from N-{3-[3-benzyloxy-4-(1,1,4-trioxo-1,2,5-thiadiazolidin-2-yl)-phenyl]-propyl}-acetamide analogous to Example 57, step D. MS (M−1)⁻=326; HPLC retention time=0.38 min. Method A.

EXAMPLES 75 TO 79

The following compounds are prepared using appropriate starting materials analogous to Example 74.

| Example | Chemical Name | MS (m/z) | Retention time (min) Method |
|---|---|---|---|
| 75 | 4-Fluoro-N-{3-[3-hydroxy-4-(1,1,4-trioxo-1,2,5-thiadiazolidin-2-yl)-phenyl]-propyl}-benzamide | (M − 1)⁻ = 406 | |
| 76 | N-{3-[3-Hydroxy-4-(1,1,4-trioxo-1,2,5-thiadiazolidin-2-yl)-phenyl]-propyl}-propionamide | (M − 1)⁻ = 340 | 0.33 A |
| 77 | N-{3-[3-Hydroxy-4-(1,1,4-trioxo-1,2,5-thiadiazolidin-2-yl)-phenyl]-propyl}-isobutyramide | (M − 1)⁻ = 354 | 0.65 A |
| 78 | N-{3-[3-Hydroxy-4-(1,1,4-trioxo-1,2,5-thiadiazolidin-2-yl)-phenyl]-propyl}-2,2-dimethyl-propionamide | (M − 1)⁻ = 368 | 0.78 A |
| 79 | Adamantane-1-carboxylic acid {3-[3-hydroxy-4-(1,1,4-trioxo-1,2,5-thiadiazolidin-2-yl)-phenyl]-propyl}-amide | (M − 1)⁻ = 446 | |

| Example | NMR |
|---|---|
| 75 | ¹H NMR (400 MHz, DMSO-D6) δ ppm 1.74-1.83 (m, J = 7.39, 7.39, 7.39, 7.39 Hz, 2H) 3.23-3.34 (m, 3H) 4.04 (s, 2H) 6.53-6.61 (m, 1H) 6.69 (d, J = 1.77 Hz, 1H) 7.22-7.31 (m, 3H) 7.87-7.94 (m, 2H) 8.49 (t, J = 5.43 Hz, 1H) |
| 79 | ¹H NMR (400 MHz, DMSO-D6) δ ppm 1.58-1.69 (m, 10H) 1.75 (d, J = 2.78 Hz, 6H) 1.95 (s, 3H) 2.41 (t, J = 7.58 Hz, 2H) 3.04 (q, J = 6.82 Hz, 2H) 4.01 (s, 2H) 7.24 (d, J = 8.08 Hz, 1H) 7.31 (s, 1H) |

EXAMPLE 80

5-[2-Hydroxy-4-((S)-5-oxopyrrolidin-2-ylmethyl)-phenyl]-1,1-dioxo-1,2,5-thiadiazolidin-3-one

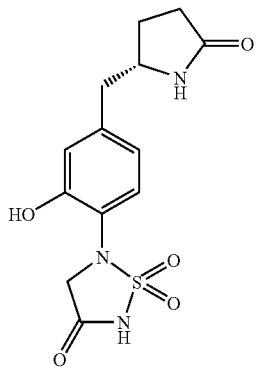

A. (S)-5-Iodomethylpyrrolidin-2-one

To a solution of imidazole (1.48 g, 21.8 mmol) in CH₂Cl₂ (20 mL) is added PPh₃ (4.55 g, 17.4 mmol). The solution is cooled to 0° C. and iodine (4.41 g, 17.4 mmol) is added in 2 portions. The mixture is allowed to warm to RT then (S)-5-hydroxymethylpyrrolidin-2-one is added and the mixture is stirred at RT for 24 h. The mixture is diluted with water and extracted with EtOAc (3×). The organic layer is washed with a 20% solution of Na₂S₂O₃. The solvent is removed and the residue is purified on a reverse phase silica cartridge eluting with a gradient of EtOH/H₂O (0-16%) to provide the title compound: (M+H)⁺=226.

B. 5-[2-Benzyloxy-4-((S)-5-oxopyrrolidin-2-ylmethyl)-phenyl]-1,1-dioxo-2-(2-trimethylsilanylethyl)-1,2,5-thiadiazolidin-3-one Zinc dust (0.69 g, 10.66 mmol) is placed in a round bottom flask and heated under vacuum to remove traces of water. After cooling, DMF (3 mL) is added, followed by 1,2-dibromoethane (0.061 mL, 0.708 mmol). The solution is heated until effervescence occurs, then cooled under N₂. To the solution is added TMSCl (0.135 mL, 1.06 mmol). A solution of (S)-5-iodomethylpyrrolidin-2-one (0.40 g, 1.78 mmol) in DMF (5 mL) is added to the mixture and stirred until TLC indicates the absence of starting material. Pd₂(dba)₃ (0.043 g, 0.047 mmol) and tri-o-tolylphosphine (0.11 g, 0.365 mmol) are added, followed by the dropwise addition of 5-(2-benzyloxy-4-iodophenyl)-1,1-dioxo-2-(2-trimethylsilanylethyl)-1,2,5-thiadiazolidin-3-one (0.645 g, 1.18 mmol) in DMF (10 mL). The mixture is stirred at RT for 4 h, then heated to 45° C. and stirred for 18 h. The mixture is allowed to cool to RT and diluted with water. A yellow precipitate forms after the addition of water. The precipitate is filtered, washed with water and dried under reduced pressure to afford the title compound: (M+H)⁺=516.

C. 5-[2-Benzyloxy-4-((S)-5-oxopyrrolidin-2-ylmethyl)-phenyl]-1,1-dioxo-1,2,5-thiadiazolidin-3-one To a suspension of PS-isocyanate resin (0.500 g) in THF is added TBAF (1M in THF, 2.5 mL) and the mixture is stirred at RT for 2 h. The resin is filtered off and the TBAF solution is added to a stirring solution of 5-[2-benzyloxy-4-((S)-5-oxopyrrolidin-2-ylmethyl)-phenyl]-1,1-dioxo-2-(2-trimethylsilanylethyl)-1,2,5-thiadiazolidin-3-one (0.660 g, 1.28 mmol) in THF (20 mL). The mixture is stirred at 50° C. for 18 h. The mixture is allowed to cool to RT then is diluted with water and extracted with EtOAc (3×). The organic layer is washed with brine, dried over Na₂SO₄ and concentrated. The residue is purified on a reverse phase silica cartridge eluting with EtOH/H$_2$O (10-60%) to provide the title compound: (M−1)$^-$=414.

D. 5-[2-Hydroxy-4-((S)-5-oxopyrrolidin-2-ylmethyl)-phenyl]-1,1-dioxo-1,2,5-thiadiazolidin-3-one To a solution of 5-[2-benzyloxy-4-((S)-5-oxopyrrolidin-2-ylmethyl)-phenyl]-1,1-dioxo-1,2,5-thiadiazolidin-3-one (0.017 g, 0.041 mmol) in EtOH/H$_2$O (1:1, 10 mL) is added 10% Pd/C (0.010 g). The mixture is stirred under an atmosphere of H$_2$ for 2 h at RT. The catalyst is filtered through Celite and is washed with EtOH. The solvent is evaporated off to the title compound. $^1$H NMR (DMSO-d$_6$) δ 7.16 (d, J=8 Hz, 1H), 6.53 is, 1H), 6.36 (d, J=5.81 Hz, 1H), 4.08 (s, 2H), 2.42 (m, 2H), 2.07 (t, J=6.57 Hz, 2H), 1.51 (m, 3H); HPLC retention time=0.55 min (method A). (M−H)$^-$=326.

EXAMPLE 81

6-[3-Hydroxy-4-(1,1,4-trioxo-1,2,5-thiadiazolidin-2-yl)-benzyl]-1H-pyridin-2-one

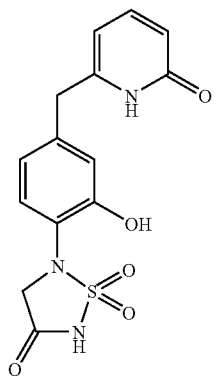

A. 5-(2-Benzyloxy-4-vinylphenyl)-1,1-dioxo-2-(2-trimethylsilanylethyl)-1,2,5-thiadiazolidin-3-one To a solution of 5-(2-benzyloxy-4-iodophenyl)-1,1-dioxo-2-(2-trimethylsilanylethyl)-1,2,5-thiadiazolidin-3-one (2.24 g, 4.1 mmol) in acetonitrile (41 mL), in a pressure vessel, is added tributyl(vinyl)tin (1.43 mL, 4.9 mmol), Pd$_2$(dba)$_3$ (73 mg, 0.16 mmol), and tri-o-tolylphosphine. The vessel is sealed and the mixture is stirred at 80° C. for 18 h. The reaction is allowed to cool to RT, then stirred vigorously with saturated KF (10 mL) for 15 min. The mixture is filtered through Celite, washing several times with acetonitrile. The solvent is removed under reduced pressure and the crude residue is purified via silica gel chromatography using a gradient of 0-40% EtOAc/hexanes to give the title compound as a colorless oil: (M+NH$_4$)$^+$=462.

B. 3-Benzyloxy-4-[1,1,4-trioxo-5-(2-trimethylsilanylethyl)-1,2,5-thiadiazolidin-2-yl]-benzaldehyde To a solution of 5-(2-benzyloxy-4-vinylphenyl)-1,1-dioxo-2-(2-trimethylsilanylethyl)-1,2,5-thiadiazolidin-3-one (1.9 g, 4.3 mmol) in 1:1:1 THF/t-BuOH/H$_2$O (60 mL) is added 1-methylmorpholine-N-oxide (551 mg, 4.74 mmol) and OsO$_4$ (2 mL of a 2.5 wt % solution in t-BuOH, 0.17 mmol). The reaction is stirred for 4 h at RT, then diluted with water (15 mL) and treated with NaIO$_4$ (4.5 g, 21.5 mmol) and NaHCO$_3$ (3.6 g, 43 mmol). The mixture is stirred vigorously for 1 h, then filtered through Celite. The solution is extracted with EtOAc. The organic phase is washed with sat. NaCl. The solution is dried over MgSO$_4$ and the solvent removed under reduced pressure. The residue is purified by column chromatography using a gradient of 0-40% EtOAc/hexane to afford the title compound as a white solid: (M+NH$_4$)$^+$=464.

C. 5-(2-Benzyloxy-4-hydroxymethylphenyl)-1,1-dioxo-2-(2-trimethylsilanylethyl)-1,2,5-thiadiazolidin-3-one To a solution of 3-benzyloxy-4-[1,1,4-trioxo-5-(2-trimethylsilanylethyl)-1,2,5-thiadiazolidin-2-yl]-benzaldehyde (1.6 g, 3.6 mmol) in benzene (20 mL), in a pressure vessel, is added triethylsilane (688 μL, 4.3 mmol) and (PPh$_3$)$_2$Re(O)$_2$I (63 mg, 0.072 mmol). The vessel is sealed and the reaction is stirred at 60° C. for 18 h. The reaction is allowed to cool to RT and the solvent is removed under reduced pressure. The crude triethylsilyl ether is immediately dissolved in MeOH (20 mL), treated with TFA (approximately 0.15 mL) and stirred for 1 h. The solvent is removed under reduced pressure and the crude alcohol is purified by silica gel chromatography using a gradient of 0-50% EtOAc/hexane as eluent to afford the title compound as a light grey solid: (M+H)$^+$=466.

D. 5-(2-Benzyloxy-4-iodomethylphenyl)-1,1-dioxo-2-(2-trimethylsilanylethyl)-1,2,5-thiadiazolidin-3-one To a 0° C. slurry of resin-bound PPh$_3$ (850 mg, 2.5 mmol) in CH$_2$Cl$_2$ (10 mL) in a pressure vessel is added imidazole (200 mg, 2.8 mmol) and iodine (650 mg, 2.5 mmol). The mixture is vigorously stirred at 0° C. for 30 min. To the mixture is added a solution of 5-(2-benzyloxy-4-hydroxymethylphenyl)-1,1-dioxo-2-(2-trimethylsilanylethyl)-1,2,5-thiadiazolidin-3-one (550 mg, 1.2 mmol) in CH$_2$Cl$_2$ (10 mL) dropwise. The vessel is sealed and heated to 45° C., with stirring, for 2 h. The reaction is allowed to cool to RT and the mixture is filtered through a plug of cotton to remove the resin. The organic solution is washed with sat. Na$_2$SO$_3$ and brine, then dried over MgSO$_4$. The solvent is removed under reduced pressure to afford the title compound as a white solid which is used in the next step without further purification: (M+H)$^+$=576.

E. 5-[2-Benzyloxy-4-(6-benzyloxypyridin-2-ylmethyl)-phenyl]-1,1-dioxo-2-(2-trimethylsilanylethyl)-1,2,5-thiadiazolidin-3-one In a pressure vessel, zinc powder (429 mg, 6.6 mmol) is dried by heating under vacuum, then cooled, placed under N$_2$, and slurried in N,N-dimethylacetamide (0.75 mL). To the slurry is added 1,2-dibromoethane (0.044 mL, 0.51 mmol) and the mixture is heated until boiling. The mixture is allowed to cool, and TMSCl (65 mL, 0.51 mmol) is added, followed by stirring for 30 min to produce a green solution. To the activated zinc is added 5-(2-benzyloxy-4-iodomethylphenyl)-1,1-dioxo-2-(2-trimethylsilanylethyl)-1,2,5-thiadiazolidin-3-one (600 mg, 1.1 mmol) in N,N-dimethylacetamide (1 mL) over 30 min. The organozinc solution is filtered and degassed with N$_2$, then to it is added Pd$_2$(dba)$_3$ (50 mg, 0.055 mmol) and 2-di-t-butylphosphino)biphenyl (66 mg, 0.22 mmol), followed by degassed 2-benzyloxy-6-bromopyridine (350 mg, 1.3 mmol) in N,N-dimethylacetamide. The vessel is sealed and the reaction is stirred at 80° C. for 18 h. The reaction is allowed to cool to RT then is filtered through Celite. The resulting solution is diluted with EtOAc (10 mL) and washed with water and brine, then dried over MgSO₄. The solvent is removed under reduced pressure and the crude residue is purified by silica gel chromatography using a gradient of 0-75% EtOAc/hexane to afford the title compound as a colorless oil: (M+H)⁺=616

F. 5-[2-Benzyloxy-4-(6-benzyloxypyridin-2-ylmethyl)-phenyl]-1,1-dioxo-1,2,5-thiadiazolidin-3-one To a solution of 5-[2-benzyloxy-4-(6-benzyloxypyridin-2-ylmethyl)-phenyl]-1,1-dioxo-2-(2-trimethylsilanylethyl)-1,2,5-thiadiazolidin-3-one (213 mg, 0.35 mmol) in DMF (3 mL) is added CsF (265 mg, 1.75 mmol). The reaction is stirred at 60° C. for 2 h. The reaction is allowed to cool to RT and the solvent is removed under reduced pressure. The crude cesium salt of the title compound is used in the next step without further purification: (M+H)⁺=516.

G. 6-[3-Hydroxy-4-(1,1,4-trioxo-1,2,5-thiadiazolidin-2-yl)-benzyl]-1H-pyridin-2-one The crude cesium salt of 5-[2-benzyloxy-4-(6-benzyloxy-pyridin-2-ylmethyl)-phenyl]-1,1-dioxo-1,2,5-thiadiazolidin-3-one (234 mg, 0.36 mmol) is dissolved in 5% EtOH/H₂O and hydrogenated at 1 atm over 10% Pd/C for 1 h. The reaction is filtered and lyophilized to afford the crude residue, which is purified by HPLC using a gradient of 0-50% acetonitrile/water containing 0.1% TFA. The purified material is treated with stoichiometric KOH and lyophilized to afford the potassium salt of the title compound as a tan solid: (M+H)⁺=336; ¹H NMR (DMSO-d₆) δ 11.64 (br s, 1H), 9.12 (br s, 1H), 7.32 (d, J=8.34 Hz, 2H), 6.75 (s, 1H), 6.70 (d, J=8.08, 1H), 6.14 (d, J=9.10 Hz, 1H), 5.95 (d, J=6.32 Hz, 1H), 4.02 (s, 2H), 3.68 (s, 2H).

EXAMPLE 82

6-[3-Hydroxy-4-(1,1,4-trioxo-1,2,5-thiadiazolidin-2-yl)-benzyl]-piperidin-2-one

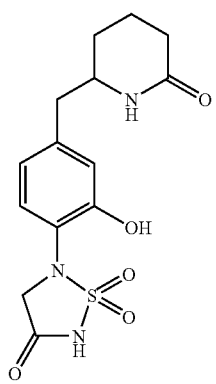

The potassium salt of 6-[3-hydroxy-4-(1,1,4-trioxo-1,2,5-thiadiazolidin-2-yl)-benzyl]-1H-pyridin-2-one (Example 81) (36 mg, 0.10 mmol) is dissolved in EtOH/H₂O (9:1) and is hydrogenated over PtO₂ (cat) at 55 psi of H₂ for 36 h. The reaction is filtered and lyophilized to afford the potassium salt of the title compound as a white solid: LC rt 0.6 (Method A); (M-H)⁻=338.

EXAMPLE 83

7-[3-Hydroxy-4-(1,1,4-trioxo-1,2,5-thiadiazolidin-2-yl)-benzyl]-azepan-2-one

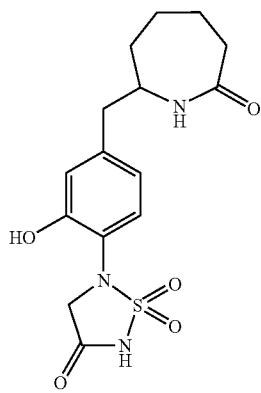

A. 3-Benzyloxy-4-nitrobenzaldehyde

To a stirred solution of benzyl bromide (6.9 g, 40.3 mmol) and 3-hydroxy-4-nitrobenzaldehyde (9.7 g, 58.0 mmol) is added potassium carbonate (8.9 g, 64.4 mmol). The mixture is stirred at RT for 18 h, diluted with water and extracted with EtOAc. The organic phase is washed with aqueous potassium carbonate and brine, dried over MgSO₄, filtered and concentrated to afford the title compound as a yellow solid: (M+1)⁺=258.

B. (3-Benzyloxy-4-nitrophenyl)-methanol

3-Benzyloxy-4-nitrobenzaldehyde (10.3 g, 0.040 mol) is dissolved in methanol (120 mL) with heating and then cooled to 0° C. To this stirred solution, sodium borohydride (1.5 g, 0.40 mol) is added in portions over a period of 5 min. The mixture is allowed to warm to RT and stirred for 18 h. The solvent is removed under reduced pressure and EtOAc is added. The organic layer is washed with 1N HCl and brine, dried over sodium sulfate/magnesium sulfate, and concentrated to afford the title compound as a yellow-brown solid: (M+NH₄)⁺=277.

C. 2-Benzyloxy-4-bromomethyl-1-nitrobenzene

To a stirred solution of (3-benzyloxy-4-nitrophenyl)-methanol (11.0 g, 0.042 mol) in anhydrous THF is added triethylamine (8.7 g, 0.86 mol). The mixture is cooled to -20° C., followed by the addition of methanesulfonyl chloride (5.8 g, 0.051 mol) and then stirred at -20° C. for 45 min. To this mixture is added lithium bromide (37.3 g, 0.43 mol) in anhydrous THF (40 mL) over 40 min followed by stirring at RT for 2 h. The suspension is concentrated under reduced pressure and diluted with EtOAc and water. The organic phase is washed with brine, dried over MgSO₄, filtered and concentrated to afford the title compound as a yellow solid.

D. 2-(3-Benzyloxy-4-nitrobenzyl)-cyclohexanone

To a stirred solution of diisopropylamine (0.44 mL, 3.1 mmol) in THF (5 mL) at 0° C. was added n-butyllithium (1.6 M in hexane, 1.94 mL, 3.1 mmol) dropwise and the solution is stirred for 20 min. After cooling the solution to −78° C., a solution of cyclohexanone (0.32 ml., 3.1 mmol) in THF (2 mL) is added dropwise. The solution is stirred at −78° C. for 1 h then a solution of 2-benzyloxy-4-bromomethyl-1-nitrobenzene (1.0 g, 3.1 mmol) in THF (3 mL) is added dropwise. The solution was warmed to RT and stirred for 18 h. Saturated NaHCO$_3$ is added and the mixture is extracted with EtOAc. The organic layer is washed with water then brine and dried over MgSO$_4$. The solvent is removed under reduced pressure and the residue is purified by flash chromatography using a gradient of 20-33% EtOAc/hexane as eluent to give the title compound as a yellow liquid. NMR (CDCl$_3$): δ 7.79-7.77 (d, J=8.33 Hz, 1H), 7.46-7.31 (m, 5H), 6.93 (d, J=1.51 Hz, 1H), 6.81-6.79 (dd, J=1.52 Hz, 8.34 Hz, 1 H), 5.22 (s, 2H), 3.20-3.16 (m, 1H), 2.53-2.39 (m, 2H), 2.33-2.25 (m, 1H), 2.11-2.05 (m, 1H), 1.96-1.90 (m, 1H), 1.85-1.79 (m, 1H), 1.66-1.55 (m, 2H), 1.35-1.25 (m, 2H).

E. 2-(3-Benzyloxy-4-nitrobenzyl)-cyclohexanone Oxime

A mixture of 2-(3-benzyloxy-4-nitrobenzyl)-cyclohexanone (1.0 g, 2.95 mmol), hydroxylamine hydrochloride (407 mg, 5.9 mmol) and sodium acetate (726 mg, 8.85 mmol) in MeOH (20 mL)/water (4 mL) is stirred at RT for 18 h. The resulting precipitate is filtered and washed with water to give the title compound as a yellow solid: (M+1)$^+$=355.

F. 7-(3-Benzyloxy-4-nitrobenzyl)-azepan-2-one

To a solution of 2-(3-benzyloxy-4-nitrobenzyl)-cyclohexanone oxime (250 mg, 0.706 mmol) in chloroform (5 mL) at −50° C. is added PCl$_5$ (148 mg, 0.71 mmol). The mixture is stirred at −50° C. for 2 h then water is added. The mixture is extracted with methylene chloride and the organic phase is washed sequentially with 5% NaOH, water and brine. The organic solution is dried over sodium sulfate and the solvent is removed under reduced pressure. The residue is purified by flash chromatography using a gradient of 50-100% EtOAc/hexanes to afford the title compound: (M+1)$^+$=355.

G. 7-(4-Amino-3-benzyloxybenzyl)-azepan-2-one

To a solution of 7-(3-benzyloxy-4-nitrobenzyl)-azepan-2-one (600 mg, 1.7 mmol) in EtOAc (20 mL) is added tin (II) chloride dihydrate. The mixture is stirred at RT for 18 h then water is added. The mixture is extracted with EtOAc and the organic phase is washed with water and brine. The solution is dried over sodium sulfate and the solvent removed under reduced pressure to give the title compound: (M+1)$^+$=325.

H. [2-Benzyloxy-4-(7-oxo-azepan-2-ylmethyl)-phenylamino]-acetic Acid Methyl Ester To a mixture of 7-(4-Amino-3-benzyloxybenzyl)-azepan-2-one (600 mg, 1.7 mmol) and potassium carbonate (345 mg, 2.5 mmol) in DMF (10 mL) is added methyl bromoacetate (383 mg, 2.5 mmol). The mixture is stirred at 60° C. for 4 h then is allowed to cool to RT. It is poured into water and extracted with EtOAc and the organic phase is washed with water (3×), brine (1×), and dried over Na$_2$SO$_4$. The solvent is removed under reduced pressure to afford the title compound which is used directly in the next step.

I. Methyl N-(t-butoxycarbonylsulfamoyl)-N-[2-Benzyloxy-4-azepin-1-ylmethyl)-phenyl]-glycinate To a cooled solution of chlorosulfonyl isocyanate (315 mg, 2.22 mmol) in CH$_2$Cl$_2$ (8 mL) is added dropwise a solution of t-butanol (165 mg, 2.22 mmol) in CH$_2$Cl$_2$ (1 mL). The solution is stirred at RT for 45 min and re-cooled, then a solution of [2-benzyloxy-4-(7-oxo-azepan-2-ylmethyl)-phenylamino]-acetic acid methyl ester (600 mg, 1.48 mmol) and triethylamine (252 mg, 2.52 mmol) in CH$_2$Cl$_2$ (2 mL) is added dropwise. The mixture is stirred at RT for 3 h then washed with water. The organic phase is dried over Na$_2$SO$_4$ and the solvent is removed under reduced pressure. The residual oil is purified by flash chromatography using EtOAc/CH$_2$Cl$_2$ (1:1) as eluent to give the title compound.

J. Methyl N-(sulfamoyl)-N-[2-Benzyloxy-4-azepin-1-ylmethyl)-phenyl]-glycinate A solution of methyl N-(t-butoxycarbonylsulfamoyl)-N-[2-benzyloxy-4-azepin-1-ylmethyl)-phenyl]-glycinate (200 mg, 0.35 mmol) in 3 mL TFA/CH$_2$Cl$_2$ (1:1) is stirred at RT for 20 min. The solvent is removed under reduced pressure. Methylene chloride is added to the residue and the solution is washed sequentially with sat. NaHCO$_3$, water and brine and dried over sodium sulfate. The solvent is removed under reduced pressure to give the title compound: (M+1)$^+$=476.

K. 7-[3-Benzyloxy-4-(1,1,4-trioxo-1,2,5-thiadiazolidin-2-yl)-benzyl]-azepan-2-one To a solution of methyl N-(sulfamoyl)-N-[2-benzyloxy-4-azepin-1-ylmethyl)-phenyl]-glycinate (170 mg, 0.35 mmol) in THF (3 mL) is added potassium t-butoxide (1.0M, 0.52 mL) in THF dropwise. The mixture is stirred at RT for 2 h. The solvent is removed under reduced pressure to afford the potassium salt of the title compound as a pale yellow solid: (M−1)$^-$=442. This is used directly in the next step.

L. 7-[3-Hydroxy-4-(1,1,4-trioxo-1,2,5-thiadiazolidin-2-yl)-benzyl]-azepan-2-one A solution of 7-[3-benzyloxy-4-(1,1,4-trioxo-1,2,5-thiadiazolidin-2-yl)-benzyl]-azepan-2-one potassium salt in 6 mL of EtOH/water (1:1) is hydrogenated over 10% Pd/C at 1 atm for 2 h. The catalyst is filtered and the solvent is removed under reduced pressure. The residue is purified by reverse phase HPLC followed by lyophilization to give the title compound as a solid: $^1$H NMR (DMSO-d6): δ 7.85-7.83 (d, J=8.09 Hz, 1H), 7.42-7.41 (d, J=2.02 Hz, 1H), 7.34-7.32 (dd, J=1.77 Hz, 8.09 Hz, 1 H), 6.49-6.50 (d, J=3.53 Hz, 1H), 4.94 (s, 2H), 4.21-4.13 (m, 2H), 3.33-3.20 (m, 3H), 2.98-2.91 (m, 1H), 2.72-2.67 (m, 1H), 2.40-2.21 (m, 3H), 2.08-1.75 (m, 3H). (M−1)$^-$=352.

EXAMPLE 84

(R)-3-[3-Hydroxy-4-(1,1,4-trioxo-1,2,5-thiadiazolidin-2-yl)-benzyl]-3,4-dihydro-2H-isoquinolin-1-one

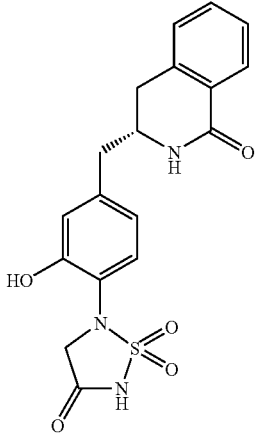

A. (S)-3-Iodomethyl-3,4-dihydro-2H-isoquinolin-1-one

The title compound is prepared from (S)-3-hydroxymethyl-3,4-dihydro-2H-isoquinolin-1-one (J. Med. Chem. 42, 4351 (1999)) analogous to Example 66, step B.

B. (R)-3-{3-Benzyloxy-4-[1,1,4-trioxo-5-(2-trimethylsilanylethyl)-1,2,5-thiadiazolidin-2-yl]-benzyl}-3,4-dihydro-2H-isoquinolin-1-one The title compound is prepared from (S)-3-iodomethyl-3,4-dihydro-2H-isoquinolin-1-one and 5-(2-benzyloxy-4-iodophenyl)-1,1-dioxo-2-(2-trimethylsilanylethyl)-1,2,5-thiadiazolidin-3-one analogous to the method used in Example 57, step B.

C. (R)-3-[3-Hydroxy-4-(1,1,4-trioxo-1,2,5-thiadiazolidin-2-yl)-benzyl]-3,4-dihydro-2H-isoquinolin-1-one The TMS-ethyl and benzyl protecting groups are removed from (R)-3-{3-benzyloxy-4-[1,1,4-trioxo-5-(2-trimethylsilanylethyl)-1,2,5-thiadiazolidin-2-yl]-benzyl}-3,4-dihydro-2H-isoquinolin-1-one analogous to the methods used in Example 57, steps C and D to give the title compound as a solid: $(M-1)^-=386$. HPLC retention time=0.77 min (Method A).

EXAMPLE 85

(S)-3-[3-Hydroxy-4-(1,1,4-trioxo-1,2,5-thiadiazolidin-2-yl)-benzyl]-2,3-dihydro-benzo[c]azepin-1-one

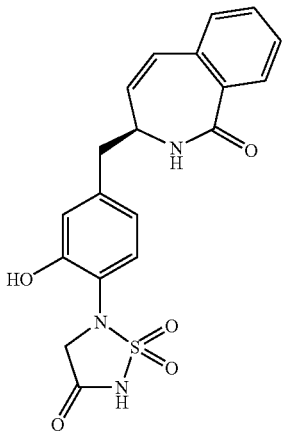

A. 2-Bromomethylbenzoic Acid Ethyl Ester

To a solution of 2-methylbenzoic acid ethyl ester (16.4 g, 99.87 mmol) in $CCl_4$ (100 mL) is added N-bromosuccinimide (17.8 g, 100 mmol) and 2,2'-azobisisobutyronitrile (3.28 g, 19.97 mmol). The resulting mixture is heated at reflux for 2 h. After the mixture is cooled to RT, the solid is filtered off and the filtrate is concentrated and extracted with EtOAc. The EtOAc solution is washed with brine and dried over $MgSO_4$, filtered and concentrated to afford the title compound as a pale yellow oil.

B. (2-Ethoxycarbonylbenzyl)-triphenylphosphonium Bromide

A mixture of 2-bromomethylbenzoic acid ethyl ester (25 g, 102.8 mmol) and triphenylphosphine (32.4 g, 123.5 mmol) in toluene is refluxed for 1 h. The solution is cooled to RT and filtered to afford the title compound as a brown solid: $(M+1)^+=243, 245$.

C. (R)-4-[2-(2-Ethoxycarbonylphenyl)-vinyl]-2,2-dimethyl-oxazolidine-3-carboxylic Acid Tert-butyl Ester To a suspension of (2-ethoxycarbonylbenzyl)-triphenylphosphonium bromide (9.0 g, 17.77 mmol) in toluene (100 mL) is added potassium bis(trimethylsilyl)amide (0.5M in toluene, 40 mL) followed by the addition of (S)-4-formyl-2,2-dimethyloxazolidine-3-carboxylic acid tert-butyl ester (3.4 g, 14.83 mmol) and the mixture is refluxed for 1 h. After cooling to RT, ice/water is added and the solution extracted with EtOAc. The organic layer is washed with brine, dried over $MgSO_4$, filtered and concentrated. The crude material is purified by column chromatography to afford the title compound as a yellow oil: $(M+1)^+=376$.

D. 2-((R)-3-Amino-4-hydroxy-but-1-enyl)-benzoic Acid Ethyl Ester

To a solution of (R)-4-[2-(2-ethoxycarbonylphenyl)-vinyl]-2,2-dimethyl-oxazolidine-3-carboxylic acid tert-butyl ester (3.3 g, 8.70 mmol) in methanol (50 mL) is added conc. HCl (4 mL) and stirred at RT for 18 h. The solvent is removed under reduced pressure and EtOAc and 2N NaOH, which is saturated by NaCl, is added. The aqueous phase is extracted with EtOAc and the organic phases are combined together, washed with brine, dried over $MgSO_4$, filtered and concentrated to afford the title compound as a white solid: $(M+1)^+=236$.

E. (R)-3-Hydroxymethyl-2,3-dihydrobenzo[c]azepin-1-one

To a solution of 2-((R)-3-amino-4-hydroxy-but-1-enyl)-benzoic acid ethyl ester (1.8 g, 7.65 mmol) in 1:1 toluene/acetonitrile (4 mL) is added DBU (1 mL, 6.45 mmol) and stirred at RT for 18 h. The white precipitate is filtered to give the title compound: $(M+1)^+=190$.

F. (R)-3-Iodomethyl-2,3-dihydrobenzo[c]azepin-1-one

The title compound is prepared from (R)-3-hydroxymethyl-2,3-dihydrobenzo[c]azepin-1-one analogous to Example 66, step B.

G. (S)-3-{3-Benzyloxy-4-[1,1,4-trioxo-5-(2-trimethylsilanylethyl)-1,2,5-thiadiazolidin-2-yl]-benzyl}-2,3-dihydrobenzo[c]azepin-1-one The title compound is prepared from (R)-3-iodomethyl-2,3-dihydrobenzo[c]azepin-1-one and 5-(2-benzyloxy-4-iodophenyl)-1,1-dioxo-2-(2-trimethylsilanylethyl)-1,2,5-thiadiazolidin-3-one analogous to the method used in Example 57, step B.

H. (S)-3-[3-Benzyloxy-4-(1,1,4-trioxo-1,2,5-thiadiazolidin-2-yl)-benzyl]-2,3-dihydrobenzo[c]azepin-1-one The TMS-ethyl group of (S)-3-{3-benzyloxy-4-[1,1,4-trioxo-5-(2-trimethylsilanylethyl)-1,2,5-thiadiazolidin-2-yl]-benzyl}-2,3-dihydrobenzo[c]azepin-1-one is removed analogous to the method described for Example 61, step E to give the title compound.

I. (S)-3-[3-Hydroxy-4-(1,1,4-trioxo-1,2,5-thiadiazolidin-2-yl)-benzyl]-2,3-dihydrobenzo[c]azepin-1-one To a solution of (S)-3-[3-benzyloxy-4-(1,1,4-trioxo-1,2,5-thiadiazolidin-2-yl)-benzyl]-2,3-dihydrobenzo[c]azepin-1-one in methylene chloride (2 mL) at −10° C. is added 0.3 mL of BBr$_3$. The mixture is stirred at −10° C. for 30 min and is quenched with water. The aqueous phase is separated and lyophilized to give the title compound: $^1$H NMR (DMSO-d$_6$) δ 9.61 (br s, 1H), 8.30 (d, J=5.56 Hz, 1H), 7.84 (d, J=7.58 Hz, 1H), 7.52 (t, J=7.07 Hz, 1H), 7.40 (t, J=7.58 Hz, 1H), 7.32 (d, J=8.0 Hz, 1H), 7.24 (d, J=8.08 Hz, 1H), 6.71 (m, 3H), 6.17 (m, 1H), 4.30 (s, 2H), 3.64 (m, 1H), 2.68 (m, 1H), 2.77 (m, 1H).

EXAMPLE 86

(R)-3-[3-Hydroxy-4-(1,1,4-trioxo-1,2,5-thiadiazolidin-2-yl)-benzyl]-2,3,4,5-tetrahydrobenzo[c]azepin-1-one

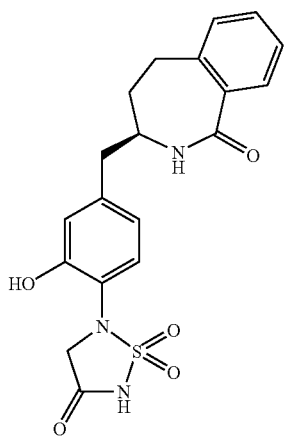

The title compound is prepared from (S)-3-[3-benzyloxy-4-(1,1,4-trioxo-1,2,5-thiadiazolidin-2-yl)-benzyl]-2,3-dihydrobenzo[c]azepin-1-one analogous to the method used in Example 44, step B. Purification by reverse phase HPLC affords the product as a white solid: (M−1)$^-$=400.

EXAMPLE 87

1-[3-Hydroxy-4-(1,1,4-trioxo-1,2,5-thiadiazolidin-2-yl)-benzyl]-1,2,4,5-tetrahydrobenzo[c]azepin-3-one

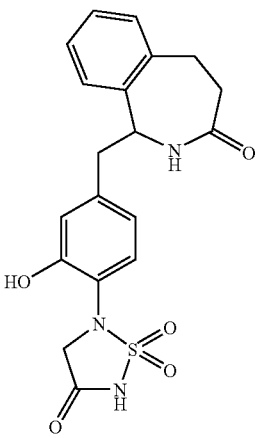

A. 1-[1-(3-Benzyloxy-4-nitrobenzyl)-3,4-dihydro-1H-naphthalen-2-ylidene]-pyrrolidinium Bromide A solution of 1-(3,4-dihydronaphthalen-2-yl)-pyrrolidine (Syn. Comm. 33, 2215 (2003)) (450 mg, 2.26 mmol) and 2-benzyloxy-4-bromomethyl-1-nitrobenzene (Example 83, step C) (730 mg, 2.26 mmol) in 20 mL CH$_3$CN is stirred at RT for 1 h. The solvent is removed under reduced pressure to give the title compound as a red solid.

B. 1-(3-Benzyloxy-4-nitrobenzyl)-3,4-dihydro-1H-naphthalen-2-one

A solution of 1-[1-(3-benzyloxy-4-nitrobenzyl)-3,4-dihydro-1H-naphthalen-2-ylidene]-pyrrolidinium bromide (700 mg, 1.59 mmol) in a mixed solvent of 10 mL H$_2$O, 1 mL CHCl$_3$ and 2 mL CH$_3$COOH is stirred at RT for 3 h. The solution is diluted with CH$_2$Cl$_2$ and the organic layer is washed well with water, brine and dried over MgSO$_4$. The solvent is removed under reduced pressure and the residue is purified by flash chromatography using a gradient of 33-50% EtOAc/hexane as eluent to give the title compound as a yellow liquid. NMR (CDCl$_3$): 7.70-7.68 (d, J=8.34 Hz, 1H), 7.40-7.29 (m, 5H), 7.23-7.15 (m, 3H), 6.96-6.94 (dd, J=6.31 Hz, 1 H), 6.57-6.55 (m, 2H), 4.96 (s, 2H), 3.75-3.72 (t, J=6.07 Hz, 1H), 3.34-3.29 (q, J=6.82 Hz, 1H), 3.19-3.14 (q, J=5.30 Hz, 1H), 2.88-2.82 (m, 1H), 2.57-2.46 (m, 3H). (M−1)$^-$=386.

C. 1-(3-Benzyloxy-4-nitrobenzyl)-3,4-dihydro-1H-naphthalen-2-one Oxime

A solution of 1-(3-benzyloxy-4-nitrobenzyl)-3,4-dihydro-1H-naphthalen-2-one (600 mg, 1.55 mmol), hydroxylamine hydrochloride (160 mg, 2.32 mmol) and sodium acetate (254 mg, 3.10 mmol) in 6 mL EtOH/H$_2$O (2:1) is refluxed for 2 h. The solution is cooled to RT and extracted with CH$_2$Cl$_2$. The organic layer is washed with water, brined and dried over MgSO$_4$. The solvent is removed under reduced pressure and the residue is purified by flash chromatography with CH$_2$Cl$_2$ to give the title compound as a yellow liquid. (M+1)$^+$=403.

D. 1-(3-Benzyloxy-4-nitrobenzyl)-1,2,4,5-tetrahydrobenzo[c]azepin-3-one

A solution of 1-(3-benzyloxy-4-nitrobenzyl)-3,4-dihydro-1H-naphthalen-2-one oxime (600 mg, 1.49 mmol) in 10 mL CHCl$_3$ is cooled to −50° C. PCl$_5$ (310 mg, 1.49 mmol) is added portionwise over 10 minutes to maintain the temperature below −30° C. The suspension is stirred until it becomes a solution then is warmed to RT and stirred for 2 hours. Water is added and the solution is extracted with CH$_2$Cl$_2$. The organic layer is washed with water, 5% NaOH and brine then is dried over MgSO$_4$. The solvent is removed under reduced pressure and the residue is purified by flash chromatography using a gradient of 14-100% EtOAc/hexane as eluent to give the title compound as a yellow solid. $^1$H NMR (CDCl$_3$): 7.85-7.83 (d, J=8.59 Hz, 1H), 7.45-7.20 (m, 8H), 7.09-7.07 (d, J=7.58 Hz, 1H), 6.88-6.86 (dd, J=1.52 Hz, 8.34 Hz, 2 H), 5.80-5.79 (d, J=4.80 Hz, 1H), 5.22-5.14 (q, J=12.12, 2H), 4.74-4.69 (m, 1H), 3.37-3.32 (q, J=5.56 Hz, 1H), 3.19-3.08 (m, 2H), 3.04-2.97 (m, 1H), 2.81-2.65 (m, 2H). (M−1)$^-$=401.

E. 1-[3-Hydroxy-4-(1,1,4-trioxo-1,2,5-thiadiazolidin-2-yl)-benzyl]-1,2,4,6-tetrahydrobenzo[c]azepin-3-one The title compound is prepared from 1-(3-benzyloxy-4-nitrobenzyl)-1,2,4,5-tetrahydrobenzo[c]azepin-3-one analogous to Example 83, steps G-L: (M−1)$^-$=400. HPLC retention time: 0.88 min. (Method A).

EXAMPLE 88

1-[3-Hydroxy-4-(1,1,4-trioxo-1,2,5-thiadiazolidin-2-yl)-benzyl]-1,3,4,5-tetrahydrobenzo[d]azepin-2-one

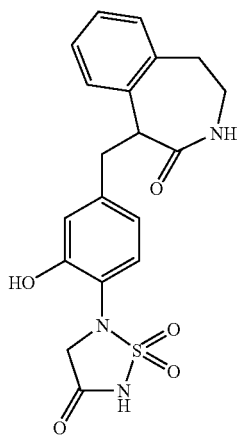

A. 1-(3-Benzyloxy-4-nitrobenzyl)-1,3,4,6-tetrahydro-benzo[d]azepin-2-one

The title compound is isolated in Example 87, step D.

B. 1-[3-Hydroxy-4-(1,1,4-trioxo-1,2,5-thiadiazolidin-2-yl)-benzyl]-1,3,4,5-tetrahydrobenzo[d]azepin-2-one The title compound is prepared from 1-(3-benzyloxy-4-nitrobenzyl)-1,3,4,5-tetrahydrobenzo[d]azepin-2-one analogous to Example 83, steps G-L: (M−1)$^-$=400. HPLC retention time: 0.82 min. (Method A).

EXAMPLE 89

7-[3-Hydroxy-4-(1,1,4-trioxo-1,2,5-thiadiazolidin-2-yl)-benzyl]-6,7-dihydro-dibenzo[c,e]azepin-5-one

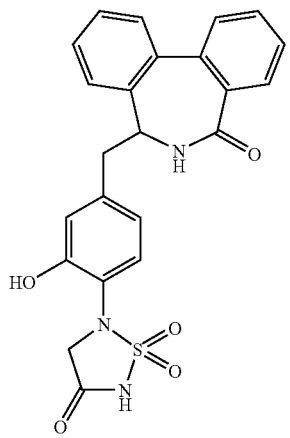

A. Bromo-(2-iodophenyl)-acetic Acid Methyl Ester

A mixture of (2-iodophenyl)-acetic acid methyl ester (14.5 g, 52.5 mmol), NBS (18.7 g, 105 mmol) and AIBN (1.72 g, 10.5 mmol) in CCl$_4$ (300 mL) is refluxed for 10 h. The mixture is cooled to RT and the precipitate filtered. The filtrate is evaporated to give the title compound.

B. Azido-(2-iodophenyl)-acetic Acid Methyl Ester

To a suspension of NaN$_3$ (10.6 g, 163 mmol) in DMF (100 mL) is added bromo-(2-iodophenyl)-acetic acid methyl ester (19.3 g, 54.4 mmol) and the mixture is stirred at RT for 18 h. Brine is added and the mixture is extracted with ether (10× 100 mL). The combined organic layers are washed with brine and dried over sodium sulfate. The solvent is removed under reduced pressure to afford the title compound which is used directly in the next step.

C. Amino-(2-iodophenyl)-acetic Acid Methyl Ester

To a solution of azido-(2-iodophenyl)-acetic acid methyl ester in THF (100 mL) is added triphenylphosphine (28.5 g, 109 mmol) in portions. The mixture is stirred at RT for 2 h then water (4 mL) is added and is heated to reflux. The solvent is removed under reduced pressure and ether (50 mL) is added followed by 2N HCl until acidic. The aqueous phase is washed with methylene chloride then is concentrated and basified with NaOH/ice until pH 12. The mixture is extracted with methylene chloride (3×200 mL) and the combined organic phases are dried over sodium sulfate. The solvent is removed under reduced pressure to give the title compound.

D. (2-Iodobenzoylamino)-(2-iodophenyl)-acetic Acid Methyl Ester

To a solution of 2-iodobenzoic acid (6.4 g, 25.8 mmol) in THF (90 mL) is added HOBt (3.5 g, 25.8 mmol). After the mixture is stirred at RT for 10 min, EDCl (4.93 g, 25.8 mmol) is added followed by triethylamine (4.9 mL, 34.4 mmol). The mixture is stirred at RT for 40 min then amino-(2-iodophenyl)-acetic acid methyl ester (5.0 g, 17.2 mmol) is added and stirring is continued for 18 h. The solvent is removed under reduced pressure and water is added to the residue. The mixture is extracted with EtOAc and the organic phase is washed with brine and dried over magnesium sulfate. The solvent is removed under reduced pressure and the residue purified by flash chromatography using a gradient of 0-60% EtOAc/hexane as eluent to give the title compound.

E. 7-Oxo-6,7-dihydro-5H-dibenzo[c,e]azepine-5-carboxylic Acid Methyl Ester

To a solution of (2-iodobenzoylamino)-(2-iodophenyl)-acetic acid methyl ester (3.4 g, 6.53 mmol) in DMF (300 mL) under argon is added PdCl$_2$(dppf) (269 mg, 0.33 mmol) and KOAc (1.28 g, 13.06 mmol) and the mixture is heated at 110° C. for 18 h. Additional PdCl$_2$(dppf) is added and heating is continued until all starting material is consumed. The solvent is removed under reduced pressure and the residue purified by flash chromatography using a gradient of 0-50% MeOH/methylene chloride as eluent to give the title compound as a yellow oil.

F. 7-Hydroxymethyl-6,7-dihydrodibenzo[c,e]azepin-5-one

To a solution of 7-oxo-6,7-dihydro-5H-dibenzo[c,e]azepine-5-carboxylic acid methyl ester (120 mg, 0.45 mmol) in MeOH (5 mL) at 0° C. is added LiBH$_4$ (20 mg, 0.9 mmol). The mixture is allowed to warm to RT and stirred there for 18 h. Additional LiBH$_4$ is added until starting material is consumed. The solvent is removed under reduced pressure and water is added. The mixture is extracted with EtOAc and the organic phase is washed with brine and dried over magnesium sulfate. The solvent is removed under reduced pressure to give the title compound which is used directly in the next step.

G. Methanesulfonic Acid 7-oxo-6,7-dihydro-5H-dibenzo[c,e]azepin-5-ylmethyl Ester To a solution of 7-hydroxymethyl-6,7-dihydro-dibenzo[c,e]azepin-5-one in pyridine (2 mL) at 0° C. is added MsCl. The mixture is stirred at 0° C. for 20 min then is quenched with ice/water. The mixture is extracted with EtOAc and the organic phase is dried over magnesium sulfate and the solvent is removed under reduced pressure to give the title compound which is used directly in the next step.

H. 7-Iodomethyl-6,7-dihydro-dibenzo[c,e]azepin-5-one

To a solution of methanesulfonic acid 7-oxo-6,7-dihydro-5H-dibenzo[c,e]azepin-5-ylmethyl ester in acetone (5 mL) is added NaI and the mixture is stirred at 50° C. for 18 h. The solvent is removed under reduced pressure and EtOAc is added. The solution is washed sequentially with sodium bisulfite solution, water and brine and is dried over magnesium sulfate. The solvent is removed under reduced pressure and the residue purified by flash chromatography using a gradient of 0-100% EtOAc/hexane as eluent to give the title compound as a yellow solid.

I. 7-{3-Benzyloxy-4-[1,1,4-trioxo-5-(2-trimethylsilanylethyl)-1,2,5-thiadiazolidin-2-yl]-benzyl}-6,7-dihydro-dibenzo[c,e]azepin-5-one The title compound is prepared from 7-iodomethyl-6,7-dihydro-dibenzo[c,e]azepin-5-one and 5-(2-benzyloxy-4-iodophenyl)-1,1-dioxo-2-(2-trimethylsilanylethyl)-1,2,5-thiadiazolidin-3-one analogous to the method used in Example 57, step B.

J. 7-[3-Benzyloxy-4-(1,1,4-trioxo-1,2,5-thiadiazolidin-2-yl)-benzyl]-6,7-dihydro-dibenzo[c,e]azepin-5-one The title compound is prepared from 7-{3-benzyloxy-4-[1,1,4-trioxo-5-(2-trimethylsilanylethyl)-1,2,5-thiadiazolidin-2-yl]-benzyl}-6,7-dihydro-dibenzo[c,e]azepin-5-one analogous to Example 611 step E.

K. 7-[3-Hydroxy-4-(1,1,4-trioxo-1,2,5-thiadiazolidin-2-yl)-benzyl]-6,7-dihydro-dibenzo[c,e]azepin-5-one The title compound is prepared from 7-[3-benzyloxy-4-(1,1,4-trioxo-1,2,5-thiadiazolidin-2-yl)-benzyl]-6,7-dihydro-dibenzo[c,e]azepin-5-one analogous to Example 44, step B: (M−1)⁻=448. HPLC retention time=1.02 min (Method A).

EXAMPLE 90

(S)-7-[3-Hydroxy-4-(1,1,4-trioxo-1,2,5-thiadiazolidin-2-yl)-benzyl]-6,7-dihydro-dibenzo[c,e]azepin-5-one

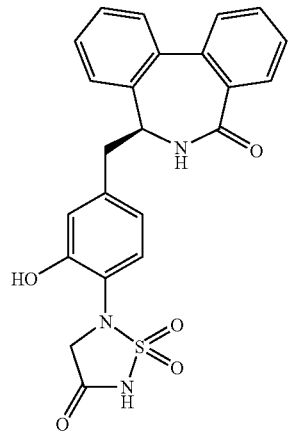

A. N—[(R)-2-(tert-Butyldimethylsilanyloxy)-1-(2-iodophenyl)-ethyl]-2-iodobenzamide To a solution of 2-iodobenzoic acid (0.66 g, 2.65 mmol) in THF (90 mL) is added HOBt (0.71 g, 5.3 mmol). After the mixture is stirred at RT for 15 min, EDCl (1.0 g, 5.3 mmol) is added followed by triethylamine (1.1 mL). The mixture is stirred at RT for 20 min then (R)-2-(tert-butyldimethylsilanyloxy)-1-(2-iodophenyl)-ethylamine (Org. Lett. 6, 513 (2004)) (1.0 g, 2.65 mmol) is added and stirring is continued for 18 h. The solvent is removed under reduced pressure and water is added to the residue. The mixture is extracted with EtOAc and the organic phase is washed with brine and dried over magnesium sulfate. The solvent is removed under reduced pressure and the residue purified by flash chromatography using a gradient of 0-60% EtOAc/hexane as eluent to give the title compound as a yellow solid.

B. (R)-7-(tert-Butyldimethylsilanyloxymethyl)-6,7-dihydrodibenzo[c,e]azepin-5-one To a mixture of N—[(R)-2-(tert-butyldimethylsilanyloxy)-1-(2-iodophenyl)-ethyl]-2-iodobenzamide (60 mg, 0.159 mmol), hydroquinone (6 mg, 0.054 mmol) and $Cs_2CO_3$ (33 mg, 0.10 mmol) is added a homogenous pre-stirred solution of $Pd(OAc)_2$ (1 mg, 0.0044 mmol) and tri-o-tolylphosphine (2 mg, 0.0065 mmol) in DMF (0.5 mL). The reaction mixture is degassed and heated under $N_2$ at 100° C. for 5 h. The reaction mixture is cooled to RT, quenched with 2N HCl, diluted with $H_2O$, and extracted with EtOAc. The organic phase is washed with 1N NaOH, $H_2O$ and brine, dried over $MgSO_4$, filtered and concentrated. The crude material is purified by flash chromatography using a gradient of 0-100%. EtOAc/hexane as eluent to give the title compound as a yellow oil: $(M+1)^+=354$.

C. (R)-7-Hydroxymethyl-6,7-dihydrodibenzo[c,e]azepin-5-one

The title compound is prepared from (R)-7-(tert-butyldimethylsilanyloxymethyl)-6,7-dihydrodibenzo[c,e]azepin-5-one analogous to Example 61, step E.

D. (S)-7-[3-Hydroxy-4-(1,1,4-trioxo-1,2,5-thiadiazolidin-2-yl)-benzyl]-6,7-dihydro-dibenzo[c,e]azepin-5-one The title compound is prepared from (R)-7-hydroxymethyl-6,7-dihydrodibenzo[c,e]azepin-5-one analogous to Example 89, steps G-K: $(M-1)^-=448$. HPLC retention time=0.96 min (Method A)

EXAMPLE 91

3-[3-Hydroxy-4-(1,1,4-trioxo-1,2,5-thiadiazolidin-2-yl)-benzyl]-3,4-dihydro-2H-naphtho[1,8-cd]azepin-1-one

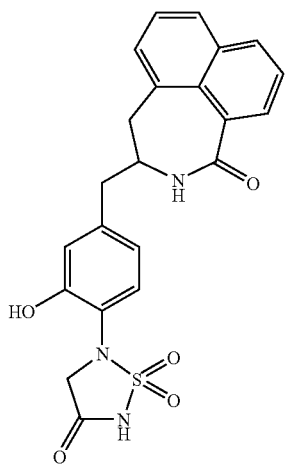

A. 8-Formylnaphthalene-1-carboxylic Acid Methyl Ester

To a solution of 1,8-naphthaldehydic acid (4.0 g, 20 mmol) in DMF (30 mL) is added potassium t-butoxide (24 mL of a 1M solution in THF, 24 mmol) and the mixture is stirred at RT for 30 min. Iodomethane (3.41 g, 24 mmol) is added and the mixture is stirred at RT for 18 h. Ethyl acetate is added and the mixture is neutralized with 1N HCl. The mixture is washed with brine (3×) and the organic phase is dried over magnesium sulfate. The solvent is removed under reduced pressure and the residue purified by flash chromatography using a gradient of 0-50% EtOAc/hexane as eluent to give the title compound.

B. Nitro-(3-oxo-1H,3H-benzo[de]isochromen-1-yl)-acetic Acid Methyl Ester

To a solution of 8-formylnaphthalene-1-carboxylic acid methyl ester (2.5 g, 11.68 mmol) in EtOH (20 mL) is added 8 drops of piperidine followed by nitroacetic acid methyl ester (2.78 g, 23.4 mmol) and the mixture is stirred at RT for 20 h. Ethyl acetate is added followed by 1N HCl. The resulting precipitate is filtered to give the title compound.

C. 1-Oxo-1,2-dihydronaphtho[1,8-cd]azepine-3-carboxylic Acid Methyl Ester

To a solution of nitro-(3-oxo-1H,3H-benzo[de]isochromen-1-yl)-acetic acid methyl ester (1.05 g, 3.33 mmol) in EtOH (12 mL) is added acetic acid (4 mL) followed by Fe (560 mg, 10 mmol) and the mixture is stirred at 100° C. for 90 min. Ethyl acetate is added to the mixture and any insoluble material is filtered. The filtrate is washed with water and the organic phase is dried over magnesium sulfate. The solvent is removed under reduced pressure and the residue purified by flash chromatography using a gradient of 0-50% EtOAc/hexane as eluent to give the title compound.

D. 1-Oxo-1,2,3,4-tetrahydronaphtho[1,8-cd]azepine-3-carboxylic Acid Methyl Ester A solution of 1-oxo-1,2-dihydronaphtho[1,8-cd]azepine-3-carboxylic acid methyl ester (129 mg, 0.5 mmol) in EtOAc (5 mL) is hydrogenated at 1 atm over 10% Pd/C (35 mg) for 18 h. The catalyst is filtered, the solvent is removed under reduced pressure and the residue purified by flash chromatography using a gradient of 0-50% EtOAc/hexane as eluent to give the title compound.

E. 3-Hydroxymethyl-3,4-dihydro-2H-naphtho[1,8-cd]azepin-1-one

To a solution of 1-oxo-1,2,3,4-tetrahydronaphtho[1,8-cd]azepine-3-carboxylic acid methyl ester (70 mg, 0.28 mmol) in MeOH (5 mL) is added $LiBH_4$ (18.3 mg, 0.83 mmol) and the mixture is stirred at RT for 1 h. Ethyl acetate is added followed by ice and 1N HCl. The mixture is washed with brine then water and the organic phase is dried over magnesium sulfate. The solvent is removed under reduced pressure and the residue purified by preparative HPLC to give the title compound.

F. 3-[3-Hydroxy-4-(1,1,4-trioxo-1,2,5-thiadiazolidin-2-yl)-benzyl]-3,4-dihydro-2H-naphtho[1,8-cd]azepin-1-one The title compound is prepared from 3-hydroxymethyl-3,4-dihydro-2H-naphtho[1,8-cd]azepin-1-one analogous to Example 89, steps G-K: (M−1)⁻=436. HPLC retention time=0.98 min (Method A).

EXAMPLE 92

5-{4-[2-(1-Acetylpiperidin-2-yl)-ethyl]-2-hydroxyphenyl}-1,1-dioxo-1,2,5-thiadiazolidin-3-one

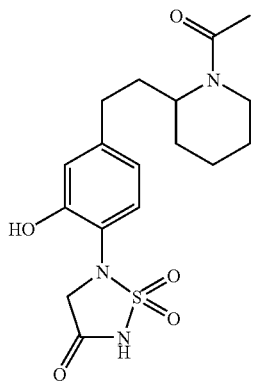

A. 5-[2-Benzyloxy-4-((E)-2-piperidin-2-yl-vinyl)-phenyl]-1,1-dioxo-2-(2-trimethylsilanylethyl)-1,2,5-thiadiazolidin-3-one A solution of 2-((E)-2-{3-benzyloxy-4-[1,1,4-trioxo-5-(2-trimethylsilanylethyl)-1,2,5-thiadiazolidin-2-yl]-phenyl}-vinyl)-piperidine-1-carboxylic acid tert-butyl ester (Example 62, step B) (240 mg, 0.353 mmol) in TFA/methylene chloride (3:8) is stirred at RT for 75 min. The solvent is removed under reduced pressure and the residue purified by preparative HPLC to give the title compound.

B. 5-{4-[(E)-2-(1-Acetylpiperidin-2-yl)-vinyl]-2-benzyloxyphenyl}-1,1-dioxo-2-(2-trimethylsilanylethyl)-1,2,5-thiadiazolidin-3-one To a solution of 5-[2-benzyloxy-4-((E)-2-piperidin-2-yl-vinyl)-phenyl]-1,1-dioxo-2-(2-trimethylsilanylethyl)-1,2,5-thiadiazolidin-3-one (101 mg, 0.192 mmol) in methylene chloride (4 mL) is added triethylamine (0.134 mL, 0.956 mmol). The solution is stirred at RT for 5 min the acetyl chloride (0.0163 mL, 0.23 mmol) is added and stirring is continued for 18 h. The mixture is diluted with EtOAc and is washed with 1N HCl and brine. The organic phase is dried over sodium sulfate and the solvent removed under reduced pressure to give the title compound.

C. 5-{4-[(E)-2-(1-Acetylpiperidin-2-yl)-vinyl]-2-benzyloxyphenyl}-1,1-dioxo-1,2,5-thiadiazolidin-3-one The title compound is prepared from 5-{4-[(E)-2-(1-acetylpiperidin-2-yl)-vinyl]-2-benzyloxyphenyl}-1,1-dioxo-2-(2-trimethylsilanyl-ethyl)-1,2,5-thiadiazolidin-3-one analogous to Example 61, step E.

D. 5-{4-[2-(1-Acetylpiperidin-2-yl)-ethyl]-2-hydroxyphenyl}-1,1-dioxo-1,2,5-thiadiazolidin-3-one The title compound is prepared from 5-{4-[(E)-2-(1-acetylpiperidin-2-yl)-vinyl]-2-benzyloxyphenyl}-1,1-dioxo-1,2,5-thiadiazolidin-3-one analogous to Example 61, step F: LC retention time 0.99 (method A); (M−1)⁻=380.

EXAMPLE 93

N-{(1R*,2S*)-2-[3-Hydroxy-4-(1,1,4-trioxo-1,2,5-thiadiazolidin-2-yl)-benzyl]-cyclohexyl}-acetamide

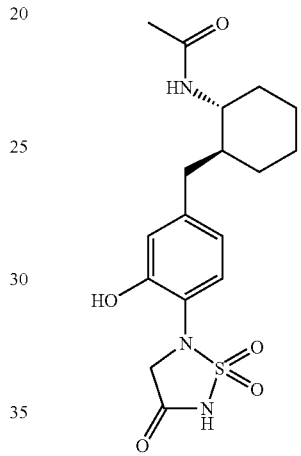

A. 5-[4-((1S*,2R*)-2-Aminocyclohexylmethyl)-2-benzyloxyphenyl]-1,1-dioxo-2-(2-trimethylsilanylethyl)-1,2,5-thiadiazolidin-3-one A solution of ((1R*,2S*)-2-{3-benzyloxy-4-[1,1,4-trioxo-5-(2-trimethylsilanylethyl)-1,2,5-thiadiazolidin-2-yl]-benzyl}-cyclohexyl)-carbamic acid tert-butyl ester (Example 66, step C) (150 mg, 0.238 mmol) in 2 mL of TFA/methylene chloride (1:1) is stirred at RT for 15 min. The solvent is removed under reduced pressure to give the title compound which is used directly in the next step.

B. N-((1R*,2S*)-2-{3-Benzyloxy-4-[1,1,4-trioxo-5-(2-trimethylsilanylethyl)-1,2,5-thiadiazolidin-2-yl]-benzyl}-cyclohexyl)-acetamide To a solution of 5-[4-((1S*,2R*)-2-aminocyclohexylmethyl)-2-benzyloxyphenyl]-1,1-dioxo-2-(2-trimethylsilanyl-ethyl)-1,2,5-thiadiazolidin-3-one in methylene chloride (5 mL) is added diisopropylethylamine (93 mg, 0.72 mmol) followed by acetyl chloride (36 mg, 0.458 mmol) and the mixture is stirred at RT for 24 h. Ethyl acetate is added and the mixture is washed with 1N HCl and brine. The organic phase is dried over magnesium sulfate and the solvent removed under reduced pressure. The residue is purified by flash chromatography using a gradient of 25-75% EtOAc/hexane as eluent to give the title compound.

C. N-{(1R*,2S*)-2-[3-Benzyloxy-4-(1,1,4-trioxo-1,2,5-thiadiazolidin-2-yl)-benzyl]-cyclohexyl}-acetamide To a solution of N-((1R*,2S*)-2-{3-benzyloxy-4-[1,1,4-trioxo-5-(2-trimethylsilanylethyl)-1,2,5-thiadiazolidin-2-yl]-benzyl}-cyclohexyl)-acetamide (76 mg, 0.133 mmol) in DMF (3 mL) is added CsF (81 mg, 0.533 mmol) and the mixture is stirred at 90° C. for 1 h. Ethyl acetate is added and the mixture is washed with 1N HCl and brine. The organic phase is dried over magnesium sulfate and the solvent removed under reduced pressure to give the title compound which is used directly in the next step.

D. N-{(1R*,2S*)-2-[3-Hydroxy-4-(1,1,4-trioxo-1,2,5-thiadiazolidin-2-yl)-benzyl]-cyclohexyl}-acetamide The title compound is prepared from N-{(1R*,2S*)-2-[3-benzyloxy-4-(1,1,4-trioxo-1,2,5-thiadiazolidin-2-yl)-benzyl]-cyclohexyl}-acetamide analogous to Example 57, step D: (M−1)⁻=380; HPLC retention time=0.73 min., Method A

EXAMPLE 94

N-{(S)-1-Benzyl-2-[3-hydroxy-4-(1,1,4-trioxo-1,2,5-thiadiazolidin-2-yl)-phenyl]-ethyl}-2,2,2-trifluoroacetamide

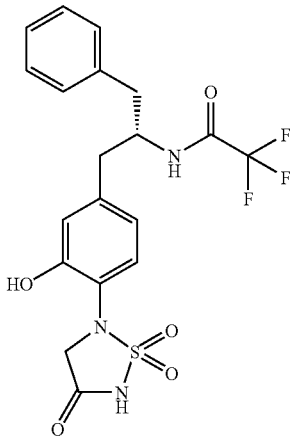

A. 5-[4-((S)-2-Amino-3-phenylpropyl)-2-benzyloxyphenyl]-1,1-dioxo-2-(2-trimethylsilanylethyl)-1,2,5-thiadiazolidin-3-one To a solution of ((S)-1-benzyl-2-{3-benzyloxy-4-[1,1,4-trioxo-5-(2-trimethylsilanylethyl)-1,2,5-thiadiazolidin-2-yl]-phenyl}-ethyl)-carbamic acid tert-butyl ester (intermediate from Example 60) (510 mg, 0.78 mmol) in methylene chloride (5 mL) is added TFA (2 mL) and the mixture is stirred at RT for 5 h. The solvent is removed under reduced pressure to give the title compound. This material is used directly in the next reaction.

B. N—((S)-1-Benzyl-2-{3-benzyloxy-4-[1,1,4-trioxo-5-(2-trimethylsilanylethyl)-1,2,5-thiadiazolidin-2-yl]-phenyl}-ethyl)-2,2,2-trifluoroacetamide To a solution of 5-[4-((S)-2-amino-3-phenylpropyl)-2-benzyloxyphenyl]-1,1-dioxo-2-(2-trimethylsilanylethyl)-1,2,5-thiadiazolidin-3-one (containing residual TFA) in methylene chloride (5 mL) at 0° C. is added triethylamine (0.2 mL) followed by benzoyl chloride (0.17 mL) and the mixture is stirred for 2 h. The mixture is diluted with EtOAc and is washed with water and NaHCO₃. The organic phase is dried over sodium sulfate and the solvent removed under reduced pressure. The residue is purified by flash chromatography using EtOAc/hexane (1:3) as eluent to give the title compound.

C. N-{(S)-1-Benzyl-2-[3-hydroxy-4-(1,1,4-trioxo-1,2,5-thiadiazolidin-2-yl)-phenyl]-ethyl}-2,2,2-trifluoroacetamide The title compound is prepared from N—((S)-1-benzyl-2-{3-benzyloxy-4-[1,1,4-trioxo-5-(2-trimethylsilanylethyl)-1,2,5-thiadiazolidin-2-yl]-phenyl}-ethyl)-2,2,2-trifluoroacetamide analogous to Example 39, steps E and F. 1H NMR (400 MHz, DMSO-D6) δ ppm 2.8 (s, 3 H) 2.9 (s, 1 H) 4.0 (s, 2 H) 4.1 (s, 1 H) 6.6 (s, 1 H) 6.7 (s, 1 H) 7.2 (s, 3 H) 7.3 (s, 3 H) 9.0 (s, 1 H) 9.3 (s, 1 H), LCMS (method 09) retention time=1.18 min,

EXAMPLE 95

N-{4-[3-Hydroxy-4-(1,1,4-trioxo-1,2,5-thiadiazolidin-2-yl)-phenyl]-butyl}-phthalamic Acid

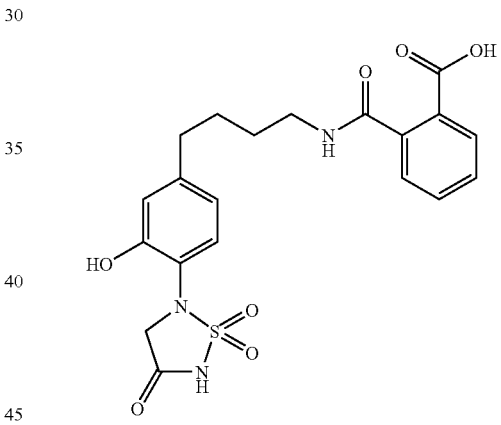

A. 2-((E)-4-{3-Benzyloxy-4-[1,1,4-trioxo-5-(2-trimethylsilanylethyl)-1,2,5-thiadiazolidin-2-yl]-phenyl}-but-3-enyl)-isoindole-1,3-dione To a solution of 5-(2-benzyloxy-4-iodophenyl)-1,1-dioxo-2-(2-trimethylsilanylethyl)-1,2,5-thiadiazolidin-3-one (100 mg, 0.184 mmol) in MeCN (5 mL) in a pressure tube is added 2-but-3-enylisoindole-1,3-dione (41 mg, 0.202 mmol), Pd(OAc)₂ (3 mg) and triethylamine (186 mg, 1.84 mmol) then the mixture is heated at 100° C. for 10 h. The solvent is removed under reduced pressure and the residue is purified by flash chromatography using a gradient of 20-40% EtOAc/hexane as eluent to give the title compound: (M+NH₄)⁺=635.

B. 2-{(E)-4-[3-Benzyloxy-4-(1,1,4-trioxo-1,2,5-thiadiazolidin-2-yl)-phenyl]-but-3-enyl}-isoindole-1,3-dione Tetrabutylammonium fluoride (1.0M in THF, 1.5 mL) is added to a suspension of PS-isocyanate resin (0.4 g) in THF (1.5 mL) and the mixture is stirred at RT for 2 h. The resin is filtered off and the filtrate is added to a solution of 2-((E)-4-{3-benzyloxy-4-[1,1,4-trioxo-5-(2-trimethylsilanylethyl)-1,2,5-thiadiazolidin-2-yl]-phenyl}-but-3-enyl)-isoindole-1,3-dione (90 mg, 0.146 mmol) in THF (1 mL). The reaction is stirred at 65° C. for 1 h and at RT for 18 h. The mixture is cooled and concentrated. The residue is partitioned between EtOAc and water and the organic layer is washed with 2N HCl (3×) and saturated aqueous sodium chloride. The organic layer is dried over $Na_2SO_4$ and the solvent removed under reduced pressure to give the title compound: $(M-1)^- = 516$.

C. N-{4-[3-Hydroxy-4-(1,1,4-trioxo-1,2,5-thiadiazolidin-2-yl)-phenyl]-butyl}-phthalamic Acid A solution of 2-{(E)-4-[3-benzyloxy-4-(1,1,4-trioxo-1,2,5-thiadiazolidin-2-yl)-phenyl]-but-3-enyl}-isoindole-1,3-dione (70 mg, 0.135 mmol) in 6 mL of EtOH/HOAc (4:2) is hydrogenated at 50 psi over 10% Pd/C (70 mg) for 18 h. The catalyst is filtered, the solvent is removed under reduced pressure and the residual yellow foam triturated with EtOAc to give the title compound as a solid: $(M-1)^- = 446$.

EXAMPLE 96

2-{4-[3-Hydroxy-4-(1,1,4-trioxo-1,2,5-thiadiazolidin-2-yl)-phenyl]-butyl}-isoindole-1,3-dione

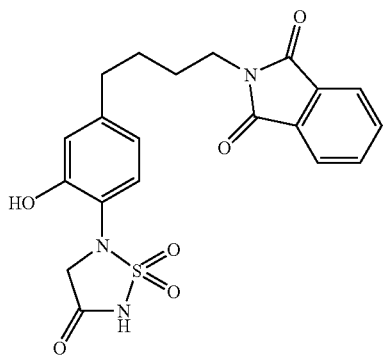

The title compound is isolated during the preparation of Example 95.

EXAMPLE 97

3-[3-Hydroxy-4-(1,1,4-trioxo-1,2,5-thiadiazolidin-2-yl)-phenyl]-N-isopropyl-N-methylpropionamide

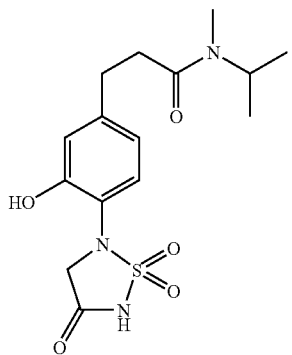

A. (E)-3-{3-Benzyloxy-4-[1,1,4-trioxo-5-(2-trimethylsilanylethyl)-1,2,5-thiadiazolidin-2-yl]-phenyl}-acrylic Acid Tert-butyl Ester To a solution of 5-(2-benzyloxy-4-iodo-phenyl)-1,1-dioxo-2-(2-trimethylsilanylethyl)-1,2,5-thiadiazolidin-3-one (544 mg, 1 mmol), t-butyl acrylate (154 mg, 1.2 mmol) and triethylamine (1.01 g, 10 mmol) in 5 mL of acetonitrile is added $Pd(OAc)_2$ (10 mg). The mixture is heated at 100° C. for 18 h. After allowing to cool to RT the solvent is removed under reduced pressure and the residual oil purified by flash chromatography using methylene chloride to elute the title compound as an oil.

B. 3-{3-Benzyloxy-4-[1,1,4-trioxo-5-(2-trimethylsilanylethyl)-1,2,5-thiadiazolidin-2-yl]-phenyl}propionic Acid Tert-butyl Ester A mixture of (E)-3-{3-benzyloxy-4-[1,1,4-trioxo-5-(2-trimethylsilanylethyl)-1,2,5-thiadiazolidin-2-yl]-phenyl}-acrylic acid tert-butyl ester (485 mg, 0.89 mmol) and 5% platinum-on-carbon (50 mg) is stirred under an atmosphere of hydrogen for 5 h. The catalyst is filtered through Celite and solvent removed under reduced pressure to give the title compound.

C. 3-{3-Benzyloxy-4-[1,1,4-trioxo-5-(2-trimethylsilanylethyl)-1,2,5-thiadiazolidin-2-yl]-phenyl}-propionic Acid A solution of 3-{3-benzyloxy-4-[1,1,4-trioxo-5-(2-trimethylsilanylethyl)-1,2,5-thiadiazolidin-2-yl]-phenyl}-propionic acid tert-butyl ester (420 mg, 0.77 mmol) in 6 mL of TFA/methylene chloride (1:1) is stirred at RT for 20 min. The solvent is removed under reduced pressure. Methylene chloride is added and removed (4×) to give the title compound as an oil: $(M-1)^- = 489$.

D. 3-{3-Benzyloxy-4-[1,1,4-trioxo-5-(2-trimethylsilanylethyl)-1,2,5-thiadiazolidin-2-yl]-phenyl}-N-isopropyl-N-methylpropionamide To a solution of 3-{3-benzyloxy-4-[1,1,4-trioxo-5-(2-trimethylsilanylethyl)-1,2,5-thiadiazolidin-2-yl]-phenyl}-propionic acid (0.10 g, 0.2 mmol), EDCl (0.38 g, 0.20 mmol) and HOAt (0.027 g, 0.20 mmol) in DMF (1 mL) is added N-isopropyl-N-methylamine (0.15 g, 0.2 mmol). The mixture is stirred at RT for 18 h, then poured into water. The mixture is extracted into EtOAc and the organic phase washed with water (3×) and sat. NaCl (1×). The organic solution is dried over $Na_2SO_4$ and the solvent removed under reduced pressure to afford the title compound. This is used directly in the next step.

E. 3-[3-Benzyloxy-4-(1,1,4-trioxo-1,2,5-thiadiazolidin-2-yl)-phenyl]-N-isopropyl-N-methylpropionamide To a solution of 3-{3-benzyloxy-4-[1,1,4-trioxo-5-(2-trimethylsilanylethyl)-1,2,5-thiadiazolidin-2-yl]-phenyl}-N-isopropyl-N-methylpropionamide (0.114 g, 0.2 mmol) in THF (2 mL) is added a 0.5M solution of TBAF (0.84 mL) in THF. The mixture is refluxed for 1 h, then allowed to cool to RT. To the mixture is added 1N HCl and EtOAc. The organic phase is washed with 1N HCl and sat. NaCl. The solution is dried over sodium sulfate and the solvent removed under reduced pressure to afford the title compound. This is used directly in the next step.

F. 3-[3-Hydroxy-4-(1,1,4-trioxo-1,2,5-thiadiazolidin-2-yl)-phenyl]-N-isopropyl-N-methylpropionamide A mixture of 3-[3-benzyloxy-4-(1,1,4-trioxo-1,2,5-thiadiazolidin-2-yl)-phenyl]-N-isopropyl-N-methylpropionamide (0.06 g) and 10% Pd/C (0.03 g) in EtOAc (25 mL) is hydrogenated at 1 atm for 18 h. The catalyst is filtered through Celite and the solvent is removed under reduced pressure. The residual gum is purified by preparative HPLC to afford the title compound as a grey solid: $^1$H NMR (DMSO-d$_6$)7.21 (d, J=8.08 Hz, 1H), 6.73 (s, 1H), 6.66 (d, J=8.08 Hz, 1H), 4.71-4.64 (m, 0.65H), 4.23 (s, 2H), 4.10-4.02 (m, 0.35H), 2.72 (s, 2H), 2.73-2.54 (m, 4H), 2.64 (s, 1H), 1.07 (d, J=6.57 Hz, 2.5H), 0.99 (d, J=6.57 Hz, 3.5H); (M−1)$^-$=354.

EXAMPLE 98

5-{4-[3-(3,4-Dihydro-1H-isoquinolin-2-yl)-3-oxo-propyl]-2-hydroxyphenyl}-1,1-dioxo-1,2,5-thiadiazolidin-3-one

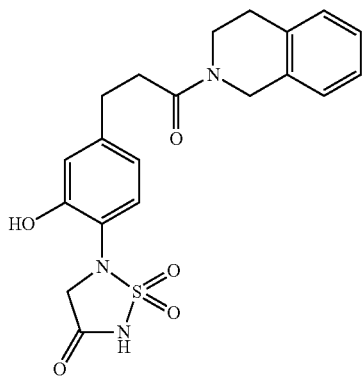

The title compound is prepared from 3-{3-benzyloxy-4-[1,1,4-trioxo-5-(2-trimethylsilanylethyl)-1,2,5-thiadiazolidin-2-yl]-phenyl}-propionic acid and tetrahydroisoquinoline analogous to Example 97, steps D, E and F: (M−1)$^-$=414.

EXAMPLE 99

N'-{3-[3-Hydroxy-4-(1,1,4-trioxo-1,2,5-thiadiazolidin-2-yl)-phenyl]-propionyl}-hydrazinecarboxylic Acid Tert-butyl Ester

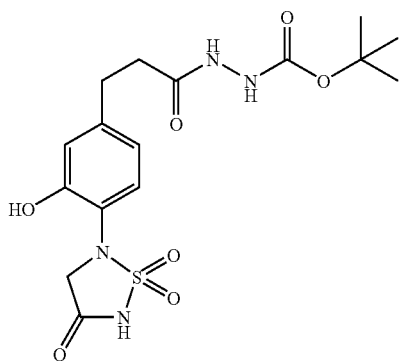

The title compound is prepared from 3-{3-benzyloxy-4-[1,1,4-trioxo-5-(2-trimethylsilanylethyl)-1,2,5-thiadiazolidin-2-yl]-phenyl}-propionic acid and t-butyl carbonate analogous to Example 97, steps D, E and F: (M−1)$^-$=413. HPLC retention time=0.74 min (Method A).

EXAMPLE 100

N-Butyl-3-[3-hydroxy-4-(1,1,4-trioxo-1,2,5-thiadiazolidin-2-yl)-phenyl]-propionamide

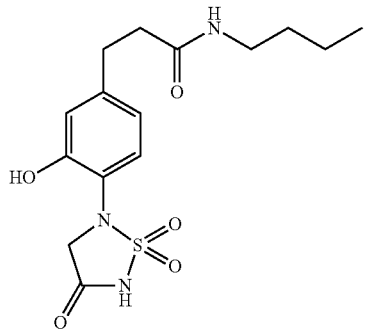

A. (E)-3-[3-Benzyloxy-4-(1,1,4-trioxo-1,2,5-thiadiazolidin-2-yl)-phenyl]-acrylic Acid Tert-butyl Ester To a mixture of 5-(2-benzyloxy-4-iodophenyl)-1,1-dioxo-1,2,5-thiadiazolidin-3-one (2.0 g, 4.49 mmol), Pd(OAc)$_2$ (100 mg) and acrylic acid t-butyl ester (0.78 mL, 5.8 mmol) in acetonitrile (15 mL) in a pressure vessel is added triethylamine (3.13, 22.5 mmol) and the mixture is stirred at 100° C. for 6 h. The solution is filtered through Celite, washed with acetonitrile and concentrated to give the title compound. This is used directly in the next step.

B. (E)-3-[3-Benzyloxy-4-(1,1,4-trioxo-1,2,5-thiadiazolidin-2-yl)-phenyl]-acrylic Acid To a solution of (E)-3-[3-benzyloxy-4-(1,1,4-trioxo-1,2,5-thiadiazolidin-2-yl)-phenyl]-acrylic acid tert-butyl ester (2.2 g, 5.18 mmol) in THF (14 mL)/MeOH (7 mL) is added 3.5 mL (20.7 mmol) of 6N NaOH solution and the mixture is stirred at RT for 18 h. The solvent is removed under reduced pressure and water is added to the residue. The mixture is acidified with 1N HCl and is extracted with methylene chloride. The organic phase is washed with water and brine then is dried over sodium sulfate. The solvent is removed under reduced pressure to give the title compound as a reddish solid: ): (M−1)$^-$=387.

C. (E)-3-[3-Benzyloxy-4-(1,1,4-trioxo-1,2,5-thiadiazolidin-2-yl)-phenyl]-N-butyl-acrylamide To a solution of (E)-3-[3-benzyloxy-4-(1,1,4-trioxo-1,2,5-thiadiazolidin-2-yl)-phenyl]-acrylic acid (10 mg, 0.25 mmol) in THF (4 mL) is added HOBt (68 mg, 0.5 mmol). After 10 min EDCl (96 mg, 0.5 mmol) and triethylamine (0.104 mL, 0.75 mmol) are added and the solution is stirred for 30 min then a solution of n-butylamine in 2 mL THF is added and the mixture is stirred at RT for 6 h. The solvent is removed under reduced pressure to afford the title compound: (M−1)$^-$=442.

D. N-Butyl-3-[3-hydroxy-4-(1,1,4-trioxo-1,2,5-thiadiazolidin-2-yl)-phenyl]-propionamide The title compound is prepared from (E)-3-[3-benzyloxy-4-(1,1,4-trioxo-1,2,5-thiadiazolidin-2-yl)-phenyl]-N-butyl-acrylamide analogous to Example 57, step D: (M−1)$^-$=354. HPLC retention time: 0.76 min. (Method A).

EXAMPLES 101 TO 107

The following compounds are prepared using (E)-3-[3-benzyloxy-4-(1,1,4-trioxo-1,2,5-thiadiazolidin-2-yl)-phenyl]-acrylic acid and the appropriate amine analogous to Example 100 steps C and D.

| Example | Chemical Name | MS (m/z) | Retention time (min) Method |
|---|---|---|---|
| 101 | 3-[3-Hydroxy-4-(1,1,4-trioxo-1,2,5-thiadiazolidin-2-yl)-phenyl]-N-pentylpropionamide | $(M - 1)^- = 368$ | |
| 102 | N-Hexyl-3-[3-hydroxy-4-(1,1,4-trioxo-1,2,5-thiadiazolidin-2-yl)-phenyl]-propionamide | $(M - 1)^- = 382$ | 1.19 A |
| 103 | 3-[3-Hydroxy-4-(1,1,4-trioxo-1,2,5-thiadiazolidin-2-yl)-phenyl]-N-(4-phenylbutyl)-propionamide | $(M - 1)^- = 430$ | 1.08 A |
| 104 | 3-[3-Hydroxy-4-(1,1,4-trioxo-1,2,5-thiadiazolidin-2-yl)-phenyl]-N-(5-phenylpentyl)-propionamide | $(M - 1)^- = 444$ | 1.16 A |
| 105 | N-(2-Hydroxyphenyl)-3-[3-hydroxy-4-(1,1,4-trioxo-1,2,5-thiadiazolidin-2-yl)-phenyl]-propionamide | $(M - 1)^- = 390$ | 0.62 A |
| 106 | 3-[3-Hydroxy-4-(1,1,4-trioxo-1,2,5-thiadiazolidin-2-yl)-phenyl]-N-phenylpropionamide | $(M - 1)^- = 374$ | 0.68 A |
| 107 | 3-[3-Hydroxy-4-(1,1,4-trioxo-1,2,5-thiadiazolidin-2-yl)-phenyl]-N-o-tolyl-propionamide | $(M - 1)^- = 388$ | 0.63 A |

EXAMPLE 108

3-[3-Hydroxy-4-(1,1,4-trioxo-1,2,5-thiadiazolidin-2-yl)-phenyl]-N-isopropyl-propionamide

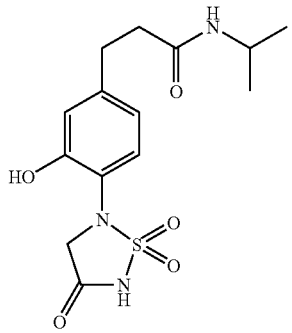

A. (E)-3-{3-Benzyloxy-4-[1,1,4-trioxo-5-(2-trimethylsilanylethyl)-1,2,5-thiadiazolidin-2-yl]-phenyl}-N-isopropylacrylamide To a mixture of 5-(2-benzyloxy-4-iodophenyl)-1,1-dioxo-2-(2-trimethylsilanylethyl)-1,2,5-thiadiazolidin-3-one (240 mg, 0.44 mmol), N-isopropylacrylamide (60 mg, 0.53 mmol) and triethylamine (445 mg, 0.44 mmol) in MeCN (5 mL) in a pressure vessel is added Pd(OAc)$_2$ (5 mg) and the mixture is heated at 100° C. for 8 h. The solvent is removed under reduced pressure and the residue is purified by flash chromatography using hexane/EtOAc (86:15) as eluent to give the title compound as a solid.

B. (E)-3-[3-Benzyloxy-4-(1,1,4-trioxo-1,2,5-thiadiazolidin-2-yl)-phenyl]-N-isopropylacrylamide The title compound is prepared from (E)-3-{3-benzyloxy-4-[1,1,4-trioxo-5-(2-trimethylsilanylethyl)-1,2,5-thiadiazolidin-2-yl]-phenyl}-N-isopropylacrylamide analogous to Example 97, step E.

C. 3-[3-Hydroxy-4-(1,1,4-trioxo-1,2,5-thiadiazolidin-2-yl)-phenyl]-N-isopropyl-propionamide The title compound is prepared from (E)-3-[3-benzyloxy-4-(1,1,4-trioxo-1,2,5-thiadiazolidin-2-yl)-phenyl]-N-isopropylacrylamide analogous to Example 95, step C: $(M-1)^-=340$.

EXAMPLE 109

2-{3-[3-Hydroxy-4-(1,1,4-trioxo-1,2,5-thiadiazolidin-2-yl)-phenyl]-propionylamino}-2-methylpropionic Acid

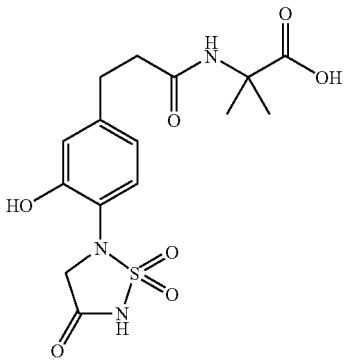

A. 5-{2-Benzyloxy-4-[(E)-2-(4,4-dimethyl-5-oxo-4,5-dihydro-oxazol-2-yl)-vinyl]-phenyl}-1,1-dioxo-2-(2-trimethylsilanylethyl)-1,2,5-thiadiazolidin-3-one The title compound is prepared using 5-(2-benzyloxy-4-iodophenyl)-1,1-dioxo-2-(2-trimethylsilanylethyl)-1,2,5-thiadiazolidin-3-one and 4,4-dimethyl-2-vinyl-4H-oxazol-5-one analogous to Example 108, step A.

B. 2-{(E)-3-[3-Benzyloxy-4-(1,1,4-trioxo-1,2,5-thiadiazolidin-2-yl)-phenyl]-acryloylamino}-2-methylpropionic Acid The title compound is prepared from 5-{2-benzyloxy-4-[(E)-2-(4,4-dimethyl-5-oxo-4,5-dihydro-oxazol-2-yl)-vinyl]-phenyl}-1,1-dioxo-2-(2-trimethylsilanylethyl)-1,2,5-thiadiazolidin-3-one analogous to Example 97, step E.

C. 2-{3-[3-Hydroxy-4-(1,1,4-trioxo-1,2,5-thiadiazolidin-2-yl)-phenyl]-propionylamino}-2-methylpropionic Acid A solution of 2-{(E)-3-[3-benzyloxy-4-(1,1,4-trioxo-1,2,5-thiadiazolidin-2-yl)-phenyl]-acryloylamino}-2-methylpropionic acid (40 mg) in EtOAc (4 mL) is hydrogenated at 1 atm over 20 mg of 10% Pd/C for 24 h. The catalyst is filtered through Celite and the solvent removed under reduced pressure to give the title compound as a yellow solid: $(M-1)^-=384$, HPLC retention time=0.71 min. (Method A).

EXAMPLE 110

2-Hydroxy-6-(4-{3-[3-hydroxy-4-(1,1,4-trioxo-1,2,5-thiadiazolidin-2-yl)-phenyl]-propionylamino}-butoxy)-benzoic Acid Methyl Ester

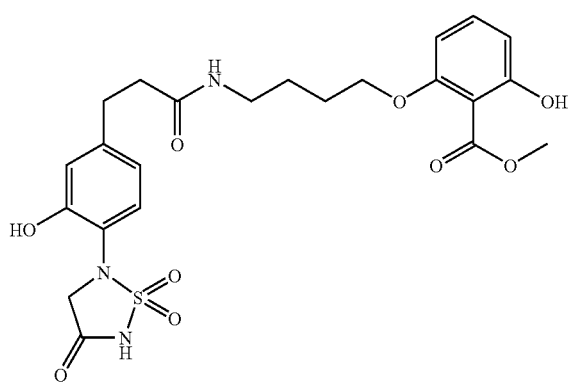

A. 2-(4-tert-Butoxycarbonylaminobutoxy)-6-hydroxybenzoic acid methyl ester (J. Med. Chem. 46, 3437 (2003))

To a solution of methyl 2,6-dihydroxybenzoate (1.0 g, 5.95 mmol) and 4-(Boc-amino)-1-butanol (1.1 mL, 5.95 mmol) in 60 mL THF is added $PPh_3$ (1.7 g, 6.5 mmol) and DEAD (2.97 mL, 6.5 mmol) and the mixture is stirred at RT overnight. The solvent is removed under reduced pressure and the residue is purified by flash chromatography eluting with hexanes/EtOAc (5:1 to 2:1) to give the title compound as a colorless liquid: $^1$H NMR (CDCl$_3$) δ 11.42 (s, 1H), 7.29 (t, J=8.34 Hz, 1H), 6.57 (d, J=8.34 Hz, 1H), 6.37 (d, J=8.34 Hz, 1H), 4.63 (s, 1H), 3.99 (t, J=6.06 Hz, 2H), 3.93 (s, 3H), 3.22-3.17 (m, 2H), 1.88-1.81 (m, 2H), 1.74-1.67 (m, 2H), 1.43 (s, 9H); $(M-1)^-=338$.

B. 2-Benzyloxy-6-(4-tert-butoxycarbonylaminobutoxy)-benzoic Acid Methyl Ester To a solution of 2-(4-tert-butoxycarbonylaminobutoxy)-6-hydroxybenzoic acid methyl ester (1.5 g, 4.4 mmol) in DMF (20 mL) is added benzyl bromide (0.56 mL, 4.6 mmol) and $K_2CO_3$ (1.8 g, 13.0 mmol). The suspension is stirred at RT for 3 h then is poured into water and extracted with EtOAc. The organic layer is washed with water and brine, and dried over sodium sulfate. The solvent is removed under reduced pressure and the residue purified by flash chromatography eluting with hexanes/EtOAc (5:1 to 1:1) to afford the title compound as a colorless liquid: $^1$H NMR (CDCl$_3$) δ 7.38-7.19 (m, 6H), 6.57-6.51 (dd, J=8.34, 12.63 Hz, 2H), 5.10 (s, 1H), 4.60 (s, 1H), 4.00 (t, J=6.06 Hz, 2H), 3.88 (s, 3H), 3.18-3.13 (m, 2H), 1.81-1.75 (m, 2H), 1.66-1.59 (m, 2H), 1.43 (s, 9H).

C. 2-(4-Aminobutoxy)-6-benzyloxybenzoic Acid Methyl Ester

A solution of 2-benzyloxy-6-(4-tert-butoxycarbonylaminobutoxy)-benzoic acid methyl ester (1.6 g, 3.7 mmol) in 30 mL of methylene chloride/TFA (2:1) is stirred at RT for 20 min. The solvent is removed under reduced pressure and the residue is re-dissolved in methylene chloride, washed with sat. NaHCO$_3$, water and brine, and dried over sodium sulfate. The solvent is removed under reduced pressure to afford the title compound as a colorless liquid: $(M+1)^+=330$.

D. 2-Hydroxy-6-(4-{3-[3-hydroxy-4-(1,1,4-trioxo-1,2,5-thiadiazolidin-2-yl)-phenyl]-propionylamino}-butoxy)-benzoic Acid Methyl Ester The title compound is prepared using (E)-3-[3-benzyloxy-4-(1,1,4-trioxo-1,2,5-thiadiazolidin-2-yl)-phenyl]-acrylic acid 2-(4-aminobutoxy)-6-benzyloxybenzoic acid methyl ester analogous to Example 100 steps C and D: white solid: mp=85-90° C.; $^1$H NMR (DMSO-d$_6$) δ 9.88 (s, 1H), 7.79 (t, J=5.31 Hz, 1H), 7.23 (d, J=8.08 Hz), 7.14 (t, J=8.34 Hz, 1 H), 6.71 (d, J=1.77 Hz), 6.63 (dd, J=1.77, 8.09 Hz), 6.47 (q, J=6.07 Hz, 2H), 4.23 (s, 2H), 3.91 (t, J=6.07 Hz, 2H), 3.72 (s, 3H), 3.05 (q, J=6.57 Hz, 2H), 2.71 (t, J=7.07 Hz, 2H), 2.31 (t, J=8.09 Hz, 2H), 1.59 (m, 2H), 1.46 (m, 2H); $(M-1)^-=520$.

EXAMPLES 111 TO 122

The following compounds are prepared using (E)-3-[3-benzyloxy-4-(1,1,4-trioxo-1,2,5-thiadiazolidin-2-yl)-phenyl]-acrylic acid and the appropriate 4-phenoxybutylamine derivative according to the general procedures outlined in Example 110. For Example 112, the methyl ester of Example 111 is converted to the acid by base hydrolysis prior to hydrogenation.

| Example | Chemical Name | MS (m/z) | Retention time (min) Method |
|---|---|---|---|
| 111 | 2-(4-{3-[3-Hydroxy-4-(1,1,4-trioxo-1,2,5-thiadiazolidin-2-yl)-phenyl]-propionylamino}-butoxy)-benzoic acid methyl ester | $(M-1)^- = 504$ | 0.96 A |

| Example | Chemical Name | MS (m/z) | Retention time (min) Method |
|---|---|---|---|
| 112 | 2-(4-{3-[3-Hydroxy-4-(1,1,4-trioxo-1,2,5-thiadiazolidin-2-yl)-phenyl]-propionylamino}-butoxy)-benzoic acid | (M − 1)⁻ = 490 | 0.55 A |
| 113 | 3-[3-Hydroxy-4-(1,1,4-trioxo-1,2,5-thiadiazolidin-2-yl)-phenyl]-N-(4-phenoxybutyl)-propionamide | (M − 1)⁻ = 446 | 1.05 A |
| 114 | 3-[3-Hydroxy-4-(1,1,4-trioxo-1,2,5-thiadiazolidin-2-yl)-phenyl]-N-[4-(2-trifluoromethylphenoxy)-butyl]-propionamide | (M − 1)⁻ = 514 | 1.35 A |
| 115 | 3-[3-Hydroxy-4-(1,1,4-trioxo-1,2,5-thiadiazolidin-2-yl)-phenyl]-N-[4-(2-methanesulfonylphenoxy)-butyl]-propionamide | (M − 1)⁻ = 524 | 1.02 A |
| 116 | 3-[3-Hydroxy-4-(1,1,4-trioxo-1,2,5-thiadiazolidin-2-yl)-phenyl]-N-[4-(3-methoxyphenoxy)-butyl]-propionamide | (M − 1)⁻ = 476 | 1.07 A |
| 117 | N-[4-(2,3-Dimethoxyphenoxy)-butyl]-3-[3-hydroxy-4-(1,1,4-trioxo-1,2,5-thiadiazolidin-2-yl)-phenyl]-propionamide | (M − 1)⁻ = 506 | 1.03 A |
| 118 | N-[4-(3-Hydroxyphenoxy)-butyl]-3-[3-hydroxy-4-(1,1,4-trioxo-1,2,5-thiadiazolidin-2-yl)-phenyl]-propionamide | (M − 1)⁻ = 462 | 0.70 A |
| 119 | N-[4-(2-Hydroxyphenoxy)-butyl]-3-[3-hydroxy-4-(1,1,4-trioxo-1,2,5-thiadiazolidin-2-yl)-phenyl]-propionamide | (M − 1)⁻ = 462 | 1.01 A |
| 120 | N-[4-(3-Hydroxy-2-methoxyphenoxy)-butyl]-3-[3-hydroxy-4-(1,1,4-trioxo-1,2,5-thiadiazolidin-2-yl)-phenyl]-propionamide | (M − 1)⁻ = 492 | 0.61 A |
| 121 | N-[4-(3-Hydroxy-2-methylphenoxy)-butyl]-3-[3-hydroxy-4-(1,1,4-trioxo-1,2,5-thiadiazolidin-2-yl)-phenyl]-propionamide | (M − 1)⁻ = 476 | 0.96 A |
| 122 | N-[4-(2-Acetyl-3-methoxyphenoxy)-butyl]-3-[3-hydroxy-4-(1,1,4-trioxo-1,2,5-thiadiazolidin-2-yl)-phenyl]-propionamide | (M − 1)⁻ = 518 | 1.01 A |

EXAMPLE 123

2-Hydroxy-6-(4-{3-[3-hydroxy-4-(1,1,4-trioxo-1,2,5-thiadiazolidin-2-yl)-phenyl]-propionylamino}-butoxy)-N,N-dimethylbenzamide

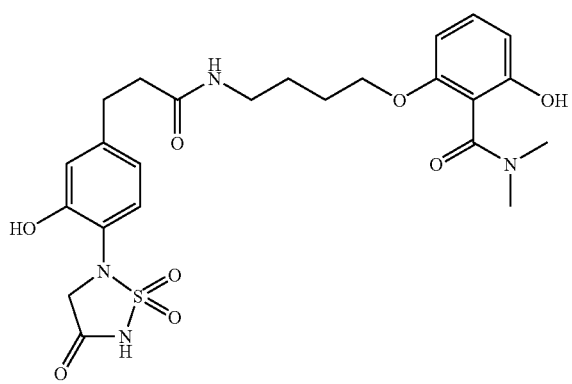

A. (4-Iodobutyl)-carbamic Acid Tert-butyl Ester

To a suspension of PPh₃-resin (16.4 g, 21.1 mmol) in methylene chloride (150 mL) at 0° C. is added iodine (5.4 g, 21.2 mmol) and imidazole (1.66 g, 24.4 mmol) then stirring is continued at 0° C. for 45 min. To this is added (4-hydroxybutyl)-carbamic acid tert-butyl ester (2.0 g, 10.6 mmol) and the suspension is refluxed for 2 h. The suspension is filtered and the organic layer is washed with a saturated sodium bisulfite solution, water and brine, and dried over sodium sulfate. The solvent is removed under reduced pressure to afford the title compound as pale yellow liquid: ¹H NMR (CDCl₃) δ 4.51 (s, 1H), 3.21-3.17 (t, J=6.82 Hz, 2H), 3.16-3.11 (q, J=6.82 Hz, 2H), 1.88-1.81 (m, 2H), 1.62-1.55 (m, 2H), 1.43 (s, 9H).

B. 2,6-Dimethoxy-N,N-dimethylbenzamide

To a stirred solution of dimethylamine (2M in THF, 3 mL) and THF (2 mL) is added 2,6-dimethoxybenzoyl chloride (200.6 mg, 1 mmol) in THF (2 mL) dropwise. After the addition, the solution is stirred at RT for 1 h. Water is added and the suspension is extracted with EtOAc. The organic layer is washed with water and brine, and dried over sodium sulfate. The solvent is removed under reduced pressure to afford the title compound: ¹H NMR (CDCl₃) δ 7.26-7.22 (t, J=8.34 Hz, 1H), 6.56-6.53 (d, J=8.33 Hz, 2H), 3.79 (s, 6H), 3.12 (s, 3H), 2.82 (s, 3H).

C. 2,6-Dihydroxy-N,N-dimethylbenzamide

To a solution of 2,6-dimethoxy-N,N-dimethylbenzamide (100 mg, 0.48 mmol) in methylene chloride (2.5 mL) is added BBr₃ (1.0M in methylene chloride, 1.4 mL) dropwise and the mixture is stirred at RT for 18 h. Water is added and the suspension is extracted with EtOAc. The organic layer is washed with water and brine, and dried over sodium sulfate. The solvent is removed under reduced pressure to give the title compound: ¹H NMR (DMSO-d₆) δ 9.35 (s, 2H), 6.93-6.89 (t, J=8.34 Hz, 1H), 6.29-6.27 (d, J=8.09 Hz, 2H), 2.89 (s, 3H), 2.86 (s, 3H).

D. 4-(3-Benzyloxy-2-dimethylcarbamoylphenoxy)-butyl]-carbamic Acid Tert-butyl Ester To a stirred solution of 2,6-dihydroxy-N,N-dimethylbenzamide (150 mg, 0.83 mmol) in DMF (10 mL) is added (4-iodobutyl)-carbamic acid tert-butyl ester (248 mg, 0.83 mmol) and $K_2CO_3$ (344 mg, 2.5 mmol). The suspension is stirred at RT for 18 h then benzyl bromide (0.10 mL, 0.83 mmol) is added and the suspension is stirred at RT for another 3 h. The suspension is poured into water and extracted with EtOAc. The organic layer is washed with water and brine, and dried over sodium sulfate. The solvent is removed under reduced pressure and the residue is purified by flash chromatography, eluting with hexanes/EtOAc (5:1 to 1:1) to afford the title compound as a pale yellow liquid: $^1$H NMR (CDCl$_3$) δ 7.38-7.25 (m, 5H), 7.19-7.15 (t, J=8.34 Hz, 1H), 6.57-6.55 (d, J=8.34 Hz, 1H), 6.54-6.52 (d, J=8.34 Hz, 1H), 5.11-5.09 (d, J=6.57 Hz, 2H), 4.92 (s, 1H), 4.01-3.98 (t, J=6.07 Hz, 2H), 3.17-3.12 (m, 2H), 3.11 (s, 3H), 2.83 (s, 3H), 1.81-1.74 (m, 2H), 1.66-1.59 (m, 2H), 1.43 (s, 9H).

E. 2-(4-Aminobutoxy)-6-benzyloxy-N,N-dimethylbenzamide

The title compound is prepared from 4-(3-benzyloxy-2-dimethylcarbamoylphenoxy)-butyl]-carbamic acid tert-butyl ester analogous to Example 110, step C.

F. 2-Hydroxy-6-(4-{3-[3-hydroxy-4-(1,1,4-trioxo-1,2,5-thiadiazolidin-2-yl)-phenyl]-propionylamino}-butoxy)-N,N-dimethylbenzamide The title compound is prepared using (E)-3-[3-benzyloxy-4-(1,1,4-trioxo-1,2,5-thiadiazolidin-2-yl)-phenyl]-acrylic acid and 2-(4-aminobutoxy)-6-benzyloxy-N,N-dimethylbenzamide analogous to Example 100 steps C and D: $^1$H NMR (DMSO-d$_6$) δ 9.78 (s, 1H), 9.54 (s, 1H), 7.83-7.80 (t, J=5.55 Hz, 1H), 7.22-7.20 (d, J=8.08 Hz, 1H), 7.09-7.05 (t, J=8.34 Hz, 1H), 6.73 (d, J=1.76 Hz, 1H), 6.66-6.63 (dd, J=1.77, 8.09 Hz, 1H), 6.46-6.44 (d, J=8.08 Hz, 2H), 4.38 (s, 2H), 3.93-3.86 (m, 2H), 3.08-3.02 (m, 2H), 2.91 (s, 3H), 2.73-2.69 (t, J=6.32 Hz, 2H), 2.71 (s, 3H), 2.33-2.29 (t, J=8.34 Hz, 2H), 1.59-1.53 (m, 2H), 1.48-1.42 (m, 2H); (M−1)$^-$=533.

EXAMPLES 124 TO 125

The following compounds are prepared using (E)-3-[3-benzyloxy-4-(1,1,4-trioxo-1,2,5-thiadiazolidin-2-yl)-phenyl]-acrylic acid and the appropriate 2-(4-aminobutoxy)-N,N-dimethylbenzamide derivative analogous to Example 123, step F.

EXAMPLE 126

2-Hydroxy-6-(4-{3-[3-hydroxy-4-(1,1,4-trioxo-1,2,5-thiadiazolidin-2-yl)-phenyl]-propionylamino}-butoxy)-benzoic Acid

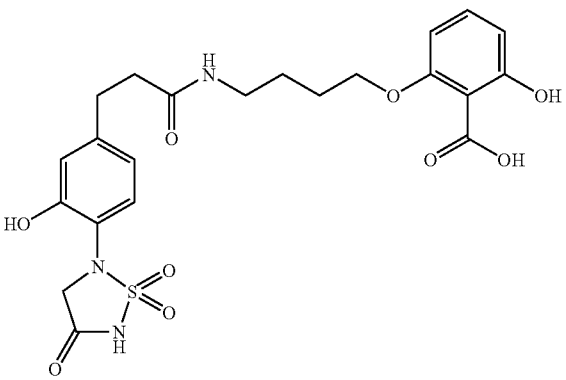

A. 2,6-Dihydroxybenzoic Acid Benzyl Ester

To a solution of 2,6-dihydroxybenzoic acid (500 mg, 3.24 mmol) in ethanol (8 mL) is added NaOH (130 mg, 3.24 mmol). After the mixture is stirred at RT for 3 h, the solvent is removed under reduced pressure. The resulting sodium salt is dissolved in DMF (10 mL) then benzyl bromide (0.39 mL, 3.24 mmol) is added and the mixture is stirred at RT for 18 h. Water is added and the mixture is extracted with EtOAc. The organic phase is washed with water and brine then is dried over sodium sulfate. The solvent is removed under reduced pressure and the residue is purified by flash chromatography using hexane/EtOAc (10:1) as eluent to give the title compound as an oil.

B. 2-(4-tert-Butoxycarbonylaminobutoxy)-6-hydroxybenzoic Acid Benzyl Ester

The title compound is prepared from 2,6-dihydroxybenzoic acid benzyl ester and 4-(Boc-amino)-1-butanol analogous to Example 1109 step A.

C. 2-Benzyloxy-6-(4-tert-butoxycarbonylaminobutoxy)-benzoic Acid Benzyl Ester The title compound is prepared from 2-(4-tert-butoxycarbonylaminobutoxy)-6-hydroxybenzoic acid benzyl ester analogous to Example 110, step B.

| Example | Chemical Name | MS (m/z) | Retention time (min) Method |
|---|---|---|---|
| 124 | 2-(4-{3-[3-Hydroxy-4-(1,1,4-trioxo-1,2,5-thiadiazolidin-2-yl)-phenyl]-propionylamino}-butoxy)-6,N,N-trimethylbenzamide | (M − 1)$^-$ = 531 | 0.92 A |
| 125 | 2-Fluoro-6-(4-{3-[3-hydroxy-4-(1,1,4-trioxo-1,2,5-thiadiazolidin-2-yl)-phenyl]-propionylamino}-butoxy)-N,N-dimethylbenzamide | (M − 1)$^-$ = 535 | 0.91 A |

D. 2-(4-Aminobutoxy)-6-benzyloxybenzoic Acid Benzyl Ester

The title compound is prepared from 2-benzyloxy-6-(4-tert-butoxycarbonylaminobutoxy)-benzoic acid benzyl ester analogous to Example 110, step C.

E. 2-Hydroxy-6-(4-{3-[3-hydroxy-4-(1,1,4-trioxo-1,2,5-thiadiazolidin-2-yl)-phenyl]-propionylamino}-butoxy)-benzoic Acid The title compound is prepared using (E)-3-[3-benzyloxy-4-(1,1,4-trioxo-1,2,5-thiadiazolidin-2-yl)-phenyl]-acrylic acid 2-(4-aminobutoxy)-6-benzyloxybenzoic acid benzyl ester analogous to Example 100 steps C and D: $(M-1)^-=506$. HPLC retention time 0.64 min. (Method A).

EXAMPLE 127

N-[4-(2-Acetyl-3-hydroxyphenoxy)-butyl]-3-[3-hydroxy-4-(1,1,4-trioxo-1,2,5-thiadiazolidin-2-yl)-phenyl]-propionamide

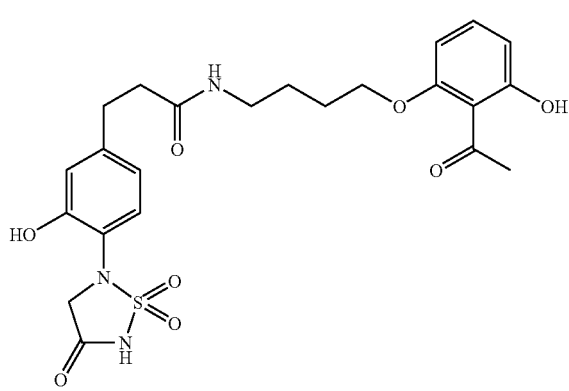

A. 1-(2-Benzyloxy-6-hydroxyphenyl)-ethanone

To a solution of 1-(2,6-dihydroxyphenyl)-ethanone (304 mg, 2 mmol) and benzyl bromide (0.255 mL, 2.1 mmol) in DMF (10 mL) is added $K_2CO_3$ (552 mg; 4 mmol) and the mixture is stirred at RT for 18 h. Water is added and the mixture is extracted with EtOAc. The organic phase is washed with water and brine then is dried over sodium sulfate. The solvent is removed under reduced pressure and the residue is purified by flash chromatography using hexane/EtOAc (10:1) as eluent to give the title compound.

B. [4-(2-Acetyl-3-benzyloxyphenoxy)-butyl]-carbamic Acid Tert-butyl Ester

To a solution of 1-(2-benzyloxy-6-hydroxyphenyl)-ethanone (100 mg, 0.41 mmol) and (4-iodobutyl)-carbamic acid tert-butyl ester (Example 123, step A) (150 mg, 0.5 mmol) in DMF (5 mL) is added $K_2CO_3$ (113 mg, 0.82 mmol) and the mixture is stirred at RT for 18 h. Water is added and the mixture is extracted with EtOAc. The organic phase is washed with water and brine then is dried over sodium sulfate. The solvent is removed under reduced pressure and the residue is purified by flash chromatography using hexane/EtOAc (10:1) as eluent to give the title compound as a white solid.

C. 1-[2-(4-Aminobutoxy)-6-benzyloxyphenyl]-ethanone

The title compound is prepared from [4-(2-acetyl-3-benzyloxyphenoxy)-butyl]-carbamic acid tert-butyl ester analogous to Example 110, step C.

D. N-[4-(2-Acetyl-3-hydroxyphenoxy)-butyl]-3-[3-hydroxy-4-(1,1,4-trioxo-1,2,5-thiadiazolidin-2-yl)-phenyl]-propionamide The title compound is prepared using (E)-3-[3-benzyloxy-4-(1,1,4-trioxo-1,2,5-thiadiazolidin-2-yl)-phenyl]-acrylic acid and 1-[2-(4-aminobutoxy)-6-benzyloxyphenyl]-ethanone analogous to Example 100 steps C and D: $(M-1)^-=504$. HPLC retention time: 1.09 min. (Method A).

EXAMPLE 128

N-[4-(2-Cyano-3-hydroxyphenoxy)-butyl]-3-[3-hydroxy-4-(1,1,4-trioxo-1,2,5-thiadiazolidin-2-yl)-phenyl]-propionamide

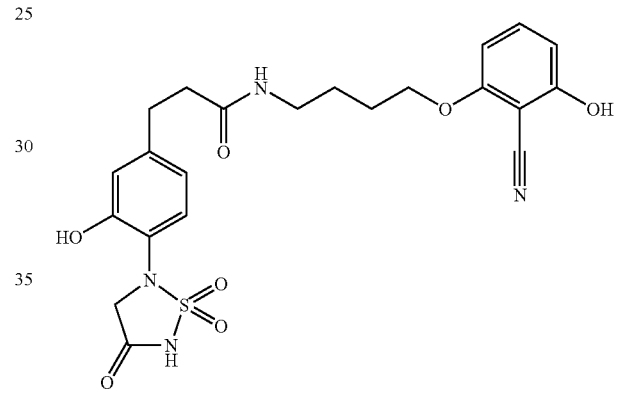

A. 2,6-Bis-benzyloxybenzoic Acid Benzyl Ester

To a solution of 2,6-dihydroxybenzoic acid (1.54 g, 10 mmol) and benzyl bromide (3.63 mL, 30.5 mmol) in DMF (20 mL) is added $K_2CO_3$ (4.83 g, 30.5 mmol) and the mixture is stirred at RT for 48 h. Water is added and the mixture is extracted with EtOAc. The organic phase is washed with water and brine then is dried over sodium sulfate. The solvent is removed under reduced pressure and the residue is purified by flash chromatography using hexane/EtOAc (8:1) as eluent to give the title compound.

B. (2,6-Bis-benzyloxyphenyl)-methanol

To a solution of 2,6-bis-benzyloxybenzoic acid benzyl ester (3.0 g, 6.6 mmol) in THF (15 mL) at 0° C. is added dropwise 7.92 mL of $LiAlH_4$ (1.0M in THF) then the mixture is stirred at RT for 18 h. Saturated sodium sulfate solution (1 ml) is added carefully and the resulting precipitate is filtered. The filtrate is evaporated to give the title compound. This is used directly in the next reaction.

C. 2,6-Bis-benzyloxybenzaldehyde

To a solution of (2,6-bis-benzyloxyphenyl)-methanol (3.0 g) in methylene chloride (40 mL) is added Dess-Martin reagent (1.5 equivalents, 15% by weight in methylene chloride) and the mixture is stirred at RT for 30 min. Saturated NaHCO₃ is added and the organic phase is washed with water and brine then is dried over sodium sulfate. The solvent is removed under reduced pressure and the residue is purified by flash chromatography using hexane/EtOAc (7:1) as eluent to give the title compound as a reddish liquid.

D. 2,6-Dihydroxybenzaldehyde

To a solution of 2,6-bis-benzyloxybenzaldehyde (1.9 g, 6 mmol) in methylene chloride (15 mL) is added BBr₃ (18 mL, 18 mmol, 1M in methylene chloride) and the mixture is stirred at RT for 18 h. Water is added to the mixture and the methylene chloride is removed under reduced pressure. The aqueous is extracted with EtOAc and the organic phase is washed with water and brine then is dried over sodium sulfate. The solvent is removed under reduced pressure and the residue is purified by flash chromatography using hexane/EtOAc (5:1) as eluent to give the title compound as a yellow solid.

E. 2,6-Dihydroxybenzonitrile

A mixture of 2,6-dihydroxybenzaldehyde (300 mg, 2.17 mmol) and hydroxylamine sulfate (758 mg, 6.51 mmol) in water (30 mL) is stirred at RT for 45 min. Methylene chloride (60 mL) is added followed by NaHCO₃ (911 mg, 10.85 mmol) and the mixture is stirred at RT for 30 min. The organic phase is separated and dried over sodium sulfate and the solvent removed under reduced pressure to give the title compound as a pale yellow solid.

F. [4-(2-Cyano-3-hydroxyphenoxy)-butyl]-carbamic Acid Tert-butyl Ester

The title compound is prepared from 2,6-dihydroxybenzonitrile and 4-(Boc-amino)-1-butanol analogous to Example 110, step A.

G. [4-(3-Benzyloxy-2-cyanophenoxy)-butyl]-carbamic Acid Tert-butyl Ester

The title compound is prepared from [4-(2-cyano-3-hydroxyphenoxy)-butyl]-carbamic acid tert-butyl ester analogous to Example 110, step B.

H. 2-(4-Aminobutoxy)-6-benzyloxybenzonitrile

The title compound is prepared from [4-(3-benzyloxy-2-cyanophenoxy)-butyl]-carbamic acid tert-butyl ester analogous to Example 110, step C.

I. N-[4-(2-Cyano-3-hydroxyphenoxy)-butyl]-3-[3-hydroxy-4-(1,1,4-trioxo-1,2,5-thiadiazolidin-2-yl)-phenyl]-propionamide The title compound is prepared using (E)-3-[3-benzyloxy-4-(1,1,4-trioxo-1,2,5-thiadiazolidin-2-yl)-phenyl]-acrylic acid and 2-(4-aminobutoxy)-6-benzyloxybenzonitrile analogous to Example 100 steps C and D: (M−1)⁻=487. HPLC retention time: 0.82 min. (Method A).

EXAMPLE 129

N-[4-(3-Hydroxy-2-methanesulfinylphenoxy)-butyl]-3-[3-hydroxy-4-(1,1,4-trioxo-1,2,5-thiadiazolidin-2-yl)-phenyl]-propionamide

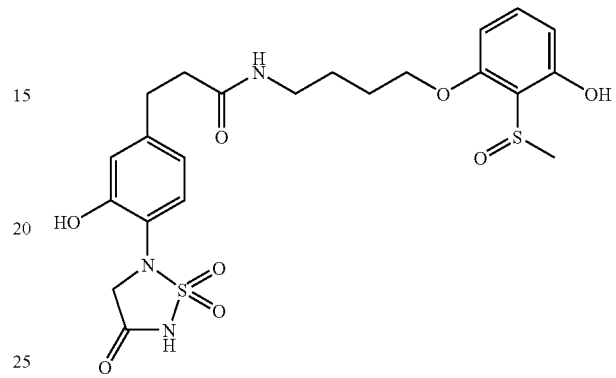

A. 1,3-Dimethoxy-2-methylsulfanylbenzene

To a solution of 1,3-dimethoxybenzene (1.94 mL, 15 mmol) and TMEDA (2.35 mL, 15.75 mmol) in ether (40 mL) a under nitrogen atmosphere at 0° C. is added dropwise n-BuLi (9.84 mL, 1.6M in hexane, 15.75 mmol). The mixture is stirred at 0° C. for 30 min then dimethyl disulfide (1.33 mL, 15 mmol) is added and stirring is continued at RT for 30 min. The mixture is poured into dilute sulfuric acid and the ether layer is separated. The aqueous is extracted with ether. The ether solutions are combined and washed with water and brine then dried over sodium sulfate. The solvent is removed under reduced pressure to give the title compound as a white solid.

B. 2-Methylsulfanylbenzene-1,3-diol

To a solution of 1,3-dimethoxy-2-methylsulfanylbenzene (2.8 g, 15 mmol) in methylene chloride (40 mL) is added BBr₃ (30 mL, 30 mmol, 1M in methylene chloride) and the mixture is stirred at RT for 18 h. Water is added and the organic phase is washed with water and brine then is dried over sodium sulfate. The solvent is removed under reduced pressure to give the title compound as a pink solid.

C. [4-(3-Hydroxy-2-methylsulfanylphenoxy)-butyl]-carbamic Acid Tert-butyl Ester The title compound is prepared from 2-methylsulfanylbenzene-1,3-diol and 4-(Boc-amino)-1-butanol analogous to Example 1101 step A.

D. [4-(3-Benzyloxy-2-methylsulfanylphenoxy)-butyl]-carbamic Acid Tert-butyl Ester The title compound is prepared from [4-(3-hydroxy-2-methylsulfanylphenoxy)-butyl]-carbamic acid tert-butyl ester analogous to Example 110, step B.

E. [4-(3-Benzyloxy-2-methanesulfinylphenoxy)-butyl]-carbamic Acid Tert-butyl Ester To a solution of [4-(3-benzyloxy-2-methylsulfanylphenoxy)-butyl]-carbamic acid tert-butyl ester (600 mg, 1.44 mmol) in methylene chloride (15 mL) is added mCPBA (355 mg, 1.44 mmol) and the mixture is stirred at RT for 2 h. Water is added the organic phase is washed with saturated NaHCO₃, water and brine then is dried over sodium sulfate. The solvent is removed under reduced pressure to give the title compound as an oil.

F. 4-(3-Benzyloxy-2-methanesulfinylphenoxy)-butylamine

The title compound is prepared from [4-(3-benzyloxy-2-methanesulfinylphenoxy)-butyl]-carbamic acid tert-butyl ester analogous to Example 110, step C.

G. N-[4-(3-Hydroxy-2-methanesulfinylphenoxy)-butyl]-3-[3-hydroxy-4-(1,1,4-trioxo-1,2,5-thiadiazolidin-2-yl)-phenyl]-propionamide The title compound is prepared using (E)-3-[3-benzyloxy-4-(1,1,4-trioxo-1,2,5-thiadiazolidin-2-yl)-phenyl]-acrylic acid and 4-(3-benzyloxy-2-methanesulfinylphenoxy)-butylamine analogous to Example 100 steps C and D: (M−1)⁻=524. HPLC retention time: 0.89 min. (Method A).

EXAMPLE 130

N-[4-(3-Hydroxy-2-methanesulfonylphenoxy)-butyl]-3-[3-hydroxy-4-(1,1,4-trioxo-1,2,5-thiadiazolidin-2-yl)-phenyl]-propionamide

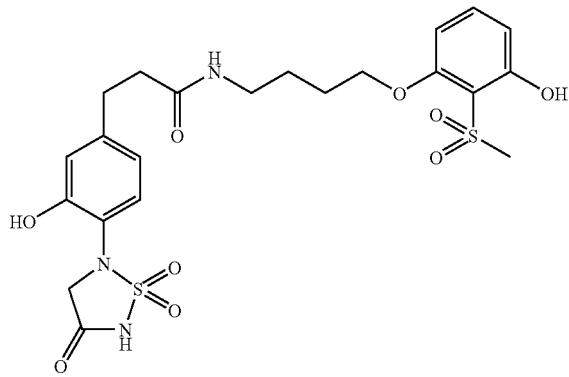

A. [4-(3-Benzyloxy-2-methanesulfonylphenoxy)-butyl]-carbamic Acid Tert-butyl Ester To a solution of [4-(3-benzyloxy-2-methylsulfanylphenoxy)-butyl]-carbamic acid tert-butyl ester (Example 129, step D) (600 mg, 1.44 mmol) in methylene chloride (15 mL) is added mCPBA (740 mg, 3.0 mmol) and the mixture is stirred at RT for 2 h. Water is added the organic phase is washed with saturated NaHCO₃, water and brine then is dried over sodium sulfate. The solvent is removed under reduced pressure to give the title compound as an oil.

B. 4-(3-Benzyloxy-2-methanesulfonylphenoxy)-butylamine

The title compound is prepared from [4-(3-benzyloxy-2-methanesulfonylphenoxy)-butyl]-carbamic acid tert-butyl ester analogous to Example 110, step C.

C. [4-(3-Benzyloxy-2-methanesulfonylphenoxy)-butyl]-carbamic Acid Tert-butyl Ester The title compound is prepared using (E)-3-[3-benzyloxy-4-(1,1,4-trioxo-1,2,5-thiadiazolidin-2-yl)-phenyl]-acrylic acid and 4-(3-benzyloxy-2-methanesulfonylphenoxy)-butylamine analogous to Example 100, steps C and D: (M−1)⁻=540. HPLC retention time: 0.92 min. (Method A).

EXAMPLE 131

2-(4-{2-Acetylamino-3-[3-hydroxy-4-(1,1,4-trioxo-1,2,5-thiadiazolidin-2-yl)-phenyl]-propionylamino}-butoxy)-6-hydroxybenzoic Acid Methyl Ester

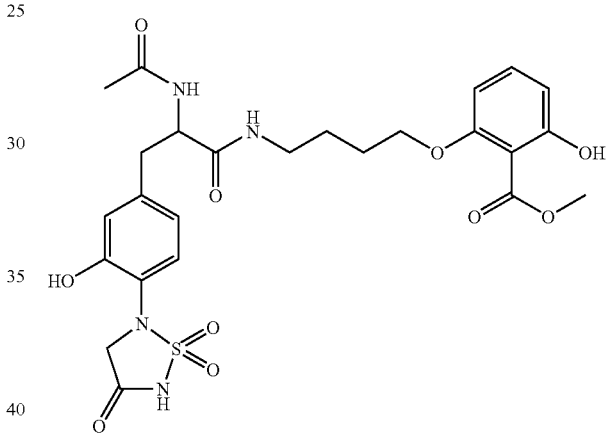

A. (E)-2-Acetylamino-3-[3-benzyloxy-4-(1,1,4-trioxo-1,2,5-thiadiazolidin-2-yl)-phenyl]-acrylic Acid Methyl Ester A mixture of 5-(2-benzyloxy-4-iodophenyl)-1,1-dioxo-1,2,5-thiadiazolidin-3-one (200 mg, 0.4 mmol), 2-acetylaminoacrylic acid methyl ester (16.6 mg, 0.54 mmol), triethylamine (0.75 mL, 5.4 mmol) and Pd(OAc)₂ (15 mg) in MeCN (5 mL) in a pressure vessel is heated at 100° C. for 18 h. The mixture is filtered and the solvent is removed under reduced pressure to give the title compound which is used directly in the next step.

B. (E)-2-Acetylamino-3-[3-benzyloxy-4-(1,1,4-trioxo-1,2,5-thiadiazolidin-2-yl)-phenyl]-acrylic Acid To a solution of (E)-2-acetylamino-3-[3-benzyloxy-4-(1,1,4-trioxo-1,2,5-thiadiazolidin-2-yl)-phenyl]-acrylic acid methyl ester is added 3 equivalents of NaOH (3N solution). After 4 h, three additional equivalents of NaOH is added and stirring is continued for 18 h. The solvent is removed under reduced pressure and the residue acidified with 1N HCl and the mixture is extracted with EtOAc. The organic phase is washed with water and brine then is dried over sodium sulfate. The solvent is removed under reduced pressure to give the title compound. This is used directly in the next step.

C. 2-(4-{(E)-2-Acetylamino-3-[3-benzyloxy-4-(1,1,4-trioxo-1,2,5-thiadiazolidin-2-yl)-phenyl]-acryloylamino}-butoxy)-6-benzyloxybenzoic Acid Methyl Ester To a solution of (E)-2-acetylamino-3-[3-benzyloxy-4-(1,1,4-trioxo-1,2,5-thiadiazolidin-2-yl)-phenyl]-acrylic acid (260 mg, 0.58 mmol) in DMF (10 mL) is added diisopropylethylamine (0.11 mL, 0.64 mmol) and HATU (243 mg, 0.64 mmol). The mixture is stirred at RT for 10 min then a solution of 2-(4-aminobutoxy)-6-benzyloxybenzoic acid methyl ester (Example 110, step C) (286 mg, 0.87 mmol) in DMF (1 mL) is added and stirring is continued for 18 h. The solvent is removed under reduced pressure to give the title compound which is used directly in the next step.

D. 2-(4-{2-Acetylamino-3-[3-hydroxy-4-(1,1,4-trioxo-1,2,5-thiadiazolidin-2-yl)-phenyl]-propionylamino}-butoxy)-6-hydroxybenzoic Acid Methyl Ester A solution of 2-(4-{(E)-2-acetylamino-3-[3-benzyloxy-4-(1,1,4-trioxo-1,2,5-thiadiazolidin-2-yl)-phenyl]-acryloylamino}-butoxy)-6-hydroxybenzoic acid methyl ester (300 mg) in 16 mL of EtOH/HOAc (1:1) is hydrogenated 1 atm over 10% Pd/C (70 mg) for 4 h. The catalyst is filtered, the solvent is removed under reduced pressure. The residue is purified by reverse phase HPLC and lyophilization to give the title compound as a white solid. This is converted to its potassium salt by addition of 1 equivalent of $KHCO_3$: $(M-1)^-=577$. HPLC retention time: 0-86 min. (Method A).

EXAMPLE 132

2-(4-{(S)-2-Acetylamino-3-[3-hydroxy-4-(1,1,4-trioxo-1,2,5-thiadiazolidin-2-yl)-phenyl]-propionylamino}-butoxy)-6-hydroxybenzoic Acid Methyl Ester

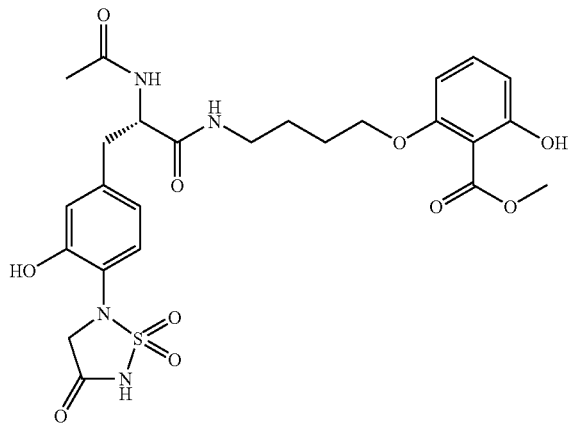

A. (R)-2-tert-Butoxycarbonylamino-3-iodopropionic Acid Tert-butyl Ester

To a suspension of $PPh_3$-resin (5 g, 6.5 mmol) in methylene chloride (50 mL) at 0° C. is added iodine (1.65 g, 6.5 mmol) and imidazole (0.485 g, 7.12 mmol) then stirring is continued at 0° C. for 45 min. To this is added (S)-2-tert-butoxycarbonylamino-3-hydroxypropionic acid tert-butyl ester (0.81 g, 3.1 mmol) and the suspension is refluxed for 45 min. The suspension is filtered and the organic layer is washed with a saturated sodium bisulfite solution, water and brine, and dried over sodium sulfate. The solvent is removed under reduced pressure to afford the title compound as a white solid.

B. (S)-3-{3-Benzyloxy-4-[1,1,4-trioxo-5-(2-trimethylsilanylethyl)-1,2,5-thiadiazolidin-2-yl]-phenyl}-2-tert-butoxycarbonylaminopropionic Acid Tert-butyl Ester To a suspension of zinc powder (645 mg, 9.9 mmol) in DMF (1 mL) under argon is added chlorotrimethylsilane (83 mg, 0.76 mmol) and the mixture is stirred at RT for 30 min. To this is added a solution of (R)-2-tert-butoxycarbonylamino-3-iodopropionic acid tert-butyl ester (1.1 g, 2.96 mmol) in DMF (1.8 mL) dropwise and the mixture is stirred at RT for 30 min. An additional 2.5 mL of DMF is added and any insoluble material is filtered. The filtrate is added to a mixture of 5-(2-benzyloxy-4-iodophenyl)-1,1-dioxo-2-(2-trimethylsilanylethyl)-1,2,5-thiadiazolidin-3-one (900 mg, 1.65 mmol), tri-o-tolylphosphine (100 mg, 0.33 mmol) and $Pd_2(dba)_3$ (74 mg, 0.08 mmol) and the mixture is stirred at RT for 90 min. Water is added and the mixture is extracted with EtOAc. The organic phase is washed with water (2×) and brine then is dried over sodium sulfate. The solvent is remover under reduced pressure and the residue is purified by flash chromatography using EtOAc/hexane (10%) as eluent to give the title compound as an off-white solid.

C. (S)-2-Amino-3-{3-benzyloxy-4-[1,1,4-trioxo-5-(2-trimethylsilanylethyl)-1,2,5-thiadiazolidin-2-yl]-phenyl}-propionic Acid Tert-butyl Ester To a solution of (S)-3-{3-benzyloxy-4-[1,1,4-trioxo-5-(2-trimethylsilanylethyl)-1,2,5-thiadiazolidin-2-yl]-phenyl}-2-tert-butoxycarbonylaminopropionic acid tert-butyl ester (760 mg, 1.15 mmol) in methylene chloride (10 mL) is added TFA (3 mL) and the mixture is stirred at RT for 45 min. The solution is carefully poured into 8% $NaHCO_3$ solution (50 mL) and the mixture is extracted with methylene chloride. The solvent is removed under reduced pressure to give the title compound which is used immediately in the next step.

D. (S)-2-Acetylamino-3-{3-benzyloxy-4-[1,1,4-trioxo-5-(2-trimethylsilanylethyl)-1,2,5-thiadiazolidin-2-yl]-phenyl}-propionic Acid Tert-butyl Ester To a Solution of (S)-2-Amino-3-{3-Benzyloxy-4-[1,1,4-Trioxo-5-(2-Trimethylsilanylethyl)-1,2,5-thiadiazolidin-2-yl]-phenyl}-propionic acid tert-butyl ester (150 mg, 0.27 mmol) and triethylamine (0.57 mL, 0.41 mmol) in methylene chloride (10 mL) at 0° C. is added acetyl chloride (0.21 mL, 0.3 mmol) dropwise then the mixture is stirred at RT for 2 h. Water and 1N HCl is added until pH 4 and the mixture is extracted with methylene chloride. The organic phase is washed with brine and dried over sodium sulfate. The solvent is removed under reduced pressure to give the title compound as an oil.

E. (S)-2-Acetylamino-3-[3-benzyloxy-4-(1,1,4-trioxo-1,2,5-thiadiazolidin-2-yl)-phenyl]-propionic Acid Tert-butyl Ester To a solution of (S)-2-acetylamino-3-{3-benzyloxy-4-[1,1,4-trioxo-5-(2-trimethylsilanylethyl)-1,2,5-thiadiazolidin- 2-yl]-phenyl}-propionic acid tert-butyl ester (137 mg, 0.23 mmol) in DMF (5 mL) is added CsF (175 mg, 1.15 mmol) and the mixture is stirred at 70° C. for 2 h. Ethyl acetate is added and the mixture is washed with 1N HCl and brine. The organic phase is dried over magnesium sulfate and the solvent removed under reduced pressure to give the title compound which is used directly in the next step.

F. (S)-2-Acetylamino-3-[3-benzyloxy-4-(1,1,4-trioxo-1,2,5-thiadiazolidin-2-yl)-phenyl]-propionic Acid A solution of (S)-2-acetylamino-3-[3-benzyloxy-4-(1,1,4-trioxo-1,2,5-thiadiazolidin-2-yl)-phenyl]-propionic acid tert-butyl ester (100 mg) in TFA/methylene chloride (1:1) is stirred at RT for 20 min. The solvent is removed under reduced pressure to give the title compound.

G. 2-(4-{(S)-2-Acetylamino-3-[3-benzyloxy-4-(1,1,4-trioxo-1,2,5-thiadiazolidin-2-yl)-phenyl]-propionylamino}-butoxy)-6-benzyloxybenzoic Acid Methyl Ester The title compound is prepared using (S)-2-acetylamino-3-[3-benzyloxy-4-(1,1,4-trioxo-1,2,5-thiadiazolidin-2-yl)-phenyl]-propionic acid and 2-(4-aminobutoxy)-6-benzyloxybenzoic acid methyl ester (Example 110, step C) analogous to Example 131, step C.

H. 2-(4-{(S)-2-Acetylamino-3-[3-hydroxy-4-(1,1,4-trioxo-1,2,5-thiadiazolidin-2-yl)-phenyl]-propionylamino}-butoxy)-6-hydroxybenzoic Acid Methyl Ester The title compound is prepared from 2-(4-{(S)-2-acetylamino-3-[3-benzyloxy-4-(1,1,4-trioxo-1,2,5-thiadiazolidin-2-yl)-phenyl]-propionylamino}-butoxy)-6-benzyloxybenzoic acid methyl ester analogous to Example 57, step D: (M−1)⁻=577. HPLC retention time: 0.91 min. (Method A)

EXAMPLE 133

3-[3-Hydroxy-4-(1,1,4-trioxo-1,2,5-thiadiazolidin-2-yl)-phenyl]-propionic Acid Methyl Ester

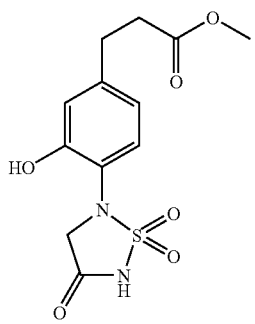

A. (E)-3-{3-Benzyloxy-4-[1,1,4-trioxo-5-(2-trimethylsilanylethyl)-1,2,5-thiadiazolidin-2-yl]-phenyl}-acrylic Acid Methyl Ester The title compound is prepared from 5-(2-benzyloxy-4-iodo-phenyl)-1,1-dioxo-2-(2-trimethylsilanylethyl)-1,2,5-thiadiazolidin-3-one and methyl acrylate analogous to Example 97, step A.

B. 3-[3-Hydroxy-4-(1,1,4-trioxo-1,2,5-thiadiazolidin-2-yl)-phenyl]-propionic Acid Methyl Ester The title compound is prepared from (E)-3-{3-benzyloxy-4-[1,1,4-trioxo-5-(2-trimethylsilanylethyl)-1,2,5-thiadiazolidin-2-yl]-phenyl}-acrylic acid methyl ester analogous to Example 51, steps B and C: (M+1)⁺=313.

EXAMPLE 134

3-[3-Hydroxy-4-(1,1,4-trioxo-1,2,5-thiadiazolidin-2-yl)-phenyl]-2-methylpropionic Acid Methyl Ester

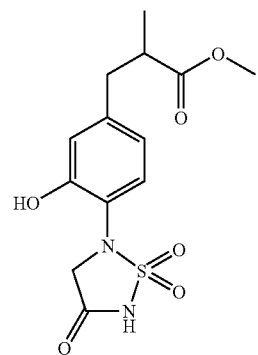

The title compound is prepared from 5-(2-benzyloxy-4-iodo-phenyl)-1,1-dioxo-2-(2-trimethylsilanylethyl)-1,2,5-thiadiazolidin-3-one and methyl methacrylate analogous to Example 133. (M+1)⁺=343. HPLC retention time=0.99 min (Method 14).

EXAMPLE 135

3-[3-Hydroxy-4-(1,1,4-trioxo-1,2,5-thiadiazolidin-2-yl)-phenyl]-2-methylpropionic Acid Tert-butyl Ester

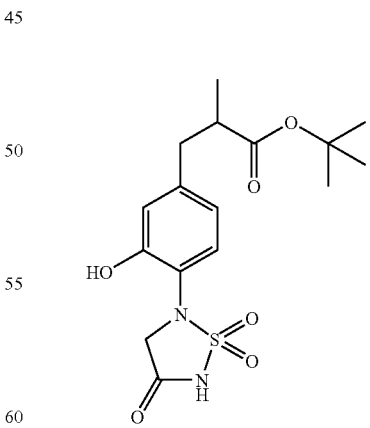

The title compound is prepared from 5-(2-benzyloxy-4-iodophenyl)-1,1-dioxo-2-(2-trimethylsilanylethyl)-1,2,5-thiadiazolidin-3-one and t-butyl methacrylate analogous to Example 133 with the modification that the TMS-ethyl group is removed after the Heck reaction.

EXAMPLE 136 AND EXAMPLE 136b (1R*,2R*)-2-[3-Hydroxy-4-(1,1,4-trioxo-1,2,5-thiadiazolidin-2-yl)-phenyl]-cyclopropanecarboxylic Acid Ethyl Ester (1R*,2S*)-2-[3-Hydroxy-4-(1,1,4-trioxo-1,2,5-thiadiazolidin-2-yl)-phenyl]-cyclopropanecarboxylic Acid Ethyl Ester

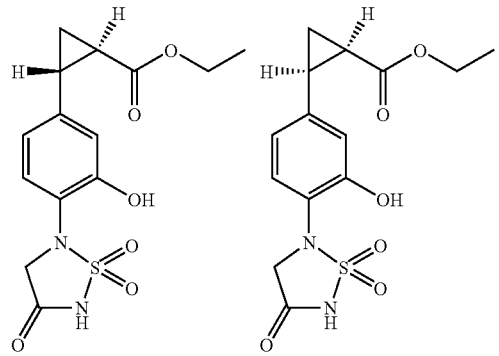

A. 2-{3-Benzyloxy-4-[1,1,4-trioxo-5-(2-trimethylsilanylethyl)-1,2,5-thiadiazolidin-2-yl]-phenyl}-cyclopropanecarboxylic Acid Ethyl Ester To a solution of 5-(2-benzyloxy-4-vinylphenyl)-1,1-dioxo-2-(2-trimethylsilanylethyl)-1,2,5-thiadiazolidin-3-one (Example 81, step A) (75 mg, 0.17 mmol) in methylene chloride is added rhodium acetate dimer (cat.). Ethyl diazoacetate (0.024 mL, 0.17 mmol) in methylene chloride (0.2 mL) is added dropwise via syringe pump over 4 h. The solvent is removed under reduced pressure and the crude material purified on silica gel using a gradient of 0-40% EtOAc/hexanes to give the title compound as a mixture of isomers (cis:trans 1:2) as a colorless oil: (M+H)$^+$=548.

B. 2-[3-Benzyloxy-4-(1,1,4-trioxo-1,2,5-thiadiazolidin-2-yl)-phenyl]-cyclopropanecarboxylic Acid Ethyl Ester To 2-{3-benzyloxy-4-[1,1,4-trioxo-5-(2-trimethylsilanylethyl)-1,2,5-thiadiazolidin-2-yl]-phenyl}-cyclopropanecarboxylic acid ethyl ester (75 mg, 0.14 mmol) in THF (3 mL) is added 1M TBAF in THF (0.21 mL) and the solution is stirred at 60° C. for 2 h. The reaction is cooled to RT and diluted with EtOAc and washed with 1N HCl and brine. The organic layer is dried over MgSO$_4$ and concentrated under reduced pressure to afford the title compound as a yellow oil, which is used in the next step without further purification: (M+H)$^+$=448.

C. 2-[3-Hydroxy-4-(1,1,4-trioxo-1,2,5-thiadiazolidin-2-yl)-phenyl]-cyclopropanecarboxylic Acid Ethyl Ester The title compounds are prepared analogous to the procedure described in Example 81, step G. The isomers are separated by reverse phase HPLC to afford (1R*,2R*)-2-[3-hydroxy-4-(1,1,4-trioxo-1,2,5-thiadiazolidin-2-yl)-phenyl]-cyclopropanecarboxylic acid ethyl ester and (1R*,2S*)-2-[3-hydroxy-4-(1,1,4-trioxo-1,2,5-thiadiazolidin-2-yl)-phenyl]-cyclopropanecarboxylic acid ethyl ester: (M−H)$^-$=339, rt 0.80 min (cis) and 0.84 min (trans); (cis) $^1$H NMR (MeOD) δ 7.26 (d, J=8.0 Hz, 1H), 6.75 (m, 1H), 6.71 (dd, J=8, 2 Hz, 1H), 4.23 (s, 2H), 3.83 (m, 2H), 2.51 (q, J=8 Hz, 1H), 2.0 (m, 1H), 1.53 (m, 1H), 1.24 (m, 2H), 0.95 (t, J=7.07 Hz, 3H); (trans) $^1$H NMR (MeOD) δ 7.23 (d, J=8.0 Hz, 1H), 6.56 (m, 1H), 6.52 (m, 1H), 4.19 (s, 2H), 4.06 (q, J=8.0 Hz, 2H), 2.25 (m, 1H), 1.75 (m, 1H), 1.38 (m, 1H), 1.20 (m, 1H), 1.17 (t, J=8.0 Hz, 3H).

EXAMPLE 137

N-[3-Hydroxy-4-(1,1,4-trioxo-1,2,5-thiadiazolidin-2-yl)-benzyl]-N-methylbenzenesulfonamide

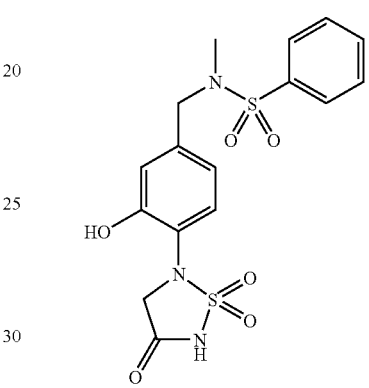

A. (3-Benzyloxy-4-nitrobenzyl)methylamine

To a solution of 3-benzyloxy-4-nitrobenzaldehyde (3.00 g, 11.673 mmol) (Example 83, step A) in CH$_2$Cl$_2$ is added methylamine (11.7 mL of 2.0 M in THF) dropwise, and the reaction stirred at RT for 10 min. Magnesium sulfate is added and the resulting slurry is stirred at RT for 4 h. The reaction is filtered to remove the magnesium sulfate and the filter cake is washed with CH$_2$Cl$_2$. The filtrate and washes are combined and concentrated under vacuum to afford a brown oil. The oil is triturated with hexanes to afford the Schiff base intermediate [1-(3-benzyloxy-4-nitrophenyl)methylidene]-methylamine, as an orange solid. The solid is dissolved in methanol/THF (4:1, 100 mL) and cooled to 0° C. in an ice/water bath. Sodium borohydride (440 mg, 11.673 mmol) is added in portions with stirring and the reaction is stirred at 0° C. for 2 h. LC/MS indicates ~50% reaction completion. Additional sodium borohydride (440 mg, 11.67 mmol) is added and the reaction allowed to warm to RT overnight. The brown reaction solution is poured into water (100 mL) and extracted with CH$_2$Cl$_2$ (3×75 mL). The extracts are combined, washed with brine, dried over Na$_2$SO$_4$, filtered, and concentrated under reduced pressure to afford the title compound.

B. N-(3-Benzyloxy-4-nitrobenzyl)-N-methylbenzenesulfonamide

To a solution of (3-benzyloxy-4-nitrobenzyl)methylamine (1.00 g, 3.672 mmol) and triethylamine (0.56 mL, 4.04 mmol) in CH$_2$Cl$_2$ (20 mL) is added dropwise benzenesulfonyl chloride (0.515 mL, 4.04 mmol) and the reaction is heated at reflux for 1 h. After cooling to RT, the reaction is diluted with CH$_2$Cl$_2$ (75 mL). The solution is washed with 1N HCl, saturated sodium bicarbonate, dried over Na₂SO₄, filtered, and concentrated under vacuum to afford an orange oil. The oil is triturated with ether to afford the title compound: (M+1)⁺=413.

C. N-(4-Amino-3-benzyloxybenzyl)-N-methylbenzenesulfonamide

To a suspension of N-(3-Benzyloxy-4-nitrobenzyl)-N-methylbenzenesulfonamide (1.09 g, 2.643 mmol) in EtOAc is added platinum oxide (60 mg). The reaction is placed under an atmosphere of H₂ and stirred at RT for 50 min. Additional platinum oxide is added (60 mg) and the reaction is stirred under an atmosphere of H₂ at RT for an additional 50 min. During this time, the reaction changes from a greenish brown slurry to a black slurry. The slurry is filtered through Celite to remove the catalyst and the filter cake is washed with several portions of EtOAc. The filtrate and washings are combined, and concentrated under vacuum to afford an orange oil. LC/MS shows a 1:1 mixture of starting material and product. The orange oil is re-dissolved in. EtOAc, slurried with platinum oxide (150 mg) and stirred under an atmosphere of H₂ at room temperature for 1.5 h. The reaction mixture is filtered through Celite and the filter cake is washed with EtOAc. The filtrate is concentrated to afford the title compound: (M+1)⁺=383.

D. N-[3-Hydroxy-4-(1,1,4-trioxo-1,2,5-thiadiazolidin-2-yl)-benzyl]-N-methylbenzenesulfonamide The synthesis of the title compound is completed using N-(4-amino-3-benzyloxybenzyl)-N-methylbenzenesulfonamide analogous to the series of reactions described for the construction of the heterocycle in Example 83, steps H-L: ¹H NMR (400 MHz, DMSO-d₆) δ ppm 2.52 (s, 3 H) 3.97 (s, 2 H) 4.07 (s, 2 H) 6.50 (br. s., 1 H) 6.70 (br. s., 1 H) 7.30 (d, J=8.08 Hz, 1 H) 7.66 (d, J=7.83 Hz, 2 H) 7.70 (d, J=7.07 Hz, 1 H) 7.83 (s, 1 H) 7.81 (d, J=1.52 Hz, 2 H)

EXAMPLE 138

N-[3-Hydroxy-4-(1,1,4-trioxo-1,2,5-thiadiazolidin-2-yl)-benzyl]-N-methylmethanesulfonamide

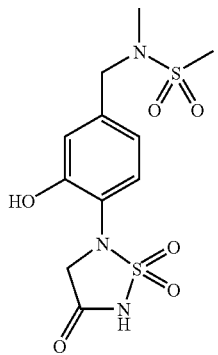

The title compound is prepared from (3-benzyloxy-4-nitrobenzyl)methylamine and methanesulfonyl chloride analogous to Example 137, steps B-D.

¹H NMR (400 MHz, DMSO-d₆) δ ppm 2.64 (s, 3 H) 2.92 (s, 3 H) 4.05 (s, 2 H) 4.09 (s, 2 H) 6.67 (br. s., 1 H) 6.79 (br. s., 1 H) 7.37 (d, J=8.08 Hz, 1 H)

EXAMPLE 139

C-Cyclohexyl-N-{2-[3-hydroxy-4-(1,1,4-trioxo-1,2,5-thiadiazolidin-2-yl)-phenyl]-ethyl}-methanesulfonamide

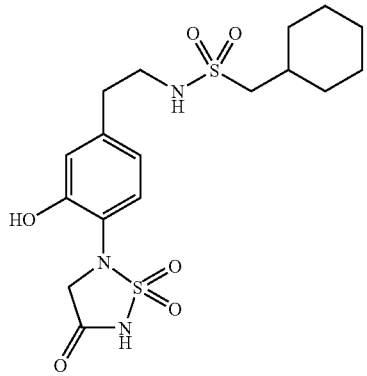

A. N-(2-{3-Benzyloxy-4-[1,1,4-trioxo-5-(2-trimethylsilanylethyl)-1,2,5-thiadiazolidin-2-yl]-phenyl}-ethyl)-C-cyclohexyl-methanesulfonamide 5-[4-(2-Aminoethyl)-2-benzyloxyphenyl]-1,1-dioxo-2-(2-trimethylsilanylethyl)-1,2,5-thiadiazolidin-3-one TFA salt (Example 67, step A) (0.49 g, 0.96 mmol) is dissolved in 5 mL of CH₂Cl₂ and triethylamine (0.27 mL, 1.92 mmol) is added. Cyclohexylmethyl sulfonyl chloride (0.19 g, 0.96 mmol) is then added and the reaction stirred for 1 h. The reaction mixture is concentrated and the residue is partitioned between EtOAc and 1N HCl and extracted with EtOAc. The combined organic layers are washed with sat. sodium bicarbonate and brine, dried over MgSO₄ and concentrated to a yellow oil. The oil is purified by chromatography over silica (hexane/EtOAc gradient) to afford the title compound as an oil.

B. N-{2-[3-Benzyloxy-4-(1,1,4-trioxo-1,2,5-thiadiazolidin-2-yl)-phenyl]ethyl}-C-cyclohexyl-methanesulfonamide N-(2-{3-Benzyloxy-4-[1,1,4-trioxo-5-(2-trimethylsilanylethyl)-1,2,5-thiadiazolidin-2-yl]-phenyl}-ethyl)-C-cyclohexyl-methanesulfonamide (0.106 g, 0.17 mmol) is dissolved in THF (3 mL) and TBAF (0.089 mg, 0.099 mL of 1N in THF, 0.34 mmol) is added. The mixture is refluxed for 30 min and then diluted with 1N HCl and extracted with EtOAc. The combined organic layers are washed with 1N HCl, dried over MgSO₄ and evaporated to afford the title compound.

C. C-Cyclohexyl-N-{2-[3-hydroxy-4-(1,1,4-trioxo-1,2,5-thiadiazolidin-2-yl)-phenyl]-ethyl}-methanesulfonamide N-{2-[3-Benzyloxy-4-(1,1,4-trioxo-1,2,5-thiadiazolidin-2-yl)-phenyl]-ethyl}-cyclohexyl-methanesulfonamide (0.086 g, 0.16 mmol) is dissolved in a small amount of EtOH and potassium bicarbonate (0.30N, 0.530 mL) is added and the reaction stirred for 10 min. Pd/C (0.075 g) is added and the mixture stirred under hydrogen for 45 min. The reaction mixture is flushed with nitrogen and then filtered through Celite. The solvent is removed under reduced pressure to afford the potassium salt of the title compound: ¹H NMR (400

MHz, DMSO-d$_6$) δ ppm 1.05 (d, J=2.78 Hz, 1 H) 1.01 (d, J=12.38 Hz, 1 H) 1.12-1.24 (m, 2 H) 1.18 (t, J=7.20 Hz, 1 H) 1.62 (td, J=10.04, 3.16 Hz, 3 H) 1.73-1.85 (m, 3 H) 2.68 (t, J=7.45 Hz, 2 H) 2.82 (d, J=6.06 Hz, 2 H) 3.12 (q, J=6.65 Hz, 2 H) 4.42 (s, 2 H) 6.71 (dd, J=8.08, 1.52 Hz, 1 H) 6.78 (s, 1 H) 7.07 (t, J=5.68 Hz, 1 H) 7.26 (d, J=8.08 Hz, 1 H) 9.84 (br. s., 1 H)

EXAMPLES 140 TO 153

The following compounds are prepared from 5-[4-(2-aminoethyl)-2-benzyloxyphenyl]-1,1-dioxo-2-(2-trimethylsilanylethyl)-1,2,5-thiadiazolidin-3-one and the appropriate sulfonyl chloride analogous to the series of reactions described in Example 139.

| Example | Chemical Name | MS (m/z) | Retention time (min) Method |
|---|---|---|---|
| 140 | N-{2-[3-Hydroxy-4-(1,1,4-trioxo-1,2,5-thiadiazolidin-2-yl)-phenyl]-ethyl}-methansulfonamide | (M − 1)⁻ = 348 | |
| 141 | Ethanesulfonic acid {2-[3-hydroxy-4-(1,1,4-trioxo-1,2,5-thiadiazolidin-2-yl)-phenyl]-ethyl}-amide | (M − 1)⁻ = 376 | 0.60 A |
| 142 | Butane-1-sulfonic acid {2-[3-hydroxy-4-(1,1,4-trioxo-1,2,5-thiadiazolidin-2-yl)-phenyl]-ethyl}-amide | (M − 1)⁻ = 390 | |
| 143 | Propane-2-sulfonic acid {2-[3-hydroxy-4-(1,1,4-trioxo-1,2,5-thiadiazolidin-2-yl)-phenyl]-ethyl}-amide | (M − 1)⁻ = 376 | |
| 144 | Octane-1-sulfonic acid {2-[3-hydroxy-4-(1,1,4-trioxo-1,2,5-thiadiazolidin-2-yl)-phenyl]-ethyl}-amide | (M − 1)⁻ = 446 | |
| 145 | N-{2-[3-Hydroxy-4-(1,1,4-trioxo-1,2,5-thiadiazolidin-2-yl)-phenyl]-ethyl}-benzenesulfonamide | (M − 1)⁻ = 410 | |
| 146 | N-{2-[3-Hydroxy-4-(1,1,4-trioxo-1,2,5-thiadiazolidin-2-yl)-phenyl]-ethyl}-C-phenyl-methansulfonamide | (M − 1)⁻ = 424 | |
| 147 | 4-Fluoro-N-{2-[3-hydroxy-4-(1,1,4-trioxo-1,2,5-thiadiazolidin-2-yl)-phenyl]-ethyl}-benzenesulfonamide | (M − 1)⁻ = 428 | |
| 148 | 3,4-Dichloro-N-{2-[3-hydroxy-4-(1,1,4-trioxo-1,2,5-thiadiazolidin-2-yl)-phenyl]-ethyl}-benzenesulfonamide | (M − 1)⁻ = 480 | |
| 150 | 3-(4-{2-[3-Hydroxy-4-(1,1,4-trioxo-1,2,5-thiadiazolidin-2-yl)-phenyl]-ethylsulfamoyl}-phenyl)-propionic acid | (M − 1)⁻ = 482 | |
| 151 | 2-Hydroxy-5-{2-[3-hydroxy-4-(1,1,4-trioxo-1,2,5-thiadiazolidin-2-yl)-phenyl]-ethylsulfamoyl}-benzoic acid | (M − 1)⁻ = 478 | |
| 152 | Naphthalene-1-sulfonic acid {2-[3-hydroxy-4-(1,1,4-trioxo-1,2,5-thiadazolidin-2-yl)-phenyl]-ethyl}-amide | (M − 1)⁻ = 460 | |
| 153 | 2-Naphthalen-1-yl-ethanesulfonic acid {2-[3-hydroxy-4-(1,1,4-trioxo-1,2,5-thiadiazolidin-2-yl)-phenyl]-ethyl}-amide | (M − 1)⁻ = 488 | |

| Example | NMR |
|---|---|
| 140 | ¹H NMR (400 MHz, DMSO-d$_6$) δ ppm 2.65 (t, J = 7.58 Hz, 2H) 2.85 (s, 3H) 3.11 (t, J = 7.58 Hz, 2H) 4.03 (s, 2H) 6.61 (dd, J = 8.21, 1.39 Hz, 1H) 6.70 (s, 1H) 7.30 (d, J = 7.83 Hz, 1H) |
| 142 | ¹H NMR (400 MHz, DMSO-D6) δ ppm 0.84 (t, J = 7.33 Hz, 3H) 1.27-1.37 (m, J = 7.39, 7.39, 7.39, 7.39 Hz, 2H) 1.50-1.59 (m, 2H) 2.65 (t, J = 7.45 Hz, 2H) 2.85-2.93 (m, 2H) 3.05-3.14 (m, 2H) 4.39 (s, 2H) 6.68 (dd, J = 8.08, 1.77 Hz, 1H) 6.76 (d, J = 1.77 Hz, 1H) 7.05 (t, J = 5.81 Hz, 1H) 7.23 (d, J = 8.08 Hz, 1H) |
| 143 | ¹H NMR (400 MHz, DMSO-d$_6$) δ ppm 1.18 (d, J = 6.82 Hz, 6H) 2.63 (t, J = 7.58 Hz, 2H) 3.04-3.15 (m, 1H) 3.10 (dd, J = 7.45, 2.91 Hz, 2H) 4.04 (s, 2H) 6.54 (d, J = 7.58 Hz, 1H) 6.66 (d, J = 1.77 Hz, 1H) 7.26 (d, J = 8.08 Hz, 1H) |
| 144 | ¹H NMR (400 MHz, DMSO-D6) δ ppm 0.78-0.86 (m, 3H) 1.19-1.31 (m, 10H) 1.51-1.60 (m, 2H) 2.65 (t, J = 7.45 Hz, 2H) 2.83-2.93 (m, 2H) 3.05-3.16 (m, 2H) 4.37 (s, 2H) 6.68 (dd, J = 8.08, 1.77 Hz, 1H) 6.75 (d, J = 1.77 Hz, 1H) 7.04 (t, J = 5.81 Hz, 1H) 7.23 (d, J = 8.08 Hz, 1H) |
| 145 | ¹H NMR (400 MHz, DMSO-D6) δ ppm 2.55 (t, J = 7.45 Hz, 2H) 2.91 (t, J = 7.58 Hz, 2H) 4.01 (s, 2H) 6.52 (dd, J = 8.08, 1.52 Hz, 1H) 6.61 (s, 1H) 7.26 (d, J = 8.08 Hz, 1H) 7.54-7.65 (m, 3H) 7.78 (d, J = 6.82 Hz, 2H) |
| 146 | ¹H NMR (400 MHz, DMSO-D6) δ ppm 2.55-2.63 (m, 2H) 3.01-3.10 (m, 2H) 4.02 (s, 2H) 4.29 (s, 2H) 6.57 (dd, J = 7.96, 1.64 Hz, 1H) 6.67 (d, J = 1.77 Hz, 1H) 7.27-7.38 (m, 5H) |

-continued

| Example | NMR |
|---|---|
| 148 | ¹H NMR (400 MHz, DMSO-d₆) δ ppm 2.61 (t, J = 7.33 Hz, 2H) 2.99 (q, J = 6.99 Hz, 2H) 4.19 (s, 2H) 6.60 (d, J = 8.08 Hz, 1H) 6.68 (s, 1H) 7.25 (d, J = 8.08 Hz, 1H) 7.72 (d, J = 2.27 Hz, 1H) 7.85-7.97 (m, 3H) 9.35 (br. s., 1H) |
| 150 | ¹H NMR (400 MHz, DMSO-d₆) δ ppm 2.58 (t, J = 7.45 Hz, 4H) \2.89 (t, J = 7.33 Hz, 4H) 4.25 (s, 2H) 6.59 (dd, J = 8.21, 1.64 Hz, 1H) 6.68 (d, J = 1.52 Hz, 1H) 7.24 (d, J = 8.08 Hz, 1H) 7.44 (d, J = 8.08 Hz, 2H) 7.61 (t, J = 5.81 Hz, 1H) 7.68 (d, J = 8.34 Hz, 2H) 9.49 (br. s., 1H) 12.19 (br. s., 1H) |
| 151 | ¹H NMR (400 MHz, DMSO-D6) δ ppm 2.51-2.56 (m, 2H) 2.83 (t, J = 7.45 Hz, 2H) 4.01 (s, 2H) 6.51 (s, 1H) 6.60 (s, 1H) 6.70 (d, J = 8.59 Hz, 1H) 7.25 (d, J = 7.83 Hz, 1H) 7.50 (d, J = 8.59 Hz, 1H) 8.10 (s, 1H) |
| 152 | ¹H NMR (400 MHz, DMSO-d₆) δ ppm 2.56 (d, J = 7.58 Hz, 2H) 3.00 (d, J = 7.83 Hz, 2H) 4.24 (s, 2H) 6.51 (dd, J = 7.96, 1.89 Hz, 1H) 6.63 (d, J = 1.77 Hz, 1H) 7.20 (d, J = 8.08 Hz, 1H) 7.64-7.75 (m, 3H) 8.05-8.15 (m, 3H) 8.24 (d, J = 8.08 Hz, 1H) 8.67 (d, J = 8.34 Hz, 1H) 9.43 (br. s., 1H) |
| 153 | ¹H NMR (400 MHz, DMSO-d₆) δ ppm 2.73 (t, J = 7.45 Hz, 2H) 3.17-3.25 (m, 1H) 3.22 (d, J = 7.33 Hz, 1H) 3.32-3.44 (m, 4H) 4.32 (s, 2H) 6.72 (dd, J = 8.08, 2.02 Hz, 1H) 6.81 (d, J = 1.77 Hz, 1H) 7.27 (d, J = 8.08 Hz, 1H) 7.34 (t, J = 5.81 Hz, 1H) 7.46 (d, J = 2.27 Hz, 1H) 7.43-7.47 (m, 1H) 7.60 (dd, J = 8.34, 1.52 Hz, 1H) 7.84 (dd, J = 5.81, 3.54 Hz, 1H) 7.95 (d, J = 1.26 Hz, 1H) 8.02 (d, J = 8.34 Hz, 1H) |

EXAMPLES 154 TO 183

The following compounds are prepared from 5-[4-(3-aminopropyl)-2-benzyloxyphenyl]-1,1-dioxo-2-(2-trimethylsilanylethyl)-1,2,5-thiadiazolidin-3-one (Example 74, step A) and the appropriate sulfonyl chloride analogous to the series of reactions described in Example 139.

| Example | Chemical Name | MS (m/z) | Retention time (min) Method |
|---|---|---|---|
| 154 | N-{3-[3-Hydroxy-4-(1,1,4-trioxo-1,2,5-thiadiazolidin-2-yl)-phenyl]-propyl}-methansulfonamide | (M − 1)⁻ = 362 | |
| 155 | N-{3-[3-Hydroxy-4-(1,1,4-trioxo-1,2,5-thiadiazolidin-2-yl)-phenyl]-propyl}-benzenesulfonamide | (M − 1)⁻ = 424 | |
| 156 | N-{3-[3-Hydroxy-4-(1,1,4-trioxo-1,2,5-thiadiazolidin-2-yl)-phenyl]-propyl}-C-phenylmethanesulfonamide | (M − 1)⁻ = 438 | |
| 157 | C-(4-Fluorophenyl)-N-{3-[3-hydroxy-4-(1,1,4-trioxo-1,2,5-thiadiazolidin-2-yl)-phenyl]-propyl}-methanesulfonamide | (M − 1)⁻ = 456 | |
| 158 | N-{3-[3-Hydroxy-4-(1,1,4-trioxo-1,2,5-thiadiazolidin-2-yl)-phenyl]-propyl}-4-isopropylbenzenesulfonamide | (M − 1)⁻ = 466 | |
| 159 | N-{3-[3-Hydroxy-4-(1,1,4)-trioxo-1,2,5-thiadiazolidin-2-yl)-phenyl]-propyl}-4-trifluoromethylbenzenesulfonamide | (M − 1)⁻ = 492 | |
| 160 | N-{3-[3-Hydroxy-4-(1,1,4-trioxo-1,2,5-thiadiazolidin-2-yl)-phenyl]-propyl}-4-trifluoromethoxybenzenesulfonamide | (M − 1)⁻ = 508 | |
| 161 | C-(3-Aminophenyl)-N-{3-[3-hydroxy-4-(1,1,4-trioxo-1,2,5-thiadiazolidin-2-yl)-phenyl]-propyl}-methanesulfonamide | (M − 1)⁻ = 453 | |
| 162 | N-{3-[3-Hydroxy-4-(1,1,4-trioxo-1,2,5-thiadiazolidin-2-yl)-phenyl]-propyl}-2,4,6-triisopropylbenzenesulfonamide | (M − 1)⁻ = 550 | |
| 163 | 2-Hydroxy-5-{3-[3-hydroxy-4-(1,1,4-trioxo-1,2,5-thiadiazolidin-2-yl)-phenyl]-propylsulfamoyl}-benzoic acid | (M − 1)⁻ = 484 | |
| 164 | 3-Amino-N-{3-[3-hydroxy-4-(1,1,4-trioxo-1,2,5-thiadiazolidin-2-yl)-phenyl]-propyl}-benzenesulfonamide | (M − 1)⁻ = 439 | |
| 165 | 4-Amino-N-{3-[3-hydroxy-4-(1,1,4-trioxo-1,2,5-thiadiazolidin-2-yl)-phenyl]-propyl}-benzenesulfonamide | (M − 1)⁻ = 439 | |
| 166 | N-{3-[3-Hydroxy-4-(1,1,4-trioxo-1,2,5-thiadiazolidin-2-yl)-phenyl]-propyl}-3,5-dimethylbenzenesulfonamide | (M − 1)⁻ = 452 | |
| 167 | N-{3-[3-Hydroxy-4-(1,1,4-trioxo-1,2,5-thiadiazolidin-2-yl)-phenyl]-propyl}-2,5-dimethylbenzenesulfonamide | (M − 1)⁻ = 452 | |

| Example | Chemical Name | MS (m/z) | Retention time (min) Method |
|---|---|---|---|
| 168 | N-{3-[3-Hydroxy-4-(1,1,4-trioxo-1,2,5-thiadiazolidin-2-yl)-phenyl]-propyl}-2,4,6-trimethylbenzenesulfonamide | (M − 1)⁻ = 466 | |
| 169 | 4-tert-Butyl-N-{3-[3-hydroxy-4-(1,1,4-trioxo-1,2,5-thiadiazolidin-2-yl)-phenyl]-propyl}-benzenesulfonamide | (M − 1)⁻ = 480 | |
| 170 | 4-(1,1-Dimethylpropyl)-N-{3-[3-hydroxy-4-(1,1,4-trioxo-1,2,5-thiadiazolidin-2-yl)-phenyl]-propyl}-benzenesulfonamide | (M − 1)⁻ = 494 | |
| 171 | N-{3-[3-Hydroxy-4-(1,1,4-trioxo-1,2,5-thiadiazolidin-2-yl)-phenyl]-propyl}-3,4-dimethoxybenzenesulfonamide | (M − 1)⁻ = 484 | |
| 172 | N-{3-[3-Hydroxy-4-(1,1,4-trioxo-1,2,5-thiadiazolidin-2-yl)-phenyl]-propyl}-2,5-bis-(2,2,2-trifluoroethoxy)-benzenesulfonamide | (M − 1)⁻ = 620 | |
| 173 | Biphenyl-4-sulfonic acid {3-[3-hydroxy-4-(1,1,4-trioxo-1,2,5-thiadiazolidin-2-yl)-phenyl]-propyl}-amide | (M − 1)⁻ = 500 | |
| 174 | N-{3-[3-Hydroxy-4-(1,1,4-trioxo-1,2,5-thiadiazolidin-2-yl-phenyl]-propyl}-2-phenoxybenzenesulfonamide | (M − 1)⁻ = 516 | |
| 175 | N-{3-[3-Hydroxy-4-(1,1,4-trioxo-1,2,5-thiadiazolidin-2-yl-phenyl]-propyl}-3-phenoxybenzenesulfonamide | (M − 1)⁻ = 516 | |
| 176 | N-{3-[3-Hydroxy-4-(1,1,4-trioxo-1,2,5-thiadiazolidin-2-yl-phenyl]-propyl}-2,5-bis-(2,2,2-trifluoroethoxy)-benzenesulfonamide | (M − 1)⁻ = 506 | |
| 177 | 2,2-Diphenylethanesulfonic acid {3-[3-hydroxy-4-(1,1,4-trioxo-1,2,5-thiadiazolidin-2-yl)-phenyl]-propyl}-amide | (M − 1)⁻ = 529 | |
| 178 | C-(2-Aminophenyl)-N{3-[3-hydroxy-4-(1,1,4-trioxo-1,2,5-thiadiazolidin-2-yl)-phenyl]-propyl}-methanesulfonamide | (M − 1)⁻ = 455 | |
| 179 | Naphthalene-1-sulfonic acid {3-[3-hydroxy-4-(1,1,4-trioxo-1,2,5-thiadiazolidin-2-yl)-phenyl]-propyl}-amide | (M − 1)⁻ = 474 | |
| 180 | C-Cyclohexyl-N-{3-[3-hydroxy-4-(1,1,4-trioxo-1,2,5-thiadiazolidin-2-yl)-pheny]-propyl}-methanesulfonamide | (M − 1)⁻ = 444 | |
| 181 | 2-Naphthalen-1-yl-ethanesulfonic acid {3-[3-hydroxy-4-(1,1,4-trioxo-1,2,5-thiadiazolidin-2-yl)-phenyl]-propyl}-amide | (M − 1)⁻ = 502 | |
| 182 | 2-Phenyl-2-(2-trifluoromethylphenyl)-ethanesulfonic acid {3-[3-hydroxy-4-(1,1,4-trioxo-1,2,5-thiadiazolidin-2-yl)-phenyl]-propyl}-amide | (M − 1)⁻ = 596 | |
| 183 | 2-Oxo-2H-chomene-6-sulfonic acid {3-[3-hydroxy-4-(1,1,4-trioxo-1,2,5-thiadiazolidin-2-yl)-phenyl]-propyl}-amide | (M − 1)⁻ = 492 | |

| Example | NMR |
|---|---|
| 154 | ¹H NMR (400 MHz, DMSO-D6) δ ppm 1.68-1.76 (m, 2H) 2.87 (m, 3H) 2.93 (q, J = 6.48 Hz, 2H) 4.02 (s, 2H) 6.60 (dd, J = 8.08, 2.02 Hz, 1H) 6.70 (d, J = 2.02 Hz, 1H) 6.95-7.07 (m, 1H) 7.27 (d, J = 8.08 Hz, 1H) |
| 155 | ¹H NMR (400 MHz, DMSO-D6) δ ppm 1.54-1.64 (m, 2H) 2.33-2.43 (m, 2H) 2.75 (t, J = 6.95 Hz, 2H) 4.02 (s, 2H) 6.44 (dd, J = 8.08, 1.77 Hz, 1H) 6.58 (d, J = 1.77 Hz, 1H) 7.21 (d, J = 8.08 Hz, 1H) 7.54-7.64 (m, 3H) 7.75-7.80 (m, 2H) |
| 156 | ¹H NMR (400 MHz, DMSO-d₆) δ ppm 1.60-1.71 (m, J = 7.39, 7.39, 7.39, 7.39 Hz, 2H) 2.42-2.49 (m, 2H) 2.89 (t, J = 6.95 Hz, 2H) 4.02 (s, 2H) 4.30 (s, 2H) 6.56 (dd, J = 8.08, 1.77 Hz, 1H) 6.66 (d, J = 2.02 Hz, 1H) 7.26 (d, J = 8.08 Hz, 1H) 7.30-7.38 (m, 5H) |
| 157 | ¹H NMR (400 MHz, DMSO-d₆) δ ppm 1.67 (qd, J = 7.37, 7.20 Hz, 2H) 2.46 (d, J = 7.83 Hz, 2H) 2.91 (t, J = 7.07 Hz, 2H) 4.01 (s, 2H) 4.31 (s, 2H) 6.58 (d, J = 7.83 Hz, 1H) 6.66 (d, J = 1.77 Hz, 1H) 7.20 (t, J = 8.84 Hz, 2H) 7.26 (d, J = 8.08 Hz, 1H) 7.40 (dd, J = 8.59, 5.56 Hz, 2H) |
| 158 | ¹H NMR (400 MHz, DMSO-d₆) δ ppm 1.23 (d, J = 6.82 Hz, 6H) 1.56-1.65 (m, 1H) 1.62 (d, J = 7.83 Hz, 1H) 2.39 (t, J = 7.83 Hz, 2H) 2.76 (t, J = 6.95 Hz, 2H) 2.99 (dt, J = 13.83, 6.85 Hz, 1H) 4.05 (s, 2H) 6.42 (dd, J = 8.08, 1.77 Hz, 1H) 6.60 (d, J = 1.77 Hz, 1H) 7.21 (d, J = 8.08 Hz, 1H) 7.46 (d, J = 8.34 Hz, 2H) 7.71 (d, J = 8.34 Hz, 2H) |
| 159 | ¹H NMR (400 MHz, DMSO-d₆) δ ppm 1.54-1.64 (m, 1H) 1.60 (d, J = 7.83 Hz, 1H) 2.40 (t, J = 8.08 Hz, 2H) 2.77 (t, J = 6.95 Hz, 2H) 3.99 (s, 2H) 6.49 (dd, |

| Example | NMR |
|---|---|
| | J = 8.08, 1.77 Hz, 1H) 6.60 (d, J = 1.77 Hz, 1H) 7.22 (d, J = 7.83 Hz, 1H) 7.87-7.96 (m, 4H) |
| 160 | ¹H NMR (400 MHz, DMSO-d₆) δ ppm 1.59 (d, J = 7.58 Hz, 2H) 2.42 (t, J = 7.71 Hz, 2H) 2.77 (t, J = 6.95 Hz, 2H) 3.99 (s, 2H) 6.50 (dd, J = 8.21, 1.64 Hz, 1H) 6.60 (d, J = 1.77 Hz, 1H) 7.23 (d, J = 7.83 Hz, 1H) 7.55 (d, J = 8.59 Hz, 2H) 7.88 (d, J = 8.84 Hz, 2H) |
| 161 | ¹H NMR (400 MHz, DMSO-d₆) δ ppm 1.58-1.70 (m, 1H) 1.67 (d, J = 7.58 Hz, 1H) 2.45 (d, J = 7.83 Hz, 2H) 2.89 (t, J = 6.95 Hz, 2H) 4.01 (s, 2H) 4.10 (s, 2H) 5.07 (s, 1H) 6.50 (dd, J = 12.76, 7.96 Hz, 2H) 6.57 (br. s., 1H) 6.57 (d, J = 1.77 Hz, 1H) 6.67 (s, 1H) 6.98 (t, J = 7.71 Hz, 1H) 7.26 (d, J = 8.08 Hz, 1H) 7.22 (d, J = 8.08 Hz, 1H) |
| 163 | ¹H NMR (400 MHz, DMSO-D6) δ ppm 1.55-1.65 (m, 2H) 2.38-2.47 (m, 2H) 2.68 (t, J = 6.82 Hz, 2H) 4.01 (s, 2H) 6.53 (dd, J = 8.08, 1.77 Hz, 1H) 6.63 (d, J = 1.77 Hz, 1H) 6.71 (d, J = 8.59 Hz, 1H) 7.24 (d, J = 8.08 Hz, 2H) 7.51 (dd, J = 8.72, 2.65 Hz, 1H) 8.10 (d, J = 2.78 Hz, 1H) |
| 164 | ¹H NMR (400 MHz, DMSO-d₆) δ ppm 1.60-1.68 (m, 1H) 1.65 (d, J = 7.58 Hz, 1H) 2.44 (t, J = 7.71 Hz, 2H) 2.76 (br. s., 2H) 4.02 (s, 2H) 5.54 (s, 2H) 6.55 (dd, J = 8.08, 1.77 Hz, 1H) 6.64 (d, J = 1.77 Hz, 1H) 6.76 (dd, J = 7.58, 1.77 Hz, 1H) 6.89 (d, J = 7.58 Hz, 1H) 7.00 (t, J = 1.89 Hz, 1H) 7.20 (t, J = 7.83 Hz, 1H) 7.26 (d, J = 8.08 Hz, 1H) 7.41 (br. s., 1H) |
| 165 | ¹H NMR (400 MHz, DMSO-d₆) δ ppm 1.59 (t, J = 7.33 Hz, 2H) 2.40 (t, J = 7.58 Hz, 2H) 2.67 (t, J = 6.82 Hz, 2H) 4.00 (s, 2H) 5.86 (s, 2H) 6.50 (dd, J = 8.08, 1.77 Hz, 1H) 6.58-6.64 (m, 3H) 7.23 (d, J = 8.08 Hz, 2H) 7.40 (d, J = 8.84 Hz, 2H) |
| 166 | ¹H NMR (400 MHz, DMSO-d₆) δ ppm 1.60 (ddd, J = 14.97, 7.39, 7.20 Hz, 2H) 2.34 (s, 6H) 2.40 (t, J = 7.71 Hz, 2H) 2.73 (t, J = 6.95 Hz, 2H) 4.01 (s, 2H) 6.44 (d, J = 7.33 Hz, 1H) 6.58 (s, 1H) 7.21 (d, J = 7.83 Hz, 1H) 7.24 (s, 1H) 7.39 (s, 2H) |
| 167 | ¹H NMR (400 MHz, DMSO-d₆) δ ppm 1.53-1.62 (m, 1H) 1.56 (d, J = 10.11 Hz, 1H) 2.33 (s, 3H) 2.35 (t, J = 8.08 Hz, 2H) 2.52 (s, 3H) 2.77 (t, J = 6.95 Hz, 2H) 4.02 (s, 2H) 6.38 (d, J = 8.08 Hz, 1H) 6.55 (d, J = 1.77 Hz, 1H) 7.19 (d, J = 8.08 Hz, 1H) 7.24-7.31 (m, 1H) 7.27 (t, J = 8.59 Hz, 1H) 7.61 (s, 1H) |
| 168 | ¹H NMR (400 MHz, DMSO-d₆) δ ppm 1.55 (qd, J = 7.37, 7.20 Hz, 2H) 2.27 (s, 3H) 2.34 (t, J = 7.58 Hz, 2H) 2.55 (s, 6H) 2.76 (t, J = 6.95 Hz, 2H) 4.04 (s, 2H) 6.35 (d, J = 8.08 Hz, 1H) 6.54 (d, J = 1.52 Hz, 1H) 7.03 (s, 2H) 7.20 (d, J = 8.08 Hz, 1H) |
| 169 | ¹H NMR (400 MHz, DMSO-d₆) δ ppm 1.30 (s, 9H) 1.59 (t, J = 7.33 Hz, 2H) 2.39 (t, J = 7.58 Hz, 2H) 2.75 (t, J = 6.82 Hz, 2H) 4.02 (s, 2H) 6.39 (br. s., 1H) 6.56 (s, 1H) 7.19 (d, J = 8.08 Hz, 1H) 7.59 (d, J = 8.34 Hz, 2H) 7.67-7.72 (m, 2H) |
| 170 | ¹H NMR (400 MHz, DMSO-d₆) δ ppm 0.61 (t, J = 7.33 Hz, 3H) 1.27 (s, 7H) 1.64 (d, J = 7.33 Hz, 4H) 2.38 (d, J = 14.91 Hz, 2H) 2.72-2.79 (m, 2H) 4.00 (s, 2H) 6.43 (br. s., 1H) 6.56 (br. s., 1H) 7.20 (d, J = 8.08 Hz, 1H) 7.53 (d, J = 8.59 Hz, 2H) 7.70 (d, J = 8.08 Hz, 2H) |
| 171 | ¹H NMR (400 MHz, DMSO-d₆) δ ppm 1.56-1.64 (m, 2H) 2.42 (t, J = 7.58 Hz, 2H) 2.72 (t, J = 6.95 Hz, 2H) 3.82 (d, J = 11.37 Hz, 7H) 4.00 (s, 2H) 6.50 (dd, J = 8.08, 1.77 Hz, 1H) 6.61 (d, J = 1.77 Hz, 1H) 7.11 (d, J = 8.59 Hz, 1H) 7.23 (d, J = 8.08 Hz, 1H) 7.29 (d, J = 2.02 Hz, 1H) 7.34 (dd, J = 8.34, 2.02 Hz, 1H) |
| 172 | ¹H NMR (400 MHz, DMSO-d₆) δ ppm 1.57-1.67 (m, 2H) 2.40 (d, J = 7.83 Hz, 2H) 2.90 (t, J = 6.95 Hz, 2H) 3.99 (s, 2H) 6.50 (dd, J = 8.08, 1.52 Hz, 1H) 6.60 (d, J = 1.77 Hz, 1H) 7.23 (d, J = 8.08 Hz, 2H) 7.33 (s, 1H) 7.38 (t, J = 1.64 Hz, 1H) |
| 173 | ¹H NMR (400 MHz, DMSO-d₆) δ ppm 1.63 (br. s., 2H) 2.43 (br. s., 2H) 2.79 (br. s., 2H) 3.99 (br. s., 2H) 6.49 (br. s., 1H) 6.60 (br. s., 1H) 7.22 (d, J = 7.33 Hz, 1H) 7.41 (br. s., 1H) 7.51 (br. s., 2H) 7.73 (br. s., 2H) 7.85 (d, J = 2.53 Hz, 4H) |
| 178 | ¹H NMR (400 MHz, DMSO-d₆) δ ppm 1.60-1.71 (m, 2H) 2.46 (d, J = 7.83 Hz, 2H) 2.93 (t, J = 6.82 Hz, 2H) 4.01 (s, 2H) 4.23 (s, 2H) 5.01 (s, 2H) 6.53-6.63 (m, 1H) 6.59 (d, J = 7.58 Hz, 1H) 6.67 (s, 1H) 6.71 (d, J = 7.83 Hz, 1H) 7.05 (t, J = 8.08 Hz, 2H) 7.27 (d, J = 8.08 Hz, 1H) |
| 179 | |
| 180 | ¹H NMR (400 MHz, DMSO-d₆) δ ppm 1.09 (d, J = 11.87 Hz, 1H) 1.06 (br. s., 1H) 1.16-1.26 (m, 2H) 1.60-1.72 (m, 2H) 1.68 (d, J = 7.58 Hz, 3H) 1.84 (br. s., 2H) 1.80 (d, J = 3.79 Hz, 2H) 2.44-2.48 (m, 2H) 2.85 (d, J = 6.06 Hz, 2H) 2.92 (t, J = 7.07 Hz, 2H) 4.03 (s, 2H) 6.49 (br. s., 1H) 6.59 (br. s., 1H) 7.21 (br. s., 1H) |
| 181 | ¹H NMR (400 MHz, DMSO-d₆) δ ppm 1.75 (qd, J = 7.45, 7.20 Hz, 2H) 2.51-2.55 (m, 2H) 3.01 (br. s., 2H) 3.32-3.38 (m, 2H) 3.40-3.47 (m, 2H) 4.01 (s, 2H) 6.61 (dd, J = 8.08, 2.02 Hz, 1H) 6.70 (d, J = 2.02 Hz, 1H) 7.27 (d, J = 8.08 Hz, 2H) 7.44-7.48 (m, 1H) 7.45 (d, J = 3.54 Hz, 1H) 7.52-7.62 (m, 2H) 7.83 (dd, J = 6.57, 3.03 Hz, 1H) 7.94 (d, J = 1.52 Hz, 1H) 8.01 (d, J = 8.34 Hz, 1H) |
| 182 | ¹H NMR (400 MHz, DMSO-d₆) δ ppm 1.56-1.63 (m, 1H) 1.60 (d, J = 7.83 Hz, 1H) 2.42 (t, J = 7.58 Hz, 2H) 2.80 (td, J = 7.14, 1.64 Hz, 2H) 3.71 (dd, J = 14.65, 6.06 Hz, 1H) 3.95 (d, J = 7.83 Hz, 1H) 4.01 (s, 2H) 4.90 (t, J = 6.69 Hz, 1H) 6.54 (d, J = 7.83 Hz, 1H) 6.63 (d, J = 1.77 Hz, 1H) 7.20 (d, J = 7.33 Hz, 1H) 7.25 (d, J = 8.08 Hz, 1H) 7.29 (t, J = 7.58 Hz, 2H) 7.37-7.45 (m, 1H) 7.39 (d, J = 7.58 Hz, 2H) 7.63-7.69 (m, 1H) 7.66 (d, J = 4.80 Hz, 1H) 7.87 (d, J = 8.08 Hz, 1H) |
| 183 | ¹H NMR (400 MHz, DMSO-D6) δ ppm 1.60-1.69 (m, 2H) 2.41-2.48 (m, 2H) 2.76-2.82 (m, 2H) 4.37 (s, 2H) 6.56-6.65 (m, 2H) 6.67 (d, J = 1.77 Hz, 1H) 7.20 (d, J = 7.83 Hz, 1H) 7.60 (d, J = 8.59 Hz, 1H) 7.75 (t, J = 5.68 Hz, 1H) 7.95 (dd, J = 8.59, 2.27 Hz, 1H) 8.18-8.23 (m, 2H) |

EXAMPLE 184

N-{3-[3-Hydroxy-4-(1,1,4-trioxo-1,2,5-thiadiazolidin-2-yl)-phenylpropyl}-N-isopropylbenzenesulfonamide

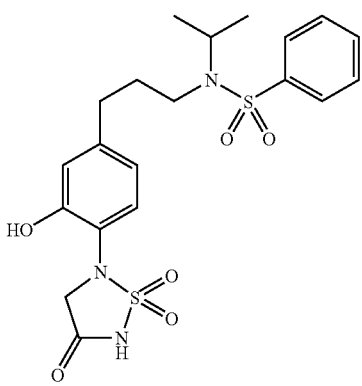

A. N-Isopropylbenzenesulfonamide

To a solution of isopropylamine (4.2 g, 70.6 mmol) in methylene chloride (50 mL) at 0-5° C. is added dropwise a solution of benzenesulfonyl chloride (5.0 g, 28.3 mmol) in methylene chloride (10 mL). After stirring the mixture at RT for 2 h, the solvent is removed under reduced pressure and 1N HCl is added to the residue. The mixture is extracted with EtOAc and the organic phase is washed with brine then dried over magnesium sulfate. The solvent is removed under reduced pressure to give the title compound as a pale yellow oil.

B. N-[3-(tert-Butyldimethylsilanyoxy)-propyl]-N-isopropylbenzenesulfonamide

A solution of N-isopropylbenzenesulfonamide (4.8 g, 24.1 mmol) in DMF (15 mL) is added dropwise to a 0° C. suspension of NaH (60%, 1.0 g, 25 mmol) in DMF (30 mL). The mixture is stirred for 15-20 min at RT then (3-bromopropoxy)-tert-butyldimethylsilane is added and stirring is continued for 2 h. The mixture is poured into sat. NaCl (100 mL) and extracted with MTBE (2×). The combined organic extracts are washed with brine, dried over MgSO$_4$. The solvent is removed under reduced pressure to afford the title compound as a light yellow oil which is used without further purification.

C. N-(3-Hydroxypropyl)-N-isopropylbenzenesulfonamide

To a solution of N-[3-(tert-butyldimethylsilanyoxy)-propyl]-N-isopropylbenzenesulfonamide in THF (40 mL) is added TBAF (26 mL of 1.0 N in THF) and the mixture is stirred at 50° C. for 2 h. The mixture is poured into 1N HCl (50 mL)/water (100 mL) and extracted with MTBE. The organic phase is washed with saturated NaHCO$_3$ and brine then dried over magnesium sulfate. The solvent is removed under reduced pressure to give a two-phase mixture. Hexane is added and decanted (3×). The remaining oil is dried under reduced pressure to give the title compound.

D. N-(3-Iodopropyl)-N-isopropylbenzenesulfonamide

To a solution of triphenylphosphine (4.4 g, 16.6 mmol) and imidazole (1.2 g, 16.7 mmol) in CH$_2$Cl$_2$ (40 mL) at RT, is added iodine (4.3 g, 17 mmol) portionwise. To this solution is added N-(3-hydroxypropyl)-N-isopropylbenzenesulfonamide (4.2 g, 16.5 mmol) in CH$_2$Cl$_2$ (8 mL) dropwise and the mixture allowed to stir at RT for 18 h. The mixture is then filtered and the filtrate concentrated to an oil, which is partitioned between ether and saturated sodium thiosulfate. The aqueous phase is extracted with ether. The combined organic layers are reduced to 10 mL and then filtered through a plug of silica, eluting with hexane. Evaporation of solvent affords the title compound.

E. N-{3-[3-Hydroxy-4-(1,1,4-trioxo-1,2,5-thiadiazolidin-2-yl)-phenylpropyl}-N-isopropylbenzenesulfonamide The title compound is prepared from 5-(2-benzyloxy-4-iodophenyl)-1,1-dioxo-2-(2-trimethylsilanylethyl)-1,2,5-thiadiazolidin-3-one and N-(3-iodopropyl)-N-isopropylbenzenesulfonamide analogous to Example 57, steps B, C and D.

$^1$H NMR (400 MHz, DMSO-D6) δ ppm 0.95 (d, J=6.82 Hz, 6 H) 1.84 (d, J=7.58 Hz, 2 H) 2.46 (d, J=7.83 Hz, 2 H) 3.03-3.11 (m, 2 H) 3.95-4.01 (m, 1 H) 4.03 (s, 2 H) 6.54 (s, 1 H) 6.64 (s, 1 H) 7.27 (d, J=7.83 Hz, 1 H) 7.56-7.66 (m, 3 H) 7.74-7.80 (m, 2 H)

EXAMPLE 185

N-(1-{2-[3-Hydroxy-4-(1,1,4-trioxo-1,2,5-thiadiazolidin-2-yl)-phenyl]-ethyl}-cyclopropyl)-benzenesulfonamide

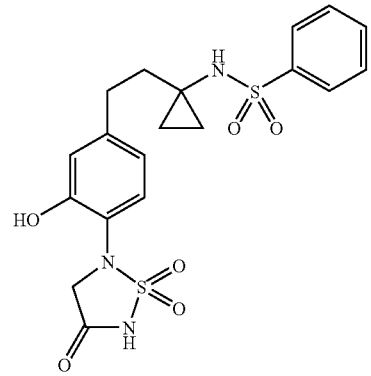

A. 1-tert-Butoxycarbonylaminocyclopropanecarboxylic Acid

To a solution of 1-aminocyclopropanecarboxylic acid (5.0 g, 50 mmol) in 80 mL dioxane/water (1:1) is added Boc$_2$O (11.9 g, 54 mmol) and Na$_2$CO$_3$ (10.5 g, 99 mmol) and the mixture is stirred at RT for 18 h. The solvent is removed under reduced pressure and the residue is dissolved in EtOAc. The mixture is acidified to pH 3 with 1N HCl and the organic phase is separated and dried over sodium sulfate. The solvent is removed under reduced pressure to give the title compound as a solid.

B. [1-(Methoxymethylcarbamoyl)-cyclopropyl]-carbamic Acid Tert-butyl Ester

The title compound is prepared from 1-tert-butoxycarbonylaminocyclopropanecarboxylic acid and N,O-dimethylhydroxylamine hydrochloride analogous to Example 61, step A.

C. (1-Vinylcyclopropyl)-carbamic Acid Tert-butyl Ester

The title compound is prepared from [1-(methoxymethylcarbamoyl)-cyclopropyl]-carbamic acid tert-butyl ester analogous to Example 61, steps B and C.

D. N-(1-{2-[3-Hydroxy-4-(1,1,4-trioxo-1,2,5-thiadiazolidin-2-yl)-phenyl]-ethyl}-cyclopropyl)-benzenesulfonamide The title compound is prepared from 5-(2-benzyloxy-4-iodophenyl)-1,1-dioxo-2-(2-trimethylsilanylethyl)-1,2,5-thiadiazolidin-3-one and (1-vinylcyclopropyl)-carbamic acid tert-butyl ester analogous to Example 61, steps D, E and F. 1H NMR (400 MHz, DMSO-D6) d ppm 0.43-0.54 (m, 2 H) 0.54-0.65 (m, 2H) 1.41-1.51 (m, 2 H) 2.39-2.48 (m, 2 H) 3.98 (s, 2 H) 6.28 (dd, J=8.08, 1.77 Hz, 1 H) 6.44 (d, J=2.02 Hz, 1 H) 7.18 (d, J=8.08 Hz, 1 H) 7.58-7.69 (m, 3 H) 7.84 (dd, J=8.21, 1.39 Hz, 2 H) 8.15 (s, 1 H) 8.79 (s, 1 H), LCMS (method 10) retention time=1.03 min, (M−H)⁻=450.

EXAMPLES 186 TO 188

The following compounds are prepared 5-[4-((S)-2-Amino-3-phenyl-propyl)-2-benzyloxy-phenyl]-1,1-dioxo-2-(2-trimethylsilanylethyl)-1,2,5-thiadiazolidin-3-one (intermediate from Example 60) and the appropriate sulfonyl chloride analogous to the series of reactions described in Example 139.

| Example | NMR |
|---|---|
| 188 | ¹H NMR (400 MHz, DMSO-D6) δ ppm 2.55-2.61 (m, 1H) 2.63-2.73 (m, 3H) 3.52-3.60 (m, 2H) 3.67-3.77 (m, 1H) 3.98-4.04 (m, 2H) 6.58 (d, J = 7.83 Hz, 1H) 6.71 (s, 1H) 7.05 (ddd, J = 3.92, 2.91, 2.78 Hz, 2H) 7.21-7.32 (m, 9H) |

EXAMPLE 189

N-{(R)-1-Benzyl-2-[3-hydroxy-4-(1,1,4-trioxo-1,2,5-thiadiazolidin-2-yl)-phenyl]-ethyl}-C-phenyl-methanesulfonamide

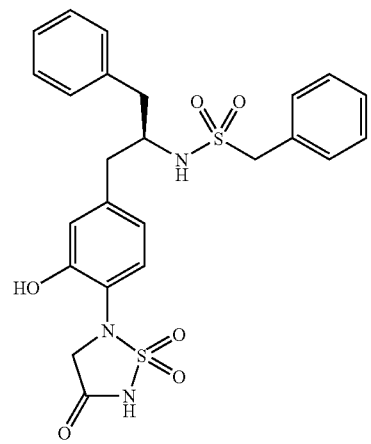

The title compound is prepared from Boc-(R)-2-amino-3-phenylpropan-1-ol analogous to Example 188. 1H NMR (400 MHz, MeOD) δ ppm 2.7 (s, 3 H) 3.2 (s, 1 H) 3.4 (s, 2 H) 3.7 (s, 1 H) 4.2 (s, 2 H) 5.0 (s, 1 H) 6.7 (s, 1 H)) 7.0 (s, 2 H) 7.1 (s, 6 H) 7.2 (s, 3 H) 7.4 (s, 2 H) 7.9 (s, 1 H), LCMS (method 09), retention time=1.39 min, (M−H)⁻=514.4.

| Example | Chemical Name | MS (m/z) | Retention time (min) Method |
|---|---|---|---|
| 186 | N-{(S)-1-Benzyl-2-[3-hydroxy-4-(1,1,4-trioxo-1,2,5-thiadiazolidin-2-yl)-phenyl]-ethyl}-methanesulfonamide | (M − 1)⁻ = 438 | 0.89 A |
| 187 | Ethanesulfonic acid {(S)-1-benzyl-2-[3-hydroxy-4-(1,1,4-trioxo-1,2,5-thiadiazolidin-2-yl)-phenyl]-ethyl}-amide | (M − 1)⁻ = 452 | 0.95 A |
| 188 | N-{(S)-1-Benzyl-2-[3-hydroxy-4-(1,1,4-trioxo-1,2,5-thiadiazolidin-2-yl)-phenyl]-ethyl}-C-phenyl-methanesulfonamide | (M − 1)⁻ = 514 | |

EXAMPLE 190

N-{4-[3-Hydroxy-4-(1,1,4-trioxo-1,2,5-thiadiazolidin-2-yl)-phenyl]-butyl}-methanesulfonamide

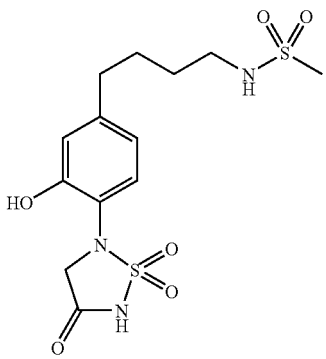

A. (4-Iodobutyl)-Carbamic Acid Tert-butyl Ester

The title compound is prepared from (4-hydroxybutyl)-carbamic acid tert-butyl ester analogous to Example 57, step A.

B. N-{4-[3-Hydroxy-4-(1,1,4-trioxo-1,2,5-thiadiazolidin-2-yl)-phenyl]-butyl}-methanesulfonamide The title compound is prepared from 5-(2-benzyloxy-4-iodophenyl)-1,1-dioxo-2-(2-trimethylsilanylethyl)-1,2,5-thiadiazolidin-3-one and (4-iodobutyl)-carbamic acid tert-butyl ester analogous to Example 57, steps B, C and D.

$^1$H NMR (400 MHz, DMSO-D6) δ ppm 1.42-1.51 (m, 2 H) 1.52-1.61 (m, 2 H) 2.43-2.49 (m, 2 H) 2.85 (s, 3 H) 2.94 (t, J=6.95 Hz, 2 H) 4.01 (s, 2 H) 6.60 (dd, J=8.08, 1.77 Hz, 1 H) 6.67 (d, J=1.77 Hz, 1 H) 7.27 (d, J=8.08 Hz, 1 H)

EXAMPLE 191

N-{5-[3-Hydroxy-4-(1,1,4-trioxo-1,2,5-thiadiazolidin-2-yl)-phenyl]-pentyl}-methanesulfonamide

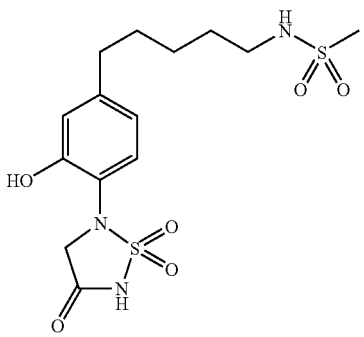

The title compound is prepared from (5-hydroxypentyl)-carbamic acid tert-butyl ester analogous to Example 190.

$^1$H NMR (400 MHz, DMSO-D6) δ ppm 1.26-1.37 (m, 2 H) 1.46-1.57 (m, 4 H) 2.46-2.53 (m, 4 H) 2.85 (s, 3 H) 2.87-2.94 (m, 2 H) 4.43 (s, 2 H) 6.67 (dd, J=7.96-1.89 Hz, 1 H) 6.75 (d, J=1.77 Hz, 1 H) 6.89 (s, 1 H) 7.22 (d, J=7.83 Hz, 1 H)

EXAMPLE 192

5-[2-Hydroxy-4-(1-methanesulfonylpiperidin-3-ylmethyl)-phenyl]-1,1-dioxo-1,2,5-thiadiazolidin-3-one

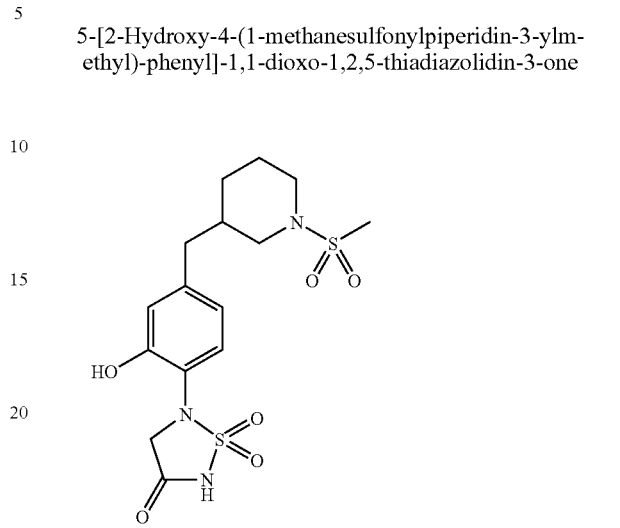

A. 5-(2-Benzyloxy-4-piperidin-3-yl-methylphenyl)-1,1-dioxo-2-(2-trimethylsilanylethyl)-1,2,5-thiadiazolidin-3-one To a solution of 3-{3-benzyloxy-4-[1,1,4-trioxo-5-(2-trimethylsilanylethyl)-1,2,5-thiadiazolidin-2-yl]-benzyl}-piperidine-1-carboxylic acid tert-butyl ester (Example 64, step B) (220 mg, 0.36 mmol) in methylene chloride (5 mL) is added TFA (1 mL) and the mixture is stirred at RT for 1 h. The solvent is removed under reduced pressure and the residue azeotroped with toluene to give the title compound as its TFA salt: (M+1)$^+$=516.

B. 5-[2-Benzyloxy-4-(1-methanesulfonylpiperidin-3-ylmethyl)-phenyl]-1,1-dioxo-2-(2-trimethylsilanylethyl)-1,2,5-thiadiazolidin-3-one To a solution of 5-(2-benzyloxy-4-piperidin-3-yl-methylphenyl)-1,1-dioxo-2-(2-trimethylsilanylethyl)-1,2,5-thiadiazolidin-3-one (112 mg, 0.179 mmol) and triethylamine (54 mg, 0.536 mmol) in methylene chloride (10 mL) is added methanesulfonyl chloride (20 mg, 0.179 mmol) and the mixture is stirred at RT for 2 h. The mixture is poured into 1N HCl and extracted with EtOAc and the organic phase is washed with saturated NaHCO$_3$. The organic phase is dried over magnesium sulfate and the solvent removed under reduced pressure to give the title compound.

C. 5-[2-Hydroxy-4-(1-methanesulfonylpiperidin-3-ylmethyl)-phenyl]-1,1-dioxo-1,2,5-thiadiazolidin-3-one The protecting groups are removed from 5-[2-benzyloxy-4-(1-methanesulfonylpiperidin-3-ylmethyl)-phenyl]-1,1-dioxo-2-(2-trimethylsilanylethyl)-1,2,5-thiadiazolidin-3-one analogous to Example 57, steps C and D. $^1$H NMR (400 MHz, DMSO-d$_6$) δ ppm 1.08 (d, J=17.18 Hz, 1 H) 1.46 (br. s., 1 H) 1.70 (br. s., 2 H) 1.75 (br. s., 1 H) 2.36-2.47 (m, 3 H) 2.67 (td, J=11.37, 2.27 Hz, 1 H) 2.82 (s, 3 H) 3.42 (d, J=12.13 Hz, 2 H) 4.03 (s, 2 H) 6.53 (br. s., 1 H) 6.63 (br. s, 1 H) 7.26 (d, J=8.08 Hz, 1 H) 8.87 (br. s., 1 H)

EXAMPLE 193

5-{2-Hydroxy-4-[2-(1-methanesulfonylpiperidin-2-yl)-ethyl]-phenyl}-1,1-dioxo-1,2,5-thiadiazolidin-3-one

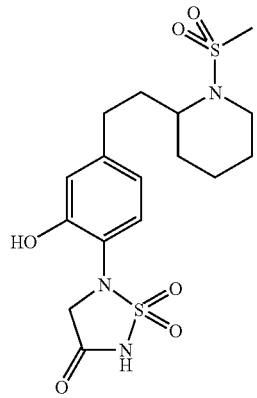

A. 5-{2-Benzyloxy-4-[(E)-2-(1-methanesulfonylpiperidin-2-yl)-vinyl]-phenyl}-1,1-dioxo-2-(2-trimethylsilanylethyl)-1,2,5-thiadiazolidin-3-one The title compound is prepared from 5-[2-benzyloxy-4-((E)-2-piperidin-2-yl-vinyl)-phenyl]-1,1-dioxo-2-(2-trimethylsilanylethyl)-1,2,5-thiadiazolidin-3-one (Example 92, step A) and methanesulfonyl chloride analogous to Example 192, step B.

B. 5-{2-Hydroxy-4-[2-(1-methanesulfonylpiperidin-2-yl)-ethyl]-phenyl}-1,1-dioxo-1,2,5-thiadiazolidin-3-one The protecting groups are removed from 5-{2-benzyloxy-4-[(E)-2-(1-methanesulfonylpiperidin-2-yl)-vinyl]-phenyl}-1,1-dioxo-2-(2-trimethylsilanylethyl)-1,2,5-thiadiazolidin-3-one analogous to Examples 39, step B and 61, step F: LC retention time=1.0 min (Method A); (M–H)⁻=416.

EXAMPLE 194

5-{4-[2-(1-Benzenesulfonylpiperidin-2-yl)-ethyl]-2-hydroxyphenyl}-1,1-dioxo-1,2,5-thiadiazolidin-3-one

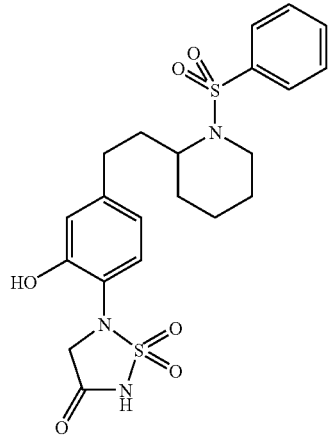

The title compound is prepared from 5-[2-benzyloxy-4-(E)-2-piperidin-2-yl-vinyl)-phenyl]-1,1-dioxo-2-(2-trimethylsilanylethyl)-1,2,5-thiadiazolidin-3-one (Example 92, step A) and benzenesulfonyl chloride analogous to Example 193: LC retention time=1.28 min (Method A); (M–1)⁻=478.

EXAMPLE 195 AND 195b.

5-{4-[2-((S)-1-Benzenesulfonylpiperidin-2-yl)-ethyl]-2-hydroxyphenyl}-1,1-dioxo-1,2,5-thiadiazolidin-3-one

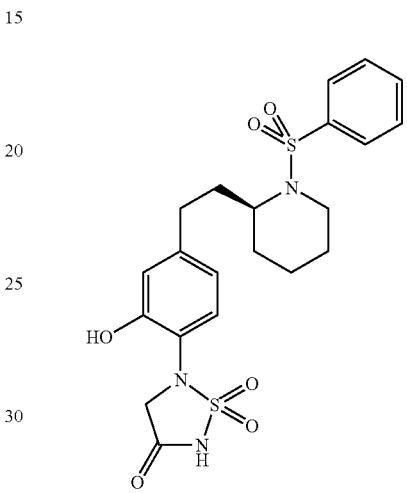

5-{4-[2-((R)-1-Benzenesulfonylpiperidin-2-yl)-ethyl]-2-hydroxyphenyl}-1,1-dioxo-1,2,5-thiadiazolidin-3-one

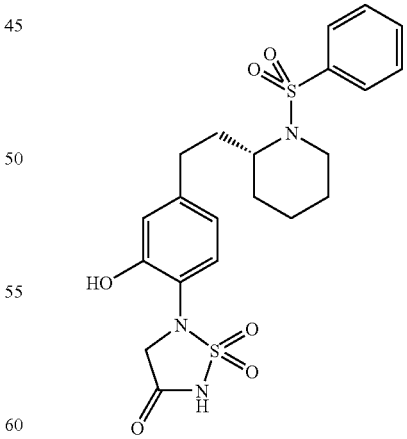

The enantiomers of Example 194 are separated by chiral HPLC (Chiracel AD, 70% EtOH in hexanes, 15 mL/min) prior to deprotection to afford the title compounds: LC retention time=1.1 min (Method A); (M–1)⁻=478

EXAMPLE 196

5-{4-[2-(1-Benzenesulfonylpyrrolidin-2-yl)-ethyl]-2-hydroxyphenyl}-1,1-dioxo-1,2,5-thiadiazolidin-3-one

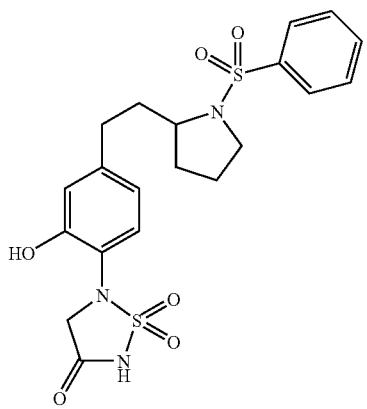

A. 1-Benzenesulfonyl-2-vinylpyrrolidine

To a suspension of methyl triphenylphosphonium bromide (357 mg, 1 mmol) in THF (10 mL) at −78° C. is added dropwise KHMDS (1 mmol, 2 mL of 0.5M solution). To this yellow solution is added dropwise a solution of 1-benzenesulfonylpyrrolidine-2-carbaldehyde (235 mg, 1 mmol) in THF (1 mL). The mixture is stirred at −78° C. for 2 h then is allowed to warm to RT. The mixture is poured into 1N HCl and extracted with EtOAc. The organic phase is washed with brine and dried over magnesium sulfate then the solvent removed under reduced pressure. The resulting oil is purified by flash chromatography using a gradient of 0-20% EtOAc/hexane as eluent to give the title compound.

B. 5-{4-[(E)-2-(1-Benzenesulfonylpyrrolidin-2-yl)-vinyl]-2-benzyloxyphenyl}-1,1-dioxo-2-(2-trimethylsilanylethyl)-1,2,5-thiadiazolidin-3-one To a solution of 5-(2-benzyloxy-4-iodophenyl)-1,1-dioxo-2-(2-trimethylsilanylethyl)-1,2,5-thiadiazolidin-3-one (100 mg, 0.183 mmol) in acetonitrile (2 mL) is added 1-benzenesulfonyl-2-vinylpyrrolidine (43 mg, 0.183 mmol), NEt$_3$ (0.038 mL, 0.274 mmol), Pd(OAc)$_2$ (2 mg, 0.034 mmol), and 2-(di-t-butylphosphino)biphenyl (4 mg) and the mixture stirred at 80° C. for 48 h. The reaction is cooled to RT and partitioned between 1N HCl and EtOAc. The organic phase is washed with brine and dried over magnesium sulfate. The solvent is removed under reduced pressure and the crude material purified by column chromatography using a gradient of 10-25% EtOAc/hexane to afford the title compound.

C. 5-{4-[(E)-2-(1-Benzenesulfonylpyrrolidin-2-yl)-vinyl]-2-benzyloxyphenyl}-1,1-dioxo-1,2,5-thiadiazolidin-3-one To a solution of 5-{4-[(E)-2-(1-benzenesulfonylpyrrolidin-2-yl)-vinyl]-2-benzyloxyphenyl}-1,1-dioxo-2-(2-trimethylsilanylethyl)-1,2,5-thiadiazolidin-3-one (53 mg) in THF (2 mL) is added 0.2 mL of a 1M solution of TBAF in THF. The mixture is stirred at 60° C. for 2 h then is allowed to cool to RT. The mixture is poured into 1N HCl (20 mL) and extracted with EtOAc. The organic phase is washed with 1N HCl and brine and is dried over magnesium sulfate. The solvent is removed under reduced pressure and the residue is purified by reverse phase Biotage using a gradient of 0-100% EtOH/water as eluent to furnish the title compound as a blue oil: (M−1)$^-$=548.

D. 5-{4-[2-(1-Benzenesulfonylpyrrolidin-2-yl)-ethyl]-2-hydroxyphenyl}-1,1-dioxo-1,2,5-thiadiazolidin-3-one To a mixture of 5-{4-[(E)-2-(1-benzenesulfonylpyrrolidin-2-yl)-vinyl]-2-benzyloxyphenyl}-1,1-dioxo-1,2,5-thiadiazolidin-3-one (22 mg) in 4 mL ethanol/water (1:3) is added 5 mg of Degussa Pd/C and the resulting mixture is hydrogenated at 1 atm for 1 h. The catalyst is filtered through Celite and the solvent is removed under reduced pressure. The residue is purified by reverse phase Biotage using a gradient of 20-60% EtOH/water as eluent to furnish the title compound: LC retention time=1.10 min (Method A); (M−H)$^-$=464.

EXAMPLE 197

5-{4-[2-(1-Benzenesulfonyl-1H-pyrrol-2-yl)-ethyl]-2-hydroxyphenyl}-1,1-dioxo-1,2,5-thiadiazolidin-3-one

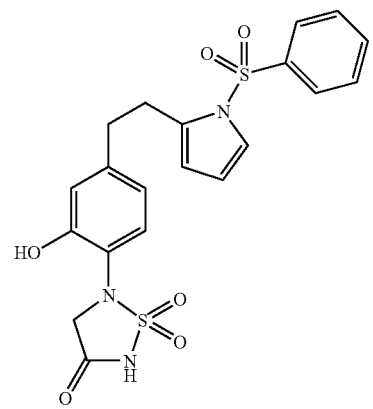

The title compound is isolated from Example 196, step D: LC retention time=1.6 min (Method A); (M−H)$^-$=460.

EXAMPLE 198

5-{4-[2-(1-Benzenesulfonylpyrrolidin-3-yl)-ethyl]-2-hydroxyphenyl}-1,1-dioxo-1,2,5-thiadiazolidin-3-one

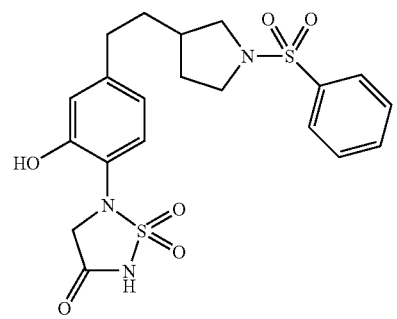

A. 3-Vinylpyrrolidine-1-carboxylic Acid Tert-butyl Ester

The title compound is prepared from 3-formylpyrrolidine-1-carboxylic acid tert-butyl ester and methyl triphenylphosphonium bromide analogous to Example 196, step A.

B. 3-((E)-2-{3-Benzyloxy-4-[1,1,4-trioxo-5-(2-trimethylsilanylethyl)-1,2,5-thiadiazolidin-2-yl]-phenyl}-vinyl)-pyrrolidine-1-carboxylic Acid Tert-butyl Ester The title compound is prepared from 5-(2-benzyloxy-4-iodophenyl)-1,1-dioxo-2-(2-trimethylsilanylethyl)-1,2,5-thiadiazolidin-3-one and 3-vinylpyrrolidine-1-carboxylic acid tert-butyl ester analogous to Example 62, step B.

C. 5-[2-Benzyloxy-4-((E)-2-pyrrolidin-3-yl-vinyl)-phenyl]-1,1-dioxo-2-(2-trimethylsilanylethyl)-1,2,5-thiadiazolidin-3-one The title compound is prepared from 3-((E)-2-{3-benzyloxy-4-[1,1,4-trioxo-5-(2-trimethylsilanylethyl)-1,2,5-thiadiazolidin-2-yl]-phenyl}-vinyl)-pyrrolidine-1-carboxylic acid tert-butyl ester analogous to Example 192, step A.

D. 5-{4-[(E)-2-(1-Benzenesulfonylpyrrolidin-3-yl)-vinyl]-2-benzyloxyphenyl}-1,1-dioxo-2-(2-trimethylsilanylethyl)-1,2,5-thiadiazolidin-3-one The title compound is prepared from 5-[2-benzyloxy-4-((E)-2-pyrrolidin-3-yl-vinyl)-phenyl]-1,1-dioxo-2-(2-trimethylsilanylethyl)-1,2,5-thiadiazolidin-3-one and benzenesulfonyl chloride analogous to Example 192, step B.

E. 5-{4-[2-(1-Benzenesulfonylpyrrolidin-3-yl)-ethyl]-2-hydroxyphenyl}-1,1-dioxo-1,2,5-thiadiazolidin-3-one The title compound is prepared from 5-{4-[(E)-2-(1-benzenesulfonylpyrrolidin-3-yl)-vinyl]-2-benzyloxyphenyl}-1,1-dioxo-2-(2-trimethylsilanylethyl)-1,2,5-thiadiazolidin-3-one analogous to Example 196, steps C and D: LC retention time=1.10 min (Method A); (M–H)⁻=464.

EXAMPLE 199

5-{4-[2-(1-Benzenesulfonylazepan-2-yl)-ethyl]-2-hydroxyphenyl}-1,1-dioxo-1,2,5-thiadiazolidin-3-one

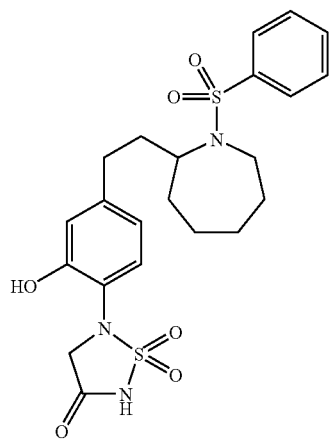

The title compound is prepared from azepane-2-carboxylic acid analogous to the series of steps described for Example 185: (M–H)⁻=492.

EXAMPLE 200

5-{2-Hydroxy-4-[2-((R)-2-methanesulfonyl-1,2,3,4-tetrahydroisoquinolin-3-yl)-ethyl]-phenyl}-1,1-dioxo-1,2,5-thiadiazolidin-3-one

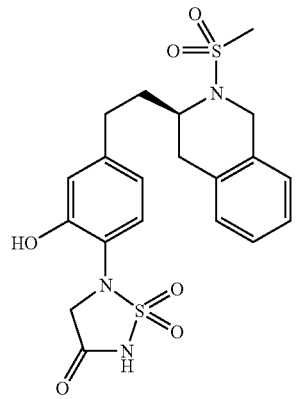

A. (S)-3-Hydroxymethyl-3,4-dihydro-1H-isoquinoline-2-carboxylic Acid Tert-butyl Ester A solution of (S)-3,4-dihydro-1H-isoquinoline-2,3-dicarboxylic acid 2-tert-butyl ester (1.0 g, 3.61 mmol) in THF (20 mL) is stirred at RT for 10 min. HATU (1.51 g, 3.97 mmol) is added and the suspension is allowed to stir at RT for 30 min. To the solution is added iPr₂NEt (1.57 mL, 9.02 mmol) and the mixture is allowed to stir at RT for 18 h. NaBH₄ is added (0.164 g, 4.33 mmol) then the mixture is quenched with MeOH (1 mL), extracted with EtOAc (2×30 mL), washed with 1N HCl (4×50 mL), saturated NaHCO₃ (2×50 mL) and brine (2×50 mL). The organic layer is dried over Na₂SO₄ and concentrated. The residue is purified by column chromatography, eluting with a gradient of 20-50% EtOAc/hexane as eluent to afford the title compound.

B. (S)-3-Formyl-3,4-dihydro-1H-isoquinoline-2-carboxylic Acid Tert-butyl Ester To a solution of oxalyl chloride (0.798 mL, 9.15 mmol) in CH₂Cl₂ (11 mL) at –78° C. is added DMSO (1.08 mL, 15.25 mmol) dropwise (evolution of gas observed) and the mixture stirred at –78° C. for 1.5 h. To this is added a solution of (S)-3-hydroxymethyl-3,4-dihydro-1H-isoquinoline-2-carboxylic acid tert-butyl ester (0.803 g, 3.05 mmol) in CH₂Cl₂ (9 mL) and the mixture is stirred at –78° C. for 1.5 h. Triethylamine (3.4 mL, 24.41 mmol) is added and the mixture is stirred for 10 min at –78° C. and then warmed to room temperature for 1.5 h. The mixture is extracted with EtOAc (2×30 mL), washed with 1N HCl (1×35 mL) and extracted again with EtOAc (1×30 mL). The combined organic layers are washed with 1N HCl (2×30 mL) and brine (2×30 mL), dried over Na₂SO₄ and concentrated to afford the title compound.

C. (S)-3-Vinyl-3,4-dihydro-1H-isoquinoline-2-carboxylic Acid Tert-butyl Ester To a solution of methyltriphenylphosphonium bromide (2.07 g, 5.8 mmol) in THF (20 mL) at −78° C. is added KHMDS (11.0 mL, 5.5 mmol) and the mixture is stirred for 1.5 h. A solution of (S)-3-formyl-3,4-dihydro-1H-isoquinoline-2-carboxylic acid tert-butyl ester (0.94 g, 3.6 mmol) in THF (10 mL) is added and the solution stirred at −78-C for 1.5 h before warming to RT. The reaction is quenched with water (10 mL) and extracted with EtOAc (2×30 mL). The organic extracts are washed with 1N HCl (3×35 mL), brine (2×30 mL) and dried over $Na_2SO_4$. Purification by flash chromatography using a gradient of 0-15% EtOAc/hexane affords the title compound.

D. (S)-3-((E)-2-{3-Benzyloxy-4-[1,1,4-trioxo-5-(2-trimethylsilanylethyl)-1,2,5-thiadiazolidin-2-yl]-phenyl}-vinyl)-3,4-dihydro-1H-isoquinoline-2-carboxylic Acid Tert-butyl Ester To a solution of 5-(2-benzyloxy-4-iodophenyl)-1,1-dioxo-2-(2-trimethylsilanylethyl)-1,2,5-thiadiazolidin-3-one (0.77 g, 1.4 mmol) and (S)-3-vinyl-3,4-dihydro-1H-isoquinoline-2-carboxylic acid tert-butyl ester (0.44 g, 1.7 mmol) in acetonitrile (5 mL) in a pressure vessel is added $Et_3N$ (0.32 mL, 2.3 mmol) followed by di-t-butyl-phosphinobiphenyl (0.017 g, 0.057 mmol). The solution is degassed by nitrogen sparging for 10 min, and then $Pd(OAc)_2$ (0.006 g, 0.028 mmol) is added and the mixture is heated to 80° C. for 18 h. The mixture is cooled to RT and is diluted with 1N HCl and extracted with EtOAc (2×30 mL). The organic layer is washed with brine (3×30 mL) and dried over $Na_2SO_4$. The solvent is removed under reduced pressure and the residue purified by flash chromatography using a gradient of 5 to 30% EtOAc in hexanes to give the title compound.

E. 5-{2-Benzyloxy-4-[(E)-(S)-2-(1,2,3,4-tetrahydroisoquinolin-3-yl)-vinyl]-phenyl}-1,1-dioxo-2-(2-trimethylsilanylethyl)-1,2,5-thiadiazolidin-3-one To a solution of (S)-3-((E)-2-{3-benzyloxy-4-[1,1,4-trioxo-5-(2-trimethylsilanylethyl)-1,2,5-thiadiazolidin-2-yl]-phenyl}-vinyl)-3,4-dihydro-1H-isoquinoline-2-carboxylic acid tert-butyl ester (0.22 g, 0.32 mmol) in $CH_2Cl_2$ (8 mL) is added TFA (3 mL). After stirring at RT for 1.5 h, the mixture is concentrated under reduced pressure to give the title compound which is used directly in the next step.

F. 5-{2-Benzyloxy-4-[(E)-2-((S)-2-methanesulfonyl-1,2,3,4-tetrahydroisoquinolin-3-yl)-vinyl]-phenyl}-1,1-dioxo-2-(2-trimethylsilanylethyl)-1,2,5-thiadiazolidin-3-one To a solution of 5-{2-benzyloxy-4-[(E)-(S)-2-(1,2,3,4-tetrahydroisoquinolin-3-yl)-vinyl]-phenyl}-1,1-dioxo-2-(2-trimethylsilanylethyl)-1,2,5-thiadiazolidin-3-one (0.12 g, 0.21 mmol) in $CH_2Cl_2$ (2 mL) is added triethylamine (0.15 mL, 1.0 mmol), followed by methanesulfonyl chloride (0.020 mL, 0.25 mmol). The mixture is stirred at RT for 1.5 h then is diluted with EtOAc (15 mL) and washed with 1N HCl (2×15 mL) and brine (1×15 mL). The organic layer is dried over $Na_2SO_4$, concentrated in vacuo and used directly in the next step without further purification.

G. 5-{2-Benzyloxy-4-[(E)-2-((S)-2-methanesulfonyl-1,2,3,4-tetrahydroisoquinolin-3-yl)-vinyl]-phenyl}-1,1-dioxo-1,2,5-thiadiazolidin-3-one To a solution of 5-{2-benzyloxy-4-[(E)-2-((S)-2-methanesulfonyl-1,2,3,4-tetrahydroisoquinolin-3-yl)-vinyl]-phenyl}-1,1-dioxo-2-(2-trimethylsilanylethyl)-1,2,5-thiadiazolidin-3-one (0.107 g, 0.164 mmol) in DMF (10 mL) is added CsF (0.980 g, 6.47 mmol). The mixture is stirred at 60° C. for 1.25 h, and then diluted with EtOAc (20 mL) and washed with 1N HCl (2×15 mL), followed by brine (2×15 mL). The organic layer is dried with $Na_2SO_4$ and the solvent removed under reduced pressure to give the title compound.

H. 5-{2-Hydroxy-4-[2-((R)-2-methanesulfonyl-1,2,3,4-tetrahydroisoquinolin-3-yl)-ethyl]-phenyl}-1,1-dioxo-1,2,5-thiadiazolidin-3-one To a solution of 5-{2-benzyloxy-4-[(E)-2-((S)-2-methanesulfonyl-1,2,3,4-tetrahydroisoquinolin-3-yl)-vinyl]-phenyl}-1,1-dioxo-1,2,5-thiadiazolidin-3-one (0.090 g, 0.16 mmol) in EtOH (4 mL) is added a slurry of 10% Pd/C (0.1 g) in EtOH (6 mL). The reaction vessel is flushed twice with $H_2$ and stirred at RT for 18 h under balloon pressure of $H_2$. The mixture is filtered and purified by reverse phase chromatography using a gradient of 15 to 40% EtOH/water to afford the title compound as a white solid: LC retention time=1.0 min (Method A); $(M+NH_4)^+=465$.

EXAMPLE 201

5-{4-[2-((R)-2-Benzenesulfonyl-1,2,3,4-tetrahydroisoquinolin-3-yl)-ethyl]-2-hydroxyphenyl}-1,1-dioxo-1,2,5-thiadiazolidin-3-one

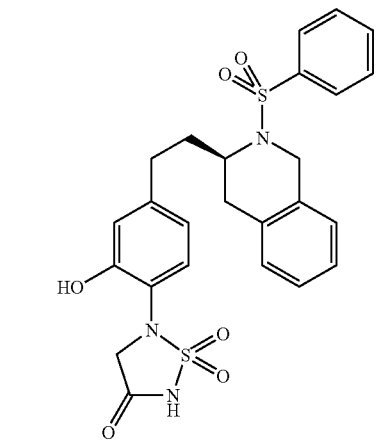

The title compound is prepared from 5-{2-benzyloxy-4-[(E)-(S)-2-(1,2,3,4-tetrahydroisoquinolin-3-yl)-vinyl]-phenyl}-1,1-dioxo-2-(2-trimethylsilanylethyl)-1,2,5-thiadiazolidin-3-one and benzenesulfonyl chloride analogous to Example 200, steps F, G and H: LC retention time=1.26 min (Method A); $(M+NH_4)^+=545$.

EXAMPLE 202

5-(2-Hydroxy-4-{2-[2-(4-trifluoromethylbenzene-sulfonyl)-1,2,3,4-tetrahydroisoquinolin-3-yl]-ethyl}-phenyl)-1,1-dioxo-1,2,5-thiadiazolidin-3-one

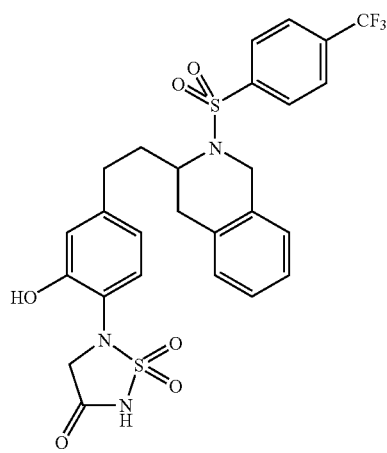

The title compound is prepared from 5-{2-benzyloxy-4-[(E)-2-(1,2,3,4-tetrahydroisoquinolin-3-yl)-vinyl]-phenyl}-1,1-dioxo-2-(2-trimethylsilanylethyl)-1,2,5-thiadiazolidin-3-one and 4-trifluoromethylbenzenesulfonyl chloride analogous to Example 200, steps F, G and H: (M−1)⁻=546.

EXAMPLE 203

5-{2-Hydroxy-4-[2-(2-phenylmethanesulfonyl-1,2,3,4-tetrahydroisoquinolin-3-yl)-ethyl]-phenyl}-1,1-dioxo-1,2,5-thiadiazolidin-3-one

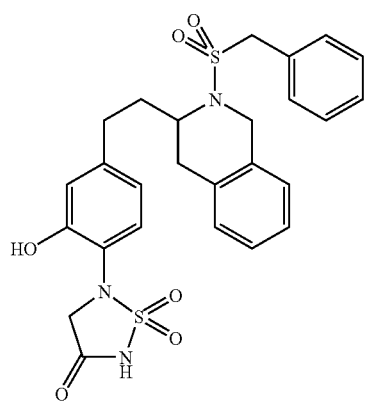

The title compound is prepared from 5-{2-benzyloxy-4-[(E)-2-(1,2,3,4-tetrahydroisoquinolin-3-yl)-vinyl]-phenyl}-1,1-dioxo-2-(2-trimethylsilanylethyl)-1,2,5-thiadiazolidin-3-one and benzylsulfonyl chloride analogous to Example 200, steps F, G and H: (M−1)⁻=492.

EXAMPLE 204

5-{4-[2-(1,1-Dioxo-1,2-thiazinan-3-yl)-ethyl]-2-hydroxyphenyl}-1,1-dioxo-1,2,5-thiadiazolidin-3-one

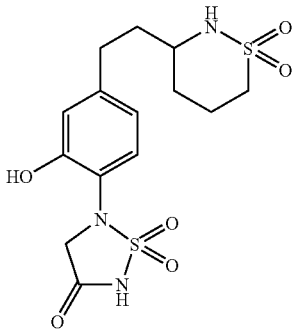

A. 5-{2-Benzyloxy-4-[(E)-2-(1,1-dioxo-1,2-thiazinan-3-yl)-vinyl]-phenyl}-1,1-dioxo-1,2,5-thiadiazolidin-3-one A mixture of 3-vinyl-[1,2]thiazinane 1,1-dioxide (107 mg, 0.664 mmol) (J. Org. Chem. 69, 6377 (2004)), 5-(2-benzyloxy-4-iodophenyl)-1,1-dioxo-2-(2-trimethylsilanylethyl)-1,2,5-thiadiazolidin-3-one (250 mg, 0.563 mmol), Pd(OAc)₂ (13 mg, 0.058 mmol) and triethylamine (0.768 mL, 5.51 mmol) in MeCN (4 mL) is heated at 120° C. for 1.5 h in a microwave apparatus. The reaction mixture is concentrated and the residue purified by preparative HPLC to afford the title compound.

B. 5-{4-[2-(1,1-Dioxo-1,2-thiazinan-3-yl)-ethyl]-2-hydroxyphenyl}-1,1-dioxo-1,2,5-thiadiazolidin-3-one The title compound is prepared from 5-{2-benzyloxy-4-[(E)-2-(1,1-dioxo-1,2-thiazinan-3-yl)-vinyl]-phenyl}-1,1-dioxo-1,2,5-thiadiazolidin-3-one analogous to Example 57, step D: (M−1)⁻=388; HPLC retention time=0.61 min. (Method A)

EXAMPLE 205

N-{(1R*,2S*)-2-[3-Hydroxy-4-(1,1,4-trioxo-1,2,5-thiadiazolidin-2-yl)-benzyl]-cyclohexyl}-methane-sulfonamide

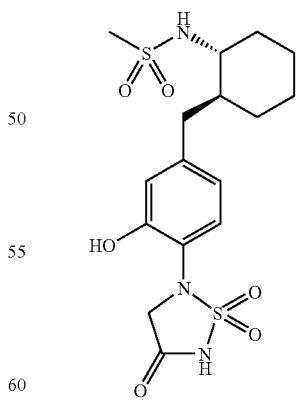

A. 5-[4-((1S*,2R*)-2-Aminocyclohexylmethyl)-2-benzyloxy-phenyl]-1,1-dioxo-2-(2-trimethylsilanyl-ethyl)-1,2,5-thiadiazolidin-3-one To a solution of ((1R*,2S*)-2-{3-benzyloxy-4-[1,1,4-tri-oxo-5-(2-trimethylsilanylethyl)-1,2,5-thiadiazolidin-2-yl]- benzyl}-cyclohexyl)-carbamic acid tert-butyl ester (Example 66, step C) (450 mg, 0.714 mmol) in methylene chloride (5 mL) is added TFA (5 mL) and the solution is stirred at RT for 15 min. The solvent is removed under reduced pressure to give the title compound which is used directly in the next step.

B. N-((1R*,2S*)-2-{3-Benzyloxy-4-[1,1,4-trioxo-5-(2-trimethylsilanylethyl)-1,2,5-thiadiazolidin-2-yl]-benzyl}-cyclohexyl)-methanesulfonamide To a solution of 5-[4-((1S*,2R*)-2-aminocyclohexylmethyl)-2-benzyloxy-phenyl]-1,1-dioxo-2-(2-trimethylsilanylethyl)-1,2,5-thiadiazolidin-3-one (153 mg, 0.238 mmol) and diisopropylethylamine (92 mg, 0.712 mmol) in methylene chloride (5 mL) is added methanesulfonyl chloride (30 mg, 0.258 mmol) and the mixture is stirred at RT for 14 h. The mixture is poured into 1N HCl and extracted with EtOAc and the organic phase is washed with saturated NaHCO$_3$. The organic phase is dried over magnesium sulfate and the solvent removed under reduced pressure to give the title compound.

C. N-{(1R*,2S*)-2-[3-Benzyloxy-4-(1,1,4-trioxo-1,2,5-thiadiazolidin-2-yl)-benzyl]-cyclohexyl}-methanesulfonamide To a solution of N-((1R*,2S*)-2-{3-Benzyloxy-4-[1,1,4-trioxo-5-(2-trimethylsilanylethyl)-1,2,5-thiadiazolidin-2-yl]-benzyl}-cyclohexyl)-methanesulfonamide (118 mg, 0.194 mmol) in DMF (3 mL) is added CsF (118 mg, 0.78 mmol) and the mixture is stirred at 90° C. for 1 h. Ethyl acetate is added and the mixture is washed with 1N HCl and brine. The organic phase is dried over magnesium sulfate and the solvent is removed under reduced pressure to give the title compound.

D. N-{(1R*,2S*)-2-[3-Hydroxy-4-(1,1,4-trioxo-1,2,5-thiadiazolidin-2-yl)-benzyl]-cyclohexyl}-methanesulfonamide The title compound is prepared from N-{(1R*,2S*)-2-[3-benzyloxy-4-(1,1,4-trioxo-1,2,5-thiadiazolidin-2-yl)-benzyl]-cyclohexyl}-methanesulfonamide analogous to Example 57, step D: (M−1)$^-$=416; HPLC retention time=0.84 min. (Method A).

EXAMPLE 206 AND 207

N-{(1R,2S)-2-[3-Hydroxy-4-(1,1,4-trioxo-1,2,5-thiadiazolidin-2-yl)-benzyl]-cyclohexyl}-methanesulfonamide

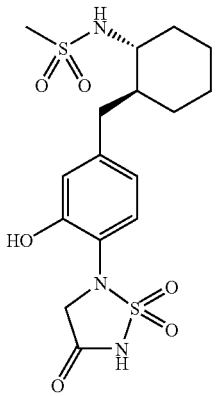

N-{(1S,2R)-2-[3-Hydroxy-4-(1,1,4-trioxo-1,2,5-thiadiazolidin-2-yl)-benzyl]-cyclohexyl}-methanesulfonamide

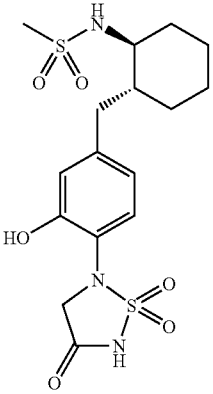

Racemic ((1R*,2S*)-2-{3-benzyloxy-4-[1,1,4-trioxo-5-(2-trimethylsilanylethyl)-1,2,5-thiadiazolidin-2-yl]-benzyl}-cyclohexyl)-carbamic acid tert-butyl ester (Example 66, step C) is separated into its enantiomers by chiral HPLC. Each enantiomer is converted to final product analogous to Example 205. Example 206: MS (M−1)$^-$=416; HPLC retention time=0.83 min. (Method A). Example 207: MS (M−1)$^-$=416; HPLC retention time=0.82 min., (Method A).

EXAMPLE 208

Ethanesulfonic acid {(1R*,2S*)-2-[3-hydroxy-4-(1,1,4-trioxo-1,2,5-thiadiazolidin-2-yl)-benzyl]-cyclohexyl}-amide

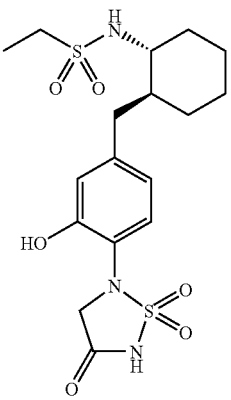

The title compound is prepared from 5-[4-((1S*,2R*)-2-aminocyclohexylmethyl)-2-benzyloxy-phenyl]-1,1-dioxo-2-(2-trimethylsilanylethyl)-1,2,5-thiadiazolidin-3-one and ethanesulfonyl chloride analogous to Example 205, steps B, C and D. MS (M−1)$^-$=430; HPLC retention time=0.91 min. (Method A).

EXAMPLE 209

N-{(1R*,2S*)-2-[3-Hydroxy-4-(1,1,4-trioxo-1,2,5-thiadiazolidin-2-yl)-benzyl]-cyclohexyl}-benzenesulfonamide

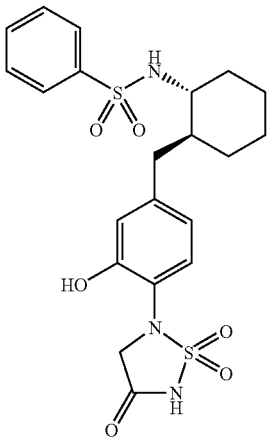

The title compound is prepared from 5-[4-((1S*,2R*)-2-aminocyclohexylmethyl)-2-benzyloxy-phenyl]-1,1-dioxo-2-(2-trimethylsilanylethyl)-1,2,5-thiadiazolidin-3-one and benzenesulfonyl chloride analogous to Example 205, steps B, C and D. MS (M−1)⁻=478; HPLC retention time=1.10 min. (Method A).

EXAMPLE 210

(S)-2-Benzenesulfonylamino-3-[3-hydroxy-4-(1,1,4-trioxo-1,2,5-thiadiazolidin-2-yl)-phenyl]-N-pentyl-propionamide

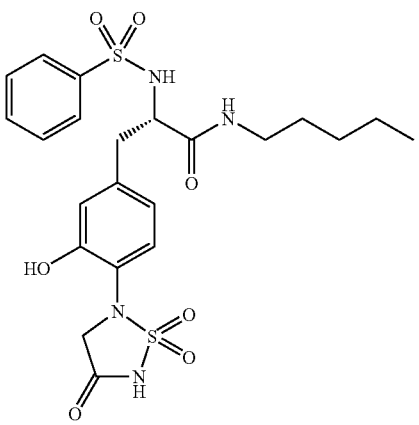

A. (S)-2-Benzenesulfonylamino-3-{3-benzyloxy-4-[1,1,4-trioxo-5-(2-trimethylsilanylethyl)-1,2,5-thiadiazolidin-2-yl]-phenyl}-propionic Acid Tert-butyl Ester To a solution of (S)-2-amino-3-{3-benzyloxy-4-[1,1,4-trioxo-5-(2-trimethylsilanylethyl)-1,2,5-thiadiazolidin-2-yl]-phenyl}-propionic acid tert-butyl ester (Example 132, step C) (10 mg, 0.249 mmol) and triethylamine (51 mg, 0.5 mmol) in MeCN (5 mL) is added benzenesulfonyl chloride (44 mg, 0.249 mmol) and the mixture is stirred at RT for 2 h. The solvent is removed under reduced pressure and the residue partitioned between methylene chloride and 1N HCl. The organic phase dried over sodium sulfate and the solvent removed under reduced pressure. The residue is purified by flash chromatography using a gradient of 0-40% EtOAc/hexane as eluent to give the title compound: (M−1)⁻=700.

B. (S)-2-Benzenesulfonylamino-3-{3-benzyloxy-4-[1,1,4-trioxo-5-(2-trimethylsilanylethyl)-1,2,5-thiadiazolidin-2-yl]-phenyl}-propionic Acid A solution of (S)-2-benzenesulfonylamino-3-{3-benzyloxy-4-[1,1,4-trioxo-5-(2-trimethylsilanylethyl)-1,2,5-thiadiazolidin-2-yl]-phenyl}-propionic acid tert-butyl ester (80 mg, 0.114 mmol) in 12 mL of TFA/CH₂Cl₂ (5:1) is stirred at RT for 1 h. The solution is concentrated, then four times redissolved in CH₂Cl₂ and reconcentrated to give the title compound: (M−1)⁻=644.

C. (S)-2-Benzenesulfonylamino-3-{3-benzyloxy-4-[1,1,4-trioxo-5-(2-trimethylsilanylethyl)-1,2,5-thiadiazolidin-2-yl]-phenyl}-N-pentylpropionamide To a solution of (S)-2-benzenesulfonylamino-3-{3-benzyloxy-4-[1,1,4-trioxo-5-(2-trimethylsilanylethyl)-1,2,5-thiadiazolidin-2-yl]-phenyl}-propionic acid (70 mg, 0.108 mmol) in methylene chloride (3 mL) is added EDCl (31 mg, 0.162 mmol) and the solution is stirred at RT for 3 min. To this is added n-pentylamine (10 mg, 0.119 mmol) and the mixture is stirred at RT for 18 h. The solvent is removed under reduced pressure and the residue purified by flash chromatography using a gradient of 0-100% EtOAc/hexane as eluent to give the title compound: (M−1)⁻=713.

D. (S)-2-Benzenesulfonylamino-3-[3-hydroxy-4-(1,1,4-trioxo-1,2,5-thiadiazolidin-2-yl)-phenyl]-N-pentylpropionamide The protecting groups are removed analogous to Example 51, steps B and C to give the title compound: (M−1)⁻=523. HPLC retention time: 0.94 min (Method A).

EXAMPLE 211

(S)-2-Benzenesulfonylamino-3-[3-hydroxy-4-(1,1,4-trioxo-1,2,5-thiadiazolidin-2-yl)-phenyl]-N-(4-phenylbutyl)-propionamide

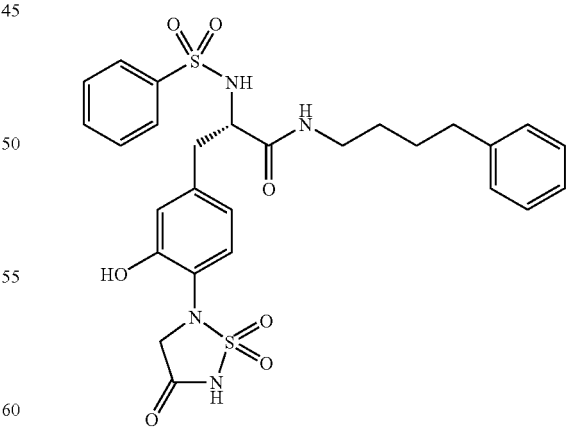

The title compound is prepared from (S)-2-benzenesulfonylamino-3-{3-benzyloxy-4-[1,1,4-trioxo-5-(2-trimethylsilanylethyl)-1,2,5-thiadiazolidin-2-yl]-phenyl}-propionic acid and 4-phenylbutylamine analogous to Example 210, steps C and D: (M−1)⁻=585. HPLC retention time: 1.27 min. (Method A).

EXAMPLE 212

N-{(S)-1-(1H-Benzoimidazol-2-yl)-2-[3-hydroxy-4-(1,1,4-trioxo-1,2,5-thiadiazolidin-2-yl)-phenyl]-ethyl}-benzenesulfonamide

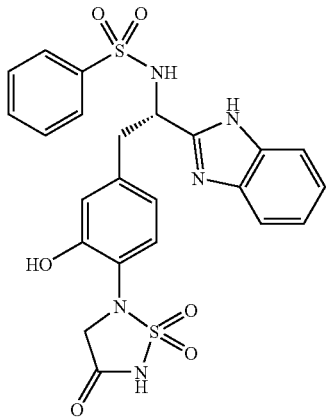

A. (S)-2-Benzenesulfonylamino-3-[3-benzyloxy-4-(1,4-trioxo-1,2,5-thiadiazolidin-2-yl)-phenyl]-propionic Acid To a solution of (S)-2-benzenesulfonylamino-3-{3-benzyloxy-4-[1,1,4-trioxo-5-(2-trimethylsilanylethyl)-1,2,5-thiadiazolidin-2-yl]-phenyl}-propionic acid (110 mg, 0.17 mmol) in DMF (5 mL) is added CsF (130 mg, 0.85 mmol) and the mixture is heated at 60° C. for 3 h. After the mixture is cooled to RT, 1N HCl is added and the mixture is extracted with EtOAc. The organic phase is washed with water and brine then dried over sodium sulfate. The solvent is removed under reduced pressure to give the title compound.

B. (S)—N-(2-Aminophenyl)-2-benzenesulfonylamino-3-[3-benzyloxy-4-(1,1,4-trioxo-1,2,5-thiadiazolidin-2-yl)-phenyl]-propionamide To a solution of (S)-2-benzenesulfonylamino-3-[3-benzyloxy-4-(1,1,4-trioxo-1,2,5-thiadiazolidin-2-yl)-phenyl]-propionic acid (110 mg, 0.2 mmol) in DMF (5 mL) is added diisopropylethylamine (0.038 mL, 0.22 mmol) and HATU (84 mg, 0.22 mmol). The mixture is stirred at RT for 10 min then a solution of 1,2-diaminobenzene (26 mg, 0.24 mmol) in DMF (1 mL) is added and stirring is continued for 48 h. The solvent is removed under reduced pressure to give the title compound which is used directly in the next step

C. N-{(S)-1-(1H-Benzoimidazol-2-yl)-2-[3-benzyloxy-4-(1,1,4-trioxo-1,2,5-thiadiazolidin-2-yl)-phenyl]-ethyl}-benzenesulfonamide A solution of (S)—N-(2-aminophenyl)-2-benzenesulfonylamino-3-[3-benzyloxy-4-(1,1,4-trioxo-1,2,5-thiadiazolidin-2-yl)-phenyl]-propionamide in acetic acid is stirred at 60° C. for 4 h. The solvent is removed under reduced pressure to give the title compound.

D. N-{(S)-1-(1H-Benzoimidazol-2-yl)-2-[3-hydroxy-4-(1,1,4-trioxo-1,2,5-thiadiazolidin-2-yl)-phenyl]-ethyl}-benzenesulfonamide A solution of N-{(S)-1-(1H-benzoimidazol-2-yl)-2-[3-benzyloxy-4-(1,1,4-trioxo-1,2,5-thiadiazolidin-2-yl)-phenyl]-ethyl}-benzenesulfonamide and $K_2CO_3$ (50 mg) in 10 mL of EtOH/water (1:1) is hydrogenated over 10% Pd/C (100 mg) at 1 atm for 18 h. The catalyst is filtered and the solvent is removed under reduced pressure. The residue is purified by reverse phase HPLC followed by lyophilization to give the title compound as a pink solid. (M−1)⁻: 526. HPLC retention time: 0.98 min. (Method A).

EXAMPLE 213

Tert-Butyl [({2-[4-(1,1-dioxido-4-oxo-1,2,5-thiadiazolidin-2-yl)-3-hydroxyphenyl]ethyl}amino)sulfonyl]carbamate

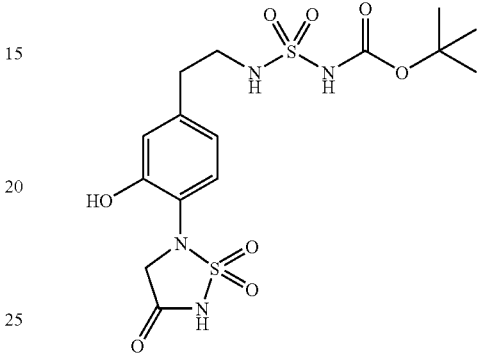

A. Tert-Butyl [({2-[4-(1,1-dioxido-4-oxo-5-(2-trimethylsilanylethyl)-1,2,5-thiadiazolidin-2-yl)-3-benzyloxyphenyl]ethyl}amino)sulfonyl]carbamate The title compound is prepared from 5-[4-(2-aminoethyl)-2-benzyloxyphenyl]-1,1-dioxo-2-(2-trimethylsilanylethyl)-1,2,5-thiadiazolidin-3-one TFA salt (Example 67, step A), chlorosulfonyl isocyanate and t-butanol analogous to Example 55, step D.

B. Tert-Butyl [({2-[4-(1,1-dioxido-4-oxo-1,2,5-thiadiazolidin-2-yl)-3-hydroxyphenyl]ethyl}aminosulfonyl]carbamate The protecting groups are removed from tert-butyl [({2-[4-(1,1-dioxido-4-oxo-5-(2-trimethylsilanylethyl)-1,2,5-thiadiazolidin-2-yl)-3-benzyloxyphenyl]ethyl}amino)sulfonyl]carbamate analogous to Example 67, steps C and D: (M−1)⁻= 449. ¹H NMR (400 MHz, DMSO-d₆) δ ppm 1.35 (br. s., 9 H) 2.63 (br. s., 2 H) 2.95 (br. s., 2 H) 4.01 (br. s., 2 H) 6.59 (d, J=7.83 Hz, 1 H) 6.68 (br. s., 2 H) 7.29 (d, J=7.83 Hz, 1 H) 8.98 (br. s., 1 H)

EXAMPLE 214

1-Cyclohexyl-3-{2-[3-hydroxy-4-(1,1,4-trioxo-1,2,5-thiadiazolidin-2-yl)-phenyl]-ethyl}-urea

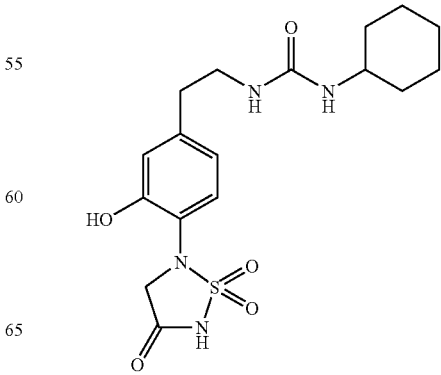

A. 1-(2-{3-Benzyloxy-4-[1,1,4-trioxo-5-(2-trimethylsilanylethyl)-1,2,5-thiadiazolidin-2-yl]-phenyl}-ethyl)-3-cyclohexylurea To 5-[4-(2-aminoethyl)-2-benzyloxyphenyl]-1,1-dioxo-2-(2-trimethylsilanylethyl)-1,2,5-thiadiazolidin-3-one (0.25 g, 0.434 mmol) (Example 67, step A) in 5 mL dioxane is added triethylamine (0.12 mL, 0.87 mmol), followed by cyclohexyl isocyanate (0.11 mL, 0.87 mmol) and the mixture heated to 85° C. for 1 h. The reaction mixture is concentrated and then partitioned between EtOAc and 1N HCl. The combined organic layers are washed with saturated sodium bicarbonate and brine, dried, and evaporated to afford a crude orange oil which is purified by flash chromatography to afford the title compound as a foam.

B. 1-Cyclohexyl-3-{2-[3-hydroxy-4-(1,1,4-trioxo-1,2,5-thiadiazolidin-2-yl)-phenyl]-ethyl}-urea The potassium salt of the title compound is prepared by removal of the protecting groups analogous to Example 67, steps C and D: $^1$H NMR (400 MHz, DMSO-$d_6$) δ ppm 1.00-1.11 (m, 1 H) 1.06 (t, J=6.95 Hz, 2 H) 1.19-1.30 (m, 2 H) 1.51 (d, J=12.13 Hz, 1 H) 1.62 (dd, J=9.09, 4.04 Hz, 2 H) 1.72 (dd, J=12.13, 3.54 Hz, 2 H) 2.59 (t, J=7.07 Hz, 2 H) 3.19 (t, J=7.07 Hz, 2 H) 3.34 (dd, J=13.89, 6.06 Hz, 1 H) 4.42 (s, 2 H) 5.70 (br. s., 1 H) 6.67<dd, J=8.08, 1.77 Hz, 1 H) 6.75 (d, J=1.52 Hz, 1 H) 7.25 (d, J=7.83 Hz, 1 H) 9.81 (br. s., 1 H)

EXAMPLES 215 TO 218

The following compounds are prepared using 5-[4-(2-aminoethyl)-2-benzyloxyphenyl]-1,1-dioxo-2-(2-trimethylsilanylethyl)-1,2,5-thiadiazolidin-3-one and an appropriate isocyanate analogous to Example 214.

EXAMPLE 219

1-(2,4-Dimethoxybenzyl)-3-{2-[3-hydroxy-4-(1,1,4-trioxo-1,2,5-thiadiazolidin-2-yl)-phenyl]-ethyl}-urea

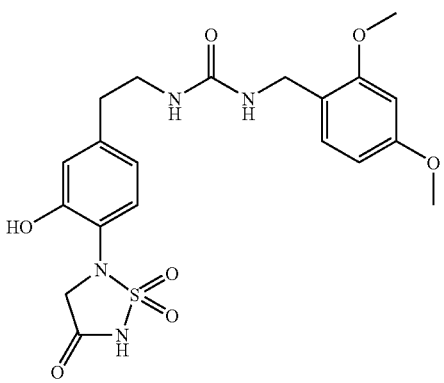

A. 5-[2-Hydroxy-4-(2-isocyanatoethyl)-phenyl]-1,1-dioxo-1,2,5-thiadiazolidin-3-one A solution of 5-[4-(2-aminoethyl)-2-benzyloxyphenyl]-1,1-dioxo-2-(2-trimethylsilanylethyl)-1,2,5-thiadiazolidin-3-one (0.266 g, 0.46 mmol) (Example 67, step A) and diisopropylethylamine (0.177 mL, 1.02 mmol) in a minimum amount of $CH_2Cl_2$ is added dropwise over a period of 30 min to triphosgene (0.051 g, 0.17 mmol) dissolved in $CH_2Cl_2$ (10 mL). This solution is used directly in the next step.

| Example | Chemical Name | MS (m/z) | Retention time (min) Method |
|---|---|---|---|
| 215 | 1-{2-[3-Hydroxy-4-(1,1,4-trioxo-1,2,5-thiadiazolidin-2-yl)-phenyl]-ethyl}-3-phenyl-urea | (M − 1)⁻ = 391 | |
| 216 | 1-Ethyl-3-{2-[3-hydroxy-4-(1,1,4-trioxo-1,2,5-thiadiazolidin-2-yl)-phenyl]-ethyl}-urea | (M − 1)⁻ = 343 | |
| 217 | 1-Adamantan-1-yl-3-{2-[3-hydroxy-4-(1,1,4-trioxo-1,2,5-thiadiazolidin-2-yl)-phenyl]-ethyl}-urea | (M − 1)⁻ = 447 | |
| 218 | Benzenesulfonyl-N-{2-[3-hydroxy-4-(1,1,4-trioxo-1,2,5-thiadiazolidin-2-yl)-phenyl]-ethyl}-urea | (M − 1)⁻ = 453 | |

| Example | NMR |
|---|---|
| 215 | $^1$H NMR (400 MHz, DMSO-$d_6$) δ ppm 2.66 (t, J = 6.95 Hz, 2H) 3.31 (d, J = 19.20 Hz, 2H) 4.20 (s, 2H) 6.03-6.12 (m, 1H) 6.68 (dd, J = 8.08, 1.77 Hz, 1H) 6.75 (d, J = 1.77 Hz, 1H) 6.87 (t, J = 7.33 Hz, 1H) 7.20 (t, J = 7.96 Hz, 2H) 7.30 (d, J = 8.08 Hz, 1H) 7.37 (d, J = 7.58 Hz, 2H) 8.47 (s, 1H) 9.36 (br. s., 1H) |
| 216 | $^1$H NMR (400 MHz, DMSO-$d_6$) δ ppm 0.97 (t, J = 7.20 Hz, 3H) 2.58 (t, J = 7.20 Hz, 2H) 2.99 (q, J = 6.91 Hz, 2H) 3.18 (t, J = 6.82 Hz, 2H) 4.24 (s, 2H) 5.76 (br. s., 2H) 6.64 (dd, J = 7.96, 1.64 Hz, 1H) 6.72 (d, J = 1.26 Hz, 1H) 7.27 (d, J = 8.08 Hz, 1H) 9.44 (br. s., 1H) |
| 218 | $^1$H NMR (400 MHz, DMSO-$d_6$) δ ppm 2.56 (br. s., 2H) 3.05 (br. s., 2H) 4.01 (s, 2H) 6.56 (d, J = 8.08 Hz, 1H) 6.66 (s, 1H) 7.26 (d, J = 7.83 Hz, 1H) 7.38 (d, J = 1.01 Hz, 3H) 7.75 (br. s., 2H) 8.94 (s, 1H) |

B. 1-(2-{3-Benzyloxy-4-[1,1,4-trioxo-5-(2-trimethylsilanylethyl)-1,2,5-thiadiazolidin-2-yl]-phenyl}-ethyl)-3-(2,4-dimethoxybenzyl)-urea To the above solution is added 2,4-dimethoxybenzylamine (0.069 mL, 0.46 mmol) and diisopropylethylamine (0.097 mL, 0.555 mmol) in $CH_2Cl_2$ (2 mL) and the mixture is stirred at RT for 10 min. The crude mixture is evaporated and partitioned between EtOAc and 1N HCl. The combined organic layers are washed with saturated sodium bicarbonate and the organic phase is dried over magnesium sulfate. The solvent is removed under reduced pressure to give the title compound as a yellow oil.

C. 1-(2,4-Dimethoxy-benzyl)-3-{2-[3-hydroxy-4-(1,1,4-trioxo-1,2,5-thiadiazolidin-2-yl)-phenyl]-ethyl}-urea The potassium salt of the title compound is prepared by removal of the protecting groups analogous to Example 67, steps C and D: $^1$H NMR (400 MHz, DMSO-$d_6$) δ ppm 2.56 (t, J=6.95 Hz, 2 H) 3.20 (d, J=19.96 Hz, 1 H) 3.20 (d, J=6.32 Hz, 1 H) 3.75 (d, J=14.65 Hz, 6 H) 4.01 (s, 2 H) 4.07 (d, J=5.81 Hz, 2 H) 5.90 (t, J=5.68 Hz, 1 H) 6.07 (t, J=5.94 Hz, 1 H) 6.47 (dd, J=8.34, 2.27 Hz, 1 H) 6.51 (d, J=2.27 Hz, 1 H) 6.58 (d, J=7.83 Hz, 1 H) 6.67 (d, J=1.52 Hz, 1 H) 7.05 (d, J=8.34 Hz, 1 H) 7.28 (d, J=8.08 Hz, 1 H) 8.91 (br. s., 1 H)

EXAMPLES 220 TO 224

The following compounds are prepared using 5-[2-hydroxy-4-(2-isocyanatoethyl)-phenyl]-1,1-dioxo-1,2,5-thiadiazolidin-3-one and an appropriate amine analogous to Example 219. For Example 224, the Boc group is removed from Example 223 with HCl/dioxane.

| Example | Chemical Name | MS (m/z) | Retention time (min) Method |
|---|---|---|---|
| 220 | 1-(2-Hydroxyethyl)-3-{2-[3-hydroxy-4-(1,1,4-trioxo-1,2,5-thiadiazolidin-2-yl)-phenyl]-ethyl}-urea | $(M-1)^- = 357$ | |
| 221 | 3-{2-[3-Hydroxy-4-(1,1,4-trioxo-1,2,5-thiadiazolidin-2-yl)-phenyl]-ethyl}-1,1-bis-(2-methoxyethyl)-urea | $(M-1)^- = 429$ | |
| 222 | Morpholine-4-carboxylic acid {2-[3-hydroxy-4-(1,1,4-trioxo-1,2,5-thiadiazolidin-2-yl)-phenyl]-ethyl}-amide | $(M-1)^- = 385$ | |
| 223 | 4-(3-{2-[3-Hydroxy-4-(1,1,4-trioxo-1,2,5-thiadiazolidin-2-yl)-phenyl]-ethyl}-ureido)-piperidine-1-carboxylic acid tert-butyl ester | $(M-1)^- = 498$ | |
| 224 | 1-{2-[3-Hydroxy-4-(1,1,4-trioxo-1,2,5-thiadiazolidin-2-yl)-phenyl]-ethyl}-3-piperidin-4-yl-urea | $(M-1)^- = 398$ | |

| Example | NMR |
|---|---|
| 220 | $^1$H NMR (400 MHz, DMSO-$d_6$) δ ppm 2.56 (t, J = 7.07 Hz, 2H) 3.04 (q, J = 5.98 Hz, 2H) 3.18 (q, J = 6.82 Hz, 2H) 3.36 (t, J = 5.81 Hz, 2H) 4.01 (s, 2H) 4.62 (br. s., 1H) 5.94 (d, J = 8.34 Hz, 1H) 5.94 (d, J = 1.77 Hz, 1H) 6.60 (dd, J = 8.08, 1.77 Hz, 1H) 6.68 (d, J = 2.02 Hz, 1H) 7.29 (d, J = 7.83 Hz, 1H) 8.92-9.04 (m, 1H) |
| 221 | $^1$H NMR (400 MHz, DMSO-$d_6$) δ ppm 2.59 (t, J = 7.33 Hz, 2H) 3.15-3.26 (m, 2H) 3.22 (s, 6H) 3.28-3.39 (m, 2H) 3.35 (dd, J = 7.20, 3.92 Hz, 4H) 4.01 (s, 2H) 6.25 (t, J = 5.43 Hz, 1H) 6.57 (dd, J = 8.08, 1.77 Hz, 1H) 6.67 (d, J = 1.77 Hz, 1H) 7.28 (d, J = 8.08 Hz, 1H) 9.12 (br. s., 1H) |
| 222 | $^1$H NMR (400 MHz, DMSO-$d_6$) δ ppm 2.59 (t, J = 7.45 Hz, 2H) 3.16-3.26 (m, 6H) 3.52 (d, J = 5.05 Hz, 4H) 4.02 (s, 2H) 6.55 (d, J = 6.82 Hz, 1H) 6.59-6.66 (m, 2H) 7.27 (d, J = 8.08 Hz, 1H) |
| 223 | $^1$H NMR (400 MHz, DMSO-$d_6$) δ ppm 1.21 (d, J = 8.84 Hz, 2H) 1.38 (s, 9H) 1.52 (s, 1H) 1.62 (d, 2H) 2.57 (t, J = 7.58 Hz, 2H) 2.69 (t, J = 11.49 Hz, 2H) 3.12-3.21 (m, 1H) 3.15 (dd, J = 6.19, 2.65 Hz, 1H) 3.85 (d, J = 13.39 Hz, 2H) 4.02 (s, 2H) 6.48-6.57 (m, 2H) 6.63 (s, 1H) 6.76 (br. s., 1H) 7.26 (d, J = 8.08 Hz, 1H) 9.04 (br. s., 1H) |
| 224 | $^1$H NMR (400 MHz, DMSO-$d_6$) δ ppm 1.38 (dd, J = 11.75, 3.66 Hz, 2H) 1.83 (br. s., 2H) 2.63 (t, J = 7.45 Hz, 2H) 2.72 (t, J = 11.87 Hz, 2H) 3.19 (t, J = 7.45 Hz, 3H) 3.95 (d, J = 13.39 Hz, 2H) 4.41 (s, 2H) 6.65 (dd, J = 8.08, 1.77 Hz, 2H) 6.79 (d, J = 1.77 Hz, 1H) 7.24 (d, J = 8.08 Hz, 1H) 8.13 (br. s., 3H) 9.84 (br. s., 1H) |

EXAMPLES 225 TO 227

The following compounds are prepared using 5-[4-(3-aminopropyl)-2-benzyloxyphenyl]-1,1-dioxo-2-(2-trimethylsilanylethyl)-1,2,5-thiadiazolidin-3-one (Example 74, step A) and an appropriate isocyanate analogous to Example 214.

| Example | Chemical Name | MS (m/z) | Retention time (min) Method |
|---|---|---|---|
| 225 | 1-{3-[3-Hydroxy-4-(1,1,4-trioxo-1,2,5-thiadiazolidin-2-yl)-phenyl]-propyl}-3-phenyl-urea | (M − 1)⁻ = 405 | |
| 226 | 1-Cyclohexyl-3-{3-[3-hydroxy-4-(1,1,4-trioxo-1,2,5-thiadiazolidin-2-yl)-phenyl]-propyl}-urea | (M − 1)⁻ = 411 | |
| 227 | 1-Adamantan-1-yl-3-{3-[3-hydroxy-4-(1,1,4-trioxo-1,2,5-thiadiazolidin-2-yl)-phenyl]-propyl}-urea | (M − 1)⁻ = 461 | |

| Example | NMR |
|---|---|
| 225 | $^1$H NMR (400 MHz, DMSO-d$_6$) δ ppm 1.69 (d, J = 7.83 Hz, 2H) 1.67 (s, 1H) 3.08 (d, J = 19.45 Hz, 1H) 3.08 (d, J = 5.81 Hz, 2H) 4.05 (s, 2H) 6.41 (t, J = 5.43 Hz, 1H) 6.56 (d, J = 7.58 Hz, 1H) 6.68 (d, J = 1.77 Hz, 1H) 6.86 (t, J = 7.33 Hz, 1H) 7.20 (t, J = 7.96 Hz, 2H) 7.25 (d, J = 8.08 Hz, 1H) 7.40 (d, J = 7.58 Hz, 2H) 8.63 (s, 1H) |
| 226 | $^1$H NMR (400 MHz, DMSO-d$_6$) δ ppm 1.05-1.15 (m, 2H) 1.08 (t, J = 9.73 Hz, 1H) 1.20-1.31 (m, 2H) 1.48-1.55 (m, 1H) 1.56-1.66 (m, 3H) 1.61 (d, J = 7.58 Hz, 2H) 1.73 (d, J = 12.38 Hz, 2H) 2.45 (s, 1H) 2.42 (d, J = 8.08 Hz, 2H) 2.97 (q, J = 6.57 Hz, 2H) 4.02 (s, 2H) 5.66 (d, J = 8.08 Hz, 1H) 5.74 (t, J = 5.68 Hz, 1H) 6.53 (d, 1H) 6.64 (s, 1H) 7.24 (d, J = 8.08 Hz, 1H) |
| 227 | $^1$H NMR (400 MHz, DMSO-D6) δ ppm 1.52-1.62 (m, 9H) 1.86 (d, J = 2.53 Hz, 6H) 1.98 (s, 3H) 2.39-2.46 (m, 2H) 2.89-2.96 (m, 2H) 4.03 (s, 2H) 5.45 (s, 1H) 5.68 (t, J = 5.56 Hz, 1H) 6.52 (s, 1H) 6.62 (s, 1H) 7.23 (d, J = 8.08 Hz, 1H) |

EXAMPLE 228

3-{3-[3-Hydroxy-4-(1,1,4-trioxo-1,2,5-thiadiazolidin-2-yl)-phenyl]-propyl}-1H-quinazoline-2,4-dione

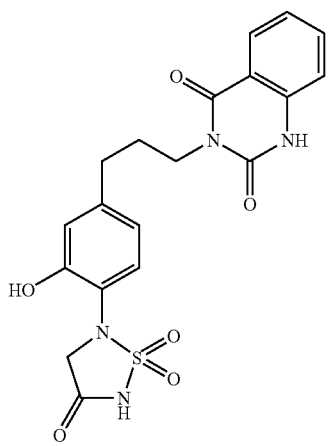

The title compound is prepared from 5-[4-(3-aminopropyl)-2-benzyloxyphenyl]-1,1-dioxo-2-(2-trimethylsilanylethyl)-1,2,5-thiadiazolidin-3-one and 2-isocyanatobenzoic acid ethyl ester analogous to Example 214. Cyclization to the quinazoline occurs during the TMS-ethyl deprotection step.

$^1$H NMR (400 MHz, DMSO-d$_6$) δ ppm 1.85 (dq, J=7.71, 7.54 Hz, 2 H) 2.51-2.56 (m, 2 H) 3.92 (d, J=7.33 Hz, 2 H) 4.00 (s, 2 H) 6.63 (dd, J=8.08, 2.02 Hz, 1 H) 6.70 (d, J=2.02 Hz, 1 H) 7.17 (d, J=7.83 Hz, 2 H) 7.26 (d, J=8.08 Hz, 1 H) 7.61 (dd, J=15.41, 1.26 Hz, 1 H) 7.91 (dd, J=8.34, 1.52 Hz, 1 H) 8.93 (br. s., 1 H) 11.36 (br. s., 1 H)

EXAMPLE 229

3-[3-Hydroxy-4-(1,1,4-trioxo-1,2,5-thiadiazolidin-2-yl)-benzyl]-piperidine-1-carboxylic Acid Ethylamide

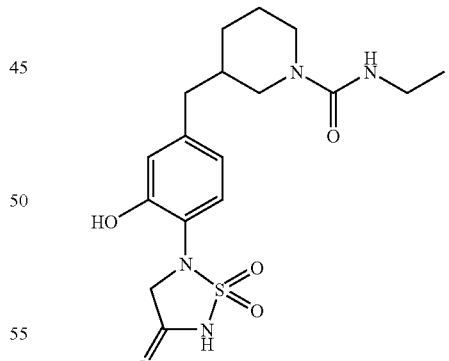

A. 3-{3-Benzyloxy-4-[1,1,4-trioxo-5-(2-trimethylsilanylethyl)-1,2,5-thiadiazolidin-2-yl]-benzyl}-piperidine-1-carboxylic Acid Ethylamide The title compound is prepared using 5-(2-benzyloxy-4-piperidin-3-yl-methylphenyl)-1,1-dioxo-2-(2-trimethylsilanylethyl)-1,2,5-thiadiazolidin-3-one (Example 192, step A) and ethyl isocyanate analogous to Example 214, step A.

B. 3-[3-Hydroxy-4-(1,1,4-trioxo-1,2,5-thiadiazolidin-2-yl)-benzyl]-piperidine-1-carboxylic Acid Ethylamide The potassium salt of the title compound is prepared by removal of the protecting groups analogous to Example 67, steps C and D: (M−1) =395. $^1$H NMR (400 MHz, DMSO-$d_6$) δ ppm 0.99 (d, J=3.28 Hz, 4 H) 1.25 (br. s., 1 H) 1.53 (br. s., 2 H) 1.61 (br. s., 1H) 2.25 (br. s., 2 H) 2.38 (d, J=11.37 Hz, 1 H) 2.63 (d, J=11.37 Hz, 1 H) 3.01 (br. s., 2 H) 3.76 (d, J=1.52 Hz, 1 H) 3.88 (d, J=1.52 Hz, 1 H) 4.02 (br. s., 2 H) 6.35 (br. s. 1 H) 6.57 (br. s., 1 H) 6.64 (br. s., 1 H) 7.27 (d, J=6.32 Hz, 1 H) 9.01 (br. s., 1 H)

EXAMPLE 230

5-(2-Hydroxy-4-methanesulfonylmethylphenyl)-1,1-dioxo-1,2,5-thiadiazolidin-3-one

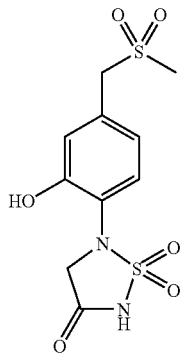

A. 2-Benzyloxy-4-methylsulfanylmethyl-1-nitrobenzene

To a solution of 2-benzyloxy-4-bromomethyl-1-nitrobenzene (Example 83, step C) (1.0 g, 3.1 mmol) in 20 mL DMF is added sodium thiomethoxide (228 mg, 3.26 mmol). The solution is stirred at RT for 2 h then water is added and the mixture is extracted with EtOAc. The organic layer is washed with water and brine, and dried over sodium sulfate. The solvent is removed under reduced pressure to give the title compound as a yellow liquid.

B. 2-Benzyloxy-4-methylsulfanylmethylphenylamine

To a stirred solution of 2-benzyloxy-4-methylsulfanylmethyl-1-nitrobenzene (900 mg, 3.11 mmol) EtOH (80 mL) is added SnCl$_2$ (3.53 g, 18.7 mmol) and the solution is refluxed for 2 h. After the mixture cools to RT the EtOH is removed under reduced pressure and EtOAc is added. The solution is washed with 1N NaOH, water, brine and dried over sodium sulfate. The solvent is removed under reduced pressure and the residue is purified by flash chromatography using hexane/EtOAc (5:1) as eluent to give the title compound as a yellow liquid. NMR (CDCl$_3$): 7.44-7.31 (m, 5H), 6.85 (d, J=1.77 Hz, 1H), 6.72-6.70 (dd, J=1.77 Hz, 7.83 Hz, 1H), 6.66-6.64 (d, J=7.84 Hz, 1H), 5.08 (s, 2H), 3.59 (s, 2H), 1.95 (s, 3H): (M+1)$^+$=260.

C. N-Sulfamoyl-N-(2-benzyloxy-4-methylsulfanylmethylphenylglycine Methyl Ester Prepared from 2-benzyloxy-4-methylsulfanylmethylphenylamine analogous to Example 83, steps H, I and J: (M−1)$^-$=441.

D. N-Sulfamoyl-N-(2-benzyloxy-4-methylsulfonylmethylphenyl)glycine Methyl Ester To a solution of N-sulfamoyl-N-(2-benzyloxy-4-methylsulfanylmethylphenyl)glycine methyl ester (100 mg, 0.24 mmol) in methylene chloride (5 mL) is added mCPBA (130 mg, 0.53 mmol) and the solution is stirred at RT for 1 h. Saturated NaHCO$_3$ is added and the mixture is extracted with EtOAc. The organic phase is washed with water and brine then dried over magnesium sulfate. The solvent is removed under reduced pressure to give the title compound as a yellowish oil.

E. 5-(2-Hydroxy-4-methanesulfonylmethylphenyl)-1,1-dioxo-1,2,5-thiadiazolidin-3-one Prepared from N-sulfamoyl-N-(2-benzyloxy-4-methylsulfonylmethylphenyl)glycine methyl ester analogously to Example 83, steps K and L: (M−1)$^-$=319. HPLC retention time: 0.82 min. (Method B).

EXAMPLE 231

5-(4-Ethanesulfonylmethyl-2-hydroxy-phenyl)-1,1-dioxo-1,2,5-thiadiazolidin-3-one

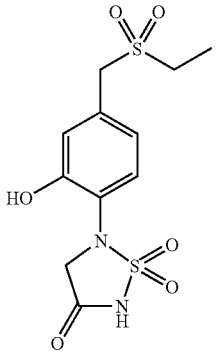

The title compound is prepared from 2-benzyloxy-4-bromomethyl-1-nitrobenzene and sodium ethanethiolate analogous to Example 230: NMR (δ, DMSO-$d_6$): 7.42 (d, 1H, J=8.5 Hz), 6.90 (s, 1H), 6.79 (d, 1H, J=6.8 Hz), 4.33 (s, 2H), 4.07 (s, 2H), 3.99 (q, 2H, J=7.3 Hz), 1.21 (t, 3H, J=7.3 Hz) (M−1)$^-$=333; High Resolution MS (M−1)$^-$=333.0224

EXAMPLE 232

5-[2-Hydroxy-4-(propane-2-sulfonylmethyl)-phenyl]-1,1-dioxo-1,2,5-thiadiazolidin-3-one

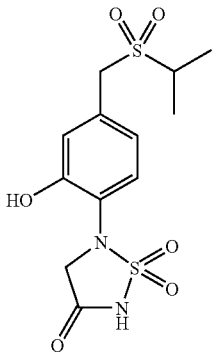

The title compound is prepared from 2-benzyloxy-4-bromomethyl-1-nitrobenzene and sodium 2-propanethiolate analogous to Example 230: (M−1)$^-$=347; HPLC retention time=0.52 min. (Method A).

EXAMPLE 233

5-(4-Benzenesulfonylmethyl-2-hydroxyphenyl)-1,1-dioxo-1,2,5-thiadiazolidin-3-one

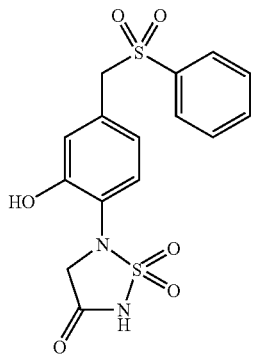

The title compound is prepared from 2-benzyloxy-4-bromomethyl-1-nitrobenzene and potassium benzenethiolate analogous to Example 230: (M−1)⁻=381. HPLC retention time: 0.79 min. (Method A).

EXAMPLES 234 TO 236

The following compounds are prepared analogous to Example 230 with the modification that one equivalent of mCPBA is used in the oxidation (step D).

| Example | Chemical Name | MS (m/z) | Retention time (min) Method |
|---|---|---|---|
| 234 | 5-(2-Hydroxy-4-methanesulfinylmethylphenyl)-1,1-dioxo-1,2,5-thiadiazolidin-3-one | (M − 1)⁻ = 303 | 0.77 B |
| 235 | 5-(4-Ethanesulfinylmethyl-2-hydroxyphenyl)-1,1-dioxo-1,2,5-thiadiazolidin-3-one | (M − 1)⁻ = 317 | 0.35 A |
| 236 | 5-[2-Hydroxy-4-(propane-2-sulfinylmethyl)-phenyl]-1,1-dioxo-1,2,5-thiadiazolidin-3-one | (M − 1)⁻ = 331 | 0.54 A |

EXAMPLES 237 TO 239

The following compounds are prepared analogous to Example 230 with the modification that the oxidation step is omitted and the benzyl protecting group is removed at the last step with BBr₃ analogous to Example 85, step I.

| Example | Chemical Name | MS (m/z) | Retention time (min) Method |
|---|---|---|---|
| 237 | 5-(2-Hydroxy-4-methylsulfanylmethylphenyl)-1,1-dioxo-1,2,5-thiadiazolidin-3-one | (M − 1)⁻ = 287 | 1.00 A |
| 238 | 5-(4-Ethylsulfanylmethyl-2-hydroxyphenyl)-1,1-dioxo-1,2,5-thiadiazolidin-3-one | (M − 1)⁻ = 301 | 0.89 A |
| 239 | 5-(2-Hydroxy-4-isopropylsulfanylmethylphenyl)-1,1-dioxo-1,2,5-thiadiazolidin-3-one | (M − 1)⁻ = 315 | 1.03 A |

EXAMPLE 240

5-[4-(2-Benzenesulfonylethyl)-2-hydroxyphenyl]-1,1-dioxo-1,2,5-thiadiazolidin-3-one

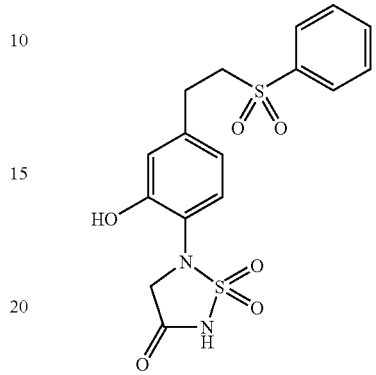

A. 5-[4-((E)-2-Benzenesulfonylvinyl)-2-benzyloxyphenyl]-1,1-dioxo-1,2,5-thiadiazolidin-3-one A mixture of 5-(2-benzyloxy-4-iodophenyl)-1,1-dioxo-1,2,5-thiadiazolidin-3-one (80 mg, 0.18 mmol), ethenesulfonylbenzene (37 mg, 0.22 mmol), Pd(OAc)₂ (2 mg) and triethylamine (186 mg, 1.84 mmol) in MeCN (2 mL) is heated at 120° C. in a microwave apparatus for 15 min. The mixture is filtered, poured into EtOAc and is washed with 1N HCl and brine then dried over magnesium sulfate. The solvent is removed under reduced pressure to give the title compound: (M−1)⁻=483.

B. 5-[4-(2-Benzenesulfonylethyl)-2-hydroxyphenyl]-1,1-dioxo-1,2,5-thiadiazolidin-3-one The title compound is prepared from 5-[4-((E)-2-benzenesulfonylvinyl)-2-benzyloxyphenyl]-1,1-dioxo-1,2,5-thiadiazolidin-3-one analogous to Example 57, step D: (M−1)⁻=395; HPLC retention time=1.04 min. (Method A).

EXAMPLE 241

5-[4-(4-Benzenesulfonylbutyl)-2-hydroxyphenyl]-1,1-dioxo-1,2,5-thiadiazolidin-3-one

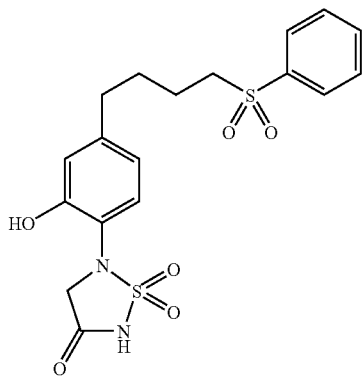

A. Acetic Acid 4-phenylsulfanylbutylester

To a suspension of NaH (60%, 0.91 g, 23 mmol) in anhydrous DMF (20 mL) at RT is added dropwise benzenethiol (2.5 g, 22.7 mmol) in DMF (5 mL). The mixture is stirred for 10-15 min, at which time it becomes clear and yellow. The mixture is cooled to 0° C. in an ice bath then 4-bromobutylacetate (4.5 g, 22.8 mmol) in DMF (5 mL) is added dropwise and the mixture is stirred at RT for 1 h. The mixture is poured into 1N HCl (50 mL) and extracted with MTBE (2×). The combined organic extracts are washed with brine (2×) and dried over MgSO₄. The solvent is removed under reduced pressure to afford the title compound as a yellow oil.

B. Acetic Acid 4-benzenesulfonylbutylester

Magnesium monoperoxyphthalate.6H₂O (80%, 17 g, 1.2 equiv) is dissolved in methanol (50 mL), then added rapidly to a cooled (0° C.) mixture of acetic acid 4-phenylsulfanylbutylester (6.4 g, 28.5 mmol). The mixture is stirred at RT for 18 h and the resulting white precipitate is filtered off and rinsed with CH₂Cl₂. The filtrate is concentrated to a yellow oil. Water (100 mL) is added (pH acidic at this point) and extracted with EtOAc. The organic extracts are washed with NaHCO₃ and brine then dried over MgSO₄. The solvent is removed under reduced pressure to afford the title compound as a light orange oil.

C. 4-Benzenesulfonylbutan-1-ol

To a mixture of acetic acid 4-benzenesulfonylbutylester (6.5 g, 25.3 mmol) in MeOH (30 mL) at RT is added NaOH (1.5 g, 37.5 mmol) in water (5 mL). The mixture is stirred at RT for 1 h then the solvent is removed under reduced pressure. To the residue is added 1N HCl (40 mL) then the mixture is extracted with EtOAc. The organic phase is dried over MgSO₄ and the solvent is removed under reduced pressure to afford the title compound as a yellow oil.

D. (4-Iodobutane-1-sulfonyl)-benzene

To a solution of imidazole (1.4 g, 20.5 mmol) in CH₂Cl₂ (20 mL) is added PPh₃ (5.4 g, 20.5 mmol). The solution is cooled to 0° C. and iodine (5.2 g, 20.5 mmol) is added in 2 portions. The mixture is allowed to warm to RT then 4-benzenesulfonylbutan-1-ol is added and the mixture is stirred at RT for 24 h. The mixture is diluted with water and extracted with EtOAc (3×). The organic layer is washed with a 20% solution of Na₂S₂O₃ and dried over magnesium sulfate. The solvent is removed under reduced pressure and the residue purified by flash chromatography using hexane/EtOAc (1:1) as eluent to give the title compound as a white solid.

E. 5-[4-(4-Benzenesulfonylbutyl)-2-hydroxyphenyl]-1,1-dioxo-1,2,5-thiadiazolidin-3-one The title compound is prepared from 5-(2-benzyloxy-4-iodophenyl)-1,1-dioxo-2-(2-trimethylsilanylethyl)-1,2,5-thiadiazolidin-3-one and (4-iodobutane-1-sulfonyl)-benzene analogous to Example 57, steps B, C and D: (M−1)⁻=423. ¹H NMR (400 MHz, DMSO-D6) δ ppm 1.49-1.60 (m, 4 H) 2.40 (t, J=6.69 Hz, 2 H) 4.01 (s, 2 H) 6.46 (s, 1 H) 6.58 (s, 1 H) 7.21 (d, J=7.83 Hz, 1 H) 7.65 (t, J=7.58 Hz, 2 H) 7.71-7.77 (m, 1 H) 7.85-7.90 (m, 2 H)

EXAMPLE 242

5-{4-[3-(1,1-Dioxotetrahydrothiophen-2-yl)-prop-1-ynyl]-2-hydroxyphenyl}-1,1-dioxo-1,2,5-thiadiazolidin-3-one

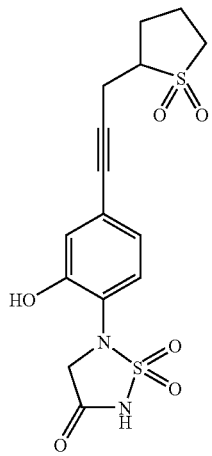

A. 2-Prop-2-ynyl-tetrahydrothiophene 1,1-dioxide

To a solution of sulfolane (1.0 g, 8.32 mmol) in THF (5 mL) at −78° C. is added n-butyllithium (5.7 mL of 1.6 M in hexane, 9.1 mmol) dropwise and the solution is stirred at −78° C. for 20 min. To this is added a solution of propargyl bromide (992 mg, 8.34 mmol) in THF (5 mL) dropwise and the mixture is allowed to warm to RT overnight. The mixture is quenched with 1N HCl and extracted with EtOAc. The organic phase is dried over magnesium sulfate and the solvent removed under reduced pressure. The residue is purified by flash chromatography using hexane/EtOAc (6:4) as eluent to give the title compound.

B. 5-{2-Benzyloxy-4-[3-(1,1-dioxotetrahydrothiophen-2-yl)-prop-1-ynyl]-phenyl}-1,1-dioxo-1,2,5-thiadiazolidin-3-one To a solution of 2-prop-2-ynyl-tetrahydrothiophene 1,1-dioxide (53 mg, 0.34 mmol) in 1 mL glyme/water (9:1) is added Pd(dppf)Cl$_2$.CH$_2$Cl$_2$ (14 mg), a solution of 5-(2-benzyloxy-4-iodophenyl)-1,1-dioxo-2-(2-trimethylsilanylethyl)-1,2,5-thiadiazolidin-3-one (164 mg, 0.37 mmol) in 1 mL glyme/water (9:1), triethylamine (68 mg, 0.67 mmol) and CuCl (13 mg, 0.13 mmol). The mixture is heated at 120° C. in a microwave apparatus for 5 min then is poured into EtOAc. The mixture is washed with 1N HCl and the organic phase is dried over magnesium sulfate. The solvent is removed under reduced pressure to give the title compound which is used directly in the next step.

C. 5-{4-[3-(1,1-Dioxotetrahydrothiophen-2-yl)-prop-1-ynyl]-2-hydroxyphenyl}-1,1-dioxo-1,2,5-thiadiazolidin-3-one To a solution of 5-{2-benzyloxy-4-[3-(1,1-dioxotetrahydrothiophen-2-yl)-prop-1-ynyl]-phenyl}-1,1-dioxo-1,2,5-thiadiazolidin-3-one in methylene chloride (5 mL) is added BBr$_3$ (0.35 mL of 1.0 M in methylene chloride) and the mixture is stirred at RT for 18 h. The solvent is removed under reduced pressure and the residue purified by preparative HPLC followed by lyophilization to give the title compound: (M−1)$^-$=383; HPLC retention time=0.72 min. (Method A)

EXAMPLE 243

5-{4-[3-(1,1-Dioxotetrahydrothiophen-2-yl)-propyl]-2-hydroxyphenyl}-1,1-dioxo-1,2,5-thiadiazolidin-3-one

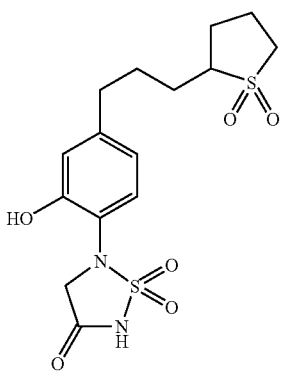

The title compound is prepared from 5-{2-benzyloxy-4-[3-(1,1-dioxotetrahydrothiophen-2-yl)-prop-1-ynyl]-phenyl}-1,1-dioxo-1,2,5-thiadiazolidin-3-one analogous to Example 571 step D. (M−1)$^-$=401, HPLC retention time=1.24 min. (Method A)

EXAMPLE 244

5-[2-Hydroxy-4-(3-oxopentyl)-phenyl]-1,1-dioxo-1,2,5-thiadiazolidin-3-one

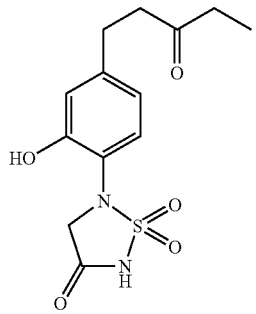

A. 5-[2-Benzyloxy-4-((E)-3-oxo-pent-1-enyl)-phenyl]-1,1-dioxo-1,2,5-thiadiazolidin-3-one To a solution of 5-(2-benzyloxy-4-iodophenyl)-1,1-dioxo-1,2,5-thiadiazolidin-3-one (160 mg, 0.36 mmol), ethylvinyl ketone (50 mg, 0.43 mmol) and Pd(OAc)$_2$ (8 mg) in MeCN (2 mL) is added triethylamine (0.5 mL, 3.6 mmol) and the mixture is heated at 100° C. in a pressure vessel for 4 h. The mixture is filtered and the solvent removed under reduced pressure to give the title compound which is used directly in the next step.

B. 5-[2-Hydroxy-4-(3-oxopentyl)-phenyl]-1,1-dioxo-1,2,5-thiadiazolidin-3-one To a solution of 5-[2-benzyloxy-4-((E)-3-oxo-pent-1-enyl)-phenyl]-1,1-dioxo-1,2,5-thiadiazolidin-3-one (130 mg, 0.325 mmol) in 7 mL of EtOH/water (2:5) is added K$_2$CO$_3$ (53 mg, 0.39 mmol) and 10% Pd/C (65 mg). The mixture is hydrogenated at 1 atm for 2 h then the catalyst is filtered and the solvent removed under reduced pressure. The residue is purified by preparative HPLC to give the title compound as a white solid: (M−1)$^-$=311. HPLC retention time: 1.31 min (Method A).

EXAMPLE 245

5-[2-Hydroxy-4-(2-methyl-3-oxopentyl)-phenyl]-1,1-dioxo-1,2,5-thiadiazolidin-3-one

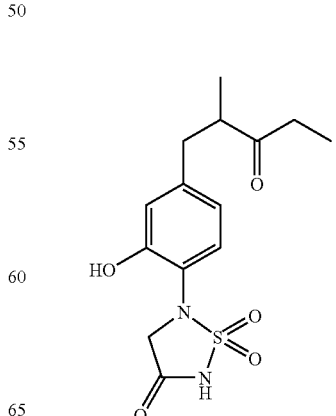

A. 1-(3-Benzyloxy-4-nitrophenyl)-2-methylpentan-3-one

To a solution of pentan-3-one (516 mg, 6 mmol) in THF (5 mL) at −78° C. is added dropwise LiHMDS (6.6 mL of 1.0 M solution in THF, 6.6 mmol) over a period of 15 min. The solution is stirred at −78° C. for 2 h then a solution of 2-benzyloxy-4-bromomethyl-1-nitrobenzene (Example 83, step C) (963 mg, 3 mmol) in THF (5 mL) is added dropwise. The mixture is allowed to warm to RT overnight and is quenched with saturated ammonium chloride solution. The mixture is extracted with EtOAc and the organic phase is washed with brine then dried over magnesium sulfate. The solvent is removed under reduced pressure and the residue is purified by flash chromatography using a gradient of 10-50% EtOAc/hexane as eluent to give the title compound.

B. 1-(4-Amino-3-benzyloxyphenyl)-2-methylpentan-3-one

A mixture of 1-(3-benzyloxy-4-nitrophenyl)-2-methylpentan-3-one (450 mg) and Pt/C (22 mg) in EtOAc (15 mL) is hydrogenated at 1 atm for 18 h. The catalyst is filtered and the filtrate evaporated to give the title compound which is used directly in the next step.

C. 5-[2-Benzyloxy-4-(2-methyl-3-oxo-pentyl)-phenyl]-1,1-dioxo-1,2,5-thiadiazolidin-3-one The title compound is prepared from 1-(4-amino-3-benzyloxyphenyl)-2-methylpentan-3-one analogous to Example 83, steps H-K.

D. 5-[2-Hydroxy-4-(2-methyl-3-oxopentyl)-phenyl]-1,1-dioxo-1,2,5-thiadiazolidin-3-one To a solution of 5-[2-benzyloxy-4-(2-methyl-3-oxo-pentyl)-phenyl]-1,1-dioxo-1,2,5-thiadiazolidin-3-one potassium salt in 5 mL of EtOH/water (1:1)) is added 20 mg of Degussa Pd/C and the resulting mixture is hydrogenated at 1 atm for 30 min. The catalyst is filtered through Celite and the solvent is removed under reduced pressure. The residue is purified by preparative HPLC to give the title compound: $^1$H NMR (Acetonitrile-d3) δ 7.30 (d, J=8.0 Hz, 1H), 6.79 (m, 1H), 6.75 (dd, J=8.0, 2.0 Hz, 1H), 4.38 (s, 2H), 2.83 (m, 2H), 2.46 (m, 2H), 2.29 (m, 1H), 1.01 (m, 3H), 0.9 (t, J=7.33 Hz, 3H). (M−1)⁻=325. HPLC retention time=0.92 min (Method A).

EXAMPLE 246

5-[2-Hydroxy-4-(2-methyl-3-oxo-3-phenylpropyl)-phenyl]-1,1-dioxo-1,2,5-thiadiazolidin-3-one

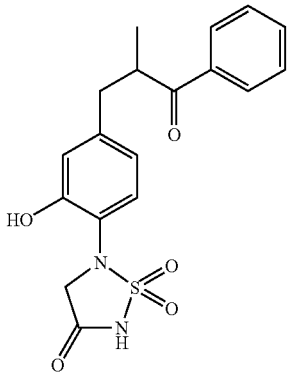

A. (E)-3-(3-Benzyloxy-4-nitrophenyl)-2-methyl-1-phenylpropenone

A mixture of 3-benzyloxy-4-nitrobenzaldehyde (83, step A) (2.57 g, 10 mmol), (1-methyl-2-oxo-2-phenylethyl)-triphenylphosphonium bromide (9.5 g, 20 mmol) and diisopropylethylamine (3.47 mL, 20 mmol) in toluene (75 mL) is heated at 100° C. for 18 h. The mixture is cooled to RT and the insoluble material filtered. The filtrate is evaporated under reduced pressure and the residue purified by flash chromatography using a gradient of 10-50% EtOAc/hexane as eluent to give the title compound as a yellow oil.

B. 3-(4-Amino-3-benzyloxyphenyl)-2-methyl-1-phenylpropan-1-one

A mixture of (E)-3-(3-benzyloxy-4-nitrophenyl)-2-methyl-1-phenylpropenone (200 mg) and Pt/C (10 mg) in EtOAc (8 mL) is hydrogenated at 1 atm for 8 h. The catalyst is filtered and the filtrate is evaporated under reduced pressure. The residue is purified by flash chromatography using a gradient of 10-25% EtOAc/hexane as eluent to give the title compound.

C. 5-[2-Benzyloxy-4-(2-methyl-3-oxo-3-phenylpropyl)-phenyl]-1,1-dioxo-1,2,5-thiadiazolidin-3-one The title compound is prepared from 3-(4-amino-3-benzyloxyphenyl)-2-methyl-1-phenylpropan-1-one analogous to Example 83, steps H-K.

D. 5-[2-Hydroxy-4-(2-methyl-3-oxo-3-phenylpropyl)-phenyl]-1,1-dioxo-1,2,5-thiadiazolidin-3-one A solution of 5-[2-benzyloxy-4-(2-methyl-3-oxo-3-phenylpropyl)-phenyl]-1,1-dioxo-1,2,5-thiadiazolidin-3-one potassium salt (15 mg) in 4 mL of EtOH/water (1:1) is hydrogenated over Degussa Pd/C (5 mg) at 1 atm for 15 min. The catalyst is filtered and the solvent is removed under reduced pressure. The residue is purified by reverse phase HPLC followed by lyophilization to give the title compound. (M−1)⁻=373. HPLC retention time=1.13 min (Method A).

EXAMPLE 247

5-[4-(2-Benzoylbutyl)-2-hydroxyphenyl]-1,1-dioxo-1,2,5-thiadiazolidin-3-one

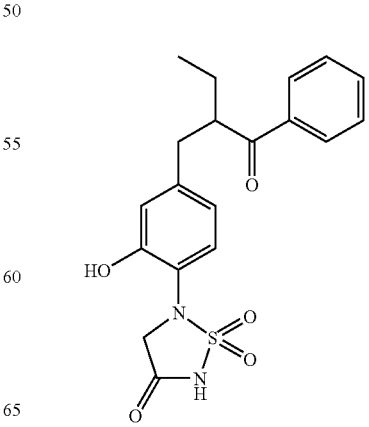

A. 2-(3-Benzyloxy-4-nitrobenzyl)-1-phenylbutan-1-one

To a solution of 1-phenylbutan-1-one (203 mg, 1.37 mmol) in THF (2.5 mL) at −78° C. is added dropwise LiHMDS (1.62 mL of 1.0 M solution in THF, 1.62 mmol) over a period of 15 min. The solution is stirred at −78° C. for 1 h then a solution of 2-benzyloxy-4-bromomethyl-1-nitrobenzene (Example 83, step C) (400 mg, 1.25 mmol) in THF (2.5 mL) is added dropwise. The mixture is allowed to warm to RT and stirred there for 1 h then is quenched with saturated ammonium chloride solution. The mixture is extracted with EtOAc and the organic phase is washed with brine then dried over magnesium sulfate. The solvent is removed under reduced pressure and the residue is purified by flash chromatography using a gradient of 5-100% EtOAc/hexane as eluent to give the title compound.

B. 5-[4-(2-Benzoylbutyl)-2-benzyloxyphenyl]-1,1-dioxo-1,2,5-thiadiazolidin-3-one The title compound is prepared from 2-(3-benzyloxy-4-nitrobenzyl)-1-phenylbutan-1-one analogous to Example 83, steps H-K.

C. 5-[4-(2-Benzoylbutyl)-2-hydroxyphenyl]-1,1-dioxo-1,2,5-thiadiazolidin-3-one A solution of 5-[4-(2-benzoylbutyl)-2-benzyloxyphenyl]-1,1-dioxo-1,2,5-thiadiazolidin-3-one potassium salt (45 mg) in 4 mL of EtOH/water (1:1) is hydrogenated over Degussa 5% Pd/C (7 mg) at 1 atm for 6 h. The catalyst is filtered and the solvent is removed under reduced pressure to give the title compound: $(M-1)^-=387$. HPLC retention time=0.60 min (Method C).

EXAMPLE 248

5-[4-(2-Benzoylpentyl)-2-hydroxyphenyl]-1,1-dioxo-1,2,5-thiadiazolidin-3-one

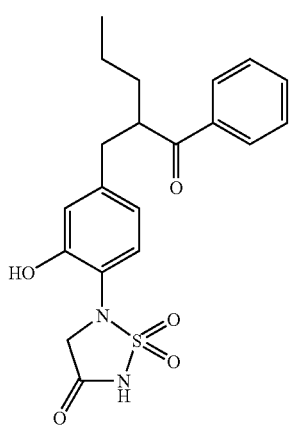

The title compound is prepared from 2-benzyloxy-4-bromomethyl-1-nitrobenzene and 1-phenylpentan-1-one analogous to Example 247: $(M-1)^-=401$.

EXAMPLE 249

5-[2-Hydroxy-4-(3-oxo-2,3-diphenylpropyl)-phenyl]-1,1-dioxo-1,2,5-thiadiazolidin-3-one

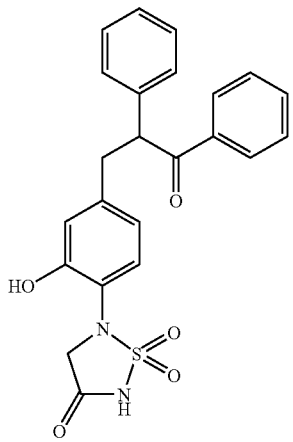

A. (E)-3-(3-Benzyloxy-4-nitrophenyl)-1,2-diphenylpropenone

A mixture of 3-benzyloxy-4-nitrobenzaldehyde (2.57 g, 10 mmol), 1,2-diphenylethanone (2.35 g, 12 mmol), piperidine (0.6 mL) and acetic acid (0.6 mL) in toluene (50 mL) is refluxed under Dean-Stark conditions for 3 h. The solvent is removed under reduced pressure and the residue purified by flash chromatography using a gradient of 6-25% EtOAc/hexane as eluent to give the title compound as a yellow oil.

B. 3-(4-Amino-3-benzyloxyphenyl)-1,2-diphenylpropan-1-one

A solution of (E)-3-(3-benzyloxy-4-nitrophenyl)-1,2-diphenylpropenone (200 mg) in EtOAc is hydrogenated over Pt/C (37.5 mg) at 1 atm for 18 h. The catalyst is filtered and the solvent evaporated to give the title compound as a yellow oil: $(M+1)^+=408$.

C. 5-[2-Hydroxy-4-(3-oxo-2,3-diphenylpropyl)-phenyl]-1,1-dioxo-1,2,5-thiadiazolidin-3-one The title compound is prepared from 3-(4-amino-3-benzyloxyphenyl)-1,2-diphenylpropan-1-one analogous to Example 247, steps B and C $(M-1)^-=435$. HPLC retention time=1.36 (Method A)

EXAMPLE 250

5-[4-(2-Benzyl-3-oxo-3-phenylpropyl)-2-hydroxyphenyl]-1,1-dioxo-1,2,5-thiadiazolidin-3-one

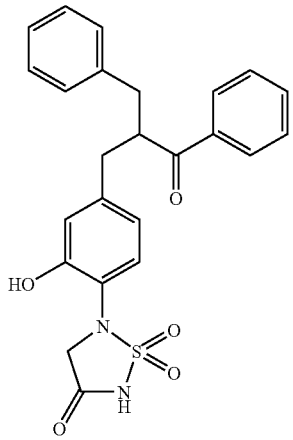

A. 2-Benzyl-3-(3-benzyloxy-4-nitrophenyl)-1-phenylpropan-1-one

To a solution of 1,3 diphenylpropan-1-one (231 mg, 1.1 mmol) in THF (2.5 mL) at −78° C. is added dropwise LiHMDS (1M in THF, 1.3 mL), over a period of 15 min. The mixture is stirred at −78° C. for 30 min then a solution of 2-benzyloxy-4-bromomethyl-1-nitrobenzene (321 mg, 1 mmol) in THF (2.5 mL) is added over a period of 15 min. The mixture is stirred at −78° C. for 15 min, then allowed to slowly warm to RT and stirred there for 45 min. The mixture is diluted with EtOAc, cooled to −25° C. and a solution of saturated ammonium chloride is added dropwise. The organic phase is washed with saturated ammonium chloride and brine, dried over MgSO$_4$, filtered and concentrated to afford crude product which is purified using flash chromatography to give the title compound as a gum.

B. 3-(4-Amino-3-benzyloxyphenyl)-1,2-diphenyl-propan-1-one

A solution of 2-benzyl-3-(3-benzyloxy-4-nitrophenyl)-1-phenylpropan-1-one (200 mg) in EtOAc (5 mL) is hydrogenated over 5% Pt/C (15 mg) at 1 atm for 18 h. The catalyst is filtered and the filtrate evaporated to give the title compound as a gum: (M+1)$^+$=422.

C. 5-[4-(2-Benzyl-3-oxo-3-phenylpropyl)-2-benzyloxyphenyl]-1,1-dioxo-1,2,5-thiadiazolidin-3-one The title compound is prepared from 3-(4-amino-3-benzyloxyphenyl)-1,2-diphenylpropan-1-one analogous to Example 83, steps H-K.

D. 5-[4-(2-Benzyl-3-oxo-3-phenylpropyl)-2-hydroxyphenyl]-1,1-dioxo-1,2,5-thiadiazolidin-3-one A mixture of 5-[4-(2-benzyl-3-oxo-3-phenylpropyl)-2-benzyloxyphenyl]-1,1-dioxo-1,2,5-thiadiazolidin-3-one (40 mg, 0.069 mmol) and 7 mg of Degussa 5% Pd/C in 4 mL of ethanol/water (1:1) is hydrogenated at 1 atm for 8 h at RT. The catalyst is filtered through Celite, washed with 1:1 ethanol/water and the filtrate concentrated under reduced pressure. The resulting residue is stripped four times with ethanol and the resulting solid is triturated with ether and dried to afford the title compound as a solid: (M−1)$^-$=449. HPLC retention time=0.88 min (Method C).

EXAMPLE 251

5-[4-(2,2-Dimethyl-3-oxo-3-phenylpropyl)-2-hydroxyphenyl]-1,1-dioxo-1,2,5-thiadiazolidin-3-one

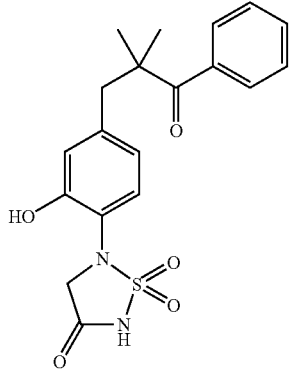

A. 5-[2-Benzyloxy-4-(2,2-dimethyl-3-oxo-3-phenylpropyl)-phenyl]-1,1-dioxo-1,2,5-thiadiazolidin-3-one The title compound is prepared from 2-benzyloxy-4-bromomethyl-1-nitrobenzene and 2-methyl-1-phenylpropan-1-one analogous to Example 247, steps A and B.

B. 5-[4-(2,2-Dimethyl-3-oxo-3-phenylpropyl)-2-hydroxyphenyl]-1,1-dioxo-1,2,5-thiadiazolidin-3-one A solution of 5-[2-benzyloxy-4-(2,2-dimethyl-3-oxo-3-phenylpropyl)-phenyl]-1,1-dioxo-1,2,5-thiadiazolidin-3-one potassium salt (60 mg) in 4 mL of EtOH/water (1:1) is hydrogenated over Degussa 5% Pd/C (15 mg) at 1 atm for 30 min. The catalyst is filtered and the solvent is removed under reduced pressure and the residue triturated with ether to give the title compound as a solid: (M−1)$^-$=387. HPLC retention time=1.42 min (Method A).

EXAMPLE 252

5-[2-Hydroxy-4-(1-oxo-indan-2-ylmethyl)-phenyl]-1,1-dioxo-1,2,5-thiadiazolidin-3-one

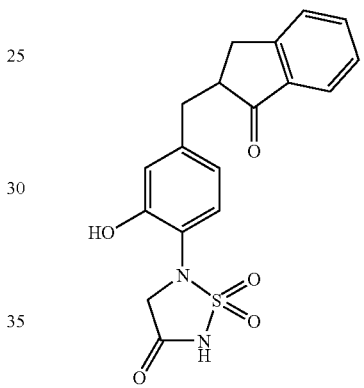

The title compound is prepared from 2-benzyloxy-4-bromomethyl-1-nitrobenzene and 1-indanone analogous to Example 251: (M−1)$^-$=371. HPLC retention time=1.17 min (Method A).

EXAMPLE 253

5-[2-Hydroxy-4-(6-oxo-6,7,8,9-tetrahydro-5H-benzocyclohepten-5-ylmethyl)-phenyl]-1,1-dioxo-1,2,5-thiadiazolidin-3-one

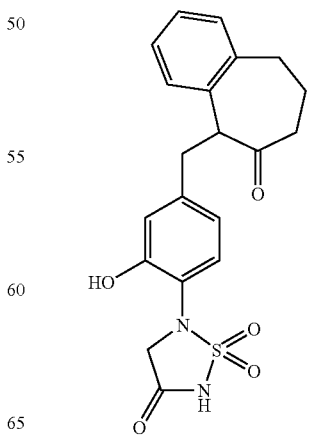

A. 5-(3-Benzyloxy-4-nitrobenzyl)-5,7,8,9-tetrahydrobenzocyclohepten-6-one

To a stirred solution of diisopropylamine (0.31 mL, 2.19 mmol) in THF (5 mL) at 0° C. is added n-butyllithium (1.6 M in hexane, 1.37 mL, 2.19 mmol) dropwise and the solution is stirred at 0° C. for 20 min then is cooled to −78° C. To this is added a solution of 5,7,8,9-tetrahydrobenzocyclohepten-6-one (J. Med. Chem. 40, 3516 (1997)) (350 mg, 2.19 mmol) in 2 THF is added dropwise. After one hour, a solution of 1-benzyloxy-4-bromomethyl-2-nitrobenzene (705 mg, 2.19 mmol) in THF (2 mL) is added dropwise and the mixture is allowed to warm to RT overnight. The mixture is quenched with saturated NaHCO$_3$ and the solution is extracted with EtOAc. The organic layer is washed with water, brined and dried over MgSO$_4$. The solvent is removed under reduced pressure and the residue is purified by flash chromatography using a gradient of 25-75% hexane/CH$_2$Cl$_2$ to give the title compound as a yellow liquid. $^1$H NMR (CDCl$_3$): 7.72-7.70 (d, J=8.08 Hz, 1H), 7.42-7.11 (m, 8H), 6.92-6.90 (dd, J=1.27 Hz, 8.08 Hz, 1 H), 6.73-6.72 (m, 2H), 5.05-5.04 (d, J=2.78 Hz, 2H), 4.0-3.96 (t, J=7.08 Hz, 1H), 3.57-3.51 (q, J=7.58 Hz, 1H), 3.05-3.01 (q, J=6.06 Hz, 1H), 2.87-2.81 (m, 1H), 2.65-2.58 (m, 1H), 2.55-2.47 (m, 1H), 2.42-2.37 (m, 1H), 2.05-1.95 (m, 1H), 1.92-1.83 (m, 1H). (M−1)$^−$=400.

B. 5-[2-Hydroxy-4-(6-oxo-6,7,8,9-tetrahydro-5H-benzocyclohepten-5-ylmethyl)-phenyl]-1,1-dioxo-1,2,5-thiadiazolidin-3-one The title compound is prepared from 5-(3-benzyloxy-4-nitrobenzyl)-5,7,8,9-tetrahydrobenzocyclohepten-6-one analogous to Example 83, steps G-L: (M−1)$^−$=399. HPLC retention time: 1.10 min. (Method A).

EXAMPLE 254

5-[2-Hydroxy-4-(2-methoxy-3-oxo-3-phenylpropyl)-phenyl]-1,1-dioxo-1,2,5-thiadiazolidin-3-one

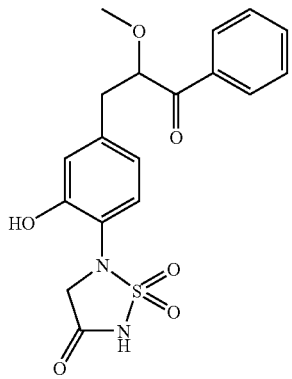

The title compound is prepared from 2-benzyloxy-4-bromomethyl-1-nitrobenzene and 2-methoxy-1-phenylethanone analogous to Example 251: (M−1)$^−$=389. HPLC retention time=1.08 min (Method A).

EXAMPLE 255

5-[2-Hydroxy-4-(3-hydroxy-2-methyl-3-phenylpropyl)-phenyl]-1,1-dioxo-1,2,5-thiadiazolidin-3-one

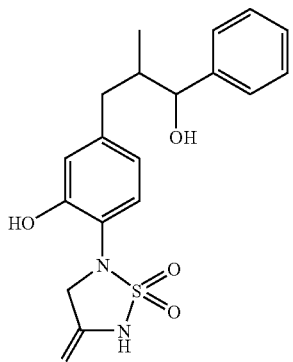

To a solution of 5-[2-benzyloxy-4-(2-methyl-3-oxo-3-phenylpropyl)-phenyl]-1,1-dioxo-1,2,5-thiadiazolidin-3-one potassium salt (Example 246, step C) in 5 mL of EtOH/water (1:1)) is added 15 mg of Degussa Pd/C and the resulting mixture is hydrogenated at 1 atm for 4 h. The catalyst is filtered through Celite and the solvent is removed under reduced pressure. The residue is purified by preparative HPLC to give the title compound: (M−1)$^−$=375.

EXAMPLES 256 TO 261

The following compounds are prepared from the appropriate ketones analogous to Example 255.

| Example | Chemical Name | MS (m/z) | Retention time (min) Method |
|---|---|---|---|
| 256 | 5-{2-Hydroxy-4-[2-(hydroxylphenylmethyl)-butyl]-phenyl}-1,1-dioxo-1,2,5-thiadiazolidin-3-one | (M − 1)$^−$ = 389 | |
| 257 | 5-{2-Hydroxy-4-[2-(hydroxyphenylmethyl)-pentyl]-phenyl}-1,1-dioxo-1,2,5-thiadiazolidin-3-one | (M − 1)$^−$ = 403 | |
| 258 | 5-[4-(2-Benzyl-3-hydroxy-3-phenylpropyl)-2-hydroxyphenyl]-1,1-dioxo-1,2,5-thiadiazolidin-3-one | (M − 1)$^−$ = 451 | |

-continued

| Example | Chemical Name | MS (m/z) | Retention time (min) Method |
|---|---|---|---|
| 259 | 5-[2-Hydroxy-4-(3-hydroxy-2,2-dimethyl-3-phenylpropyl)-phenyl]-1,1-dioxo-1,2,5-thiadiazolidin-3-one | $(M-1)^- = 389$ | 1.32 A |
| 260 | 5-[2-Hydroxy-4-(1-hydroxyindan-2-ylmethyl)-phenyl]-1,1-dioxo-1,2,5-thiadiazolidin-3-one | $(M-1)^- = 373$ | 1.11 A |
| 261 | 5-[2-Hydroxy-4-(3-hydroxy-2-methoxy-3-phenyl-propyl)-phenyl]-1,1-dioxo-1,2,5-thiadiazolidin-3-one | $(M-1)^- = 391$ | 0.95 A |

EXAMPLE 262

5-(2-Hydroxy-4-vinylphenyl)-1,1-dioxo-1,2,5-thiadiazolidin-3-one

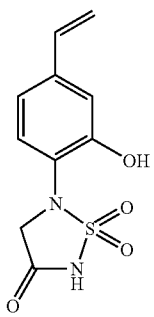

A. 5-(2-Benzyloxy-4-vinylphenyl)-1,1-dioxo-1,2,5-thiadiazolidin-3-one

The title compound is prepared from 5-(2-benzyloxy-4-vinylphenyl)-1,1-dioxo-2-(2-trimethylsilanylethyl)-1,2,5-thiadiazolidin-3-one (Example 81, step A) analogous to Example 136, step B.

B. 5-(2-Hydroxy-4-vinylphenyl)-1,1-dioxo-1,2,5-thiadiazolidin-3-one

To a solution of 5-(2-benzyloxy-4-vinylphenyl)-1,1-dioxo-1,2,5-thiadiazolidin-3-one (73 mg, 0.21 mmol) in $CH_2Cl_2$ (4 mL) at 0° C. is added dropwise 1M $BBr_3$ (0.32 mL, 0.32 mmol) in $CH_2Cl_2$ and the reaction is stirred at 0° C. for 30 min. The mixture is quenched with water (1 mL) followed by washing with $Et_2O$. The aqueous layer is concentrated under reduced pressure and the crude residue is purified by chromatography on a C18 column using a gradient of 0-15% EtOH/water as eluent to give the title compound: $(M-H)^-=253$; $^1H$ NMR (MeOD) δ 7.32 (d, J=8.0 Hz, 1H), 6.87 (d, J=2.0 Hz, 1H), 6.79 (dd, J=8, 2 Hz, 1H), 4.69 (q, J=6.48 Hz, 1H), 4.26 (s, 2H), 2.63 (s, 1H), 1.34 (d, J=6.57 Hz, 3H).

EXAMPLE 263

5-[2-Hydroxy-4-(1-hydroxyethyl)-phenyl]-1,1-dioxo-1,2,5-thiadiazolidin-3-one

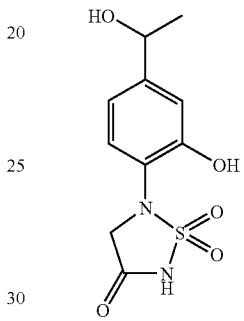

The title compound is isolated as a side product from the deprotection of 5-(2-benzyloxy-4-vinylphenyl)-1,1-dioxo-1,2,5-thiadiazolidin-3-one (example 262, step B): $(M-H)^-=271$; $^1H$ NMR (MeOD) δ 7.3 (d J=8.0 Hz, 1H), 6.89 (d, J=2.0 Hz, 1H), 6.85 (dd, J=8.0, 2.0 Hz, 1H), 6.58 (m, 1H), 5.62 (m, 1H), 5.13 (m, 1H), 4.28 (s, 2H).

EXAMPLE 264

5-[2-Hydroxy-4-(2-hydroxyhexyl)-phenyl]-1,1-dioxo-1,2,5-thiadiazolidin-3-one

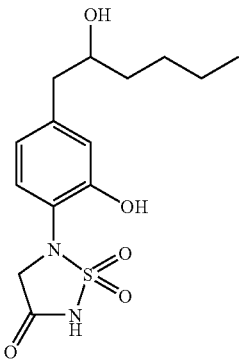

A. 5-[2-benzyloxy-4-((E)-hex-1-enyl)-phenyl]-1,1-dioxo-1,2,5-thiadiazolidin-3-one A mixture of 5-(2-benzyloxy-4-iodophenyl)-1,1-dioxo-1,2,5-thiadiazolidin-3-one (200 mg, 0.45 mmol), trans-1-hexen-1-ylboronic acid (77 mg, 0.676 mmol), resin-bound $PPh_3Pd$ (692 mg, loading 0.13 mmol/g) and aqueous $Na_2CO_3$ (0.9 mL of a 2M solution) in DME (3 mL) is placed in a microwave vial and heated at 110° C. for 30 min. The mixture is filtered, diluted with EtOAc and washed with 1N HCl. The organic phase is dried over magnesium sulfate and the solvent removed under reduced pressure. The residue is purified by preparative HPLC to give the title compound.

B. 5-[2-Benzyloxy-4-(3-butyloxiranyl)-phenyl]-1,1-dioxo-1,2,5-thiadiazolidin-3-one To a stirred solution of 5-[2-benzyloxy-4-((E)-hex-1-enyl)-phenyl]-1,1-dioxo-1,2,5-thiadiazolidin-3-one (10 mg, 0.275 mmol) in acetone (10 mL) is added a solution of DMDO (0.56 mM, 4.9 mL, 0.413 mmol) in acetone. This mixture is stirred at RT for 1 h, at which point LCMS of the reaction shows clean conversion to the desired epoxide. The reaction mixture is diluted with EtOAc and concentrated 3× to fully remove the volatile DMDO. The remaining EtOAc is removed under reduced pressure to afford the title compound which is used directly in the next step.

C. 5-[2-Hydroxy-4-(2-hydroxyhexyl)-phenyl]-1,1-dioxo-1,2,5-thiadiazolidin-3-one A mixture of 5-[2-benzyloxy-4-(3-butyloxiranyl)-phenyl]-1,1-dioxo-1,2,5-thiadiazolidin-3-one (110 mg) and Pd(OH)$_2$ (11 mg) in EtOAc (5 mL) is hydrogenated at 1 atm for 48 h. The catalyst is filtered and the filtrate evaporated. The residue is purified by preparative HPLC to give the title compound: $(M-1)^-=327$; HPLC retention time=0.93 min (method A).

EXAMPLE 265

5-[2-Hydroxy-4-(3-hydroxybutyl)-phenyl]-1,1-dioxo-1,2,5-thiadiazolidin-3-one

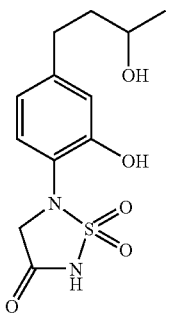

The title compound is prepared from 5-(2-benzyloxy-4-iodophenyl)-1,1-dioxo-1,2,5-thiadiazolidin-3-one and but-3-en-2-ol analogous to Example 44: $(M-1)^-=299$; HPLC retention time=1.16 min (method B)

EXAMPLE 266

5-{2-Hydroxy-4-[2-(1-hydroxycyclohexyl)-ethyl]-phenyl}-1,1-dioxo-1,2,5-thiadiazolidin-3-one

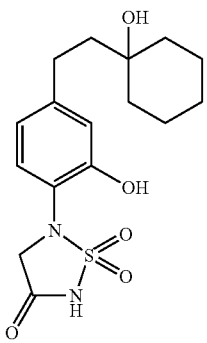

The title compound is prepared from 5-(2-benzyloxy-4-iodophenyl)-1,1-dioxo-1,2,5-thiadiazolidin-3-one and 1-vinyl-cyclohexanol analogous to Example 44: $(M-1)^-=353$; HPLC retention time=1.35 min (method A).

EXAMPLE 267

5-[2-Hydroxy-4-(4,4,4-trifluoro-3-hydroxy-3-phenylbutyl)-phenyl]-1,1-dioxo-1,2,5-thiadiazolidin-3-one

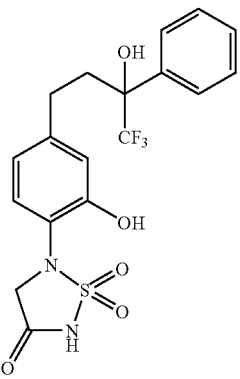

The title compound is prepared from 5-(2-benzyloxy-4-iodophenyl)-1,1-dioxo-1,2,5-thiadiazolidin-3-one and 1,1,1-trifluoro-2-phenyl-but-3-en-2-ol analogous to Example 44: $(M-1)^-=429$; HPLC retention time=1.29 min (method A).

EXAMPLE 268

5-(3-Hydroxybiphenyl-4-yl)-1,1-dioxo-1,2,5-thiadiazolidin-3-one

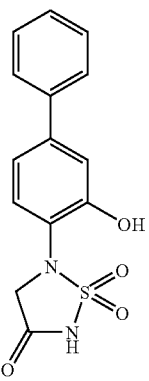

A. 5-(3-Benzyloxybiphenyl-4-yl)-1,1-dioxo-1,2,5-thiadiazolidin-3-one

A mixture of 5-(2-benzyloxy-4-iodophenyl)-1,1-dioxo-1,2,5-thiadiazolidin-3-one (200 mg, 0.45 mmol), phenylboronic acid (180 mg, 0.83 mmol), Pd(PPh$_3$)$_4$ (100 mg, 20 mol %) and aqueous Na$_2$CO$_3$ (0.83 mL of a 2M solution) in DME (3 mL) is placed in a microwave vial and heated at 110° C. for 15 min. The mixture is filtered, diluted with EtOAc and washed with 1N HCl. The organic phase is dried over magnesium sulfate and the solvent removed under reduced pressure to give the title compound which is used directly in the next step.

B. 5-(3-Hydroxybiphenyl-4-yl)-1,1-dioxo-1,2,5-thiadiazolidin-3-one

The potassium salt of the title compound is prepared from 5-(3-benzyloxybiphenyl-4-yl)-1,1-dioxo-1,2,5-thiadiazolidin-3-one analogous to Example 57, step D: (M−1)⁻= 303.__¹H NMR (400 MHz, DMSO-D6) δ ppm 4.11 (t, J=4.29 Hz, 2 H) 7.27-7.35 (m, 3 H) 7.37-7.47 (m, 3 H) 7.48-7.51 (m, 1 H) 7.53-7.57 (m, 1 H) 7.59-7.68 (m, 1 H)

EXAMPLE 269

5-(3,3'-Dihydroxybiphenyl-4-yl)-1,1-dioxo-1,2,5-thiadiazolidin-3-one

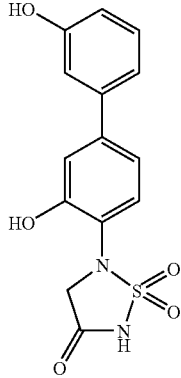

The potassium salt of the title compound is prepared from 5-(2-benzyloxy-4-iodophenyl)-1,1-dioxo-1,2,5-thiadiazolidin-3-one and 3-(4,4,5,5-tetramethyl-[1,3,2]dioxaborolan-2-yl)-phenol analogous to Example 268: (M−1)⁻=319. ¹H NMR (400 MHz, DMSO-D6) δ ppm 4.14 (s, 2 H) 6.70 (s, 1 H) 6.89-7.00 (m, 3 H) 7.19 (t, J=7.83 Hz, 1 H) 7.41 (s, 1 H)

EXAMPLE 270

[3'-Hydroxy-4'-(1,1,4-trioxo-1,2,5-thiadiazolidin-2-yl)-biphenyl-4-yl]-acetic Acid

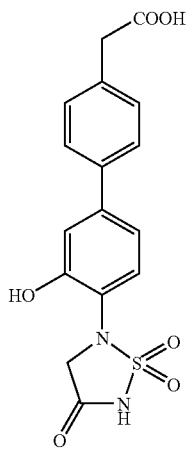

The potassium salt of the title compound is prepared from 5-(2-benzyloxy-4-iodophenyl)-1,1-dioxo-1,2,5-thiadiazolidin-3-one, [4-(4,4,5,5-tetramethyl-[1,3,2]dioxaborolan-2-yl)-phenyl]-acetic acid and resin-bound PPh₃Pd analogous to Example 268: (M−1)⁻=361.__¹H NMR (400 MHz, DMSO-D6) δ ppm 3.21 (d, J=9.85 Hz, 3 H) 4.15 (s, 2 H) 6.95 (s, 1 H) 7.17 (d, J=7.83 Hz, 1 H) 7.25 (d, J=8.08 Hz, 2 H) 7.32 (s, 1 H) 7.38 (d, J=8.34 Hz, 2 H) 7.58 (d, J=8.08 Hz, 1 H)

EXAMPLE 271

5,5'-(3,3'-Dihydroxybiphenyl-4-yl)-1,1,1',1'-tetraoxo-1,1',2,2',5,5'-dithiadiazolidin-3,3'-one

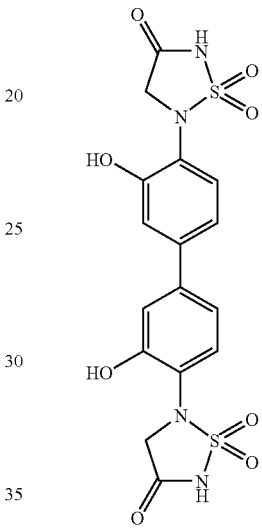

A. 5,5'-(3,3'-Bis-benzyloxybiphenyl-4-yl)-1,1,1',1'-tetraoxo-2,2'-(2,2'-bis-trimethylsilanylethyl)-1,1',2,2', 5,5'-dithiadiazolidin-3,3'-one The title compound is isolated as a minor dimeric by-product from the zinc coupling reactions (e.g. Examples 57, 59, 80, etc.)

B. 5,5'-(3,3'-Bis-benzyloxybiphenyl-4-yl)-1,1,1',1'-tetraoxo-1,1',2,2',5,5'-dithiadiazolidin-3,3'-one To a solution of 5,5'-(3,3'-bis-benzyloxybiphenyl-4-yl)-1, 1,1',1'-tetraoxo-2,2'-(2,2'-bis-trimethylsilanylethyl)-1,1'2,2', 5,5'-dithiadiazolidin-3,3'-one (0.55 g, 0.47 mmol) in THF (5 mL) is added a 1.0M solution of TBAF (2 mL) in THF and the mixture is stirred at RT for 18 h. To the mixture is added 1N HCl and EtOAc. The organic phase is washed with 1N HCl and sat. NaCl. The solution is dried over sodium sulfate and the solvent partially removed under reduced pressure. Ether and hexane is added and the resulting precipitate is filtered to give the title compound as an orange powder.

C. 5,5'-(3,3'-Dihydroxybiphenyl-4-yl)-1,1,1',1'-tetraoxo-1,1',2,2',5,5'-dithiadiazolidin-3,3'-one The dipotassium salt of the title compound is prepared from 5,5'-(3,3'-bis-benzyloxybiphenyl-4-yl)-1,1,1',1'-tetraoxo-1,1',2,2',5,5'-dithiadiazolidin-3,3'-one analogous to Example 57, step D: ¹H NMR (DMSO-d₆ δ7.39 (d, J=8.08

Hz, 2H), 7.0 (s, 2H), 6.85 (m, 2H), 4.15 (s, 4H). $^1$H NMR (400 MHz, DMSO-D6) δ ppm 4.15 (s, 4 H) 6.85 (s, 2 H) 7.00 (s, 2 H) 7.34-7.43 (m, 2 H)

EXAMPLE 272

5-(4-Furan-3-yl-2-hydroxyphenyl)-1,1-dioxo-1,2,5-thiadiazolidin-3-one

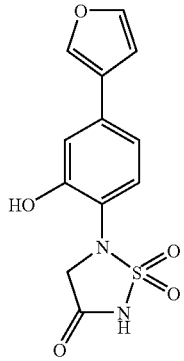

A. 5-(2-Benzyloxy-4-furan-3-yl-phenyl)-1,1-dioxo-1,2,5-thiadiazolidin-3-one

A mixture of 5-(2-benzyloxy-4-iodophenyl)-1,1-dioxo-1,2,5-thiadiazolidin-3-one (163 mg, 0.37 mmol), furan-3-boronic acid (62 mg, 0.550 mmol), potassium phosphate (235 mg, 1.1 mmol), and palladium dppf (9 mg, 0.011 mmol) in 6 mL of glyme/water (9:1) is heated in a microwave apparatus at 120° C. for 25 min. The mixture is poured into EtOAc and extracted with 1N HCl and saturated NaCl. The organic phase is dried and the solvent removed is under reduced pressure to leave a crude semi-solid that is chromatographed on a $C_{18}$ column using a gradient of 0-60% water/acetonitrile as eluent. The aqueous is lyophilized to afford the title compound as a hygroscopic solid: $^1$H NMR (DMSOd$_6$) δ 8.1 (s, 1H), 7.7 (s, 1H), 7.5 (d, J=8.3 Hz, 1H), 7.4 (m, 6H), 7.1 (dd, J=8.3, 1.8 Hz, 1H), 6.9 (s, 1H), 5.2 (s, 2H), 4.0 (s, 2H); (M–1)$^-$=383.

B. 5-(4-Furan-3-yl-2-hydroxyphenyl)-1,1-dioxo-1,2,5-thiadiazolidin-3-one

To a solution of 5-(2-benzyloxy-4-furan-3-yl-phenyl)-1,1-dioxo-1,2,5-thiadiazolidin-3-one (73 mg, 0.190 mmol) in EtOH (1 mL) is added aqueous potassium bicarbonate (0.190 mmol) and water (4 mL) and stirred for 10 min. The resulting solution is hydrogenated at 1 atm over 10% Pd/C (7 mg) for 4 h. The mixture is filtered through Celite and lyophilized to afford the potassium salt of the title compound as a dark powder: mp=230-235° C., $^1$H NMR (DMSO-d$_6$) δ 8.0 (s, 1H), 7.7 (m, 1H), 7.4 (d, J=8.1 Hz, 1H), 7.0 (d, J=1.8 Hz, 1H), 7.0 (dd, J=8.3, 1.8 Hz, 1H), 6.8 (d, 2.0 Hz, 1H), 4.0 (s, 1H); (M–1)$^-$=293.

EXAMPLE 273

5-(2-Hydroxy-4-thiophen-3-yl-phenyl)-1,1-dioxo-1,2,5-thiadiazolidin-3-one

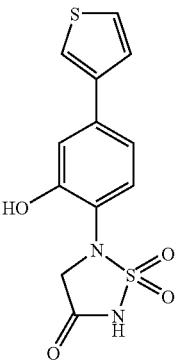

The title compound is prepared using 5-(2-benzyloxy-4-iodophenyl)-1,1-dioxo-1,2,5-thiadiazolidin-3-one and thiophene-3-boronic acid analogous to Example 272: $^1$H NMR (DMSO-d$_6$ δ 9.68 (br s, 1H), 7.75 (m, 1H), 7.61 (m, 1H), 7.43 (m, 1H), 7.38 (m, 1H), 7.15 (m, 2H), 4.32 (s, 2H); (M–1)$^-$=309.

EXAMPLE 274

5-(4-Benzofuran-3-yl-2-hydroxyphenyl)-1,1-dioxo-1,2,5-thiadiazolidin-3-one

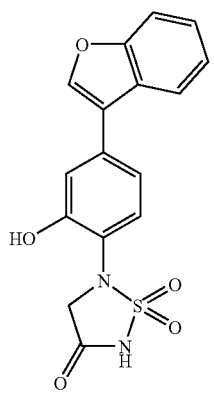

A. Trifluoromethanesulfonic Acid Benzofuran-3-yl Ester

To a solution of benzofuran-3-one (500 mg, 3.73 mmol) in methylene chloride (30 mL) at −20° C. is added triethylamine (1.13 g, 11.2 mmol) then a solution of trifluoromethanesulfonic anhydride (1.58 g, 5.59 mmol) in methylene chloride (5 mL) is added dropwise. The mixture is stirred at −20° C. for 1 h then it is quenched with 8% NaHCO$_3$ solution. The organic phase is dried over magnesium sulfate and the solvent is removed under reduced pressure at a temperature less than 30° C. to give the title compound which is used directly in the next step.

B. 3-(4,4,5,5-Tetramethyl-[1,3,2]dioxaborolan-2-yl)-benzofuran

To a solution of trifluoromethanesulfonic acid benzofuran-3-yl ester (half of the amount from step A) in THF is added triethylamine (732 mg, 7.23 mmol), 4,4,5,5-tetramethyl-[1,3,2]dioxaborolane (3.2 mL of a 1.0M in THF, 3.2 mmol) and Pd(dppf)Cl$_2$.CH$_2$Cl$_2$ (76 mg, 0.096 mmol). The mixture is heated at 150° C. under microwave conditions for 3 min. The mixture is filtered and the filtrate evaporated under reduced pressure. The residual oil is purified by flash chromatography using hexane/EtOAc (9:1) as eluent to give the title compound.

C. 5-(4-Benzofuran-3-yl-2-benzyloxyphenyl)-1,1-dioxo-1,2,5-thiadiazolidin-3-one A mixture of 5-(2-benzyloxy-4-iodophenyl)-1,1-dioxo-1,2,5-thiadiazolidin-3-one (80 mg, 0.18 mmol), 3-(4,4,5,5-tetramethyl-[1,3,2]dioxaborolan-2-yl)-benzofuran (44 mg, 0.18 mmol), Cs$_2$CO$_3$ (235 mg, 0.72 mmol) and Pd(PPh$_3$)$_4$ (8 mg) in DMF (5 mL) is stirred at 80° C. for 7 h. The mixture is cooled to RT and is diluted with EtOAc, washed with water and bride and dried over magnesium sulfate. The solvent is removed under reduced pressure to give the title compound.

D. 5-(4-Benzofuran-3-yl-2-hydroxyphenyl)-1,1-dioxo-1,2,5-thiadiazolidin-3-one The title compound is prepared from 5-(4-benzofuran-3-yl-2-benzyloxyphenyl)-1,1-dioxo-1,2,5-thiadiazolidin-3-one analogous to Example 57, step D: (M−1)$^−$=343. HPLC retention time=0.73 min (Method A).

EXAMPLE 275

5-[2-Hydroxy-4-(6-methoxybenzofuran-3-yl)-phenyl]-1,1-dioxo-1,2,5-thiadiazolidin-3-one

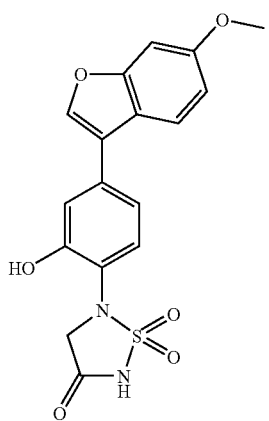

The title compound is prepared from 5-(2-benzyloxy-4-iodophenyl)-1,1-dioxo-1,2,5-thiadiazolidin-3-one and 6-methoxybenzofuran-3-one analogous to Example 274: (M−1)$^−$=373; HPLC retention time=1.09 min. (Method A).

EXAMPLE 276

5-(2-Hydroxy-4-thiazol-5-yl-phenyl)-1,1-dioxo-1,2,5-thiadiazolidin-3-one

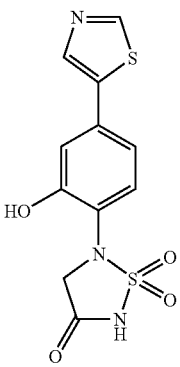

A. 5-Tributylstannanyl-2-trimethylsilanylthiazole

To a solution of n-BuLi (2.5M in hexane, 6.0 mL, 15 mmol) in ether (60 mL) at −78° C. is added a solution of 2-(trimethylsilyl)thiazole (2.0 mL, 12.5 mmol) in ether (20 mL) dropwise. The mixture is stirred at −78° C. for 1 h then tributyltin chloride (4.04 mL, 15 mmol) in ether (25 mL) is added dropwise and stirring is continued at −78° C. for 1 h. The reaction mixture is washed with saturated NaHCO$_3$, dried over anhydrous MgSO$_4$ and concentrated to afford the title compound as a yellow oil which used in the next step without further purification: $^1$H NMR (CDCl$_3$) δ 0.41 (s, 9H), 0.90 (t, J=8 Hz, 9H), 1.14 (q, 6H), 1.13 (q, 6H), 1.54 (m, 6H), 8.06 (s, 1H); (M+1)$^+$=447.

B. 5-Tributylstannanylthiazole

To a solution of 5-tributylstannanyl-2-trimethylsilanylthiazole (4.0 g, 9.0 mmol) in THF is added slowly HCl (1.0N, 3 mL) and the solution is stirred at RT for 1 h. The reaction mixture is extracted with ether, washed with sat. NaHCO$_{31}$ dried over anhydrous MgSO$_4$ and concentrated to afford the title compound as a yellow oil which is used in the next step without further purification: (M+1)$^+$=375.

C. 5-(2-Benzyloxy-4-thiazol-5-yl-phenyl)-1,1-dioxo-2-(2-trimethylsilanylethyl)-1,2,5-thiadiazolidin-3-one To a solution of 5-tributylstannanylthiazole (515 mg, 1.38 mmol) in MeCN (8 mL) is added 5-(2-benzyloxy-4-iodophenyl)-1,1-dioxo-2-(2-trimethylsilanylethyl)-1,2,5-thiadizolidin-3-one (500 mg, 0.919 mmol), Pd$_2$(dba)$_3$ (42 mg, 0.046 mmol) and tri-o-tolylphosphine (70 mg, 0.23 mmol). The mixture is heated at 75° C. for 18 h then cooled to RT. The insoluble material is filtered through Celite and the filtrate concentrated. The residue is purified by flash column chromatography using hexane/EtOAc (1:1) as eluent to afford the title compound as a yellow solid; $^1$H NMR (CDCl$_3$) δ 0.01 (s, 9H), 1.01 (m, 2H), 3.53 (m, 2H), 4.32 (s, 2H), 5.12 (s, 2H), 7.14 (m, 2H), 7.25-7.30 (m, 5H) 7.45 (d, J=8 Hz, 1H), 7.98 (s, 1H), 8.73 (s, 1H); (M+1)$^+$=502.

D. 5-(2-Benzyloxy-4-thiazol-5-yl-phenyl)-1,1-dioxo-1,2,5-thiadiazolidin-3-one

To a mixture of PS-isocyanate resin (2.0 g) in THF (5 mL) is added tetrabutylammonium fluoride (1.0 M in THF, 2.17 mL) and the mixture is stirred at RT for 2 h. The resin is filtered off and the filtrate is added to a solution of 5-(2-benzyloxy-4-thiazol-5-yl-phenyl)-1,1-dioxo-2-(2-trimethylsilanylethyl)-1,2,5-thiadiazolidin-3-one (272 mg, 0.543 mmol) in THF (1 mL) and the mixture is stirred at 50° C. for 18 h. The reaction mixture is cooled and diluted with EtOAc, washed with 1N HCl and dried over MgSO$_4$. The solvent is removed under reduced pressure and the residue is purified by column chromatography eluting with MeOH/EtOAc to afford the title compound as a yellow solid: (M+1)$^+$=402.

E. 5-(2-Hydroxy-4-thiazol-5-yl-phenyl)-1,1-dioxo-1,2,5-thiadiazolidin-3-one

To a solution of 5-(2-benzyloxy-4-thiazol-5-yl-phenyl)-1,1-dioxo-1,2,5-thiadiazolidin-3-one (87 mg, 0.217 mmol) in EtOH (2.5 mL) and water (22.5 mL) is added 10% Pd/C (100 mg) and the mixture is stirred under an atmosphere of H$_2$ for 2.5 h. The mixture is filtered through Celite and the filtrate evaporated. The residue is purified by reverse phase HPLC (CH$_3$CN/water/0.1% TFA) to afford the title compound as a light yellow solid: $^1$H NMR (CD$_3$OD $\delta$ 4.37 (s, 1H), 7.04 (d, J=8 Hz, 1H), 7.08 (s, 1H), 7.35 (d, J=8 Hz, 1H), 7.97 (s, 1H), 8.79 (s, 1H); (M−1)$^−$=310.

EXAMPLE 277

5-(2-Hydroxy-4-thiazol-2-yl-phenyl)-1,1-dioxo-1,2,5-thiadiazolidin-3-one

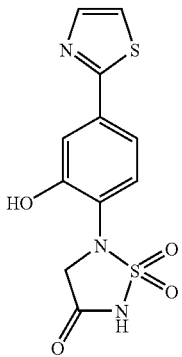

A. 5-(2-Benzyloxy-4-thiazol-2-yl-phenyl)-1,1-dioxo-2-(2-trimethylsilanylethyl)-1,2,5-thiadiazolidin-3-one To a solution of n-BuLi (2.5M in hexane, 0.44 mL, 1.1 mmol) in Et$_2$O (1 mL) at −78° C. is added 2-(trimethylsilyl)thiazole (0.16 mL, 1.0 mmol) and the reaction mixture is stirred at −78° C. for 30 min. Zinc chloride (1.0 M in Et$_2$O, 3.0 mL, 3.0 mmol) is added and the mixture is warmed to RT over 30 min. The ether is removed under reduced pressure then a solution of 5-(2-benzyloxy-4-iodophenyl)-1,1-dioxo-2-(2-trimethylsilanylethyl)-1,2,5-thiadiazolidin-3-one (250 mg, 0.46 mmol) and Pd(PPh$_3$)$_4$ (55 mg, 0.046 mmol) in THF (1 mL) is added. The yellow solution is stirred at RT for 1 h then is heated at reflux for 2 h. The mixture is quenched with 1N HCl, extracted with EtOAc, washed with brine, dried over MgSO$_4$ and concentrated. The residue is purified by chromatography using EtOAc/hexane as eluent to afford the title compound as a yellow solid: $^1$H NMR (CDCl$_3$) $\delta$ 0.01 (s, 9H), 0.83 (m, 2H), 3.51 (m, 2H), 4.33 (s, 2H), 5.13 (s, 2H), 7.27-7.37 (m, 6H) 7.48 (m, 2H), 7.73 (br s, 1H), 7.82 (d, J=4 Hz, 1H); (M+1)$^+$=502.

B. 5-(2-Benzyloxy-4-thiazol-2-yl-phenyl)-1,1-dioxo-1,2,5-thiadiazolidin-3-one

The title compound is prepared from 5-(2-benzyloxy-4-thiazol-2-yl-phenyl)-1,1-dioxo-2-(2-trimethylsilanylethyl)-1,2,5-thiadiazolidin-3-one analogous to Example 276 and is used in the next step without further purification: (M+1)$^+$=402.

C. 5-(2-Hydroxy-4-thiazol-2-yl-phenyl)-1,1-dioxo-1,2,5-thiadiazolidin-3-one

To a suspension of 5-(2-benzyloxy-4-thiazol-2-yl-phenyl)-1,1-dioxo-1,2,5-thiadiazolidin-3-one (50 mg, 0.125 mmol) in CH$_2$Cl$_2$ (5 mL) at −10° C. is added BBr$_3$ (1.0M in CH$_2$Cl$_2$, 0.68 mL) dropwise. The yellow mixture is stirred at −10° C. for 30 min. Water is added to the reaction mixture and the aqueous layer is separated and neutralized with 1N NaOH. The water is removed under reduced pressure and the residue is purified by reverse phase HPLC (MeCN/water/0.1% TFA) to afford the title compound as a light yellow solid: $^1$H NMR (D$_2$O $\delta$ 4.45 (s, 1H), 7.48-7.54 (m, 3H), 7.61 (d, J=4 Hz, 1H), 7.85 (d, J=4 Hz, 1H); (M−1)$^−$=310.

EXAMPLE 278

5-[2-Hydroxy-4-(1H-pyrrol-3-yl)-phenyl]-1,1-dioxo-1,2,5-thiadiazolidin-3-one

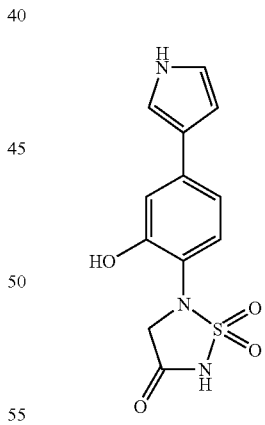

A. 5-[2-Benzyloxy-4-(1-triisopropylsilanyl-1H-pyrrol-3-yl)-phenyl]-1,1-dioxo-1,2,5-thiadiazolidin-3-one To a solution of 5-(2-benzyloxy-4-iodophenyl)-1,1-dioxo-1,2,5-thiadiazolidin-3-one (100 mg, 0.225 mmol) in DME (5 mL) is added 1-triisopropylsilylpyrrole-3-boronic acid (120 mg, 0.450 mmol), Pd(PPh$_3$)$_4$ (27 mg, 0.023 mmol) and 0.5 mL of Na$_2$CO$_3$ (2M aqueous solution) and the mixture is heated in a microwave apparatus at 120° C. for 5 min. The mixture is concentrated under reduced pressure and the residue purified by reverse phase MPLC using a gradient of 10-50% MeCN/water as eluent to afford the title compound: $(M-1)^-=538$.

B. 5-[2-Hydroxy-4-(1-triisopropylsilanyl-1H-pyrrol-3-yl)-phenyl]-1,1-dioxo-1,2,5-thiadiazolidin-3-one To a slurry of Pd/C (10 mg) in 10 mL of EtOH/EtOAc (1:1) is added a solution of 5-[2-benzyloxy-4-(1-triisopropylsilanyl-1H-pyrrol-3-yl)-phenyl]-1,1-dioxo-1,2,5-thiadiazolidin-3-one in EtOH. The mixture is stirred under an atmosphere of $H_2$ for 18 h then the catalyst is removed by filtration through a pad of Celite. The filtrate is concentrated under reduced pressure to afford the title compound which is used directly in the next step: $(M-1)^-=448$.

C. 5-[2-Hydroxy-4-(1H-pyrrol-3-yl)-phenyl]-1,1-dioxo-1,2,5-thiadiazolidin-3-one To a solution of 5-[2-hydroxy-4-(1-triisopropylsilanyl-1H-pyrrol-3-yl)-phenyl]-1,1-dioxo-1,2,5-thiadiazolidin-3-one in MeCN (10 mL) is added HF-Pyridine (0.2 mL, 2.23 mmol) and the reaction mixture is stirred at RT for 2 h. TMSOMe (5 mL) is added to consume unreacted HF, and the crude reaction mixture is concentrated in vacuo. The residue is purified by reverse phase MPLC using 1-40% MeCN/$H_2O$ as eluent to give the title compound: $(M-1)^-=292$.

EXAMPLE 279

5-[2-Hydroxy-4-(1H-pyrazol-3-yl)-phenyl]-1,1-dioxo-1,2,5-thiadiazolidin-3-one

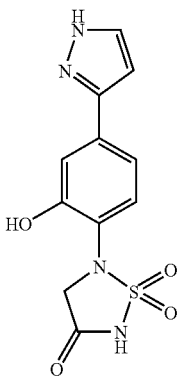

A. 1-Benzyloxymethyl-1H-pyrazole

To a solution of pyrazole (4.92 g, 72.2 mmol) in THF (100 mL) at −78° C. is added n-BuLi (28.9 mL of 2.5M in hexane) dropwise. The mixture is warmed to RT then re-cooled to −78° C. then Bom-Cl (11.3 g, 72.2 mmol) is added and the mixture is allowed to warm to RT. The solvent is removed under reduced pressure and 1N NaOH (25 mL) is added to the residual solid. The mixture is extracted with ether and the organic phase is washed with brine and dried over sodium sulfate. The solvent is removed under reduced pressure and the residue purified by reverse phase-MPLC using a gradient of 25-50% MeCN/water as eluent to give the title compound.

B. 1-Benzyloxymethyl-1H-pyrazole-3-boronic Acid

To a solution of 1-benzyloxymethyl-1H-pyrazole (200 mg, 1.06 mmol) in THF (5 mL) at 0° C. is added n-BuLi (0.51 mL of 2.5M in THF, 1.28 mmol) and the mixture is stirred at 0° C. for 30 min. To this is added trimethyl borate (551 mg, 5.3 mmol) dropwise then the mixture is allowed to warm to RT overnight. The light yellow solution is acidified with 1N HCl (12.8 mL) and the THF is removed under reduced pressure. The aqueous phase is purified by reverse phase MPLC using a gradient of 0-60% MeCN/water as eluent. The solvent is concentrated until a precipitate forms. The mixture is cooled to 0° C. and the solid filtered to give the title compound.

C. 5-[2-Benzyloxy-4-(1-benzyloxymethyl-1H-pyrazol-3-yl)-phenyl]-1,-dioxo-1,2,5-thiadiazolidin-3-one To a solution of 5-(2-benzyloxy-4-iodophenyl)-1,1-dioxo-1,2,5-thiadiazolidin-3-one (100 mg, 0.225 mmol) in DME (5 mL), in a microwave vessel is added 1-benzyloxymethyl-1H-pyrazole-3-boronic acid (104 mg, 0.450 mmol), Pd(PPh$_3$)$_4$ (27 mg, 0.023 mmol) and 0.45 mL of Na$_2$CO$_3$ (2M aqueous solution). The reaction mixture is heated in a microwave apparatus at 120° C. for 5 min. The mixture is concentrated under reduced pressure and the residue purified by reverse phase MPLC using a gradient of 10-50% MeCN/water as eluent to afford the title compound.

D. 5-[2-Hydroxy-4-(1H-pyrazol-3-yl)-phenyl]-1,1-dioxo-1,2,5-thiadiazolidin-3-one A solution of 5-[2-benzyloxy-4-(1-benzyloxymethyl-1H-pyrazol-3-yl)-phenyl]-1,1-dioxo-1,2,5-thiadiazolidin-3-one in 10 mL of EtOH/water (1:1) is hydrogenated over 10% Pd/C (15 mg) at 1 atm for 18 h. The catalyst is filtered and the filtrate evaporated. The residue is re-dissolved in EtOH/HOAc (3:1) and hydrogenated over 10% Pd/C for 18 h. The catalyst is filtered and the filtrate evaporated to give the title compound: $(M-1)^-=293$.

EXAMPLE 280

5-[2-Hydroxy-4-(1H-pyrazol-4-yl)-phenyl]-1,1-dioxo-1,2,5-thiadiazolidin-3-one

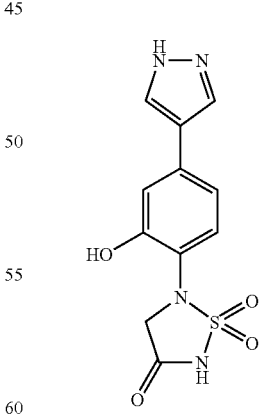

A. 5-[2-Benzyloxy-4-(1H-pyrazol-4-yl)-phenyl]-1,1-dioxo-1,2,5-thiadiazolidin-3-one A mixture of 5-(2-benzyloxy-4-iodophenyl)-1,1-dioxo-1,2,5-thiadiazolidin-3-one (100 mg, 0.225 mmol), 4-pyrazoleboronic acid (87 mg, 0.45 mmol), resin-bound PPh₃Pd (346 mg, loading 0.13 mmol/g) and aqueous Na₂CO₃ (0.45 mL of a 2M solution) in DME (3 mL) is heated in a microwave apparatus at 110° C. for 30 min. The mixture is filtered and the solvent removed under reduced pressure. The residue is purified by reverse phase MPLC to give the title compound.

B. 5-[2-Hydroxy-4-(1H-pyrazol-4-yl)-phenyl]-1,1-dioxo-1,2,5-thiadiazolidin-3-one A mixture of 5-[2-benzyloxy-4-(1H-pyrazol-4-yl)-phenyl]-1,1-dioxo-1,2,5-thiadiazolidin-3-one (50 mg) and Pd(OH)₂ (5 mg) in 3 mL of EtOH/EtOAc (1:1) is hydrogenated at 1 atm for 18 h. The catalyst is filtered and the filtrate evaporated. The residue is purified by preparative HPLC to give the title compound: (M−1)⁻=293; HPLC retention time=0.88 min (method A).

EXAMPLE 281

5-[2-Hydroxy-4-(1-propyl-1H-pyrazol-4-yl)-phenyl]-1,1-dioxo-1,2,5-thiadiazolidin-3-one

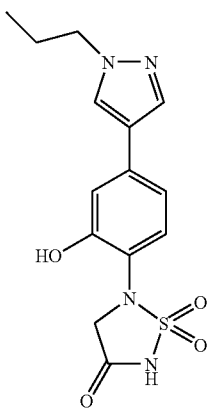

A. 5-[2-Benzyloxy-4-(1-propyl-1H-pyrazol-4-yl)-phenyl]-1,1-dioxo-1,2,5-thiadiazolidin-4-one A mixture of 5-(2-benzyloxy-4-iodophenyl)-1,1-dioxo-1,2,5-thiadiazolidin-3-one (100 mg, 0.225 mmol), 1-propyl-4-(4,4,5,5-tetramethyl-[1,3,2]dioxaborolan-2-yl)-1H-pyrazole (106 mg, 0.45 mmol), resin-bound PPh₃Pd (177 mg, loading 0.13 mmol/g) and aqueous Na₂CO₃ (0.45 mL of a 2M solution) in DME (3 mL) is heated in a microwave apparatus at 110° C. for 10 min. The mixture is filtered and the solvent removed under reduced pressure to give the title compound which is used directly in the next step.

B. 5-[2-Hydroxy-4-(1-propyl-1H-pyrazol-4-yl)-phenyl]-1,1-dioxo-1,2,5-thiadiazolidin-3-one The title compound is prepared from 5-[2-benzyloxy-4-(1-propyl-1H-pyrazol-4-yl)-phenyl]-1,1-dioxo-1,2,5-thiadiazolidin-3-one analogous to Example 280, step B: (M−1)⁻=335; HPLC retention time=0.87 min (method A).

EXAMPLES 282 TO 283

The following compounds are prepared from 5-(2-benzyloxy-4-iodophenyl)-1,1-dioxo-1,2,5-thiadiazolidin-3-one and the appropriately substituted 4-(4,4,5,5-tetramethyl-[1,3,2]dioxaborolan-2-yl)-1H-pyrazole analogous to Example 281.

| Example | Chemical Name | MS (m/z) | Retention time (min) Method |
|---|---|---|---|
| 282 | 5-[2-Hydroxy-4-(1-isobutyl-1H-pyrazol-4-yl)-phenyl]-1,1-dioxo-1,2,5-thiadiazolidin-3-one | (M − 1)⁻ = 349 | 0.98 A |
| 283 | 5-{2-Hydroxy-4-[1-(3-methylbutyl)-1H-pyrazol-4-yl]-phenyl}-1,1-dioxo-1,2,5-thiadiazolidin-3-one | (M − 1)⁻ = 363 | 0.83 A |

EXAMPLE 284

5-[2-Hydroxy-4-(tetrahydrofuran-3-yl)-phenyl]-1,1-dioxo-1,2,5-thiadiazolidin-3-one

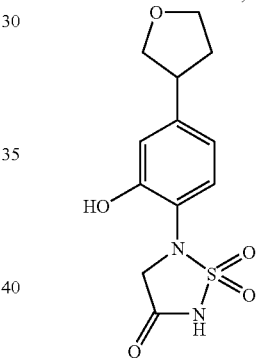

The title compound is isolated as a by-product from the reduction step of Example 272: (M−1)⁻=297; HPLC retention time=0.64 min. (Method A)

EXAMPLE 285

5-[4-(2,3-Dihydrobenzofuran-3-yl)-2-hydroxyphenyl]-1,1-dioxo-1,2,5-thiadiazolidin-3-one

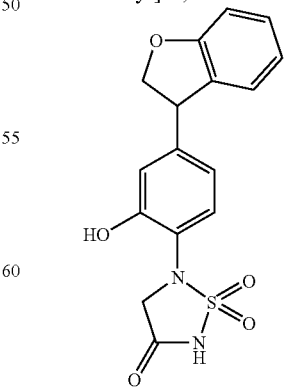

The title compound is isolated as a by-product from the reduction step of Example 274: (M−1)⁻=345; HPLC retention time=1.04 min. (Method A)

EXAMPLE 286

5-(2-Hydroxy-4-thiazol-2-ylmethylphenyl)-1,1-di-oxo-1,2,5-thiadiazolidin-3-one

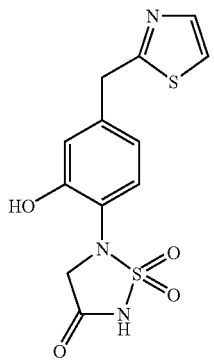

A.
(3-Benzyloxy-4-nitrophenyl)-thiazol-2-yl-methanol

To a solution of n-BuLi (1.9 mL, 2.5 M in hexane) in ether (8 mL) at −78° C. is added 2-bromothiazole (0.34 mL, 3.80 mmol) dropwise. The yellow solution is stirred at −78° C. for 30 min and 3-benzyloxy-4-nitrobenzaldehyde (83, step A) (0.81 g, 3.16 mmol) in THF (2 mL) is added. After stirring for 30 min, the purple suspension is poured into a sat. NH$_4$Cl solution (50 mL) and is extracted with EtOAc. The organic layer is washed with brine, dried over MgSO$_4$ and concentrated. The residue is then purified by column chromatography to give the title compound: (M+1)$^+$=343.

B. 2-Benzlyoxy-4-thiazol-2-ylmethylphenylamine

To a solution of (3-benzyloxy-4-nitrophenyl)-thiazol-2-yl-methanol (0.62 g, 1.81 mmol) in HOAc/EtOH (3:1, 8 mL) is added iron powder (0.30 g, 5.43 mmol). The mixture is heated at 100° C. for 3 h and the precipitate is filtered through Celite. The filtrate is concentrated, extracted with CH$_2$Cl$_2$ and filtered again. The crude material is purified by flash chromatography using a gradient of 10-60% EtOAc/hexane as eluent to afford the title compound as a yellow oil: (M+1)$^+$=297.

C 5-(2-Benzyloxy-4-thiazol-2-ylmethylphenyl)-1,1-dioxo-1,2,5-thiadiazolidin-3-one The title compound is prepared analogous to Example 83, steps H-K: (M−1)$^-$=416.

D. 5-(2-Hydroxy-4-thiazol-2-ylmethylphenyl)-1,1-dioxo-1,2,5-thiadiazolidin-3-one To a suspension of 5-(2-benzyloxy-4-thiazol-2-ylmethylphenyl)-1,1-dioxo-1,2,5-thiadiazolidin-3-one (20 mg, 0.05 mmol) in CH$_2$Cl$_2$ (5 mL) at −10° C. is added BBr$_3$ (0.2 mL, 1.0 M in CH$_2$Cl$_2$) and the yellow mixture is stirred at −10° C. for 30 min. The reaction is quenched with water and the aqueous layer is neutralized to pH=7 with 1N NaOH. The aqueous layer is then concentrated and the residue is purified by reverse phase HPLC (CH$_3$CN/water/0.1% TFA) to give the title compound as a light yellow solid: $^1$H NMR (MeOD$\delta$ 4.16 (s, 2H), 4.18 (s, 2H), 6.68 (d, J=8 Hz, 1H), 7.73 (s, 1H), 7.28 (d, J=8 Hz, 1H), 7.34 (d, J=4 Hz, 1H) 7.56 (d, J=4 Hz, 1H); (M−1)$^-$=324.

EXAMPLE 287

5-[2-Hydroxy-4-(2H-pyrazol-3-ylmethyl)-phenyl]-1,1-dioxo-1,2,5-thiadiazolidin-3-one

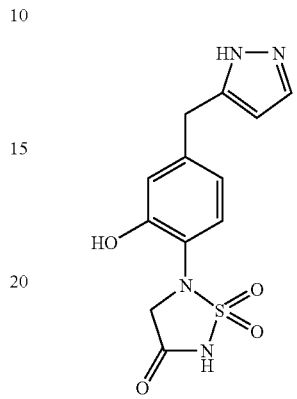

A. (2-Benzyloxymethyl-2H-pyrazol-3-yl)-(3-benzyloxy-4-nitrophenyl)-methanol

To a solution of 1-benzyloxymethyl-1H-pyrazole (Example 279, step A) (278 mg, 1.48 mmol) in THF (4 mL) at −78° C. is added n-BuLi (2.5 M in hexanes, 0.60 mL, 1.5 mmol) dropwise. The mixture is stirred at −78° C. for 20 min then a solution of 3-benzyloxy-4-nitrobenzaldehyde (Example 83, step A) (315 mg, 1.23 mmol) in THF (4 mL) is added dropwise. The mixture is stirred at −78° C. for 30 min and then is partitioned between EtOAc and aq. NH$_4$Cl. The organic phase is dried over MgSO$_4$ and concentrated. The crude material is chromatographed to afford the title compound as a light brown oil: (M+1)$^+$=446, (M+HCO$_2^-$)=490.

B. 1-Benzyloxymethyl-5-[(3-benzyloxy-4-nitrophenyl)-(tert-butyldimethylsilanyloxy)-methyl]-1H-pyrazole A mixture of (2-benzyloxymethyl-2H-pyrazol-3-yl)-(3-benzyloxy-4-nitrophenyl)-methanol (392 mg, 0.881 mmol), TBSOTf (0.25 mL, 1.09 mmol) and 2,6-lutidine (0.153 mL, 1.32 mmol) in CH$_2$Cl$_2$ is stirred at RT for 2 h. The mixture is partitioned between CH$_2$Cl$_2$ and aqueous NaHCO$_3$. The organic phase is dried over MgSO$_4$ and concentrated. The residue is purified by flash chromatography to give the title compound.

C. 2-Benzyloxy-4-[(2-benzyloxymethyl-2H-pyrazol-3-yl)-(tert-butyl-dimethyl-silanyloxy)-methyl]-phenylamine The title compound is prepared from 1-benzyloxymethyl-5-[(3-benzyloxy-4-nitrophenyl)-(tert-butyldimethylsilanyloxy)-methyl]-1H-pyrazole analogous to Example 246, step B.

D. 5-[2-Hydroxy-4-(2H-pyrazol-3-ylmethyl)-phenyl]-1,1-dioxo-1,2,5-thiadiazolidin-3-one The title compound is prepared from 2-benzyloxy-4-[(2-benzyloxymethyl-2H-pyrazol-3-yl)-(tert-butyl-dimethyl-silanyloxy)-methyl]-phenylamine analogous to Example 83, steps H-L: (M+1)⁺=309, (M−1)⁻=307; ¹H NMR (CD₃OD) δ 7.40 (br s, 1H), 7.23 (d, J=8.0 Hz, 1H), 6.66 (s, 1H), 6.63 (d, J=8.0 Hz, 1H), 5.98 (s, 1H), 4.24 (s, 2H), 3.82 (s, 2H).

EXAMPLE 288

5-(2-Hydroxy-4-pyrazol-1-ylmethyl-phenyl)-1,1-dioxo-1,2,5-thiadiazolidin-3-one

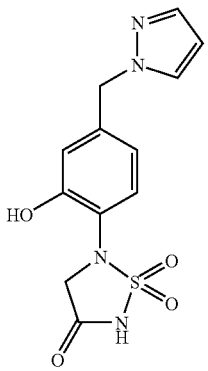

A. 1-(3-Benzyloxy-4-nitrobenzyl)-1H-pyrazole

A mixture of pyrazole (93 mg, 1.4 mmol), K₂CO₃ (180 mg, 1.30 mmol) and 2-benzyloxy-4-bromomethyl-1-nitrobenzene (Example 83, step C) (193 mg, 0.599 mmol) in MeCN (5 mL) is stirred at RT for 1 h. Additional pyrazole (500 mg, 7.34 mmol) and K₂CO₃ (200 mg, 1.45 mmol) are added and the mixture is stirred at RT for an additional 15 h. The mixture is partitioned between EtOAc and water and the organic phase is dried over MgSO₄. The solvent is removed under reduced pressure to give the title compound.

B. 2-Benzyloxy-4-pyrazol-1-ylmethyl-phenylamine

The title compound is prepared from 1-(3-benzyloxy-4-nitrobenzyl)-1H-pyrazole analogous to Example 246, step B.

C. 5-(2-Hydroxy-4-pyrazol-1-ylmethyl-phenyl)-1,1-dioxo-1,2,5-thiadiazolidin-3-one The title compound is prepared from 2-benzyloxy-4-pyrazol-1-ylmethyl-phenylamine analogous to Example 83, steps H-L: (M+1)⁺=309, (M−1)⁻=307; ¹H NMR (CD₃OD) δ 7.57 (d, J=4.0 Hz, 1H), 7.41 (d, J=4.0 Hz, 1H), 7.30 (d, J=8.0 Hz, 1H), 6.61 (s, 1H), 6.60 (d, J=8.0 Hz, 1H), 6.23 (t, J=4.0 Hz, 1H), 5.18 (s, 2H), 4.20 (s, 2H).

EXAMPLE 289

5-[2-Hydroxy-4-(3-trifluoromethylpyrazole-1-ylmethyl)-phenyl]-1,1-dioxo-1,2,5-thiadiazolidin-3-one

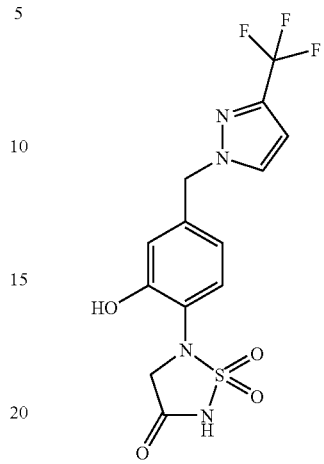

A. 1-(3-Benzyloxy-4-nitrobenzyl)-3-trifluoromethyl-1H-pyrazole

To a solution of 3-trifluoromethyl-1H-pyrazole (632 mg, 4.65 mmol) and 2-benzyloxy-4-bromomethyl-1-nitrobenzene (1.0 g, 3.1 mmol) in DMF (8 mL) is added K₂CO₃ (642 mg, 4.65 mmol) and the mixture is stirred at RT for 48 h. The mixture is partitioned between EtOAc and water and the organic phase is washed with brine and dried over MgSO₄. The solvent is removed under reduced pressure to give the title compound: (M+1)⁺=378.

B. 5-[2-Hydroxy-4-(3-trifluoromethylpyrazole-1-ylmethyl)-phenyl]-1,1-dioxo-1,2,5-thiadiazolidin-3-one The title compound is prepared from 1-(3-benzyloxy-4-nitrobenzyl)-3-trifluoromethyl-1H-pyrazole analogous to Example 288, steps B and C: ¹H NMR (DMSO) δ 4.03 (s, 2H), 5.30 (s, 2H), 6.69-7.73 (m, 3H), 7.39 (d, J=8 Hz, 1H), 8.05 (s, 1H), 9.29 (br, 1H); (M−1)⁻=375.

EXAMPLE 290

5-[3-Hydroxy-4-(1,1,4-trioxo-1,2,5-thiadiazolidin-2-yl)-phenyl]-pentanoic Acid

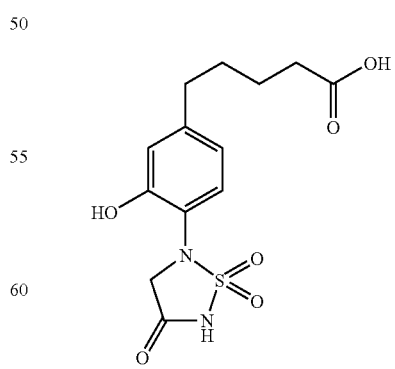

The title compound is prepared from 5-(2-benzyloxy-4-iodophenyl)-1,1-dioxo-1,2,5-thiadiazolidin-3-one and pent-4-enoic acid analogous to Example 44: (M−1)⁻=327.

EXAMPLE 291

4-[3-Hydroxy-4-(1,1,4-trioxo-1,2,5-thiadiazolidin-2-yl)-phenyl]-butane-1-sulfinic Acid

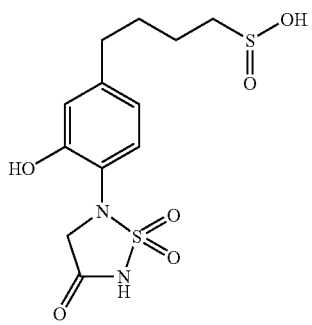

A. Acetic acid 4-benzylsulfanylbutyl Ester

To a suspension of NaH (0.45 g, 60% in mineral oil, 11.1 mmol) in DMF (5 mL) is added benzylmercaptan (1.43 mL, 11.03 mmol) and the resulting yellow solution is stirred at RT for 30 min. The mixture is cooled to 0° C. then acetic acid 4-bromobutyl ester (2.2 g, 11.2 mmol) is added dropwise (exothermic). The mixture is allowed to warm to RT and is quenched with 1N HCl (35 mL). The mixture is extracted with MTBE and the organic phase is dried over magnesium sulfate. The solvent is removed under reduced pressure and the residue is purified by flash chromatography using EtOAc/hexane (4:1) as eluent to give the title compound as an oil.

B. Acetic Acid 4-phenylmethanesulfonylbutyl Ester

To a solution of acetic acid 4-benzylsulfanylbutyl ester (2.5 g, 10.4 mmol) in methylene chloride (50 mL) at 0° C. is added mCPBA (5.0 g, 70%) and the mixture is stirred at 0° C. for 1 h. The precipitate is filtered and the filtrate evaporated. The residue is dissolved in EtOAc and washed with brine. The organic phase is dried over magnesium sulfate and the solvent removed under reduced pressure to give the title compound as a white solid.

C. 4-Phenylmethanesulfonylbutan-1-ol

To a solution of acetic acid 4-phenylmethanesulfonylbutyl ester (1.6 g, 5.93 mmol) in MeOH (20 mL) is added NaOH (6.0 ml of 1.0N) and the mixture is stirred at RT for 90 min. The MeOH is removed under reduced pressure and the aqueous extracted with EtOAc. The organic solution is dried over magnesium sulfate and the solvent is removed under reduced pressure. The resulting solid is triturated with hexane to give the title compound as a white solid.

D. (4-Iodobutane-1-sulfonylmethyl)-benzene

To a mixture of iodine (1.2 g, 4.5 mmol), imidazole (0.34 g, 4.4 mmol) and Ph$_3$P (1.2 g, 4.4 mmol) in methylene chloride (10 mL) is added 4-phenylmethanesulfonylbutan-1-ol (0.99 g, 4.34 mmol) and the mixture is stirred at RT for 1 h. The mixture is filtered and the filtrate evaporated. The resulting oil is dissolved in EtOAc and washed with saturated sodium thiosulfate and brine. The organic phase is dried over magnesium sulfate and the solvent removed under reduced pressure. The resulting solid is washed with ether and the filtrate is evaporated to give the title compound as a white solid.

E. 5-[2-Benzyloxy-4-(4-phenylmethanesulfonylbutyl)-phenyl]-1,1-dioxo-2-(2-trimethylsilanylethyl)-1,2,5-thiadiazolidin-3-one The title compound is prepared from 5-(2-benzyloxy-4-iodophenyl)-1,1-dioxo-2-(2-trimethylsilanylethyl)-1,2,5-thiadiazolidin-3-one and (4-iodobutane-1-sulfonylmethyl)-benzene analogous to Example 571 step B.

F. 5-[2-Benzyloxy-4-(4-phenylmethanesulfonylbutyl)-phenyl]-1,1-dioxo-1,2,5-thiadiazolidin-3-one The title compound is prepared from 5-[2-benzyloxy-4-(4-phenylmethanesulfonylbutyl)-phenyl]-1,1-dioxo-2-(2-trimethylsilanylethyl)-1,2,5-thiadiazolidin-3-one analogous to Example 57, step C.

G. 4-[3-Hydroxy-4-(1,1,4-trioxo-1,2,5-thiadiazolidin-2-yl)-phenyl]-butane-1-sulfinic Acid A mixture of 5-[2-benzyloxy-4-(4-phenylmethanesulfonylbutyl)-phenyl]-1,1-dioxo-1,2,5-thiadiazolidin-3-one (450 mg), 10% Pd/C (400 mg) and KHCO$_3$ (1.6 mL of 0.52M) in EtOH (1 mL)/water (10 mL) is hydrogenated at 1 atm for 2 h. The catalyst is filtered and the filtrate evaporated. The residue is treated with 1N HCl and extracted with EtOAc. The organic phase is dried over magnesium sulfate and the solvent removed under reduced pressure to give the title compound: (M−1)$^-$=347 $^1$H NMR (400 MHz, DMSO-D6) δ ppm 1.38-1.48 (m, 2 H) 1.49-1.58 (m, J=7.67, 7.67, 7.52, 7.20 Hz, 3 H) 1.79-1.85 (m, 2 H) 2.43 (t, J=7.45 Hz, 2 H) 4.01 (s, 2 H) 6.56 (dd, J=8.08, 1.77 Hz, 1 H) 6.67 (d, J=1.77 Hz, 1 H) 7.25 (d, J=8.08 Hz, 1 H)

EXAMPLE 292

4-[3-Hydroxy-4-(1,1,4-trioxo-1,2,5-thiadiazolidin-2-yl)-phenyl]-butyronitrile

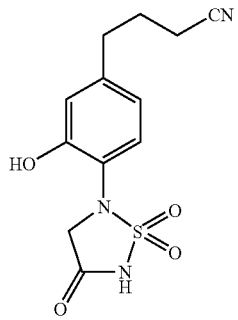

A. 4-{3-Benzyloxy-4-[1,1,4-trioxo-5-(2-trimethylsilanylethyl)-1,2,5-thiadiazolidin-2-yl]-phenyl}-butyronitrile To a solution of 4-bromobutyronitrile (0.074 mL, 0.75 mmol) in DMF (2 mL) is added Rieke zinc (0.9 mmol) and a catalytic amount of NaI. The mixture is stirred at RT for 5 h then P(o-tolyl)$_3$ (22.8 mg, 15 mol %), Pd$_2$(dba)$_3$ (13.7 mg, 3 mol %) and 5-(2-benzyloxy-4-iodophenyl)-1,1-dioxo-2-(2- trimethylsilanylethyl)-1,2,5-thiadiazolidin-3-one (272 mg, 0.5 mmol) is added and the mixture is stirred at RT for 18 h. The mixture is partitioned between EtOAc and 1N HCl and the organic phase is washed with brine and dried over sodium sulfate. The solvent is removed under reduced pressure and the residue is purified by column chromatography using a gradient of 0-15% EtOAc/hexane as eluent to give the title compound.

B. 4-[3-Benzyloxy-4-(1,1,4-trioxo-1,2,5-thiadiazolidin-2-yl)-phenyl]-butyronitrile To a solution of 4-{3-benzyloxy-4-[1,1,4-trioxo-5-(2-trimethylsilanylethyl)-1,2,5-thiadiazolidin-2-yl]-phenyl}-butyronitrile (45.7 mg, 0.094 mmol) in THF (4 mL) is added 0.188 mL of a 1M solution of TBAF in THF. The mixture is stirred at 65° C. for 1 h then is allowed to cool to RT. The mixture is poured into 1N HCl and extracted with EtOAc. The organic phase is washed with brine and dried over magnesium sulfate. The solvent is removed under reduced pressure and the residue is purified by reverse phase Biotage using a gradient of 0-30% EtOH/water as eluent to furnish the title compound.

C. 4-[3-Hydroxy-4-(1,1,4-trioxo-1,2,5-thiadiazolidin-2-yl)-phenyl]-butyronitrile A solution of 4-[3-benzyloxy-4-(1,1,4-trioxo-1,2,5-thiadiazolidin-2-yl)-phenyl]-butyronitrile (30 mg) in ethanol (30 mL) is hydrogenated over 10% Pd/C at 1 atm for 1 h. The catalyst is removed by filtration through Celite and the solvent is removed under reduced pressure to give the title compound. It is converted to a potassium salt by addition of 1 equivalent of $KHCO_3$: $(M-1)^-=294$.

EXAMPLE 293

4-[3-Hydroxy-4-(1,1,4-trioxo-1,2,5-thiadiazolidin-2-yl)-phenyl]-2-methyl-butyronitrile

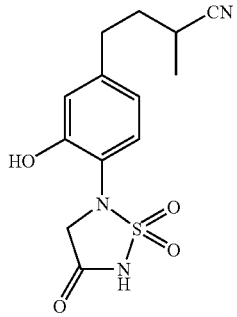

A. (E)-4-[3-Benzyloxy-4-(1,1,4-trioxo-1,2,5-thiadiazolidin-2-yl)-phenyl]-2-methyl-but-3-enenitrile A mixture of 2-methyl-but-3-enenitrile (18 mg, 0.225 mmol), 5-(2-benzyloxy-4-iodophenyl)-1,1-dioxo-1,2,5-thiadiazolidin-3-one (50 mg, 0.113 mmol), Pd(OAc)₂ (5 mg, 0.023 mmol) and triethylamine (11 mg, 0.107 mmol) in THF (3 mL) is placed in a microwave vial and heated at 110° C. for 10 min. The mixture is filtered and the filtrate concentrated. The residue is purified by reverse phase HPLC to give the title compound.

B. 4-[3-Hydroxy-4-(1,1,4-trioxo-1,2,5-thiadiazolidin-2-yl)-phenyl]-2-methyl-butyronitrile A mixture of (E)-4-[3-benzyloxy-4-(1,1,4-trioxo-1,2,5-thiadiazolidin-2-yl)-phenyl]-2-methyl-but-3-enenitrile (10 mg) and Pd(OH)₂ (1 mg) in EtOAc/EtOH (3 mL) is hydrogenated at 1 atm for 2 h. The catalyst is filtered and the filtrate evaporated. The residue is washed with 1N HCl and the residue is purified by preparative HPLC to give the title compound: $(M-1)^-=308$; HPLC retention time=0.78 min (method A).

EXAMPLE 294

4-[3-Hydroxy-4-(1,1,4-trioxo-1,2,5-thiadiazolidin-2-yl)-phenyl]-3,3-dimethylbutyronitrile

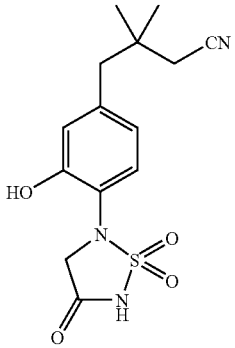

A. Toluene-4-sulfonic Acid 3-cyano-2,2-dimethylpropyl Ester

To a solution of toluene-4-sulfonic acid 3-toluene-4-sulfonyloxy-2,2-dimethylpropyl ester (5.0 g, 12.1 mmol) in DMSO (15 mL) is added KCN (789 mg, 12.1 mmol). The mixture is stirred at 80° C. for 18 h then cooled to RT. The mixture is poured into water and extracted with ether. The organic layer is dried over sodium sulfate the filtrate concentrated. The crude material is purified by column chromatography to give the title compound.

B. 4-Iodo-3,3-dimethylbutyronitrile

To a solution of toluene-4-sulfonic acid 3-cyano-2,2-dimethylpropyl ester (132 mg, 0.494 mmol) in DMF (1 mL) in a microwave vial, is added NaI (150.1 mg, 1.0 mmol). The mixture is heated in a microwave apparatus at 150° C. for 10 min. The solution is filtered and concentrated to afford the title compound.

C. 4-{3-Benzyloxy-4-[1,1,4-trioxo-5-(2-trimethylsilanylethyl)-1,2,5-thiadiazolidin-2-yl]-phenyl}-3,3-dimethylbutyronitrile The title compound is prepared 5-(2-benzyloxy-4-iodophenyl)-1,1-dioxo-2-(2-trimethylsilanylethyl)-1,2,5-thiadiazolidin-3-one and 4-iodo-3,3-dimethylbutyronitrile analogous to Example 292, step A.

D. 4-[3-Benzyloxy-4-(1,1,4-trioxo-1,2,5-thiadiazolidin-2-yl)-phenyl]-3,3-dimethylbutyronitrile To a suspension of PS-isocyanate resin (100 mg) in THF is added TBAF (1M in THF, 0.5 mL) and the mixture is stirred at RT for 2 h. The resin is filtered off and the TBAF solution is added to a solution of 4-{3-benzyloxy-4-[1,1,4-trioxo-5-(2-trimethylsilanylethyl)-1,2,5-thiadiazolidin-2-yl]-phenyl}-3,3-dimethylbutyronitrile (25 mg, 0.047 mmol) in THF (5 mL). The mixture is stirred at RT for 18 h then is diluted with 1N HCl and extracted with EtOAc. The organic layer is washed with brine, dried over $Na_2SO_4$ and concentrated to give the title compound which is used directly in the next step.

E. 4-[3-Hydroxy-4-(1,1,4-trioxo-1,2,5-thiadiazolidin-2-yl)-phenyl]-3,3-dimethylbutyronitrile A mixture of 4-[3-benzyloxy-4-(1,1,4-trioxo-1,2,5-thiadiazolidin-2-yl)-phenyl]-3,3-dimethylbutyronitrile (25 mg) and $Pd(OH)_2$ (25 mg) in EtOAc (5 mL) is hydrogenated at 1 atm for 6 h. The catalyst is filtered and the filtrate evaporated. The residue is purified by preparative HPLC to give the title compound: $(M-1)^-=322$.

EXAMPLE 295

[3-Hydroxy-4-(1,1,4-trioxo-1,2,5-thiadiazolidin-2-yl)-phenoxy]-acetic Acid 2-trimethylsilanylethyl Ester

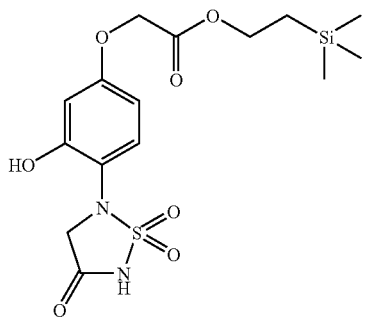

A. 2-Trimethylsilanylethyl (3-benzyloxy-4-nitrophenoxy)acetate

A mixture of 2-trimethylsilylethyl bromoacetate (J. Org. Chem. 51, 1537 (1986) (13.72 g, 56.0 mmol), 3-benzyloxy-4-nitrophenol (EP application 095121) (13.38 g, 55.9 mmol), and potassium carbonate (15.46 g, 112 mmol) in DMF (40 mL) is stirred at RT for 18 h. The mixture is poured into EtOAc and extracted once with water and five times with brine. The organic layer is dried, filtered, and concentrated to afford the title compound as a pale brown liquid: $^1$H NMR $(CDCl_3)$ δ 7.93 (d, J=9.1 Hz, 1H), 7.42 (d, J=7.1 Hz, 2H), 7.34 (t, J=7.1 Hz, 2H), 7.28 (t, J=7.1 Hz, 1H), 6.60 (d, J=2.5 Hz, 1H), 6.41 (dd, J=9.1, 2.5 Hz, 1H), 5.15 (s, 2H), 4.57 (s, 2H), 4.25 (m, 2H), 0.97 (m, 2H), 0.00 (s, 9H).

B. 2-Trimethylsilanylethyl (4-amino-3-benzyloxyphenoxy)acetate

A mixture of 2-trimethylsilylethyl (3-benzyloxy-4-nitrophenoxy)acetate (5.0 g) and 5% Pt/C (500 mg) in EtOAc (50 mL) is hydrogenated at 1 atm for 3 h. The catalyst is filtered off through Celite and the solvent removed under reduced pressure to afford the title compound: $^1$H NMR $(CDCl_3)$ δ 7.31 (m, 5H), 6.73 (d, J=8.6 Hz, 1H), 6.56 (d, J=2.8 Hz, 1H), 6.29 (dd, J=8.6, 2.8 Hz, 1H), 5.01 (s, 2H), 4.45 (s, 2H), 4.94 (m, 2H), 0.98 (m, 2H), 0.00 (s, 9H).

C. [3-Benzyloxy-4-(methoxycarbonylmethylamino)-phenoxy]-acetic Acid 2-trimethylsilanylethyl Ester To a mixture of 2-trimethylsilanylethyl (4-amino-3-benzyloxyphenoxy)acetate (4.56 g, 12.2 mmol) and potassium carbonate (3.37 g, 24.4 mmol) in DMF (25 mL) is added methyl bromoacetate (1.87 g, 12.2 mmol). The mixture is stirred at 60° C. for 1 h then is allowed to cool to RT. It is poured into water and extracted with EtOAc and the organic phase is washed with water (1×), brine (5×), and dried over $Na_2SO_4$. The solvent is removed under reduced pressure to afford the title compound which is used directly in the next step.

D. Methyl N-(2-(benzyloxy)-4-{2-oxo-2-[2-(trimethylsilyl)ethoxy]ethoxy}phenyl)-N-{[(tert-butoxycarbonyl)amino]sulfonyl}glycinate To an ice cooled solution of chlorosulfonyl isocyanate (2.55 g, 18 mmol) in methylene chloride (50 mL) is added dropwise a solution of t-butanol (1.33 g, 18 mmol) in methylene chloride (5 mL). The mixture is allowed to wart to RT, stirred for 15 min then re-chilled to 0° C. To this is added dropwise a solution of [3-benzyloxy-4-(methoxycarbonylmethylamino)-phenoxy]-acetic acid 2-trimethylsilanylethyl ester (5.35 g, 12 mmol) and triethylamine (2.07 g, 20.4 mmol) in methylene chloride (15 mL) and the mixture is stirred at RT for 2 h. The mixture is washed with water and the organic phase is dried over $NaSO_4$. The solvent is removed under reduced pressure and the residue is purified by column chromatography to using EtOAc/hexane (3:7) as eluent to give the title compound.

E. Methyl N-(aminosulfonyl)-N-(2-(benzyloxy)-4-{2-oxo-2-[2-(trimethylsilyl)ethoxy]ethoxy}phenyl) glycinate A mixture of methyl N-(2-(benzyloxy)-4-{2-oxo-2-[2-(trimethylsilyl)ethoxy]ethoxy}phenyl)-N-{[(tert-butoxycarbonyl)amino]sulfonyl}glycinate (50 mg, 0.08 mmol) in HCl/dioxane (3 mL, 4.0 M) is stirred at RT for 30 min. The solvent is removed under reduced pressure and water is added. The mixture is extracted with EtOAc and the organic phase dried over magnesium sulfate. The solvent is removed under reduced pressure to give the title compound.

F. [3-Benzyloxy-4-(1,1,4-trioxo-1,2,5-thiadiazolidin-2-yl)-phenoxy]-acetic Acid 2-trimethylsilanylethyl Ester To a solution of methyl N-(aminosulfonyl)-N-(2-(benzyloxy)-4-{2-oxo-2-[2-(trimethylsilyl)ethoxy]ethoxy}phenyl) glycinate in THF is added potassium t-butoxide (1.1 equivalent) in THF dropwise. The mixture is stirred at RT for 18 h. The solvent is removed under reduced pressure to afford the title compound which is used directly in the next step.

G. [3-Hydroxy-4-(1,1,4-trioxo-1,2,5-thiadiazolidin-2-yl)-phenoxy]-acetic Acid 2-trimethylsilanylethyl Ester A solution of [3-benzyloxy-4-(1,1,4-trioxo-1,2,5-thiadiazolidin-2-yl)-phenoxy]-acetic acid 2-trimethylsilanylethyl ester in water is hydrogenated at 1 atm over 10% Pd/C for 48 h. The catalyst is filtered through Celite and the filtrate evaporated. The residue is purified by reverse phase HPLC and the aqueous fractions lyophilized to give the title compound as a white powder: (M−1)⁻=401; HPLC retention time=1.24 min. (Method A)

EXAMPLE 296

[3-Hydroxy-4-(1,1,4-trioxo-1,2,5-thiadiazolidin-2-yl)-phenoxy]-acetic Acid

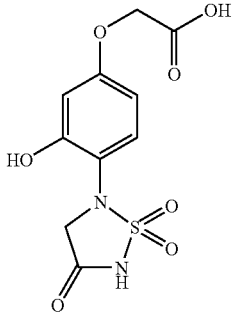

A. N-(Aminosulfonyl)-N-(2-(benzyloxy)-4-{2-oxo-2-[2-(trimethylsilyl)ethoxy]ethoxy}phenyl)glycine A solution of methyl N-(2-(benzyloxy)-4-{2-oxo-2-[2-(trimethylsilyl)ethoxy]ethoxy}phenyl)-N-{[(tert-butoxycarbonyl)amino]sulfonyl}glycinate (1.15 g, 1.84 mmol) in 20 mL of TFA/methylene chloride (1:1) is stirred at RT for 30 min. The solvent is removed under reduced pressure and the residue is dissolved in methylene chloride and the solvent evaporated (4×) to give the title compound.

B. [3-Hydroxy-4-(1,1,4-trioxo-1,2,5-thiadiazolidin-2-yl)-phenoxy]-acetic Acid

The title compound is prepared from N-(aminosulfonyl)-N-(2-(benzyloxy)-4-{2-oxo-2-[2-(trimethylsilyl)ethoxy]ethoxy}phenyl)glycine analogous to Example 295, steps F and G with the modification of using two equivalents of potassium t-butoxide in step F: mp=185-188° C.; ¹H NMR (DMSO-d₆) δ 9.87 (br s, 1H), 7.22 (d, J=8.6 Hz, 1H), 6.43 (d, J=2.8 Hz, 1H), 6.38 (dd, J=8.8, 2.8 Hz, 1H), 4.62 (s, 2H), 4.32 (s, 2H); (M−1)⁻=301.

EXAMPLE 297

3-[3-Hydroxy-4-(1,1,4-trioxo-1,2,5-thiadiazolidin-2-yl)-phenoxy]-1,3,4,5-tetrahydro-benzo[b]azepin-2-one

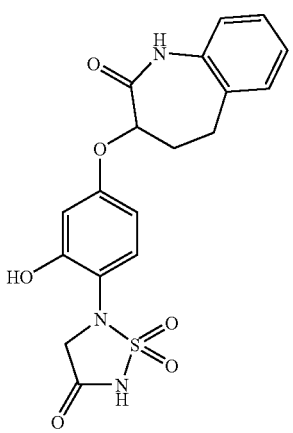

A. 3-(3-Benzyloxy-4-nitrophenoxy)-1,3,4,5-tetrahydrobenzo[b]azepin-2-one

A mixture of 3-benzyloxy-4-nitrophenol (2.45 g, 10 mmol), 3-bromo-1,3,4,5-tetrahydrobenzo[b]azepin-2-one (2.4 g, 10 mmol) and potassium carbonate (3.1 g, 23 mmol) in MeCN (10 mL) is refluxed for 10 h. Upon cooling a precipitate forms. The solid is filtered, washed with water and crystallized from EtOAc to give the title compound: mp=188-189° C.

B. 3-(4-Amino-3-benzyloxyphenoxy)-1,3,4,5-tetrahydrobenzo[b]azepin-2-one

A solution of 3-(3-benzyloxy-4-nitrophenoxy)-1,3,4,5-tetrahydrobenzo[b]azepin-2-one (3.0 g, 7.4 mmol) in 50 mL EtOAc/MeOH (1:1) is hydrogenated at 1 atm over platinum oxide for 2.5 h. The catalyst is filtered and the filtrate evaporated to give the title compound which is used directly in the next step.

C. [2-Benzyloxy-4-(2-oxo-2,3,4,6-tetrahydro-1H-benzo[b]azepin-3-yloxy)-phenylamino]-acetic Acid Ethyl Ester A mixture of 3-(4-amino-3-benzyloxyphenoxy)-1,3,4,5-tetrahydrobenzo[b]azepin-2-one (7.4 mmol) and ethyl glyoxylate (1.44 mL, 7.4 mmol) in THF (5 mL) is stirred at RT for 5 h. The mixture is diluted with 38 mL of EtOH/HOAc (9:1) then NaCNBH₃ (0.91 g, 14 mmol) is added and stirring is continued for 18 h. The solvent is removed under reduced pressure and the residue triturated with water. The solid is purified by column chromatography using a gradient of 33-50% EtOAc/hexane as eluent to give the title compound.

D. 3-[3-Benzyloxy-4-(1,1,4-trioxo-1,2,5-thiadiazolidin-2-yl)-phenoxy]-1,3,4,5-tetrahydro-benzo[b]azepin-2-one The title compound is prepared from [2-benzyloxy-4-(2-oxo-2,3,4,5-tetrahydro-1H-benzo[b]azepin-3-yloxy)-phenylamino]-acetic acid ethyl ester analogous to Example 83, steps I, J and K: (M−1)⁻=492.

E. 3-[3-Hydroxy-4-(1,1,4-trioxo-1,2,5-thiadiazolidin-2-yl)-phenoxy]-1,3,4,5-tetrahydro-benzo[b]azepin-2-one A solution of 3-[3-benzyloxy-4-(1,1,4-trioxo-1,2,5-thiadiazolidin-2-yl)-phenoxy]-1,3,4,5-tetrahydro-benzo[b]azepin-2-one (244 mg) in 30 mL of EtOH/HOAc (2:1) is hydrogenated at 1 atm over Pd/C (100 mg) for 4 h. The catalyst is filtered and the filtrate evaporated. The residual solid is triturated with ether to give the title compound: (M−1)⁻=402.

EXAMPLE 298

5-(4-Ethyl-2-hydroxyphenyl)-1,1-dioxo-1,2,5-thiadiazolidin-3-one

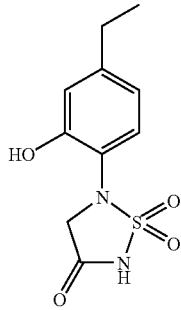

The title compound is prepared from the reduction of 5-(2-benzyloxy-4-vinylphenyl)-1,1-dioxo-1,2,5-thiadiazolidin-3-one (Example 262, step A) analogous to Example 55, step K: LC retention time=0.85 (Method A); (M−H)⁻=255.

EXAMPLE 299

5-(4-Hexyl-2-hydroxyphenyl)-1,1-dioxo-1,2,5-thiadiazolidin-3-one

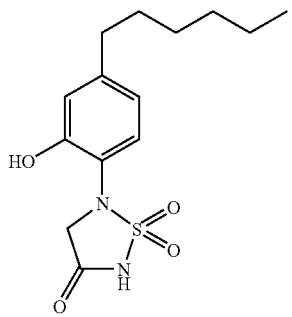

The title compound is prepared from the reduction of 5-[2-benzyloxy-4-((E)-hex-1-enyl)-phenyl]-1,1-dioxo-1,2,5-thiadiazolidin-3-one (Example 264, step A) analogous to Example 280, step B: (M−H)⁻=311; HPLC retention time=1.33 min (method A).

EXAMPLE 300

5-(2-Hydroxy-4-isobutylphenyl)-1,1-dioxo-1,2,5-thiadiazolidin-3-one

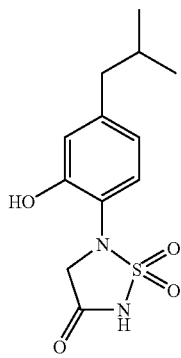

A. 5-[2-Benzyloxy-4-(2-methylpropenyl)-phenyl]-1,1-dioxo-1,2,5-thiadiazolidin-3-one A mixture of 5-(2-benzyloxy-4-iodophenyl)-1,1-dioxo-1,2,5-thiadiazolidin-3-one (150 mg, 0.338 mmol) and 2,2-dimethylethenylboronic acid (67 mg, 0.670 mmol), resin-bound PPh₃Pd (519 mg, 0.069 mmol) and Na₂CO₃ (0.338 mL, 2M) in DME (3 mL) is heated in a microwave apparatus at 12° C. for 20 min. The mixture is filtered through Celite, washed with MeCN and concentrated. The residue is purified by reverse phase chromatography using a gradient of 10-60% EtOH/H₂O as eluent to afford the title compound: (M−1)⁻=371.

B. 5-(2-Hydroxy-4-isobutylphenyl)-1,1-dioxo-1,2,5-thiadiazolidin-3-one

The title compound is prepared from 5-[2-benzyloxy-4-(2-methylpropenyl)-phenyl]-1,1-dioxo-1,2,5-thiadiazolidin-3-one analogous to Example 61, step F: ¹H-NMR (MeOD) δ 7.22 (d, J=8.08 Hz, 1H), 6.62 (d, J=1.77 Hz, 1H), 6.52 (dd, J=8.08, 1.77 Hz, 1H), 4.24 (s, 2H), 2.32 (d, J=7.07 Hz, 2H), 1.75 (m, 1H), 0.85 (s, 3H), 0.83 (s, 3H); (M−1)⁻=283; HPLC retention time=1.08 min (method A).

EXAMPLE 301

5-[4-(3,3-Dimethylbutyl)-2-hydroxyphenyl]-1,1-dioxo-1,2,5-thiadiazolidin-3-one

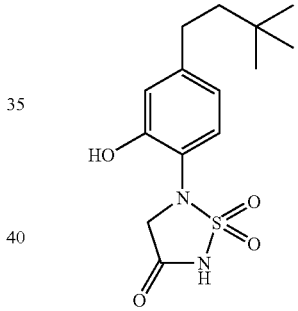

The title compound is prepared from 5-(2-benzyloxy-4-iodophenyl)-1,1-dioxo-1,2,5-thiadiazolidin-3-one and 3,3-dimethylbut-1-ene analogous to Example 300: (M−1)⁻=311; HPLC retention time=1.20 min (method A).

EXAMPLE 302

5-[2-Hydroxy-4-(3,3,3-trifluoropropyl)-phenyl]-1,1-dioxo-1,2,5-thiadiazolidin-3-one

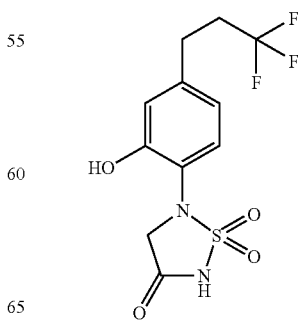

A. 5-[2-Benzyloxy-4-(3,3,3-trifluoropropyl)-phenyl]-1,1-dioxo-2-(2-trimethylsilanylethyl)-1,2,5-thiadiazolidin-3-one To a solution of 1,1,1-trifluoro-3-iodopropane (0.088 mL, 0.75 mmol) in DMF (2 mL) is added Rieke zinc (0.9 mmol) and the mixture is stirred at RT for 5 h then P(o-tolyl)$_3$ (22.8 mg, 15 mol %), Pd$_2$(dba)$_3$ (13.7 mg, 3 mol %) and 5-(2-benzyloxy-4-iodophenyl)-1,1-dioxo-2-(2-trimethylsilanylethyl)-1,2,5-thiadiazolidin-3-one (272 mg, 0.5 mmol) is added and the mixture is stirred at RT for 18 h. The mixture is partitioned between EtOAc and 1N HCl and the organic phase is washed with brine and dried over sodium sulfate. The solvent is removed under reduced pressure and the residue is purified by column chromatography using a gradient of 0-15% EtOAc/hexane as eluent to give the title compound.

B. 5-[2-Hydroxy-4-(3,3,3-trifluoropropyl)-phenyl]-1,1-dioxo-1,2,5-thiadiazolidin-3-one The title compound is prepared from 5-[2-benzyloxy-4-(3,3,3-trifluoropropyl)-phenyl]-1,1-dioxo-2-(2-trimethylsilanylethyl)-1,2,5-thiadiazolidin-3-one analogous to Example 292, steps B and C with the modification that Pd(OH)$_2$ is used as the catalyst in the reduction step: (M−1)$^-$=323.

EXAMPLE 303

5-(4-Cyclopentylmethyl-2-hydroxyphenyl)-1,1-dioxo-1,2,5-thiadiazolidin-3-one

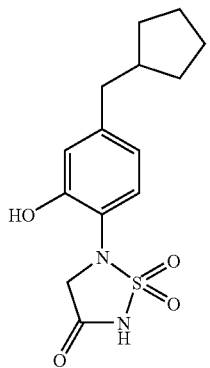

A. 5-(2-Benzyloxy-4-cyclopentylmethylphenyl)-1,1-dioxo-1,2,5-thiadiazolidin-3-one To a solution of methylenecyclopentane (246 mg, 3 mmol) in THF (7.5 mL) is added 9-BBN (7.5 mL, 0.5M in THF, 3 mmol) and the mixture is stirred at RT for 18 h. A mixture of 5-(2-benzyloxy-4-iodophenyl)-1,1-dioxo-1,2,5-thiadiazolidin-3-one (200 mg, 0.45 mmol), 3.38 mL of the borane solution previously prepared (0.675 mmol), resin-bound PPh$_3$Pd (100 mg) and Na$_2$CO$_3$ (0.9 mL, 2M) in DME (5 mL) is heated in a microwave apparatus at 110° C. for 15 min. The mixture is filtered and the solvent removed under reduced pressure to give the title compound which is used directly in the next step.

B. 5-(4-Cyclopentylmethyl-2-hydroxyphenyl)-1,1-dioxo-1,2,5-thiadiazolidin-3-one A solution of 5-(2-benzyloxy-4-cyclopentylmethylphenyl)-1,1-dioxo-1,2,5-thiadiazolidin-3-one in EtOH (2 mL)/water (6 mL) is hydrogenated at 1 atm over 10% Pd/C for 18 h. The catalyst is filtered and the filtrate evaporated. The residue is purified by preparative HPLC to give the title compound: (M−1)$^-$=309. HPLC retention time: 1.14 min. (Method A).

EXAMPLE 304

5-(4-Cyclohexylmethyl-2-hydroxyphenyl)-1,1-dioxo-1,2,5-thiadiazolidin-3-one

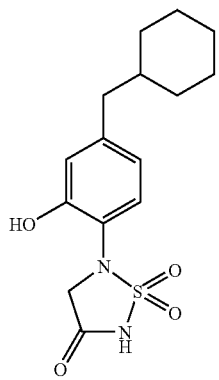

The title compound is prepared from 5-(2-benzyloxy-4-iodophenyl)-1,1-dioxo-2-(2-trimethylsilanylethyl)-1,2,5-thiadiazolidin-3-one and iodomethylcyclohexane analogous to Example 57, steps B, C and D: (M−1)$^-$=323. $^1$H NMR (400 MHz, DMSO-d$_6$) δ ppm 0.89 (d, J=11.37 Hz, 2 H) 1.09-1.19 (m, 2 H) 1.14 (d, J=9.60 Hz, 1 H) 1.44 (dd, J=14.78, 3.66 Hz, 1 H) 1.62 (d, J=10.86 Hz, 5 H) 2.34 (d, J=7.07 Hz, 2 H) 4.00 (s, 2 H) 6.54 (dd, J=7.96, 1.89 Hz, 1 H) 6.61 (d, J=1.77 Hz, 1 H) 7.25 (d, J=8.08 Hz, 1 H) 8.85 (s, 1 H)

EXAMPLE 305

5-{2-Hydroxy-4-[1-(2,4,6-trimethylphenyl)-ethyl]-phenyl}-1,1-dioxo-1,2,5-thiadiazolidin-3-one

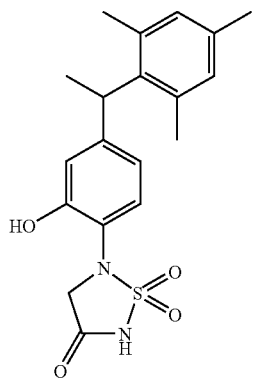

A. 5-{2-Benzyloxy-4-[1-(2,4,6-trimethylphenyl)-ethyl]-phenyl}-1,1-dioxo-1,2,5-thiadiazolidin-3-one A mixture of 1,3,5-trimethyl-2-vinylbenzene (0.058 mL, 0.36 mmol), 5-(2-benzyloxy-4-iodophenyl)-1,1-dioxo-1,2,5- thiadiazolidin-3-one (80 mg, 0.18 mmol), Pd(OAc)$_2$ (5 mg, 0.09 mmol) and triethylamine (0.13 mL, 0.9 mmol) in acetonitrile (1.5 mL) is heated in a microwave apparatus at 120° C. for 1 h. The mixture is filtered over Celite and the filtrate is evaporated to give the title compound which is used directly in the next step.

B. 5-{2-Hydroxy-4-[1-(2,4,6-trimethylphenyl)-ethyl]-phenyl}-1,1-dioxo-1,2,5-thiadiazolidin-3-one A solution of 5-{2-benzyloxy-4-[1-(2,4,6-trimethylphenyl)-ethyl]-phenyl}-1,1-dioxo-1,2,5-thiadiazolidin-3-one and K$_2$CO$_3$ (60 mg) in EtOH (5 mL)/water (7 mL) is hydrogenated at 1 atm over 10% Pd/C (50 mg) for 10 days. The catalyst is filtered and the solvent evaporated to give the title compound as a pale-yellow solid: (M−1)$^-$=373. HPLC retention time: 1.45 min (Method A).

EXAMPLE 306

5-[4-(2-Aminobenzyl)-2-hydroxyphenyl]-1,1-dioxo-1,2,5-thiadiazolidin-3-one

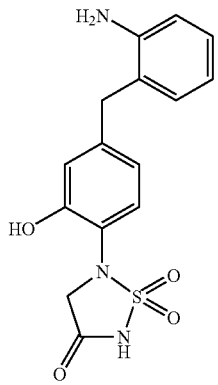

A. (2-Hydroxymethylphenyl)-carbamic Acid Tert-butyl Ester

To a solution of 2-aminobenzyl alcohol (2.0 g, 8.13 mmol) in methylene chloride (20 mL) is added a solution of Boc$_2$O (1.82 g, 8.3 mmol) in methylene chloride (20 mL) dropwise. The mixture is stirred at RT for 48 h then is washed with 0.15N HCl and water. The organic phase is dried over magnesium sulfate and the solvent removed under reduced pressure to give the title compound.

B. (2-Iodomethylphenyl)-carbamic Acid Tert-butyl Ester

To a solution of imidazole (404 mg, 5.94 mmol) and triphenylphosphine (1.56 g, 5.94 mmol) in methylene chloride (50 mL) is added iodine (1.51 g, 5.94 mmol) in portions. When the reaction is complete, a solution of (2-hydroxymethylphenyl)-carbamic acid tert-butyl ester (1.2 g, 5.4 mmol) in methylene chloride (20 mL) is added dropwise and the mixture is stirred at RT for 75 min. The mixture is concentrated and the insoluble material is filtered. The filtrate is evaporated and the residue is purified by column chromatography using a gradient of 25-50% MTBE/methylene chloride as eluent to give the title compound.

C. (2-{3-Benzyloxy-4-[1,1,4-trioxo-5-(2-trimethylsilanylethyl)-1,2,5-thiadiazolidin-2-yl]-benzyl}-phenyl)-carbamic Acid Tert-butyl Ester The title compound is prepared from 5-(2-benzyloxy-4-iodophenyl)-1,1-dioxo-2-(2-trimethylsilanylethyl)-1,2,5-thiadiazolidin-3-one and (2-iodomethylphenyl)-carbamic acid tert-butyl ester analogous to Example 57, step B.

D. 5-[4-(2-Aminobenzyl)-2-benzyloxyphenyl]-1,1-dioxo-2-(2-trimethylsilanylethyl)-1,2,5-thiadiazolidin-3-one To a solution of (2-{3-benzyloxy-4-[1,1,4-trioxo-5-(2-trimethylsilanylethyl)-1,2,5-thiadiazolidin-2-yl]-benzyl}-phenyl)-carbamic acid tert-butyl ester (1.7 g, 2.73 mmol) in methylene chloride (10 mL) is added TFA (5 mL) and the mixture is stirred at RT for 20 min. The solvent is removed under reduced pressure and methylene chloride is added to the residue and evaporated (6×) to give the title compound as its TFA salt.

E. 5-[4-(2-Aminobenzyl)-2-benzyloxyphenyl]-1,1-dioxo-1,2,5-thiadiazolidin-3-one

The title compound is prepared from 5-[4-(2-aminobenzyl)-2-benzyloxyphenyl]-1,1-dioxo-2-(2-trimethylsilanylethyl)-1,2,5-thiadiazolidin-3-one analogous to Example 97, step E.

F. 5-[4-(2-Aminobenzyl)-2-hydroxyphenyl]-1,1-dioxo-1,2,5-thiadiazolidin-3-one

The title compound is prepared from 5-[4-(2-aminobenzyl)-2-benzyloxyphenyl]-1,1-dioxo-1,2,5-thiadiazolidin-3-one analogous to Example 62, step D. (M+1)$^+$=334. HPLC retention time=0.87 min (Method B).

EXAMPLE 307

5-[2-Hydroxy-4-(2-hydroxybenzyl)-phenyl]-1,1-dioxo-1,2,5-thiadiazolidin-3-one

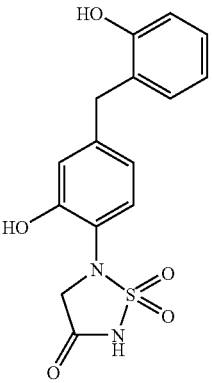

A. 2-Methanesulfonyloxybenzoic Acid Methyl Ester

To a solution of methyl salicylate (3.04 g, 20 mmol) in pyridine (25 mL) is added dropwise methanesulfonyl chloride (2.17 g, 19 mmol) and the mixture is stirred at RT for 18 h. The solvent is removed under reduced pressure and the residue partitioned between EtOAc and water. The organic phase is washed sequentially with 1N HCl, 2N Na$_2$CO$_3$, 1N HCl, water and brine then is dried over magnesium sulfate. The solvent is removed under reduced pressure and the residue purified by column chromatography using a gradient of 0-100% EtOAc/hexane as eluent to give the title compound as a solid.

B. Methanesulfonic Acid 2-hydroxymethylphenyl Ester

To a solution of 2-methanesulfonyloxybenzoic acid methyl ester (1.0 g, 4.3 mmol) in THF (10 mL) is added LiBH$_4$ (375 mg, 17.2 mmol) in portions. The mixture is heated at 45° C. for 2 h then at 60° C. for 2 h. The mixture is diluted with EtOAc and ice and 1N HCl is added. The organic phase is separated and washed with 1N HCl and brine then dried over magnesium sulfate. The solvent is removed under reduced pressure to give the title compound as a solid.

C. Methanesulfonic Acid 2-iodomethylphenyl Ester

The title compound is prepared from methanesulfonic acid 2-hydroxymethylphenyl ester analogous to Example 306, step B.

D. 5-[2-Hydroxy-4-(2-hydroxybenzyl)-phenyl]-1,1-dioxo-1,2,5-thiadiazolidin-3-one The title compound is prepared from 5-(2-benzyloxy-4-iodophenyl)-1,1-dioxo-2-(2-trimethylsilanylethyl)-1,2,5-thiadiazolidin-3-one and methanesulfonic acid 2-iodomethylphenyl ester analogous to Example 306, steps C-F: (M−1)$^-$=333. HPLC retention time=1.04 min (Method A).

EXAMPLE 308

5-[2-Hydroxy-4-(2-hydroxy-5-methylbenzyl)-phenyl]-1,1-dioxo-1,2,5-thiadiazolidin-3-one

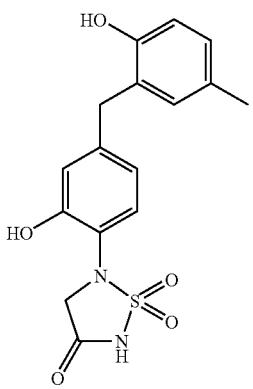

A. 2-(4-Methoxybenzyloxy)-5-methylbenzoic Acid Methyl Ester

A mixture of 2-hydroxy-5-methylbenzoic acid methyl ester (4.98 g, 30 mmol), 4-methoxybenzyl chloride (4.69 g, 30 mmol) and K$_2$CO$_3$ (4.55 g, 33 mmol) in DMF (50 mL) is stirred at 60° C. for 48 h. The mixture is diluted with EtOAc and washed with 1N HCl and brine then the organic phase is dried over magnesium sulfate. The solvent is removed under reduced pressure and the residue is purified by column chromatography using a gradient of 0-100% EtOAc/hexane as eluent to give the title compound as a colorless oil.

B. [2-(4-Methoxybenzyloxy)-5-methylphenyl]-methanol

To a solution of 2-(4-methoxybenzyloxy)-5-methylbenzoic acid methyl ester (7.32 g, 25.6 mmol) in THF (20 mL) is added LiAlH$_4$ solution (26 mL, 1M in THF) dropwise and the mixture is stirred at RT for 1 h. The mixture is diluted with THF (80 mL) and cooled in an ice bath then saturated sodium sulfate solution (1 mL) is added dropwise. The mixture is filtered and the filtrate dried over magnesium sulfate and evaporated to give the title compound.

C. 2-Iodomethyl-1-(4-methoxybenzyloxy)-4-methylbenzene

To a solution of imidazole (1.52 g, 22.32 mmol) and triphenylphosphine (5.85 g, 22.32 mmol) in methylene chloride (30 mL)/THF (15 mL) is added iodine (5.67 g, 22.32 mmol) in portions and the mixture is stirred at RT for 3 h. To this is added dropwise a solution of [2-(4-methoxybenzyloxy)-5-methylphenyl]-methanol (4.80 g, 18.6 mmol) in THF (15 mL) and the mixture is stirred at RT for 18 h. The mixture is concentrated and the insoluble material is filtered. The filtrate is evaporated and the residue is purified by column chromatography using a gradient of 0-75% EtOAc/hexane as eluent to give the title compound as a brown oil.

D. 5-{2-Benzyloxy-4-[2-(4-methoxybenzyloxy)-5-methylbenzyl]-phenyl}-1,1-dioxo-2-(2-trimethylsilanylethyl)-1,2,5-thiadiazolidin-3-one The title compound is prepared from 5-(2-benzyloxy-4-iodophenyl)-1,1-dioxo-2-(2-trimethylsilanylethyl)-1,2,5-thiadiazolidin-3-one and 2-iodomethyl-1-(4-methoxybenzyloxy)-4-methylbenzene analogous to Example 57, step B.

E. 5-[2-Benzyloxy-4-(2-hydroxy-5-methylbenzyl)-phenyl]-1,1-dioxo-2-(2-trimethylsilanylethyl)-1,2,5-thiadiazolidin-3-one A solution of 5-{2-benzyloxy-4-[2-(4-methoxybenzyloxy)-5-methylbenzyl]-phenyl}-1,1-dioxo-2-(2-trimethylsilanylethyl)-1,2,5-thiadiazolidin-3-one (50 mg) in 10% TFA/methylene chloride (1 mL) is stirred at RT for 2 h. The solvent is removed under reduced pressure to give the title compound.

F. 5-[2-Hydroxy-4-(2-hydroxy-5-methylbenzyl)-phenyl]-1,1-dioxo-1,2,5-thiadiazolidin-3-one The title compound is prepared from 5-[2-benzyloxy-4-(2-hydroxy-5-methylbenzyl)-phenyl]-1,1-dioxo-2-(2-trimethylsilanylethyl)-1,2,5-thiadiazolidin-3-one analogous to Example 306, steps E and F: (M−1)$^-$=347. HPLC retention time=0.94 min (Method A)

EXAMPLE 309

5-[4-(2-Aminomethylbenzyl)-2-hydroxyphenyl]-1,1-dioxo-1,2,5-thiadiazolidin-3-one

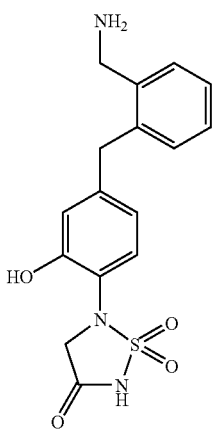

A. 2-{3-Benzyloxy-4-[1,1,4-trioxo-5-(2-trimethylsilanylethyl)-1,2,5-thiadiazolidin-2-yl]-benzyl}-benzonitrile Zinc dust (240 mg, 3.69 mmol) is placed in a flask and heated under vacuum to remove traces of water. DMF (10 mL) is then added under nitrogen atmosphere. Dibromoethane (0.03 mL) is added and the mixture heated until effervescence occurs. The mixture is allowed to cool to RT and chlorotrimethylsilane (0.03 mL) is added. After 30 min, NaI (165 mg, 1.1 mmol) is added followed by 2-cyanobenzyl bromide (216 mg, 1.1 mmol) and the mixture is stirred at RT for 30 min. To this mixture is added tri-o-tolylphosphine (33.5 mg) and Pd$_2$(dba)$_3$ (20.2 mg) followed by the dropwise addition of a solution of 5-(2-benzyloxy-4-iodophenyl)-1,1-dioxo-2-(2-trimethylsilanylethyl)-1,2,5-thiadiazolidin-3-one (400 mg, 0.74 mmol) in DMF (10 mL). The reaction mixture is stirred at RT for 18 h and then diluted with EtOAc and filtered through Celite. The filtrate is washed with 0.1N HCl and brine then is dried over sodium sulfate. The solvent is removed under reduced pressure and the residue purified by column chromatography using a gradient of 0-10% EtOAc/hexane as eluent to give the title compound.

B. 2-[3-Benzyloxy-4-(1,1,4-trioxo-1,2,5-thiadiazolidin-2-yl)-benzyl]-benzonitrile To a solution of 2-{3-benzyloxy-4-[1,1,4-trioxo-5-(2-trimethylsilanylethyl)-1,2,5-thiadiazolidin-2-yl]-benzyl}-benzonitrile (57 mg, 0.107 mmol) in THF (10 mL) is added TBAF (0.16 mL, 1.5 equiv) and the mixture is stirred at 60° C. for 2 h. The mixture is partitioned between EtOAc and 1N HCl. The organic phase is washed with 1N HCl and brine then is dried over sodium sulfate. The solvent is removed under reduced pressure and the residue purified by column chromatography using a gradient of 0-40% EtOAc/hexane as eluent to give the title compound.

C. 5-[4-(2-Aminomethylbenzyl)-2-hydroxyphenyl]-1,1-dioxo-1,2,5-thiadiazolidin-3-one A solution of 2-[3-benzyloxy-4-(1,1,4-trioxo-1,2,5-thiadiazolidin-2-yl)-benzyl]-benzonitrile in EtOH/water (1:1) is hydrogenated at 1 atm over 10% Pd/C for 40 min. The catalyst is filtered, the solvent evaporated and the residue purified by preparative HPLC to give the title compound.

EXAMPLE 310

5-[2-Hydroxy-4-(2-methoxymethylbenzyl)-phenyl]-1,1-dioxo-1,2,5-thiadiazolidin-3-one

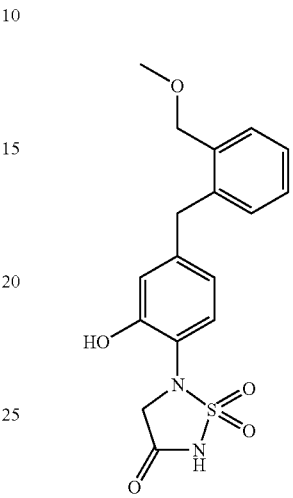

A. (2-Methoxymethylphenyl)-methanol

To a solution of 1,2-benzenedimethanol (1.38 g, 10 mmol) in DMF (10 mL) cooled in an ice bath is added NaH (400 mg, 60% in mineral oil, 10 mmol) in portions. The mixture is stirred at 0° C. for 15 min then at RT for 30 min. To this is added iodomethane (1.45 g, 10.2 mmol) dropwise and the mixture is stirred at RT for 1 h. Ice, EtOAc and water is added and the mixture is acidified with 1N HCl. The organic phase is washed with water and brine then is dried over magnesium sulfate. The solvent is removed under reduced pressure and the residue purified by column chromatography using a gradient of 0-100% EtOAc/hexane as eluent to give the title compound.

B. 1-Iodomethyl-2-methoxymethylbenzene

To a solution of imidazole (338 mg, 4.98 mmol) and triphenylphosphine (1.3 g, 4.98 mmol) in methylene chloride (10 mL) is added iodine (1.26 g, 4.98 mmol) in portions. The mixture is stirred at RT for 45 min then a solution of (2-methoxymethylphenyl)-methanol (630 mg, 4.14 mmol) in methylene chloride (3 mL) is added dropwise and stirring is continued for 3 h. The mixture is concentrated and the insoluble material is filtered. The filtrate is evaporated and the residue is purified by column chromatography using a gradient of 0-50% EtOAc/hexane as eluent to give the title compound.

C. 5-[2-Benzyloxy-4-(2-methoxymethylbenzyl)-phenyl]-1,1-dioxo-2-(2-trimethylsilanylethyl)-1,2,5-thiadiazolidin-3-one The title compound is prepared from 5-(2-benzyloxy-4-iodophenyl)-1,1-dioxo-2-(2-trimethylsilanylethyl)-1,2,5-thiadiazolidin-3-one and 1-iodomethyl-2-methoxymethylbenzene analogous to Example 57, step B.

D. 5-[2-Benzyloxy-4-(2-methoxymethylbenzyl)-phenyl]-1,1-dioxo-1,2,5-thiadiazolidin-3-one To a solution of 5-[2-benzyloxy-4-(2-methoxymethylbenzyl)-phenyl]-1,1-dioxo-2-(2-trimethylsilanylethyl)-1,2,5-thiadiazolidin-3-one (375 mg, 0.679 mmol) in DMF (5 mL) is added CsF (361 mg, 2.37 mmol) and the mixture is stirred at 65° C. for 3 h. The mixture is diluted with EtOAc and water then is acidified with 1N HCl. The organic phase is washed with 1N HCl, water and brine. The organic phase is dried over sodium sulfate and the solvent is removed under reduced pressure to give the title compound as a foam.

E. 5-[2-Hydroxy-4-(2-methoxymethylbenzyl)-phenyl]-1,1-dioxo-1,2,5-thiadiazolidin-3-one A solution of 5-[2-benzyloxy-4-(2-methoxymethylbenzyl)-phenyl]-1,1-dioxo-1,2,5-thiadiazolidin-3-one (270 mg) in ethanol (5 mL) is hydrogenated over 5% Pd/C at 1 atm for 2 h. The catalyst is removed by filtration through Celite and the solvent is removed under reduced pressure. The residue is purified by preparative HPLC to give the title compound. $(M-1)^- = 361$. HPLC retention time=1.01 min (Method A).

EXAMPLE 311

{2-[3-Hydroxy-4-(1,1,4-trioxo-1,2,5-thiadiazolidin-2-yl)-benzyl]-phenyl}-acetonitrile

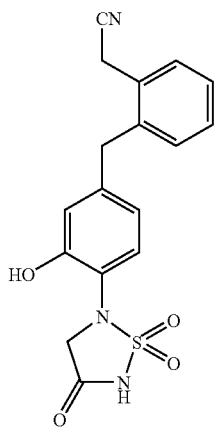

A. (2-Hydroxymethylphenyl)-acetonitrile

To a solution of 2-cyanomethylbenzoic acid methyl ester (1.75 g, 10 mmol) in THF (15 mL) is added LiBH4 (660 mg, 30 mmol) and the mixture is stirred at RT for 3 h. The mixture is quenched with MeOH then water is added. The mixture is extracted with EtOAc and the organic phase is washed with 1N HCl and brine then is dried over magnesium sulfate. The solvent is removed under reduced pressure to give the title compound which is used directly in the next step.

B. (2-Iodomethylphenyl)-acetonitrile

The title compound is prepared from (2-hydroxymethylphenyl)-acetonitrile analogous to Example 308, step C.

C. {2-[3-Hydroxy-4-(1,1,4-trioxo-1,2,5-thiadiazolidin-2-yl)-benzyl]-phenyl}-acetonitrile The title compound is prepared from 5-(2-benzyloxy-4-iodophenyl)-1,1-dioxo-2-(2-trimethylsilanylethyl)-1,2,5-thiadiazolidin-3-one and (2-iodomethylphenyl)-acetonitrile analogous to Example 310, steps C, D and E. $(M-1)^- = 356$. HPLC retention time=0.93 min (Method A).

EXAMPLE 312

{2-[3-Hydroxy-4-(1,1,4-trioxo-1,2,5-thiadiazolidin-2-yl)-benzyl]-phenyl}-acetic Acid Methyl Ester

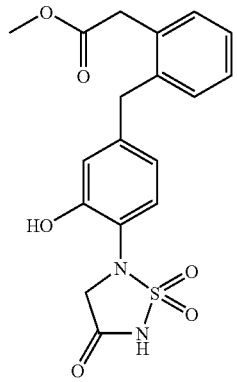

A. (2-Hydroxymethylphenyl)-acetic Acid Methyl Ester

To a solution of 2-methoxycarbonylmethylbenzoic acid (1.84 g, 9.48 mmol) (Tetrahedron Lett. 39, 8563 (1998)) in THF (20 mL) at 0° C. is added dropwise borane THF solution (10.4 mL, 10.4 mmol) and the mixture is stirred at 0° C. for 4 h. The mixture is quenched with MeOH and the solvent is evaporated. To the residue is added EtOAc and the mixture is washed with brine. The organic phase is dried over magnesium sulfate and the solvent is removed under reduced pressure. The residue is purified by column chromatography using a gradient of 0-100% EtOAc/hexane as eluent to give the title compound as an oil.

B. (2-Iodomethylphenyl)-acetic Acid Methyl Ester

The title compound is prepared from (2-hydroxymethylphenyl)-acetic acid methyl ester analogous to Example 308, step C.

C. {2-[3-Benzyloxy-4-(1,1,4-trioxo-1,2,5-thiadiazolidin-2-yl)-benzyl]-phenyl}-acetic Acid Methyl Ester The title compound is prepared from 5-(2-benzyloxy-4-iodophenyl)-1,1-dioxo-2-(2-trimethylsilanylethyl)-1,2,5-thiadiazolidin-3-one and (2-iodomethylphenyl)-acetic acid methyl ester analogous to Example 310, steps C and D.

D. {2-[3-Hydroxy-4-(1,1,4-trioxo-1,2,5-thiadiazolidin-2-yl)-benzyl]-phenyl}-acetic Acid Methyl Ester The title compound is prepared from {2-[3-benzyloxy-4-(1,1,4-trioxo-1,2,5-thiadiazolidin-2-yl)-benzyl]-phenyl}-acetic acid methyl ester analogous to Example 310, step E.

EXAMPLE 313

{2-[3-Hydroxy-4-(1,1,4-trioxo-1,2,5-thiadiazolidin-2-yl)-benzyl]-phenyl}-acetic Acid

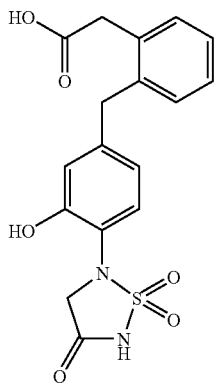

To a solution of {2-[3-hydroxy-4-(1,1,4-trioxo-1,2,5-thiadiazolidin-2-yl)-benzyl]-phenyl}-acetic acid methyl ester in water/MeOH/MeCN (1:1:1) is added KOH and the mixture is heated at 60° C. for 1 h. The mixture is cooled to RT and is acidified with 1N HCl. The mixture is purified by preparative HPLC to give the title compound. $(M-1)^-=375$. HPLC retention time=0.63 min (Method A).

EXAMPLE 314

N-Ethyl-2-{2-[3-hydroxy-4-(1,1,4-trioxo-1,2,5-thiadiazolidin-2-yl)-benzyl]-phenyl}-acetamide

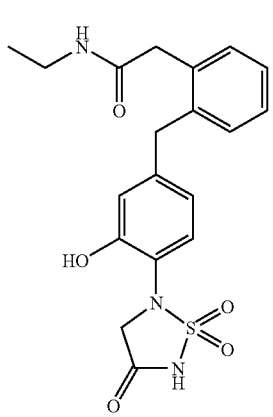

A. {2-[3-Benzyloxy-4-(1,1,4-trioxo-1,2,5-thiadiazolidin-2-yl)-benzyl]-phenyl}-acetic Acid To a solution of {2-[3-benzyloxy-4-(1,1,4-trioxo-1,2,5-thiadiazolidin-2-yl)-benzyl]-phenyl}-acetic acid methyl ester (Example 512, step C) in water/MeOH/MeCN (1:1:1) is added KOH and the mixture is heated at 60° C. for 1 h. The mixture is cooled to RT, acidified with 1N HCl and extracted with EtOAc. The organic phase is washed with brine and dried over magnesium sulfate. The solvent is removed under reduced pressure to give the title compound which is used directly in the next step.

B. 2-{2-[3-Benzyloxy-4-(1,1,4-trioxo-1,2,5-thiadiazolidin-2-yl)-benzyl]-phenyl}-N-ethylacetamide To a solution of {2-[3-benzyloxy-4-(1,1,4-trioxo-1,2,5-thiadiazolidin-2-yl)-benzyl]-phenyl}-acetic acid (40 mg, 0.86 mmol) in DMSO (0.7 mL) is added HATU (49 mg, 0.129 mmol) and diisopropylethylamine (0.045 mL, 0.256 mmol). The mixture is stirred for 5 min then ethylamine (0.086 mL, 2M in THF) is added dropwise. Upon completion of the reaction, the mixture is acidified with 1N HCl and extracted with EtOAc. The organic phase is washed with brine and dried over magnesium sulfate. The solvent is removed under reduced pressure to give the title compound which is used directly in the next step.

C. N-Ethyl-2-{2-[3-hydroxy-4-(1,1,4-trioxo-1,2,5-thiadiazolidin-2-yl)-benzyl]-phenyl}-acetamide The title compound is prepared from 2-{2-[3-benzyloxy-4-(1,1,4-trioxo-1,2,5-thiadiazolidin-2-yl)-benzyl]-phenyl}-N-ethylacetamide analogous to Example 310, step E.

EXAMPLE 315

5-(2-Hydroxy-4-{2-[2-(4-methylpiperidin-1-yl)-2-oxo-ethyl]-benzyl}-phenyl)-1,1-dioxo-1,2,5-thiadiazolidin-3-one

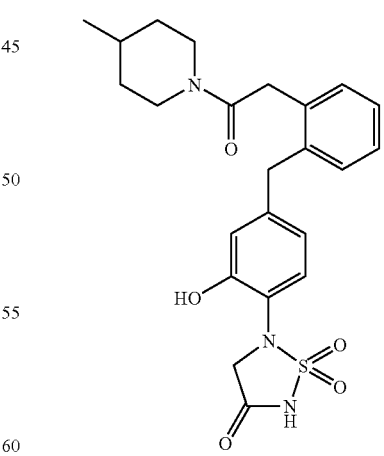

The title compound is prepared from {2-[3-benzyloxy-4-(1,1,4-trioxo-1,2,5-thiadiazolidin-2-yl)-benzyl]-phenyl}-acetic acid and 4-methylpiperidine analogous to Example 314, steps B and C. $(M-1)^-=456$. HPLC retention time=1.07 min (Method A).

EXAMPLE 316

5-{2-Hydroxy-4-[2-(2-hydroxyethyl)-benzyl]-phenyl}-1,1-dioxo-1,2,5-thiadiazolidin-3-one

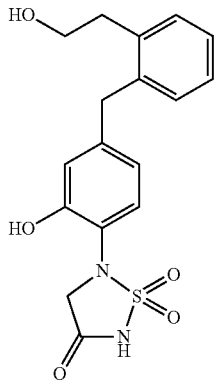

A. 5-{2-Benzyloxy-4-[2-(2-hydroxyethyl)-benzyl]-phenyl}-1,1-dioxo-1,2,5-thiadiazolidin-3-one To a solution of {2-[3-benzyloxy-4-(1,1,4-trioxo-1,2,5-thiadiazolidin-2-yl)-benzyl]-phenyl}-acetic acid methyl ester (32 mg, 0.067 mmol) in THF (4 mL) is added LiBH$_4$ (25 mg, 0.115 mmol) and the mixture is stirred at RT for 2 h. The mixture is cooled in an ice bath and is acidified with 1N HCl. The mixture is extracted with EtOAc and the organic phase is washed with 1N HCl and brine then is dried over magnesium sulfate. The solvent is removed under reduced pressure to give the title compound as a gum.

B. 5-{2-Hydroxy-4-[2-(2-hydroxyethyl)-benzyl]-phenyl}-1,1-dioxo-1,2,5-thiadiazolidin-3-one To a solution of 5-{2-benzyloxy-4-[2-(2-hydroxyethyl)-benzyl]-phenyl}-1,1-dioxo-1,2,5-thiadiazolidin-3-one (25 mg) in EtOH (2 mL) is added KHCO$_3$ (0.102 mL, 0.516M) and the mixture is hydrogenated at 1 atm over 10% Pd/C for 1 h. The catalyst is filtered and the filtrate evaporated. The residue is dissolved in water and washed with ether. The aqueous phase is lyophilized to give the potassium salt of the title compound: $(M-1)^-=361$. HPLC retention time=0.88 min (Method A).

EXAMPLE 317

5-[2-Hydroxy-4-(pyridine-2-carbonyl)-phenyl]-1,1-dioxo-1,2,5-thiadiazolidin-3-one

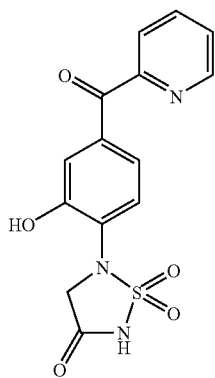

A. 5-[2-Benzyloxy-4-(hydroxypyridin-2-yl-methyl)-phenyl]-1,1-dioxo-2-(2-trimethylsilanylethyl)-1,2,5-thiadiazolidin-3-one To a solution of 3-benzyloxy-4-[1,1,4-trioxo-5-(2-trimethylsilanylethyl)-1,2,5-thiadiazolidin-2-yl]-benzaldehyde (Example 81, step B) (75 mg, 0.17 mmol) in anhydrous THF (4 mL) at −78° C. is added dropwise 2-pyridyl magnesium bromide (0.25M in THF, 1.36 mL, 0.34 mmol). The reaction is stirred at −78° C. for 1 h, then is quenched with saturated NH$_4$Cl. The mixture is extracted with EtOAc and the organic phase is dried over MgSO$_4$. The solvent is removed under reduced pressure and the crude material is purified by column chromatography using a gradient of 0-50% EtOAc/hexane to afford the title compound as a colorless oil: $(M-H)^-=526$.

B. 5-[2-Benzyloxy-4-(pyridine-2-carbonyl)-phenyl]-1,1-dioxo-2-(2-trimethylsilanylethyl)-1,2,5-thiadiazolidin-3-one To a solution of 5-[2-benzyloxy-4-(hydroxypyridin-2-yl-methyl)-phenyl]1,1-dioxo-2-(2-trimethylsilanylethyl)-1,2,5-thiadiazolidin-3-one (45 mg, 0.085 mmol) in acetic acid (2 mL) is added iron powder (24 mg, 0.43 mmol) and the mixture is refluxed for 2 h. The reaction is diluted with EtOAc and filtered. The solvent is removed under reduced pressure and the crude material is purified by flash chromatography using a gradient of 0-50% EtOAc/hexane to afford the title compound as a yellow oil: $(M+H)^+=524$.

C. 5-[2-Benzyloxy-4-(pyridine-2-carbonyl)-phenyl]-1,1-dioxo-1,2,5-thiadiazolidin-3-one The title compound is prepared from 5-[2-benzyloxy-4-(pyridine-2-carbonyl)-phenyl]-1,1-dioxo-2-(2-trimethylsilanylethyl)-1,2,5-thiadiazolidin-3-one analogous to Example 81, step F.

D. 5-[2-Hydroxy-4-(pyridine-2-carbonyl)-phenyl]-1,1-dioxo-1,2,5-thiadiazolidin-3-one The title compound is prepared from 5-[2-benzyloxy-4-(pyridine-2-carbonyl)-phenyl]-1,1-dioxo-1,2,5-thiadiazolidin-3-one analogous to Example 262, step B: LC retention time=0.77 min (Method A); $(M+H)^+=334$.

EXAMPLE 318

5-(4-Benzenesulfonyl-2-hydroxyphenyl)-1,1-dioxo-1,2,5-thiadiazolidin-3-one

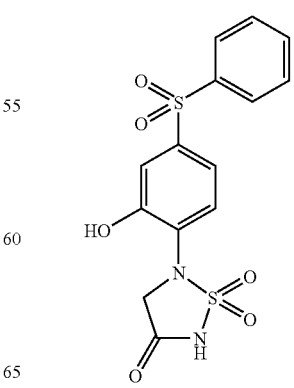

A. 2-Benzyloxy-4-nitrodiphenylsulfone

A solution of benzenesulfinic acid sodium salt (2.0 g, 12.1 mmol) and 2-benzyloxy-4-fluoronitrobenzene (3.0 g, 12.1 mmol) in (10 mL) is heated at 130° C. for 18 h. The mixture is poured into EtOAc and washed with water (1×), 1N NaOH (2×), water (1×), and brine (1×). The organic layer is dried over magnesium sulfate and the solvent is removed under reduced pressure. The residue is triturated with ether to afford the title compound as a solid: mp=137-144° C.; $^1$H NMR (CDCl$_3$) δ 7.84 (m, 3H), 7.70 (d, J=1.5 Hz, 1H), 7.60 (dt, J=7.4, 1.5 Hz, 1H), 7.51 (m, 3H), 7.40 (m, 5H), 5.31 (s, 2H).

B. 2-Benzyloxy-4-aminodiphenylsulfone

A mixture of 2-benzyloxy-4-nitrodiphenylsulfone (1.55 g, 4.59 mmol) and indium (2.11 g, 18.4 mmol) in THF (30 mL) is vigorously stirred. Concentrated HCl (3.1 mL) is added cautiously and the mixture stirred at RT for 3 h. The mixture is diluted with water and ether and basified with 50% NaOH. The mixture is centrifuged and the supernatant decanted. The residue is treated with water (3×) and EtOAc and recentrifuged. Combined supernatants are separated and the organic layer is dried over magnesium sulfate. The solvent is removed under reduced pressure and the residue is purified by chromatography on a Biotage 40M column using hexane/EtOAc (65:35) as eluent to afford the title compound: $^1$H NMR (CDCl$_3$) δ 7.83 (m, 2H), 7.42 (m, 10H), 6.70 (d, J=7.8 Hz, 1H), 5.11 (s, 2H), 4.32 (br s, 2H); (M+1)$^+$=340.

C. Methyl (4-benzenesulfonyl-2-benzyloxyphenylamino)acetate

A mixture of 2-benzyloxy-4-aminodiphenylsulfone (930 mg, 3.03 mmol), methyl bromoacetate (1.14 mL, 12.1 mmol) and potassium carbonate (836 mg, 6.05 mmol) in DMF (15 mL) is stirred at 90° C. for 42 h. The mixture is poured into EtOAc and extracted with water (1×) and brine (5×). The organic layer is dried over magnesium sulfate and the solvent removed under reduced pressure. The residue is chromatographed on a Biotage 40M column using a gradient of 40-60% EtOAc/hexane as eluent to give the title compound as an oil: $^1$H NMR (CDCl$_3$) δ 7.82 (m, 2H), 7.43 (m, 10H), 6.46 (d, J=8.1 Hz, 1H), 5.36 (br t, J=5.5 Hz, 1H), 5.14 (s, 2H), 3.95 (d, J=6.1 Hz, 2H), 3.78 (s, 3H); (M+1)$^+$=411.

D. N-(t-Butoxycarbonylsulfamoyl)-N-(4-benzenesulfonyl-2-benzyloxyphenyl)glycine Methyl Ester To a solution of chlorosulfonylisocyanate (346 mg, 2.45 mmol) in CH$_2$Cl$_2$ (15 mL) at 0° C. is added dropwise a solution of t-butanol (181 mg, 2.45 mmol) in CH$_2$Cl$_2$ (5 mL) and the mixture is stirred at 0-5° C. for 30 min. To this is added dropwise a solution of methyl (4-benzenesulfonyl-2-benzyloxyphenylamino)acetate (620 mg, 1.63 mmol) and triethylamine (281 mg, 278 mmol) in CH$_2$Cl$_2$ (5 mL) and the mixture is stirred at RT for 4 h. The mixture is washed with water and the organic layer is dried over magnesium sulfate. The solvent is removed under reduced pressure to afford an oil that is chromatographed on a Biotage 40M column using CH$_2$Cl$_2$/EtOAc (95:5) as eluent to afford the title compound as an oil: $^1$H NMR (CDCl$_3$) δ 7.82 (m, 3H), 7.47 (m, 11H), 5.24 (s, 2H), 4.54 (br s, 2H), 3.67 (s, 3H), 1.41 (s, 9H); (M−1)$^-$=589.

E. N-Sulfamoyl-N-(4-benzenesulfonyl-2-benzyloxyphenyl)glycine Methyl Ester

A solution of N-(t-butoxycarbonylsulfamoyl)-N-(4-benzenesulfonyl-2-benzyloxyphenyl)glycine methyl ester (620 mg, 1.05 mmol) in 10 mL TFA/CH$_2$Cl$_2$ (1:1) is stirred at RT for 30 min. The solvent is removed under reduced pressure and the residue is redissolved in CH$_2$Cl$_2$ and restripped (4×). The residual oil is chromatographed on a Biotage 40M column using CH$_2$Cl$_2$/EtOAc (90:10) as eluent to afford the title compound: $^1$H NMR (CDCl$_3$) δ 7.87 (m, 2H), 7.72 (d, J=8.2 Hz, 1H), 7.60 (m, 2H), 7.50 (m, 3H), 7.41 (m, 5H), 5.18 (s, 2H), 4.92 (br s, 2H), 4.32 (s, 2H), 3.87 (s, 3H); MS (M−1)$^-$=489.

F. 5-(4-Benzenesulfonyl-2-benzyloxyphenyl)-1,1-dioxo-1,2,5-thiadiazolidin-3-one Potassium Salt To a solution of N-sulfamoyl-N-(4-benzenesulfonyl-2-benzyloxyphenyl)glycine methyl ester (239 mg, 0.487 mmol) in THF (2 mL) is added potassium t-butoxide (0.487 mL, 1M in THF) and the mixture is stirred at RT for 18 h. The solvent is removed under reduced pressure and the residue triturated with CH$_2$Cl$_2$. The solvent from the triturate is removed under reduced pressure to give the title compound which is used directly in the next step: (M−1)$^-$=457.

G. 5-(4-Benzenesulfonyl-2-hydroxyphenyl)-1,1-dioxo-1,2,5-thiadiazolidin-3-one To a solution of 5-(4-benzenesulfonyl-2-benzyloxyphenyl)-1,1-dioxo-1,2,5-thiadiazolidin-3-one potassium in CH$_2$Cl$_2$ (5 mL), cooled in an ice/salt bath, is added dropwise BBr$_3$ (4.8 mL, 1M in CH$_2$Cl$_2$). The mixture is stirred for 30 min then is quenched with water, basified with potassium carbonate, and separated. The aqueous layer is washed with ether, then lyophilized, and purified by preparative HPLC to afford the title compound as an amorphous solid: mp=126-180° C.; $^1$H NMR (DMSO-d$_6$) δ 10.89 (br s, 1H), 7.93 (d, J=7.0 Hz, 2H), 7.66 (m, 4H), 7.42 (m, 2H), 4.56 (s, 2H); (M−1)$^-$=367.

EXAMPLE 319

5-(2-Hydroxy-4-trifluoromethylphenyl)-1,1-dioxo-1,2,5-thiadiazolidin-3-one

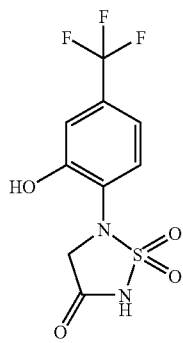

A. 2-Nitro-5-trifluoromethylphenol

A solution of 3-trifluoromethylphenol (3.0 mL, 25 mmol) in HOAc (10 mL) is added dropwise to a solution of 65% nitric acid (2.0 mL, 278 mmol) in HOAc (10 mL) at 0° C. The mixture is warmed to 40° C. and when the reaction is complete it is cooled to RT and partitioned between water and EtOAc. The organic layer is concentrated and the residue is chromatographed using 10% EtOAc/hexane as eluent to afford the title compound as a yellow oil: (M−1)⁻=206.

B. 2-Benzyloxy-1-nitro-4-trifluoromethylbenzene

A mixture of 2-nitro-5-trifluoromethylphenol (730 mg, 3.5 mmol), benzyl bromide (0.42 mL, 3.5 mmol), and potassium carbonate (200 mg) in DMF (10 mL) is stirred at RT for 48 h. The mixture is partitioned between water and EtOAc, the organic layer is concentrated and the residue is chromatographed using a gradient of 5-20% EtOAc/hexane as eluent to afford the title compound as a light yellow solid.

C. 2-Benzyloxy-4-trifluoromethylphenylamine

To a solution of 2-benzyloxy-1-nitro-4-trifluoromethylbenzene (1.0 g, 3.4 mmol) in 16 mL HOAc/EtOH (1:3) is added iron powder and the mixture is refluxed for 2 h. The mixture is cooled to RT and water is added and it is extracted with EtOAc. The organic phase is dried over sodium sulfate and the solvent removed under reduced pressure to give the title compound as a reddish oil.

D. 5-(2-Hydroxy-4-trifluoromethylphenyl)-1,1-dioxo-1,2,5-thiadiazolidin-3-one

The title compound is prepared from 2-benzyloxy-4-trifluoromethylphenylamine analogous to Example 83, steps H-K: $^1$H NMR (CD$_3$OD) δ 7.60 (d, J=8.0 Hz, 1H), 7.17 (m, 2H), 4.57 (s, 2H); (M−1)⁻=295.

EXAMPLE 320

5-(2-Hydroxy-4-methoxyphenyl)-1,1-dioxo-1,2,5-thiadiazolidin-3-one

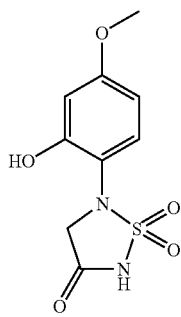

A. 2-Benzyloxy-4-methoxy-1-nitrobenzene

A mixture of 2-hydroxy-4-methoxy-1-nitrobenzene (520 mg, 3.08 mmol), benzyl bromide (522 mg, 3.08 mmol) and potassium carbonate (637 mg, 4.61 mmol) in DMF (3 mL) is stirred at 65° C. for 18 h. The mixture is poured into water and the mixture extracted with EtOAc. The organic phase is washed with water (3×) and brine (1×) and is dried over sodium sulfate. The solvent is removed under reduced pressure to give the title compound as an oil.

B. 2-Benzyloxy-4-methoxyphenylamine

A solution of 2-benzyloxy-4-methoxy-1-nitrobenzene (700 mg) in EtOAc (15 mL) is hydrogenated over platinum oxide (70 mg) at 20 psi for 1 h. The catalyst is filtered and the filtrate evaporated to give the title compound as an oil.

C. 5-(2-Hydroxy-4-methoxyphenyl)-1,1-dioxo-1,2,5-thiadiazolidin-3-one

The title compound is prepared from 2-benzyloxy-4-methoxyphenylamine analogous to Example 83, steps H-K: $^1$H NMR (DMSO-d$_6$) δ 10.03 (s, broad, 1H), 7.23 (d, J=8.67 Hz, 1H), 6.50-6.40 (m, 2H), 4.40 (s, 2H), 3.71 (s, 3H). (M−1)⁻=257.

EXAMPLE 321

3-Hydroxy-4-(1,1,4-trioxo-1,2,5-thiadiazolidin-2-yl)-benzonitrile

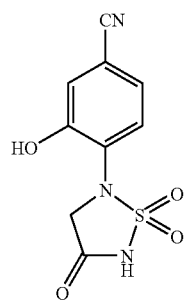

A. 3-Benzyloxy-4-(1,1,4-trioxo-1,2,5-thiadiazolidin-2-yl)-benzonitrile

To a solution of 5-(2-benzyloxy-4-iodophenyl)-1,1-dioxo-1,2,5-thiadiazolidin-3-one (108.4 mg, 0.243 mmol) in DMF (2 mL) is added KHCO$_3$ (0.488 mL, 0.5M aqueous solution), CuCN (19 mg, 0.212 mmol) and resin-bound PPh$_3$Pd (10 mol %) in DMF (2 mL) and the mixture is heated in a microwave apparatus at 110° C. for 20 min. The solvent is removed under reduced pressure and the residue purified by reverse phase MPLC to give the title compound.

B. 3-Hydroxy-4-(1,1,4-trioxo-1,2,5-thiadiazolidin-2-yl)-benzonitrile

The title compound is prepared from 3-benzyloxy-4-(1,1,4-trioxo-1,2,5-thiadiazolidin-2-yl)-benzonitrile analogous to Example 61, step F: (M−1)⁻=252.

EXAMPLE 322

5-(4-Chloro-2-hydroxyphenyl)-1,1-dioxo-1,2,5-thiadiazolidin-3-one

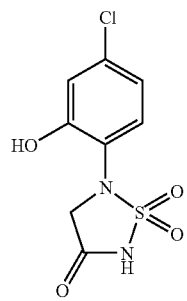

A. 2-Benzyloxy-4-chlorobenzoic Acid Benzyl Ester

To a suspension of 4-chloro-2-hydroxybenzoic acid (10.0 g, 57.9 mmol) and $K_2CO_3$ (20.8 g, 151 mmol) in DMF (115 mL) is added benzyl bromide (14.5 mL, 122 mmol) and the mixture is stirred at 85° C. for 7 h. The mixture is allowed to cool to RT and is partitioned between EtOAc and 1N HCl. The organic phase is washed with 1N HCl and brine then is dried over sodium sulfate. The solvent is removed under reduced pressure to give the title compound which is used directly in the next step.

B. 2-Benzyloxy-4-chlorobenzoic Acid

To a solution of 2-benzyloxy-4-chlorobenzoic acid benzyl ester in EtOH (500 mL) is added 1N NaOH (100 mL) and the mixture is stirred at 60° C. for 24 h. The mixture is allowed to cool to RT and is acidified with 1N HCl. The volume of the solution is reduced to 250 mL and the resulting precipitate is filtered, washed with water and dried to give the title compound as an off-white solid.

C. (2-Benzyloxy-4-chlorophenyl)-carbamic Acid Tert-butyl Ester

To a solution of 2-benzyloxy-4-chlorobenzoic acid (12.9 g, 46.6 mmol), t-butanol (17.5 mL, 186 mmol) and triethylamine (7.79 mL, 55.9 mmol) in toluene (250 mL) is added DPPA (11.1 mL, 51.3 mmol) and the mixture is stirred at 85° C. for 3 h then at 65° C. for 48 h. The mixture is diluted with EtOAc (500 mL) and is washed with 1N HCl (3×150 mL), $NaHCO_3$ (3×150 mL) and brine (150 mL). The organic phase is dried over sodium sulfate and the solvent evaporated to give a brown solid which is triturated with hexane to give the title compound: $(M-1)^-=332$.

D. [(2-Benzyloxy-4-chlorophenyl)-tert-butoxycarbonylamino]-acetic Acid Methyl Ester To a solution of (2-benzyloxy-4-chlorophenyl)-carbamic acid tert-butyl ester (14.75 g, 44.2 mmol) in DMF (150 mL) at 0° C. is added NaH (1.94 g, 60% in mineral oil, 48.6 mmol) and the mixture is stirred at 0° C. for 10 min. To this is added methyl bromoacetate (5.04 mL, 53 mmol) and the mixture is stirred at RT for 8 h. The mixture is poured into ice/water (150 mL) and is extracted with EtOAc (700 mL). The organic phase is washed with 1N HCl (3×150 mL) and brine (150 mL) then is dried over sodium sulfate. The solvent is removed under reduced pressure and the residue purified by flash chromatography using a gradient of 5-10% EtOAc/hexane as eluent to give the title compound.

E. (2-Benzyloxy-4-chlorophenylamino)-acetic Acid Methyl Ester

A solution of [(2-benzyloxy-4-chlorophenyl)-tert-butoxycarbonylamino]-acetic acid methyl ester (14.95 g, 36.8 mmol) in 180 mL of TFA/methylene chloride (1:2) is stirred at RT for 45 min. The solvent is removed under reduced pressure and the residue is dissolved in EtOAc (500 mL). To this solution is added diisopropylethylamine (13.11 g) and the resulting precipitate is filtered. The filtrate is evaporated to give the title compound as a tan solid. $(M+1)=306$.

F. 5-(2-Benzyloxy-4-chlorophenyl)-1,1-dioxo-1,2,5-thiadiazolidin-3-one

The title compound is prepared from (2-benzyloxy-4-chlorophenylamino)-acetic acid methyl ester analogous to Example 83, steps 1, J and K: $(M-1)^-=351$.

G. 5-(4-Chloro-2-hydroxyphenyl)-1,1-dioxo-1,2,5-thiadiazolidin-3-one

To a solution of 5-(2-benzyloxy-4-chlorophenyl)-1,1-dioxo-1,2,5-thiadiazolidin-3-one (388 mg, 1.1 mmol) in methylene chloride (10 mL) at 0° C. is added dropwise $BBr_3$ (1.65 mL of 1.0M in methylene chloride, 1.65 mmol) and the mixture is stirred at 0° C. for 30 min. Ice is added and the organic phase is washed with 1N HCl. The aqueous phase is washed with methylene chloride and the combined organic layers are dried over sodium sulfate. The solvent is removed under reduced pressure and the residue is purified by preparative HPLC to give the title compound as a white solid: $(M-1)^-=261$.

EXAMPLE 323

5-(4-Fluoro-2-hydroxyphenyl)-1,1-dioxo-1-[1,2,5]thiadiazolidin-3-one

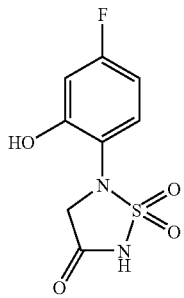

A. 2-Benzyloxy-4-fluoro-1-nitrobenzene

To a stirred solution of 5-fluoro-2-nitrophenol (1.57 g, 10 mmol) and benzyl bromide (1.25 mL, 10.5 mmol) in DMF (20 mL) is added $K_2CO_3$ (2.07 g, 15 mmol) and the suspension is stirred at RT overnight. The reaction is quenched with water and the aqueous layer is extracted with EtOAc. The combined organic layers are washed with water and brine, then dried over $MgSO_4$ and filtered. The solvent is removed under reduced pressure to give the product as a pale yellow solid.

B. 2-Benzyloxy-4-fluorophenylamine

To a stirred solution of 2-benzyloxy-4-fluoro-1-nitrobenzene (2.4 g, 10 mmol) in EtOH (20 mL) is added $SnCl_2$ (9.45 g, 50 mmol) and the suspension is stirred at RT overnight. The solvent is removed under reduced pressure and the residue is adjusted to pH >8. The aqueous layer is extracted with EtOAc and the combined organic layers are washed with water and brine, then dried over MgSO₄ and filtered. The solvent is removed under reduced pressure to give the product as a red oil.

C. 5-(4-Fluoro-2-hydroxyphenyl)-1,1-dioxo-1-[1,2,5]thiadiazolidin-3-one

The potassium salt of the title compound is prepared from 2-benzyloxy-4-fluorophenylamine analogous to Example 83 steps H-L: ¹H NMR (DMSO-d6): 9.70 (s, 1H), 7.39-7.35 (q, J=6.82 Hz, 1H), 6.62-6.53 (m, 2H), 3.98 (s, 2H). MS (M−1): 245.

EXAMPLE 324

5-(2-Hydroxy-4-methylphenyl)-1,1-dioxo-[1,2,5]thiadiazolidin-3-one

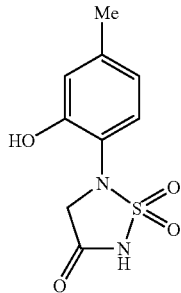

The title compound is prepared from 2-benzyloxy-4-methylphenylamine analogous to Example 83, steps H-L: ¹H NMR (DMSO-d6): δ 7.20 (d, J=8.09 Hz, 1H), 6.73 (s, 1H), 6.64 (d, J=8.09 Hz, 1H), 5.70-4.54 (s, broad, 2H), 4.41 (s, 2H), 2.23 (s, 3H); MS (M−1): 241.

EXAMPLE 325

5-(2-Hydroxy-4,6-dimethylphenyl)-1,1-dioxo-[1,2,5]thiadiazolidin-3-one

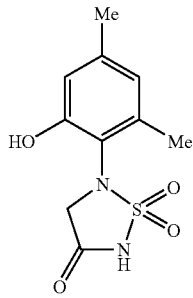

A. 2-Benzyloxy-6-methylphenylamine

To a stirred solution of 1-benzyloxy-3-methyl-2-nitrobenzene (5.0 g, 20.6 mmol) in EtOAc (150 mL) is added SnCl₂ (23.2 g, 103 mmol) and the suspension is heated at 80° C. overnight. The suspension is filtered and the filtrate washed with sat. NaHCO₃ and extracted with EtOAc. The combined organic layers are washed with water, brine, then dried over MgSO₄ and filtered. The solvent is removed under reduced pressure and the residue is purified by flash chromatography (hexanes/EtOAc=10:1 to 5:1) to give the title compound as a yellow oil.

B. 2-Benzyloxy-4-bromo-6-methyl-phenylamine

A solution of 2-benzyloxy-6-methyl-phenylamine (3.4 g, 16 mmol) in MeOH/AcOH (50 mL/20 mL) is cooled to 0° C. then a solution of Br₂ (0.82 mL, 16 mmol) in AcOH (10 mL) is added dropwise. After the addition, the solution is stirred at RT overnight. The solvent is removed under reduced pressure and the residue adjusted to pH>8 with aqueous K₂CO₃ solution. The suspension is extracted with EtOAc and the combined organic layers are washed with water, brine, then dried over MgSO₄ and filtered. The solvent is removed under reduced pressure and the residue is purified by flash chromatography (hexanes/EtOAc=10:1 to 5:1) to give the title compound as a red solid.

C. 5-(2-Benzyloxy-4-bromo-6-methylphenyl)-1,1-dioxo-1-[1,2,5]thiadiazolidin-3-one The title compound is prepared from 2-benzyloxy-4-bromo-6-methyl-phenylamine analogous to Example 83, steps H-K.

D. 5-(2-Benzyloxy-4,6-dimethylphenyl)-1,1-dioxo-1-[1,2,5]thiadiazolidin-3-one

A mixture of 5-(2-benzyloxy-4-bromo-6-methyl-phenyl)-1,1-dioxo-1-[1,2,5]thiadiazolidin-3-one (100 mg, 0.24 mmol), methylboronic acid (17.4 mg, 0.29 mmol), Pd(PPh₃)-resin (50 mg, 50% w), and 2N Na₂CO₃ (0.48 mL) in DME (5 mL) is placed in a microwave vial and heated under microwave irradiation at 140° C. for 1 h. The suspension is filtered and the solvent is removed under reduced pressure to give the product as a red oil. This was used directly in the next step.

E. 5-(2-Hydroxy-4,6-dimethylphenyl)-1,1-dioxo-[1,2,5]thiadiazolidin-3-one

The title compound is prepared from 5-(2-benzyloxy-4,6-dimethylphenyl)-1,1-dioxo-1-[1,2,5]thiadiazolidin-3-one analogous to Example 83, step L: ¹H NMR (DMSO-d6): 9.72 (s, 1H), 7.30-7.27 (m, 2H), 7.22-7.16 (m, 3H), 6.60 (d, J=1.26 Hz, 1H), 6.54-6.53 (d, J=1.77 Hz, 1H), 4.28 (s, 2H), 3.80 (s, 2H), 2.26 (s, 3H). MS (M−1): 331.

EXAMPLE 326

5-(4,5-Difluoro-2-hydroxyphenyl)-1,1-dioxo-[1,2,5]thiadiazolidin-3-one

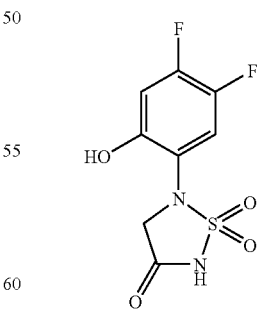

A. 4,5-Difluoro-2-nitrophenol

To a solution of 3,4-difluorophenol (1.56 g, 7.69 mmol) in dichloromethane (10 mL) under a blanket of nitrogen is added ammonium nickel sulfate (2.0 g, 5.07 mmol), with vigorous stirring, followed by the addition of nitric acid (69%, 0.770 mL, 7.69 mmol). The resulting heterogeneous mixture is then stirred at RT for 5-10 min; at this point a bright orange solution was observed along with a mild exothermic gaseous emission. (LC/MS indicated the formation of one single product.) Anhydrous magnesium sulfate (~1 g) is then added to the reaction mixture, which is stirred and filtered to afford an orange solution. Removal of dichloromethane under reduced pressure affords an orange solid residue. (low melting solid, sublimed upon storage) $^1$H NMR (400 MHz, δ, CDCl$_3$): 10.61 (s, 1H), 8.01 (m, 1H), 7.00 (m, 1H).

B. 2-Benzyloxy-4,5-difluoronitrobenzene

To a vigorously stirred mixture of 4,5-difluoro-2-nitrophenol (1 g, 5.71 mmol) and anhydrous potassium carbonate (1.9 g, 14.28 mmol) in acetone (20 mL). is added benzyl bromide (750 μl, 6.28 mmol) and the dark heterogeneous mixture is heated to reflux for 10 h; or until all starting material had been consumed according to LC/MS analysis. The dark mixture is then filtered, dried over magnesium sulfate, and filtered again to afford, after solvent removal, a light brown crystalline solid that was used in the next step without further purification.

C. 2-Benzyloxy-4,5-difluorophenylamine

A mixture of 2-benzyloxy-4,5-difluoronitrobenzene (2.35 g, 8.86 mmol) and 10% platinum on carbon (235 mg) in ethyl acetate (50 mL) is hydrogenated at atmospheric pressure for 6 h. The catalyst is filtered through Celite and solvent removed under reduced pressure. The residue is purified by silica gel chromatography on an Isco Companion using a gradient of 90:10 to 50:50 hexane/ethyl acetate to afford the title compound. $^1$H NMR (δ, CDCl$_3$): 7.39 (m, 5H), 6.68 (dd, 1H, J=11.6, 7.3 Hz), 6.52 (dd, 1H, J=11.6, 7.8 Hz), 5.01 (s, 2H), 3.74 (br s, 2H). MS (M+1): 236.

D. 5-(4,5-Difluoro-2-hydroxyphenyl)-1,1-dioxo-[1,2,5]thiadiazolidin-3-one

The potassium salt of the title compound is prepared from 2-benzyloxy-4,5-difluorophenylamine analogous to Example 83, steps H-L: $^1$H NMR (δ, DMSO-d$_6$): 7.42 (dd, 1H, J=12.1, 9.1 Hz), 6.76 (dd, 1H, J=12.4, 8.1 Hz), 4.05 (s, 2H). MS (M−1): 368.

EXAMPLE 327

5-(3,5-Difluoro-2-hydroxy-4-methylphenyl)-1,1-dioxo-1,2,5-thiadiazolidin-3-one

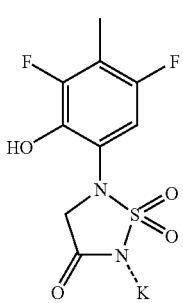

A. 2,4-Difluoro-6-nitrophenol

The title compound is prepared analogous to Example 326, step A, starting from 2,4-difluorophenol, which is used directly to the next step without purification.

B. 2-Benzyloxy-1,5-difluoro-3-nitrobenzene

The title compound is prepared analogous to Example 326, step B, starting from 2,4-difluoro-6-nitrophenol: MS (M−H)$^-$=264.

C. 2-Benzyloxy-3,5-difluorophenylamine

To a solution of 2-benzyloxy-1,5-difluoro-3-nitrobenzene (2.60 g, 9.80 mmol) in EtOH (20 mL)/water (10 mL) is added zinc (3.4 g, 49 mmol) and ammonium chloride (1.0 g, 19.6 mmol) and the mixture is heated at 60° C. for 2 h. The mixture is extracted with EtOAc and the solvent is removed under reduced pressure. The residue is dissolved in methylene chloride and the solution washed with water. The organic phase is dried over sodium sulfate. The solvent is removed under reduced pressure to give the title compound which is used directly to the next step without purification.

D. 2-Benzyloxy-4-bromo-3,5-difluorophenylamine

To a suspension of NBS (1.60 g, 9.01 mmol) in methylene chloride (20 mL) at 0° C. is added a solution of 2-benzyloxy-3,5-difluorophenylamine (2.12 g, 9.01 mmol) and the mixture is stirred at 0° C. for 30 min then at RT for 30 min. The Mixture is washed with water and the solvent evaporated under reduced pressure. The residue is purified by column chromatography to give the title compound: MS (M−H)$^-$=313.

E. 5-(2-Benzyloxy-4-bromo-3,5-difluorophenyl)-1,1-dioxo-[1,2,5]thiadiazolidin-3-one The title compound is prepared analogous to Example 83, steps H-K, starting from 2-benzyloxy-4-bromo-3,5-difluorophenylamine, the resulting potassium salt is neutralized with aqueous HCl during workup to afford the product: MS (M−H)$^-$=432.

F. 5-(2-Benzyloxy-3,5-difluoro-4-methylphenyl)-1,1-dioxo-[1,2,5]thiadiazolidin-3-one The title compound is prepared from 5-(2-benzyloxy-4-bromo-3,5-difluorophenyl)-1,1-dioxo-1,2,5]thiadiazolidin-3-one and methylboronic acid analogous to Example 325, Step D at 150° C. for 30 min.

G. 5-(3,5-Difluoro-2-hydroxy-4-methylphenyl)-1,1-dioxo-1,2,5-thiadiazolidin-3-one Potassium Salt The title compound is prepared from 5-(2-benzyloxy-4-bromo-3,5-difluoro-phenyl)-1,1-dioxo-1,2,5]thiadiazolidin-3-one analogous to Example 83, step L: HPLC retention time 0.75 min (Method A), MS (M−H)$^-$=277. The potassium salt is formed by treatment with one equivalent of KHCO$_3$.

EXAMPLE 328

5-(3,5-Difluoro-2-hydroxyphenyl)-1,1-dioxo-1,2,5]thiadiazolidin-3-one Potassium Salt

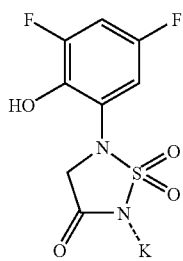

The title compound is prepared from 2,4-difluorophenol analogous to Example 326: HPLC retention time 0.64 min (Method A), MS (M–H)⁻=263.

EXAMPLE 329

5-(2-Hydroxyphenyl)-1,1-dioxo-1-[1,2,5]thiadiazolidin-3-one

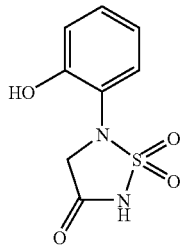

The title compound is prepared from 2-nitrophenol analogous to Example 323 with the modification that the reduction step B is performed by catalytic hydrogenation over platinum oxide: $^1$H NMR (6, DMSO-$d_6$): 9.20 (s, broad, 1H), 7.40 (dd, J=8.09 and 1.47 Hz, 1H), 7.04-6.98 (m, 1H), 6.84 (d, J=8.09 Hz, 1H), 6.75 (t, 1H), 4.06 (s, 2H). MS (M–H)_=227.

What is claimed is:
1. A compound of the formula

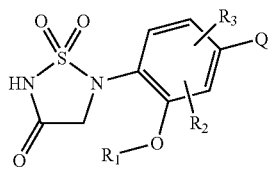

(I)

wherein
Q is:
i) —X, or
ii) —Y—(CH$_2$)$_n$—(CR$_8$R$_9$)$_p$—(CH$_2$)$_m$—Z—X in which;
Y is oxygen or S(O)$_q$ in which q is zero or an integer of 1 or 2; or
Y is —C≡C— or —C═C—; or
Y is cyclopropyl or Y is absent;
n and m are, independently from each other, zero or an integer from 1 to 8;
R$_8$ and R$_9$ are, independently from each other, hydrogen, hydroxyl, alkoxy, alkanoyl, alkanoylamino, alkoxycarbonyl, aralkyl, heteroaryl, carbamoyl, aryl, or alkyl; or
R$_8$ and R$_9$ combined are alkylene which together with the carbon atom to which they are attached form a 3- to 7-membered ring;
p is zero or an integer selected from 1 or 2
Z is absent;
Z is —C(O)—O—; or
Z is —C(O)—; or
Z is —C(O)—NRα-alkylene- or —C(O)—NRα-alkylene-O—, wherein Rα is H or lower alkyl; or
Z is —CO—NRα-(CH$_2$)$_n$—(CR$_8$R$_9$)$_{p'}$—(CH$_2$)$_{m'}$—, or —C(O)—NRα-(CH$_2$)$_{n'}$—(CR$_8$R$_9$)$_{p'}$—(CH$_2$)$_{m'}$—O—, wherein p' is zero or an integer of 1, n' and m' are, independently from each other, zero or an integer from 1 to 8, R$_{8'}$ and R$_{9'}$ are, independently from each other, hydrogen or lower alkyl, Rα is H or lower alkyl; or
Z is —NRα'-C(O)—, or —NRα'-C(O)—O—, wherein Rα' is H or lower alkyl, or Rα' and R$_9$ combined are alkylene which together with the carbon atom to which they are attached form a 3- to 7-membered ring; or
Z is —C(O)—NH—NH—C(O)—O—; or
Z is —S(O)$_2$—, or —S(O)—; or
Z is —NRβ-S(O)$_2$—, wherein Rβ is H, lower alkyl, or Rβ and R$_9$ combined are alkylene which together with the carbon atom to which they are attached form a 3- to 7-membered ring; or
Z is —NH—S(O)$_2$—NH—C(O)—O—; or
Z is —NRγ-C(O)—NRγ'—; wherein Rγ' is H, alkyl, aryl, heterocyclyl, or lower alkoxy and Rγ is H, lower alkyl, or Rγ and R9 combined are alkylene which together with the carbon atom to which they are attached form a 3- to 7-membered ring; or Rγ' and X combined are alkylene which together with the carbon atom to which they are attached form a 3- to 7-membered ring or
Z is —NRτ-C(O)—NH—S(O)$_2$—, wherein Rτ is H or lower alkyl,
X is hydrogen, hydroxy, NH$_2$, halogen, alkoxy, alkylthio, alkyl, —S(O)—OH, cycloalkyl, cycloalkoxy, acyl, acyloxy, carbamoyl, optionally substituted amino, cyano, trifluoromethyl, free or esterified carboxy, heterocyclyl, heterocyclooxy, heteroaryl, heteroaralkyl, aryl, aralkyl, aralkoxy, aryloxy, aralkylthio, arylthio, wherein the alkyl, cycloalkyl, aryl, heteroaryl and heterocylclyl groups are unsubstituted or optionally substituted by 1, 2, 3, 4, or 5 susbtituents; wherein heterocyclyl is selected from the group consisting of pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyrazinyl, pyrimidinyl, pyridazinyl, tetrahydropyranyl, dioxotetrahydrothiophen, morpholinyl, thiamorpholinyl, thiamorpholinyl sulfoxide, thiamorpholinyl sulfone, 1,3-dioxolane, 1,1-dioxo-1,2,5-thiadiazolidin-3-one, 1,1-Dioxo-1,2-thiazinanyl, tetrahydro-1,1-dioxothienyl, 1,1,4-trioxo-1,2,5-thiadiazolidin-2-yl, indolyl, dihydroidolyl, benzothiazolyl, benzoxazinyl, benzoxazolyl, benzothienyl, benzothiazinyl, quinuclidinyl, quinazoline, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, chromenenyl, isoindole-1,3-dione, coumarinyl, benzopyranyl, cinnolinyl, quinoxalinyl, indazolyl, pyrrolopyridyl, furopyridinyl, dihydroisoindolyl, 1,3-dioxo-1,3-dihydroisoindol-2-yl, dihydroquinazolinyl, tetrahydroisoquinolinyl, tetrahydro-benzo[b]azepine, phthalazinyl, carbazolyl, dibenzoazepinyl, dithienoazepinyl, benzindolyl, phenanthrolinyl, acridinyl, phenanthridinyl, phenoxazinyl, phenothiazinyl, xanthenyl, and carbolinyl; and wherein heteroaryl, either alone or as part of a heteroaralkyl, is selected from the group consisting of pyrrolyl, pyrazolyl, imidazolyl, oxazolyl, isoxazolyl, thiazolyl, isothiazolyl, furyl, thienyl, pyrazinyl, pyrimidinyl, pyridazinyl, indolyl, benzothiazolyl, benzoxazolyl, benzothienyl, quinolinyl, isoquinolinyl, benzimidazolyl, and benzofuryl;

$R_1$ is hydrogen $R_2$ and $R_3$ are hydrogen;

or a pharmaceutically acceptable salt thereof, and wherein n +m +p is >1 or is 0, when X is aryl, and Y and Z are absent, n+m+p is not 0 when X is —O-aryl, and Y and Z are absent, or n+m+p is not 0 when X is —S-aryl, and Y and Z are absent, or n+m+p is not 0 when X is —CH$_2$-aryl, and Y and Z are absent, or n+m+p is not 0 when X is aryl, Z is absent and Y is —O— or Y is —S—, or wherein Q cannot be —CH$_2$-aryl, —S-aryl or —O-aryl.

2. The compound according to claim 1, wherein

Y is oxygen; or

Y is —C≡C— or —C=C—; or

Y is cyclopropyl or

Y is absent; and

X is, hydrogen, hydroxy, NH$_2$, halogen, substituted or unsubstituted alkoxy, substituted or unsubstituted alkylthio, substituted or unsubstituted alkyl, —S(O)—OH, substituted or unsubstituted alkyl, substituted or unsubstituted cycloalkyl, cyano, trifluoromethyl, carboxy, substituted or unsubstituted esterified carboxy, substituted or unsubstituted heterocyclyl, substituted or unsubstituted heteroaryl, substituted or unsubstituted heteroaralkyl, substituted or unsubstituted aryl, substituted or unsubstituted aralkyl, substituted or unsubstituted aryloxy;

or a pharmaceutically acceptable salt thereof.

3. The compound according to claim 1, wherein

Q is —Y—(CH$_2$)$_n$—(CR$_8$R$_9$)$_p$—(CH$_2$)$_m$—Z—X, in which

Y is oxygen or S(O)$_q$ in which q is zero or an integer of 1 or 2; or

Y is —C≡C— or —C=C—; or

Y is cyclopropyl; or

Y is absent;

n and m are, independently from each other, zero or an integer from 1 to 8;

$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl;

p is zero or an integer selected from 1 or 2

Z is absent;

Z is —CO—O—; or

Z is —CO—; or

X is hydrogen, hydroxy, NH$_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio;

or a pharmaceutically acceptable salt thereof.

4. The compound according to claim 3, wherein

Y is oxygen; or

Y is cyclopropyl; or

Y is absent;

or a pharmaceutically acceptable salt thereof.

5. The compound according to claim 3, wherein $R_8$ and $R_9$ are, independently from each other, hydrogen, alkoxy, alkanoyl, alkoxycarbonyl, aralkyl, aryl, or alkyl;

or a pharmaceutically acceptable salt thereof.

6. The compound according to claim 3, wherein

X is hydrogen, hydroxy, substituted or unsubstituted alkyl, substituted or unsubstituted heterocyclyl, substituted or unsubstituted heteroaryl, substituted or unsubstituted aryl;

or a pharmaceutically acceptable salt thereof.

7. The compound according to claim 1, wherein

Q is —Y—(CH$_2$)$_n$—(CR$_8$R$_9$)$_p$—(CH$_2$)$_m$—Z—X, in which

Y is oxygen or S(0)$_q$ in which q is zero or an integer of 1 or 2; or

Y is —C≡C— or —C=C—; or

Y is cyclopropyl; or

Y is absent;

n and m are, independently from each other, zero or an integer from 1 to 8;

$R_8$ and $R_9$ are, independently from each other, hydrogen, hydroxyl, alkoxy, alkanoyl, alkanoylamino, alkoxycarbonyl, aralkyl, heteroaryl, heterocyclyl, carbamoyl, aryl, or alkyl; or $R_8$ and $R_9$ combined are alkylene which together with the carbon atom to which they are attached form a 3- to 7-membered ring;

p is zero or an integer selected from 1 or 2

Z is absent;

X is hydrogen, hydroxy, NH$_2$, halogen, substituted or unsubstituted alkoxy, substituted or unsubstituted alkylthio, —SO—OH, substituted or unsubstituted alkyl, substituted or unsubstituted cycloalkyl, substituted or unsubstituted cycloalkoxy, substituted or unsubstituted acyl, substituted or unsubstituted acyloxy, substituted or unsubstituted carbamoyl, optionally substituted amino, cyano, trifluoromethyl, carboxy, substituted or unsubstituted esterified carboxy, substituted or unsubstituted heterocyclyl, substituted or unsubstituted heterocyclooxy, substituted or unsubstituted heteroaryl, substituted or unsubstituted heteroaralkyl, substituted or unsubstituted aryl, substituted or unsubstituted aralkyl, substituted or unsubstituted aralkoxy, substituted or unsubstituted aryloxy, substituted or unsubstituted aralkylthio, substituted or unsubstituted arylthio;
or a pharmaceutically acceptable salt thereof.

8. The compound according to claim 7, wherein
$R_8$ and $R_9$ are, independently from each other, hydrogen, alkoxy, alkanoyl, alkoxycarbonyl, aralkyl, or alkyl;
or a pharmaceutically acceptable salt thereof.

9. A compound according to claim 1 which is selected from the group consisting of:
- 3-{2-[3-Hydroxy-4-(1,1,4-trioxo-1,2,5-thiadiazolidin-2-yl)-phenyl]-ethyl}-benzamide
- 3-{2-[3-Hydroxy-4-(1,1,4-trioxo-1,2,5-thiadiazolidin-2-yl)-phenyl]-ethyl}-N-methyl benzamide
- 3-{2-[3-Hydroxy-4-(1,1,4-trioxo-1,2,5-thiadiazolidin-2-yl)-phenyl]-ethyl}-N,N-dimethylbenzamide
- 4-{2-[3-Hydroxy-4-(1,1,4-trioxo-1,2,5-thiadiazolidin-2-yl)-phenyl]-ethyl}-N,N-dimethylbenzamide
- 4-{2-[3-Hydroxy-4-(1,1,4-trioxo-1,2,5-thiadiazolidin-2-yl)-phenyl]-ethyl}-benzamide
- 4-{2-[3-Hydroxy-4-(1,1,4-trioxo-1,2,5-thiadiazolidin-2-yl)-phenyl]-ethyl}-N-methylbenzamide
- 3-{2-[3-Hydroxy-4-(1,1,4-trioxo-1,2,5-thiadiazolidin-2-yl)-phenyl]-ethyl}-benzoic acid
- 4-{2-[3-Hydroxy-4-(1,1,4-trioxo-1,2,5-thiadiazolidin-2-yl)-phenyl]-ethyl}-benzoic acid
- 4-{2-[3-Hydroxy-4-(1,1,4-trioxo-1,2,5-thiadiazolidin-2-yl)-phenyl]-ethyl}-benzonitrile
- 2-{2-[3-Hydroxy-4-(1,1,4-trioxo-1,2,5-thiadiazolidin-2-yl)-phenyl]-ethyl}-benzonitrile
- 5-(2-Hydroxy-4-phenethylphenyl)-1,1-dioxo-1,2,5-thiadiazolidin-3-one
- 5-{2-Hydroxy-4-[2-(3-methoxyphenyl)-ethyl]-phenyl}-1,1-dioxo-1,2,5-thiadiazolidin-3-one
- 5-{4-[2-(3-Fluorophenyl)-ethyl]-2-hydroxyphenyl}-1-1,1-dioxo-1,2,5-thiadiazolidin-3-one
- 5-{4-[2-(2-Fluorophenyl)-ethyl]-2-hydroxyphenyl}-1,1-dioxo-1,2,5-thiadiazolidin-3-one
- 5-[2-Hydroxy-4-(2-pentafluorophenylethyl)-phenyl]-1,1-dioxo-1,2,5-thiadiazolidin-3-one
- 5-[2-Hydroxy-4-(2-p-tolylethyl)-phenyl]-1,1-dioxo-1,2,5-thiadiazolidin-3-one
- 5-{2-Hydroxy-4-[2-(4-octylphenyl)-ethyl]-phenyl}-1,1-dioxo-1,2,5-thiadiazolidin-3-one
- 5-[4-(2-Biphenyl-4-yl-ethyl)-2-hydroxyphenyl]-1,1-dioxo-1,2,5-thiadiazolidin-3-one
- 5-{4-[2-(4-tert-Butylphenyl)-ethyl]-2-hydroxyphenyl}-1,1-dioxo-1,2,5-thiadiazolidin-3-one
- 5-{4-[2-(2,5-Dimethylphenyl)-ethyl]-2-hydroxyphenyl}-1,1-dioxo-1,2,5-thiadiazolidin-3-one
- 5-{4-[2-(2,4-Dimethylphenyl)-ethyl]-2-hydroxyphenyl}-1,1-dioxo-1,2,5-thiadiazolidin-3-one
- 5-{2-Hydroxy-4-[2-(4-trifluoromethylphenyl)-ethyl]-phenyl}-1,1-dioxo-1,2,5-thiadiazolidin-3-one
- Acetic acid 4-{2-[3-hydroxy-4-(1,1,4-trioxo-1,2,5-thiadiazolidin-2-yl)-phenyl]-ethyl}-phenyl ester
- 5-{2-Hydroxy-4-[2-(4-phenoxyphenyl)-ethyl]-phenyl}-1,1-dioxo-1,2,5-thiadiazolidin-3-one
- 5-[2-Hydroxy-4-(2-naphthalenethyl)-phenyl]-1,1-dioxo-1,2,5-thiadiazolidin-3-one
- 5-[2-Hydroxy-4-(2-quinolin-3-yl-ethyl)-phenyl]-1,1-dioxo-1,2,5-thiadiazolidin-3-one
- 5-{4-[2-(4,6-Diamino-[1,3,5]triazin-2-yl)-ethyl]-2-hydroxy-phenyl}-1,1-dioxo-1,2,5thiadiazolidin-3-one
- 5-[2-Hydroxy-4-(2-phenylpropyl)-phenyl]-1,1-dioxo-1,2,5-thiadiazolidin-3-one
- 5-{4-[2-(2-Aminophenyl)-propyl]-2-hydroxyphenyl}-1,1-dioxo-1,2,5-thiadiazolidin-3-one
- 3-[3-Hydroxy-4-(1,1,4-trioxo-1,2,5-thiadiazolidin-2-yl)-phenyl]-2-phenylpropionic acid ethyl ester
- 5-[2-Hydroxy-4-(1-methyl-2-phenylethyl)-phenyl]-1,1-dioxo-1,2,5-thiadiazolidin-3-one
- 5-[2-Hydroxy-4-(1-methoxy-2-phenylethyl)-phenyl]-1,1-dioxo-1,2,5-thiadiazolidin-3-one
- 5-[2-Hydroxy-4-(3-oxo-2-phenylbutyl)-phenyl]-1,1-dioxo-1,2,5-thiadiazolidin-3-one
- 5-{2-Hydroxy-4-[2-(2H-pyrazol-3-yl)-ethyl]-phenyl}-1,1-dioxo-1,2,5-thiadiazolidin-3-one
- 5-{2-Hydroxy-4-[2-(1H-pyrazol-4-yl)-ethyl]-phenyl}-1,1-dioxo-1,2,5-thiadiazolidin-3-one
- 5-{2-Hydroxy-4-[2-(1-methyl-1H-pyrazol-4-yl)-ethyl]-phenyl}-1,1-dioxo-1,2,5-thiadiazolidin-3-one
- 5-[2-Hydroxy-4-(2-thiazol-5-yl-ethyl)-phenyl]-1,1-dioxo-1,2,5-thiadiazolidin-3-one
- 5-{4-[2-(2,4-Dimethyl-thiazol-5-yl)-ethyl]-2-hydroxyphenyl}-1,1-dioxo-1,2,5-thiadiazolidin-3-one
- 5-[2-Hydroxy-4-(2-[1,2,4]triazol-yl-ethyl)-phenyl]-1,1-dioxo-1,2,5-thiadiazolidin-3-one
- 5-[2-Hydroxy-4-(2-imidazol-1-yl-ethyl)-phenyl]-1,1-dioxo-1,2,5-thiadiazolidin-3-one
- 5-{2-Hydroxy-4-[2-(2-methyl-thiazol-5-yl)-ethyl]-phenyl}-1,1-dioxo-1,2,5-thiadiazolidin-3-one
- 5-{2-Hydroxy-4-[2-(2-propyl-thiazol-5-yl)-ethyl]-phenyl}-1,1-dioxo-1,2,5-thiadiazolidin-3-one
- 5-(2-Hydroxy-4-{2-[4-methyl-2-(4-trifluoromethyl-phenyl)-thiazol-5-yl]-ethyl}-phenyl)-1,1-dioxo-1,2,5-thiadiazolidin-3-one
- 5-{2-Hydroxy-4-[2-(2-methyl-4-trifluoromethyl-thiazol-5-yl)-ethyl]-phenyl}-1,1-dioxo-1,2,5-thiadiazolidin-3-one
- 5-{4-[2-(1H-Benzoimidazol-2-yl)-ethyl]-2-hydroxyphenyl}-1,1-dioxo-1,2,5-thiadiazolidin-3-one
- 5-[2-Hydroxy-4-(3-phenylpropyl)-phenyl]-1,1-dioxo-1,2,5-thiadiazolidin-3-one
- 5-{4-[3-(3,4-Dimethoxyphenyl)-propyl]-2-hydroxyphenyl}-1,1-dioxo-1,2,5-thiadiazolidin-3-one
- 5-[2-Hydroxy-4-(2-methyl-3-phenylpropyl)-phenyl]-1,1-dioxo-1,2,5-thiadiazolidin-3-one
- 5-[2-Hydroxy-4-(3-hydroxy-3-phenylpropyl)-phenyl]-1,1-dioxo-1,2,5-thiadiazolidin-3-one
- 5-(2-Hydroxy-4-phenethyloxyphenyl)-1,1-dioxo-1,2,5-thiadiazolidin-3-one
- 5-[2-Hydroxy-4-(4-phenylbutyl)-phenyl]-1,1-dioxo-1,2,5-thiadiazolidin-3-one
- {3-[3-Hydroxy-4-(1,1,4-trioxo-1,2,5-thiadiazolidin-2-yl)-phenyl]-propyl}-carbamic acid tert-butyl ester
- 5-[4-(3-Aminopropyl)-2-hydroxyphenyl]-1,1-dioxo-1,2,5-thiadiazolidin-3-one
- {2-[3-Hydroxy-4-(1,1,4-trioxo-1,2,5-thiadiazolidin-2-yl)-phenyl]-ethyl}-carbamic acid tert-butyl ester
- {(S)-1-Benzyl-2-[3-hydroxy-4-(1,1,4-trioxo-1,2,5-thiadiazolidin-2-yl)-phenyl]-ethyl}-carbamic acid tert-butyl ester
- {3-[3-Hydroxy-4-(1,1,4-trioxo-1,2,5-thiadiazolidin-2-yl)-phenyl]-1,1-dimethylpropyl}-carbamic acid tert-butyl ester
- 2-{2-[3-Hydroxy-4-(1,1,4-trioxo-1,2,5-thiadiazolidin-2-yl)-phenyl]-ethyl}-piperidine-1-carboxylic acid tert-butyl ester 2-{2-[3-Hydroxy-4-(1,1,4-trioxo-1,2,5-thiadiazolidin-2-yl)-phenyl]-ethyl}-azepane-1-carboxylic acid tert-butyl ester
3-[3-Hydroxy-4-(1,1,4-trioxo-1,2,5-thiadiazolidin-2-yl)-benzyl]-piperidine-1-carboxylic acid tert-butyl ester
5-(2-Hydroxy-4-piperidin-3-ylmethylphenyl)-1,1-dioxo-1,2,5-thiadiazolidin-3-one
{(1R*,2S*)-2-[3-Hydroxy-4-(1,1,4-trioxo-1,2,5-thiadiazolidin-2-yl)-benzyl]-cyclohexyl}-carbamic acid tert-butyl ester
N-{2-[3-Hydroxy-4-(1,1,4-trioxo-1,2,5-thiadiazolidin-2-yl)-phenyl]-ethyl}-benzamide
4-Fluoro-N-{2-[3-hydroxy-4-(1,1,4-trioxo-1,2,5-thiadiazolidin-2-yl)-phenyl]-ethyl}-benzamide
N-{2-[3-Hydroxy-4-(1,1,4-trioxo-1,2,5-thiadiazolidin-2-yl)-phenyl]-ethyl}-acetamide
N-{2-[3-Hydroxy-4-(1,1,4-trioxo-1,2,5-thiadiazolidin-2-yl)-phenyl]-ethyl}-propionamide
N-{2-[3-Hydroxy-4-(1,1,4-trioxo-1,2,5-thiadiazolidin-2-yl)-phenyl]-ethyl}-isobutyramide
N-{2-[3-Hydroxy-4-(1,1,4-trioxo-1,2,5-thiadiazolidin-2-yl)-phenyl]-ethyl}-2,2-dimethyl-propionamide
Adamantane-1-carboxylic acid {2-[3-hydroxy-4-(1,1,4-trioxo-1,2,5-thiadiazolidin-2-yl)-phenyl]-ethyl}-amide
N-{3-[3-Hydroxy-4-(1,1,4-trioxo-1,2,5-thiadiazolidin-2-yl)-phenyl]-propyl}-acetamide
4-Fluoro-N-{3-[3-hydroxy-4-(1,1,4-trioxo-1,2,5-thiadiazolidin-2-yl)-phenyl]-propyl}-benzamide
-{3-[3-Hydroxy-4-(1,1,4-trioxo-1,2,5-thiadiazolidin-2-yl)-phenyl]-propyl}-propionamide
N-{3-[3-Hydroxy-4-(1,1,4-trioxo-1,2,5-thiadiazolidin-2-yl)-phenyl]-propyl}-isobutyramide
N-{3-[3-Hydroxy-4-(1,1,4-trioxo-1,2,5-thiadiazolidin-2-yl)-phenyl]-propyl}-2,2-dimethyl-propionamide
Adamantane-1-carboxylic acid {3-[3-hydroxy-4-(1,1,4-trioxo-1,2,5-thiadiazolidin-2-yl)-phenyl]-propyl}-amide
5[2-Hydroxy-4-((S)-5-oxopyrrolidin-2-ylmethyl)-phenyl]-1,1-dioxo-1,2,5-thiadiazolidin-3-one
6-[3-Hydroxy-4-(1,1,4-trioxo-1,2,5-thiadiazolidin-2-yl)-benzyl]-piperidin-2-one
7-[3-Hydroxy-4-(1,1,4-trioxo-1,2,5-thiadiazolidin-2-yl)-benzyl]-azepan-2-one
(R)-3-[3-Hydroxy-4-(1,1,4-trioxo-1,2,5-thiadiazolidin-2-yl)-benzyl]-3,4-dihydro-2H-isoquinolin-1-one
(S)-3-[3-Hydroxy-4-(1,1,4-trioxo-1,2,5-thiadiazolidin-2-yl)-benzyl]-2,3-dihydro-benzo[c]azepin-1-one
(R)-3-[3-Hydroxy-4-(1,1,4-trioxo-1,2,5-thiadiazolidin-2-yl)-benzyl]-2,3,4,5-tetrahydrobenzo[c]azepin-1-one
1-[3-Hydroxy-4-(1,1,4-trioxo-1,2,5-thiadiazolidin-2-yl)-benzyl]-1,2,4,5-tetrahydrobenzo[c]azepin-3-one
1-[3-Hydroxy-4-(1,1,4-trioxo-1,2,5-thiadiazolidin-2-yl)-benzyl]-1,3,4,5-tetrahydrobenzo[d]azepin-2-one
7[3-Hydroxy-4-(1,1,4-trioxo-1,2,5-thiadiazolidin-2-yl)-benzyl]-6,7-dihydro-dibenzo[c,e]azepin-5-one
(S)-7-[3-Hydroxy-4-(1,1,4-trioxo-1,2,5-thiadiazolidin-2-yl)-benzyl]-6,7-dihydro-dibenzo[c,e]azepin-5-one
3-[3-Hydroxy-4-(1,1,4-trioxo-1,2,5-thiadiazolidin-2-yl)-benzyl]-3,4-dihydro-2H-naphtho[1,8-cd]azepin-1-one
5-{4-[2-(1-Acetylpiperidin-2-yl)-ethyl]-2-hydroxyphenyl}-1,1-dioxo-1,2,5-thiadiazolidin-3-one
N-{(1R*,2S*)-2-[3-Hydroxy-4-(1,1,4-trioxo-1,2,5-thiadiazolidin-2-yl)-benzyl]-cyclohexyl}-acetamide
N-{(S)-1-Benzyl-2-[3-hydroxy-4-(1,1,4-trioxo-1,2,5-thiadiazolidin-2-yl)-phenyl]-ethyl}-2,2,2-trifluoroacetamide
N-{4-[3-Hydroxy-4-(1,1,4-trioxo-1,2,5-thiadiazolidin-2-yl)-phenyl]-butyl}-phthalamic acid
2-{4-[3-Hydroxy-4-(1,1,4-trioxo-1,2,5-thiadiazolidin-2-yl)-phenyl]-butyl}-isoindole-1,3-dione
3-[3-Hydroxy-4-(1,1,4-trioxo-1,2,5-thiadiazolidin-2-yl)-phenyl]-N-isopropyl-N-methylpropionamide
5-{4-[3-(3,4-Dihydro-1H-isoquinolin-2-yl)-3-oxopropyl]-2-hydroxyphenyl}-1,1-dioxo-1,2,5-thiadiazolidin-3-one
N'-{3-[3-Hydroxy-4-(1,1,4-trioxo-1,2,5-thiadiazolidin-2-yl)-phenyl]-propionyl}-hydrazinecarboxylic acid tert-butyl ester
N-Butyl-3-[3-hydroxy-4-(1,1,4-trioxo-1,2,5-thiadiazolidin-2-yl)-phenyl]-propionamide
3-[3-Hydroxy-4-(1,1,4-trioxo-1,2,5-thiadiazolidin-2-yl)-phenyl]-N-pentylpropionamide
N-Hexyl-3-[3-hydroxy-4-(1,1,4-trioxo-1,2,5-thiadiazolidin-2-yl)-phenyl]-propionamide
3-[3-Hydroxy-4-(1,1,4-trioxo-1,2,5-thiadiazolidin-2-yl)-phenyl]-N-(4-phenylbutyl)-propionamide
3-[3-Hydroxy-4-(1,1,4-trioxo-1,2,5-thiadiazolidin-2-yl)-phenyl]-N-(5-phenylpentyl)-propionamide
N-(2-Hydroxyphenyl)-3-[3-hydroxy-4-(1,1,4-trioxo-1,2,5-thiadiazolidin-2-yl)-phenyl]-propionamide
3-[3-Hydroxy-4-(1,1,4-trioxo-1,2,5-thiadiazolidin-2-yl)-phenyl]-N-phenylpropionamide
3-[3-Hydroxy-4-(1,1,4-trioxo-1,2,5-thiadiazolidin-2-yl)-phenyl]-N-o-tolyl-propionamide
3-[3-Hydroxy-4-(1,1,4-trioxo-1,2,5-thiadiazolidin-2-yl)-phenyl]-N-isopropyl-propionamide
2-{3-[3-Hydroxy-4-(1,1,4-trioxo-1,2,5-thiadiazolidin-2-yl)-phenyl]-propionylamino}-2-methylpropionic acid
2-Hydroxy-6-(4-{3-[3-hydroxy-4-(1,1,4-trioxo-1,2,5-thiadiazolidin-2-yl)-phenyl]-propionylamino}-butoxy)-benzoic acid methyl ester
2-(4-{3-[3-Hydroxy-4-(1,1,4-trioxo-1,2,5-thiadiazolidin-2-yl)-phenyl]-propionylamino}-butoxy)-benzoic acid methyl ester
2-(4-{3-[3-Hydroxy-4-(1,1,4-trioxo-1,2,5-thiadiazolidin-2-yl)-phenyl]-propionylamino}-butoxy)-benzoic acid
3-[3-Hydroxy-4-(1,1,4-trioxo-1,2,5-thiadiazolidin-2-yl)-phenyl]-N-(4-phenoxybutyl)-propionamide
3-[3-Hydroxy-4-(1,1,4-trioxo-1,2,5-thiadiazolidin-2-yl)-phenyl]-N-[4-(2-trifluoromethylphenoxy)-butyl]-propionamide
3-[3-Hydroxy-4-(1,1,4-trioxo-1,2,5-thiadiazolidin-2-yl)-phenyl]-N-[4-(2-methanesulfonylphenoxy)-butyl]-propionamide
3-[3-Hydroxy-4-(1,1,4-trioxo-1,2,5-thiadiazolidin-2-yl)-phenyl]-N-[4-(3-methoxyphenoxy)-butyl]-propionamide
N-[4-(2,3-Dimethoxyphenoxy)-butyl]-3-[3-hydroxy-4-(1,1,4-trioxo-1,2,5-thiadiazolidin-2-yl)-phenyl]-propionamide
N-[4-(3-Hydroxyphenoxy)-butyl]-3-[3-hydroxy-4-(1,1,4-trioxo-1,2,5-thiadiazolidin-2-yl)-phenyl]-propionamide
N-[4-(2-Hydroxyphenoxy)-butyl]-3-[3-hydroxy-4-(1,1,4-trioxo-1,2,5-thiadiazolidin-2-yl)-phenyl]-propionamide
N-[4-(3-Hydroxy-2-methoxyphenoxy)-butyl]-3-[3-hydroxy-4-(1,1,4-trioxo-1,2,5-thiadiazolidin-2-yl)-phenyl]-propionamide
N-[4-(3-Hydroxy-2-methylphenoxy)-butyl]-3-[3-hydroxy-4-(1,1,4-trioxo-1,2,5-thiadiazolidin-2-yl)-phenyl]-propionamide N-[4-(2-Acetyl-3-methoxyphenoxy)-butyl]-3-[3-hydroxy-4-(1,1,4-trioxo-1,2,5-thiadiazolidin-2-yl)-phenyl]-propionamide
2-Hydroxy-6-(4-{3-[3-hydroxy-4-(1,1,4-trioxo-1,2,5-thiadiazolidin-2-yl)-phenyl]-propionylamino}-butoxy)-N,N-dimethylbenzamide2-(4-{3-[3-Hydroxy-4-(1,1,4-trioxo-1,2,5-thiadiazolidin-2-yl)-phenyl]-propionylamino}-butoxy)-6,N,N-trimethylbenzamide
2-Fluoro-6-(4-{3-[3-hydroxy-4-(1,1,4-trioxo-1,2,5-thiadiazolidin-2-yl)-phenyl]-propionylamino}-butoxy)-N,N-dimethylbenzamide
2-Hydroxy-6-(4-{3-[3-hydroxy-4-(1,1,4-trioxo-1,2,5-thiadiazolidin-2-yl)-phenyl]-propionylamino}-butoxy)-benzoic acid
N-[4-(2-Acetyl-3-hydroxyphenoxy)-butyl]-3-[3-hydroxy-4-(1,1,4-trioxo-1,2,5-thiadiazolidin-2-yl)-phenyl]-propionamide
N-[4-(2-Cyano-3-hydroxyphenoxy)-butyl]-3-[3-hydroxy-4-(1,1,4-trioxo-1,2,5-thiadiazolidin-2-yl)-phenyl]-propionamide
N-[4-(3-Hydroxy-2-methanesulfinylphenoxy)-butyl]-3-[3-hydroxy-4-(1,1,4-trioxo-1,2,5-thiadiazolidin-2-yl)-phenyl]-propionamide
N-[4-(3-Hydroxy-2-methanesulfonylphenoxy)-butyl]-3-[3-hydroxy-4-(1,1,4-trioxo-1,2,5-thiadiazolidin-2-yl)-phenyl]-propionamide
2-(4-{2-Acetylamino-3-[3-hydroxy-4-(1,1,4-trioxo-1,2,5-thiadiazolidin-2-yl)-phenyl]-propionylamino}-butoxy)-6-hydroxybenzoic acid methyl ester
2-(4-{(S)-2-Acetylamino-3-[3-hydroxy-4-(1,1,4-trioxo-1,2,5-thiadiazolidin-2-yl)-phenyl]-propionylamino}-butoxy)-6-hydroxybenzoic acid methyl ester
3-[3-Hydroxy-4-(1,1,4-trioxo-1,2,5-thiadiazolidin-2-yl)-phenyl]-propionic acid methyl ester
3-[3-Hydroxy-4-(1,1,4-trioxo-1,2,5-thiadiazolidin-2-yl)-phenyl]-2-methylpropionic acid methyl ester
3-[3-Hydroxy-4-(1,1,4-trioxo-1,2,5-thiadiazolidin-2-yl)-phenyl]-2-methylpropionic acid tert-butyl ester
(1R*,2R*)-2-[3-Hydroxy-4-(1,1,4-trioxo-1,2,5-thiadiazolidin-2-yl)-phenyl]-cyclopropanecarboxylic acid ethyl ester
(1R*,231-2-[3-Hydroxy-4-(1,1,4-trioxo-1,2,5-thiadiazolidin-2-yl)-phenyl]-cyclopropanecarboxylic acid ethyl ester
N-[3-Hydroxy-4-(1,1,4-trioxo-1,2,5-thiadiazolidin-2-yl)-benzyl]-N-methylbenzenesulfonamide
N-[3-Hydroxy-4-(1,1,4-trioxo-1,2,5-thiadiazolidin-2-yl)-benzyl]-N-methylmethansulfonamide
C-Cyclohexyl-N-{2-[3-hydroxy-4-(1,1,4-trioxo-1,2,5-thiadiazolidin-2-yl)-phenyl]-ethyl}-methanesulfonamide
N-{2-[3-Hydroxy-4-(1,1,4-trioxo-1,2,5-thiadiazolidin-2-yl)-phenyl]-ethyl}-methansulfonamide
Ethanesulfonic acid {2-[3-hydroxy-4-(1,1,4-trioxo-1,2,5-thiadiazolidin-2-yl)-phenyl]-ethyl}-amide
Butane-1-sulfonic acid {2-[3-hydroxy-4-(1,1,4-trioxo-1,2,5-thiadiazolidin-2-yl)-phenyl]-ethyl}-amide
Propane-2-sulfonic acid {2-[3-hydroxy-4-(1,1,4-trioxo-1,2,5-thiadiazolidin-2-yl)-phenyl]-ethyl}-amide
Octane-1-sulfonic acid {2-[3-hydroxy-4-(1,1,4-trioxo-1,2,5-thiadiazolidin-2-yl)-phenyl]-ethyl}-amide
N-{2-[3-Hydroxy-4-(1,1,4-trioxo-1,2,5-thiadiazolidin-2-yl)-phenyl]-ethyl}-benzenesulfonamide
N-{2-[3-Hydroxy-4-(1,1,4-trioxo-1,2,5-thiadiazolidin-2-yl)-phenyl]-ethyl}-C-phenyl-methansulfonamide
4-Fluoro-N-{2-[3-hydroxy-4-(1,1,4-trioxo-1,2,5-thiadiazolidin-2-yl)-phenyl]-ethyl}-benzenesulfonamide
3,4-Dichloro-N-{2-[3-hydroxy-4-(1,1,4-trioxo-1,2,5-thiadiazolidin-2-yl)-phenyl]-ethyl}-benzenesulfonamide
3-(4-{2-[3-Hydroxy-4-(1,1,4-trioxo-1,2,5-thiadiazolidin-2-yl)-phenyl]-ethylsutfamoyl}-phenyl)-propionic acid
2-Hydroxy-5-{2-[3-hydroxy-4-(1,1,4-trioxo-1,2,5-thiadiazolidin-2-yl)-phenyl]-ethylsulfamoyl}-benzoic acid
Naphthalene-1-sulfonic acid {2-[3-hydroxy-4-(1,1,4-trioxo-1,2,5-thiadiazolidin-2-yl)-phenyl]-ethyl}-amide
2-Naphthalen-1-yl-ethanesulfonic acid {2-[3-hydroxy-4-(1,1,4-trioxo-1,2,5-thiadiazolidin-2-yl)-phenyl]-ethyl}-amide
N-{3-[3-Hydroxy-4-(1,1,4-trioxo-1,2,5-thiadiazolidin-2-yl)-phenyl]-propyl}-methansulfonamide
N-{3-[3-Hydroxy-4-(1,1,4-trioxo-1,2,5-thiadiazolidin-2-yl)-phenyl]- propyl}-benzenesulfonamide
N-{3-[3-Hydroxy-4-(1,1,4-trioxo-1,2,5-thiadiazolidin-2-yl)-phenyl]-propyl}-C-phenylmethanesulfonamide
C-(4-Fluorophenyl)-N-{3-[3-hydroxy-4-(1,1,4-trioxo-1,2,5-thiadiazolidin-2-yl)-phenyl]-propyl}-methanesulfonamide
N-{3-[3-Hydroxy-4-(1,1,4-trioxo-1,2,5-thiadiazolidin-2-yl)-phenyl]-propyl}-4-isopropylbenzenesulfonamide
N-{3-[3-Hydroxy-4-(1,1,4)-trioxo-1,2,5-thiadiazolidin-2-yl)-phenyl]-propyl}-4-trifluoromethylbenzenesulfonamide
N-{3-[3-Hydroxy-4-(1,1,4-trioxo-1,2,5-thiadiazolidin-2-yl)-phenyl]-propyl}-4-trifluoromethoxybenzenesulfonamide
C-(3-Aminophenyl)-N-{3-[3-hydroxy-4-(1,1,4-trioxo-1,2,5-thiadiazolidin-2-yl)-phenyl]-propyl}-methanesulfonamide
N-{3-[3-Hydroxy-4-(1,1,4-trioxo-1,2,5-thiadiazolidin-2-yl)-phenyl]-propyl}-2,4,6-triisopropylbenzenesulfonamide
2-Hydroxy-5-{3-[3-hydroxy-4-(1,1,4-trioxo-1,2,5-thiadiazolidin-2-yl)-phenyl]-propylsulfamoyl}-benzoic acid
3-Amino-N-{3-[3-hydroxy-4-(1,1,4-trioxo-1,2,5-thiadiazolidin-2-yl)-phenyl]-propyl}-benzenesulfonamide
4-Amino-N-{3-[3-hydroxy-4-(1,1,4-trioxo-1,2,5-thiadiazolidin-2-yl)-phenyl]-propyl}-benzenesulfonamide
N-{3-[3-Hydroxy-4-(1,1,4-trioxo-1,2,5-thiadiazolidin-2-yl)-phenyl]-propyl}-3,5-dimethylbenzenesulfonamide
N-{3-[3-Hydroxy-4-(1,1,4-trioxo-1,2,5-thiadiazolidin-2-yl)-phenyl]-propyl}-2,5-dimethylbenzenesulfonamide
N-{3-[3-Hydroxy-4-(1,1,4-trioxo-1,2,5-thiadiazolidin-2-yl)-phenyl]-propyl}-2,4,6-trimethylbenzenesulfonamide
4-tert-Butyl-N-{3-[3-hydroxy-4-(1,1,4-trioxo-1,2,5-thiadiazolidin-2-yl)-phenyl]-propyl}-benzenesulfonamide
4-(1,1-Dimethylpropyl)-N-{3-[3-hydroxy-4-(1,1,4-trioxo-1,2,5-thiadiazolidin-2-yl)-phenyl]-propyl}-benzenesulfonamide
N-{3-[3-Hydroxy-4-(1,1,4-trioxo-1,2,5-thiadiazolidin-2-yl)-phenyl]-propyl}-3,4-dimethoxybenzenesulfonamide
N-{3-[3-Hydroxy-4-(1,1,4-trioxo-1,2,5-thiadiazolidin-2-yl)-phenyl]-propyl}-2,5-bis-(2,2,2-trifluoroethoxy)-benzenesulfonamide
Biphenyl-4-sulfonic acid {3-[3-hydroxy-4-(1,1,4-trioxo-1,2,5-thiadiazolidin-2-yl)-phenyl]-propyl}-amide
N-{3-[3-Hydroxy-4-(1,1,4-trioxo-1,2,5-thiadiazolidin-2-yl)-phenyl]-propyl}-2-phenoxybenzenesulfonamide
N-{3-[3-Hydroxy-4-(1,1,4-trioxo-1,2,5-thiadiazolidin-2-yl)-phenyl]-propyl}-3-phenoxybenzenesulfonamide N-{3-[3-Hydroxy-4-(1,1,4-trioxo-1,2,5-thiadiazolidin-2-yl)-phenyl]-propyl}-2,5-bis-(2,2,2-trifluoroethoxy)-benzenesulfonamide 2,2-Diphenylethanesulfonic acid {3-[3-hydroxy-4-(1,1,4-trioxo-1,2,5-thiadiazolidin-2-yl)-phenyl]-propyl}-amide C-(2-Aminophenyl)-N{3-[3-hydroxy-4-(1,1,4-trioxo-1,2,5-thiadiazolidin-2-yl)-phenyl]-propyl}-methanesulfonamide Naphthalene-1-sulfonic acid {3-[3-hydroxy-4-(1,1,4-trioxo-1,2,5-thiadiazolidin-2-yl)-phenyl]-propyl}-amide C-Cyclohexyl-N-{3-[3-hydroxy-4-(1,1,4-trioxo-1,2,5-thiadiazolidin-2-yl)-phenyl]-propyl}-methanesulfonamide 2-Naphthalen-1-yl-ethanesulfonic acid {3-[3-hydroxy-4-(1,1,4-trioxo-1,2,5-thiadiazolidin-2-yl)-phenyl]-propyl}-amide 2-Phenyl-2-(2-trifluoromethylphenyl)-ethanesulfonic acid {3-[3-hydroxy-4-(1,1,4-trioxo-1,2,5-thiadiazolidin-2-yl)-phenyl]-propyl}-amide 2-Oxo-2H-chomene-6-sulfonic acid {3-[3-hydroxy-4-(1,1,4-trioxo-1,2,5-thiadiazolidin-2-yl)-phenyl]-propyl}-amide N-{3-[3-Hydroxy-4-(1,1,4-trioxo-1,2,5-thiadiazolidin-2-yl)-phenylpropyl}-N-isopropylbenzenesulfonamide N-(1-{2-[3-Hydroxy-4-(1,1,4-trioxo-1,2,5-thiadiazolidin-2-yl)-phenyl]-ethyl}-cyclopropyl)-benzenesulfonamide N-{(S)-1-Benzyl-2-[3-hydroxy-4-(1,1,4-trioxo-1,2,5-thiadiazolidin-2-yl)-phenyl]-ethyl}-methanesulfonamide Ethanesulfonic acid {(S)-1-benzyl-2-[3-hydroxy-4-(1,1,4-trioxo-1,2,5-thiadiazolidin-2-yl)-phenyl]-ethyl}-amide N-{(S)-1-Benzyl-2-[3-hydroxy-4-(1,1,4-trioxo-1,2,5-thiadiazolidin-2-yl)-pheny]-ethyl}-C-phenyl-methanesulfonamide N-{(R)-1-Benzyl-2-[3-hydroxy-4-(1,1,4-trioxo-1,2,5-thiadiazolidin-2-yl)-phenyl]-ethyl}-C-phenylmethanesulfonamide N-{4-[3-Hydroxy-4-(1,1,4-trioxo-1,2,5-thiadiazolidin-2-yl)-phenyl]-butyl}-methanesulfonamide N-{5-[3-Hydroxy-4-(1,1,4-trioxo-1,2,5-thiadiazolidin-2-yl)-phenyl]-pentyl}-methanesulfonamide 5-[2-Hydroxy-4-(1-methanesulfonylpiperidin-3-ylmethyl)-phenyl]-1,1-dioxo-1,2,5-thiadiazolidin-3-one 5-{2-Hydroxy-4-[2-(1-methanesulfonylpiperidin-2-yl)-ethyl]-phenyl}-1,1-dioxo-1,2,5-thiadiazolidin-3-one 5-{4-[2-(1-Benzenesulfonylpiperidin-2-yl)-ethyl]-2-hydroxyphenyl}-1,1-dioxo-1,2,5-thiadiazolidin-3-one 5-{4-[2((S)-1-Benzenesulfonylpiperidin-2-yl)-ethyl]-2-hydroxyphenyl}-1,1-dioxo-1,2,5-thiadiazolidin-3-one 5-{4-[2-((R)-1-Benzenesulfonylpiperidin-2-yl)-ethyl]-2-hydroxyphenyl}-1,1-dioxo-1,2,5-thiadiazolidin-3-one 5-{4-[2-(1-Benzenesulfonylpyrrolidin-2-yl)-ethyl]-2-hydroxyphenyl}-1,1-dioxo-1,2,5-thiadiazolidin-3-one 5-{4-[2-(1-Benzenesulfonyl-1H-pyrrol-2-yl)-ethyl]-2-hydroxyphenyl}-1,1-dioxo-1,2,5-thiadiazolidin-3-one 5-{4-[2-(1-Benzenesulfonylpyrrolidin-3-yl)-ethyl]-2-hydroxyphenyl}-1,1-dioxo-1,2,5-thiadiazolidin-3-one 5-{4-[2-(1-Benzenesulfonylazepan-2-yl)-ethyl]-2-hydroxyphenyl}-1,1-dioxo-1,2,5-thiadiazolidin-3-one 5-{2-Hydroxy-4-[2-((R)-2-methanesulfonyl-1,2,3,4-tetrahydroisoquinolin-3-yl)-ethyl]-phenyl}-1,1-dioxo-1,2,5-thiadiazolidin-3-one 5-{4-[2-((R)-2-Benzenesulfonyl-1,2,3,4-tetrahydroisoquinolin-3-yl)-ethyl]-2-hydroxyphenyl}-1,1-dioxo-1,2,5-thiadiazolidin-3-one 5-(2-Hydroxy-4-{2-[2-(4-trifluoromethylbenzenesulfonyl)-1,2,3,4-tetrahydroisoquinolin-3-yl]-ethyl}-phenyl)-1,1-dioxo-1,2,5-thiadiazolidin-3-one 5-{2-Hydroxy-4-[2-(2-phenylmethanesulfonyl-1,2,3,4-tetrahydroisoquinolin-3-yl)-ethyl]-phenyl}-1,1-dioxo-1,2,5-thiadiazolidin-3-one 5-{4-[2-(1,1-Dioxo-1,2-thiazinan-3-yl)-ethyl]-2-hydroxyphenyl}-1,1-dioxo-1,2,5-thiadiazolidin-3-one N-{(1R*,2S*)-2-[3-Hydroxy-4-(1,1,4-trioxo-1,2,5-thiadiazolidin-2-yl)-benzyl]-cyclohexyl}-methanesulfonamide N-{(1R,2S)-2-[3-Hydroxy-4-(1,1,4-trioxo-1,2,5-thiadiazolidin-2-yl)-benzyl]-cyclohexyl}-methanesulfonamide N-{(1S,2R)-2-[3-Hydroxy-4-(1,1,4-trioxo-1,2,5-thiadiazolidin-2-yl)-benzyl]-cyclohexyl}-methanesulfonamide Ethanesulfonic acid {(1R*,2S*)-2-[3-hydroxy-4-(1,1,4-trioxo-1,2,5-thiadiazolidin-2-yl)-benzyl]-cyclohexyl}-amide N-{(1 R*,2S*)-2-[3-Hydroxy-4-(1,1,4-trioxo-1,2,5-thiadiazolidin-2-yl)-benzyl]-cyclohexyl}-benzenesulfonamide (S)-2-Benzenesulfonylamino-3-[3-hydroxy-4-(1,1,4-trioxo-1,2,5-thiadiazolidin-2-yl)-phenyl]-N-pentylpropionamide (S)-2-Benzenesulfonylamino-3-[3-hydroxy-4-(1,1,4-trioxo-1,2,5-thiadiazolidin-2-yl)-phenyl]-N-(4-phenylbutyl)-propionamide N-{(S)-1-(1H-Benzoimidazol-2-yl)-2-[3-hydroxy-4-(1,1,4-trioxo-1,2,5-thiadiazolidin-2-yl)-phenyl]-ethyl}-benzenesulfonamide tert-Butyl [({2-[4-(1,1-dioxido-4-oxo-1,2,5-thiadiazolidin-2-yl)-3-hydroxyphenyl]ethyl}amino)sulfonyl]carbamate 1-Cyclohexyl-3-{2-[3-hydroxy-4-(1,1,4-trioxo-1,2,5-thiadiazolidin-2-yl)-phenyl]-ethyl}-urea 1-{2-[3-Hydroxy-4-(1,1,4-trioxo-1,2,5-thiadiazolidin-2-yl)-phenyl]-ethyl}-3-phenyl-urea 1-Ethyl-3-{2-[3-hydroxy-4-(1,1,4-trioxo-1,2,5-thiadiazolidin-2-yl)-phenyl]-ethyl}-urea 1-Adamantan-1-yl-3-{2-[3-hydroxy-4-(1,1,4-trioxo-1,2,5-thiadiazolidin-2-yl)-phenyl]-ethyl}-urea Benzenesulfonyl-N-{2-[3-hydroxy-4-(1,1,4-trioxo-1,2,5-thiadiazolidin-2-yl)-phenyl]-ethyl}-urea 1-(2,4-Dimethoxybenzyl)-3-{2-[3-hydroxy-4-(1,1,4-trioxo-1,2,5-thiadiazolidin-2-yl)-phenyl]-ethyl}-urea 1-(2-Hydroxyethyl)-3-{2-[3-hydroxy-4-(1,1,4-trioxo-1,2,5-thiadiazolidin-2-yl)-phenyl]-ethyl}-urea 3-{2-[3-Hydroxy-4-(1,1,4-trioxo-1,2,5-thiadiazolidin-2-yl)-phenyl]-ethyl}-1,1-bis-(2-methoxyethyl)-urea Morpholine-4-carboxylic acid {2-[3-hydroxy-4-(1,1,4-trioxo-1,2,5-thiadiazolidin-2-yl)-phenyl]-ethyl}-amide 4-(3-{2-[3-Hydroxy-4-(1,1,4-trioxo-1,2,5-thiadiazolidin-2-yl)-phenyl]-ethyl}-ureido)-piperidine-1-carboxylic acid tert-butyl ester 1-{2-[3-Hydroxy-4-(1,1,4-trioxo-1,2,5-thiadiazolidin-2-yl)-phenyl]-ethyl}-3-piperidin-4-yl-urea 1-{3-[3-Hydroxy-4-(1,1,4-trioxo-1,2,5-thiadiazolidin-2-yl)-phenyl]-propyl}-3-phenyl-urea 1-Cyclohexyl-3-{3-[3-hydroxy-4-(1,1,4-trioxo-1,2,5-thiadiazolidin-2-yl)-phenyl]-propyl}-urea 1-Adamantan-1-yl-3-{3-[3-hydroxy-4-(1,1,4-trioxo-1,2,5-thiaidiazolidin-2-yl)-phenyl]-propyl}-urea 3-{3-[3-Hydroxy-4-(1,1,4-trioxo-1,2,5-thiadiazolidin-2-yl)-phenyl]-propyl}-1H-quinazoline-2,4-dione 3-[3-Hydroxy-4-(1,1,4-trioxo-1,2,5-thiadiazolidin-2-yl)-benzyl]-piperidine-1-carboxylic acid ethylamide 5-(2-Hydroxy-4-methanesutfonylmethylphenyl)-1,1-dioxo-1,2,5-thiadiazolidin-3-one
5-(4-Ethanesulfonylmethyl-2-hydroxy-phenyl)-1,1-dioxo-1,2,5-thiadiazolidin-3-one
5-[2-Hydroxy-4-(propane-2-sutfonylmethyl)-phenyl]-1,1-dioxo-1,2,5-thiadiazolidin-3-one
5-(4-Benzenesulfonylmethyl-2-hydroxyphenyl)-1,1-dioxo-1,2,5-thiadiazolidin-3-one
5-(2-Hydroxy-4-methanesulfinylmethylphenyl)-1,1-dioxo-1,2,5-thiadiazolidin-3-one
5-(4-Ethanesulfinylmethyl-2-hydroxyphenyl)-1,1-dioxo-1,2,5-thiadiazolidin-3-one
5-[2-Hydroxy-4-(propane-2-sulfinylmethyl)-phenyl]-1,1-dioxo-1,2,5-thiadiazolidin-3-one
5-(2-Hydroxy-4-methylsulfanylmethylphenyl)-1,1-dioxo-1,2,5-thiadiazolidin-3-one
5-(4-Ethylsulfanylmethyl-2-hydroxyphenyl)-1,1-dioxo-1,2,5-thiadiazolidin-3-one
5-(2-Hydroxy-4-isopropylsulfanylmethylphenyl)-1,1-dioxo-1,2,5-thiadiazolidin-3-one
5-[4-(2-Benzenesulfonylethyl)-2-hydroxyphenyl]-1,1-dioxo-1,2,5-thiadiazolidin-3-one
5-[4-(4-Benzenesulfonylbutyl)-2-hydroxyphenyl]-1,1-dioxo-1,2,5-thiadiazolidin-3-one
5-{4-[3-(1,1-Dioxotetrahydrothiophen-2-yl)-prop-1-ynyl]-2-hydroxyphenyl}-1,1-dioxo-1,2,5-thiadiazolidin-3-one
5-{4-[3-(1,1-Dioxotetrahydrothiophen-2-yl)-propyl]-2-hydroxyphenyl}-1,1-dioxo-1,2,5-thiadiazolidin-3-one
5-[2-Hydroxy-4-(3-oxopentyl)-phenyl]-1,1-dioxo-1,2,5-thiadiazolidin-3-one
5-[2-Hydroxy-4-(2-methyl-3-oxopentyl)-phenyl]-1,1-dioxo-1,2,5-thiadiazolidin-3-one
5-[2-Hydroxy-4-(2-methyl-3-oxo-3-phenylpropyl)-phenyl]-1,1-dioxo-1,2,5-thiadiazolidin-3-one
5-[4-(2-Benzoylbutyl)-2-hydroxyphenyl]-1,1-dioxo-1,2,5-thiadiazolidin-3-one
5-[4-(2-Benzoylpentyl)-2-hydroxyphenyl]-1,1-dioxo-1,2,5-thiadiazolidin-3-one
5-[2-Hydroxy-4-(3-oxo-2,3-diphenylpropyl)-phenyl]-1,1-dioxo-1,2,5-thiadiazolidin-3-one
5-[4-(2-Benzyl-3-oxo-3-phenylpropyl)-2-hydroxyphenyl]-1,1-dioxo-1,2,5-thiadiazolidin-3-one
5-[4-(2,2-Dimethyl-3-oxo-3-phenylpropyl)-2-hydroxyphenyl]-1,1-dioxo-1,2,5-thiadiazolidin-3-one
5-[2-Hydroxy-4-(1-oxo-indan-2-ylmethyl)-phenyl]-1,1-dioxo-1,2,5-thiadiazolidin-3-one
5-[2-Hydroxy-4-(6-oxo-6,7,8,9-tetrahydro-5H-benzocyclohepten-5-ylmethyl)-phenyl]-1,1-dioxo-1,2,5-thiadiazolidin-3-one
5-[2-Hydroxy-4-(2-methoxy-3-oxo-3-phenylpropyl)-phenyl]-1,1-dioxo-1,2,5-thiadiazolidin-3-one
5-[2-Hydroxy-4-(3-hydroxy-2-methyl-3-phenylpropyl)-phenyl]-1,1-dioxo-1,2,5-thiadiazolidin-3-one
5-{2-Hydroxy-4-[2-(hydroxylphenylmethyl)-butyl]-phenyl}-1,1-dioxo-1,2,5-thiadiazolidin-3-one
5-{2-Hydroxy-4-[2-(hydroxyphenylmethyl)-pentyl]-phenyl}-1,1-dioxo-1,2,5-thiadiazolidin-3-one
5-[4-(2-Benzyl-3-hydroxy-3-phenylpropyl)-2-hydroxyphenyl]-1,1-dioxo-1,2,5-thiadiazolidin-3-one
5-[2-Hydroxy-4-(3-hydroxy-2,2-dimethyl-3-phenylpropyl)-phenyl]-1,1-dioxo-1,2,5-thiadiazolidin-3-one
5-[2-Hydroxy-4-(1-hydroxyindan-2-ylmethyl)-phenyl]-1,1-dioxo-1,2,5-thiadiazolidin-3-one
5-[2-Hydroxy-4-(3-hydroxy-2-methoxy-3-phenyl-propyl)-phenyl]-1,1-dioxo-1,2,5-thiadiazolidin-3-one
5-(2-Hydroxy-4-vinylphenyl)-1,1-dioxo-1,2,5-thiadiazolidin-3-one
5-[2-Hydroxy-4-(1-hydroxyethyl)-phenyl]-1,1-dioxo-1,2,5-thiadiazolidin-3-one
5-[2-Hydroxy-4-(2-hydroxyhexyl)-phenyl]-1,1-dioxo-1,2,5-thiadiazolidin-3-one
5-[2-Hydroxy-4-(3-hydroxybutyl)-phenyl]-1,1-dioxo-1,2,5-thiadiazolidin-3-one
5-{Hydroxy-4-[2-(1-hydroxycyclohexyl)-ethyl]-phenyl}-1,1-dioxo-1,2,5-thiadiazolidin-3-one
5-[2-Hydroxy-4-(4,4,4-trfluoro-3-hydroxy-3-phenylbutyl)-phenyl]-1,1-dioxo-1,2,5-thiadiazolidin-3-one
5-(3-Hydroxybiphenyl-4-yl)-1,1-dioxo-1,2,5-thiadiazolidin-3-one
5-(3,3'-Dihydroxybiphenyl-4-yl)-1,1-dioxo-1,2,5-thiadiazolidin-3-one
[3'-Hydroxy-4'-(1,1,4-trioxo-1,2,5-thiadiazolidin-2-yl)-biphenyl-4-yl]-acetic acid
5,5'-(3,3'-Dihydroxybiphenyl-4-yl)-1,1,1',1'-tetraoxo-1,1',2,2',5,5'-dithiadiazolidin-3,3'-one
5-(4-Furan-3-yl-2-hydroxyphenyl)-1,1-dioxo-1,2,5-thiadiazolidin-3-one
5-(2-Hydroxy-4-thiophen-3-yl-phenyl)-1,1-dioxo-1,2,5-thiadiazolidin-3-one
5-(4-Benzofuran-3-yl-2-hydroxyphenyl)-1,1-dioxo-1,2,5-thiadiazolidin-3-one
5-[2-Hydroxy-4-(6-methoxybenzofuran-3-yl)-phenyl]-1,1-dioxo-1,2,5-thiadiazolidin-3-one
5-(2-Hydroxy-4-thiazol-5-yl-phenyl)-1,1-dioxo-1,2,5-thiadiazolidin-3-one
5-(2-Hydroxy-4-thiazol-2-yl-phenyl)-1,1-dioxo-1,2,5-thiadiazolidin-3-one
5-[2-Hydroxy-4-(1H-pyrrol-3-yl)-phenyl]-1,1-dioxo-1,2,5-thiadiazolidin-3-one
5-[2-Hydroxy-4-(1H-pyrazol-3-yl)-phenyl]-1,1-dioxo-1,2,5-thiadiazolidin-3-one
5-[2-Hydroxy-4-(1H-pyrazol-4-yl)-phenyl]-1,1-dioxo-1,2,5-thiadiazolidin-3-one
5-[2-Hydroxy-4-(1-propyl-1H-pyrazol-4-yl)-phenyl]-1,1-dioxo-1,2,5-thiadiazolidin-3-one
5-[2-Hydroxy-4-(1-isobutyl-1H-pyrazol-4-yl)-phenyl]-1,1-dioxo-1,2,5-thiadiazolidin-3-one
5-{2-Hydroxy-4-[1-(3-methylbutyl)-1H-pyrazol-4-yl]-phenyl}-1,1-dioxo-1,2,5-thiadiazolidin-3-one
5-[2-Hydroxy-4-(tetrahydrofuran-3-yl)-phenyl]-1,1-dioxo-1,2,5-thiadiazolidin-3-one
5-[4-(2,3-Dihydrobenzofuran-3-yl)-2-hydroxyphenyl]-1,1-dioxo-1,2,5-thiadiazolidin-3-one
5-(2-Hydroxy-4-thiazol-2-ylmethylphenyl)-1,1-dioxo-1,2,5-thiadiazolidin-3-one
5-[2-Hydroxy-4-(2H-pyrazol-3-ylmethyl)-phenyl]-1,1-dioxo-1,2,5-thiadiazolidin-3-one
5-(2-Hydroxy-4-pyrazol-1-ylmethyl-phenyl)-1,1-dioxo-1,2,5-thiadiazolidin-3-one
5-[2-Hydroxy-4-(3-trifluoromethylpyrazole-1-ylmethyl)-phenyl]-1,1-dioxo-1,2,5-thiadiazolidin-3-one
5-[3-Hydroxy-4-(1,1,4-trioxo-1,2,5-thiadiazolidin-2-yl)-phenyl]-pentanoic acid
4-[3-Hydroxy-4-(1,1,4-trioxo-1,2,5-thiadiazolidin-2-yl)-phenyl]-butane-1-sulfinic acid
4-[3-Hydroxy-4-(1,1,4-trioxo-1,2,5-thiadiazolidin-2-yl)-phenyl]-butyronitrile
4-[3-Hydroxy-4-(1,1,4-trioxo-1,2,5-thiadiazolidin-2-yl)-phenyl]-2-methyl-butyronitrile
4-[3-Hydroxy-4-(1,1,4-trioxo-1,2,5-thiadiazolidin-2-yl)-phenyl]-3,3-dimethylbutyronitrile

[3-Hydroxy-4-(1,1,4-trioxo-1,2,5-thiadiazolidin-2-yl)-phenoxy]-acetic acid 2-trimethylsilanylethyl ester

[3-Hydroxy-4-(1,1,4-trioxo-1,2,5-thiadiazolidin-2-yl)-phenoxy]-acetic acid

3-[3-Hydroxy-4-(1,1,4-trioxo-1,2,5-thiadiazolidin-2-yl)-phenoxy]-1,3,4,5-tetrahydro-benzo[b]azepin-2-one 5-(4-Ethyl-2-hydroxyphenyl)-1,1-dioxo-1,2,5-thiadiazolidin-3-one 5-(4-Hexyl-2-hydroxyphenyl)-1,1-dioxo-1,2,5-thiadiazolidin-3-one 5-(2-Hydroxy-4-isobutylphenyl)-1,1-dioxo-1,2,5-thiadiazolidin-3-one 5-[4-(3,3-Dimethylbutyl)-2-hydroxyphenyl]-1,1-dioxo-1,2,5-thiadiazolidin-3-one 5-[2-Hydroxy-4-(3,3,3-trifluoropropyl)-phenyl]-1,1-dioxo-1,2,5-thiadiazolidin-3-one 5-(4-Cyclopentylmethyl-2-hydroxyphenyl)-1,1-dioxo-1,2,5-thiadiazolidin-3-one 5-(4-Cyclohexylmethyl-2-hydroxyphenyl)-1,1-dioxo-1,2,5-thiadiazolidin-3-one 5-{2-Hydroxy-4-[1-(2,4,6-trimethylphenyl)-ethyl]-phenyl}-1,1-dioxo-1,2,5-thiadiazolidin-3-one 5-[4-(2-Aminobenzyl)-2-hydroxyphenyl]-1,1-dioxo-1,2,5-thiadiazolidin-3-one 5-[2-Hydroxy-4-(2-hydroxybenzyl)-phenyl]-1,1-dioxo-1,2,5-thiadiazolidin-3-one 5-[2-Hydroxy-4-(2-hydroxy-5-methylbenzyl)-phenyl]-1,1-dioxo-1,2,5-thiadiazolidin-3-one 5-[4-(2-Aminomethylbenzyl)-2-hydroxyphenyl]-1,1-dioxo-1,2,5-thiadiazolidin-3-one 5-[2-Hydroxy-4-(2-methoxymethylbenzyl)-phenyl]-1,1-dioxo-1,2,5-thiadiazolidin-3-one {2-[3-Hydroxy-4-(1,1,4-trioxo-1,2,5-thiadiazolidin-2-yl)-benzyl]-phenyl}-acetonitrile {2-[3-Hydroxy-4-(1,1,4-trioxo-1,2,5-thiadiazolidin-2-yl)-benzyl]-phenyl}-acetic acid methyl ester {2-[3-Hydroxy-4-(1,1,4-trioxo-1,2,5-thiadiazolidin-2-yl)-benzyl]-phenyl}-acetic acid N-Ethyl-2-{2-[3-hydroxy-4-(1,1,4-trioxo-1,2,5-thiadiazolidin-2-yl)-benzyl]-phenyl}-acetamide 5-(2-Hydroxy-4-{2-[2-(4-methylpiperidin-1-yl)-2-oxo-ethyl]-benzyl}-phenyl)-1,1-dioxo-1,2,5-thiadiazolidin-3-one 5-{2-Hydroxy-4-[2-(2-hydroxyethyl)-benzyl]-phenyl}-1,1-dioxo-1,2,5-thiadiazolidin-3-one 5-(4-Benzenesulfonyl-2-hydroxyphenyl)-1,1-dioxo-1,2,5-thiadiazolidin-3-one 5-(2-Hydroxy-4-trifluoromethylphenyl)-1,1-dioxo-1,2,5-thiadiazolidin-3-one 5-(2-Hydroxy-4-methoxyphenyl)-1,1-dioxo-1,2,5-thiadiazolidin-3-one 3-Hydroxy-4-(1,1,4-trioxo-1,2,5-thiadiazolidin-2-yl)-benzonitrile 5-(4-Chloro-2-hydroxyphenyl)-1,1-dioxo-1,2,5-thiadiazolidin-3-one, 5-(4-Fluoro-2-hydroxyphenyl)-1,1-dioxo-1-[1,2,5]thiadiazolidin-3-one, and 5-(2-Hydroxy-4-methylphenyl)-1,1-dioxo-[1,2,5]thiadiazolidin-3-one, or a pharmaceutically acceptable salt thereof.

10. A method for the treatment of a condition mediated by PTPase activity, wherein the treatment is palliative, comprising: administering to a mammal in need thereof a therapeutically effective amount of a compound of claim 1, or a pharmaceutically acceptable salt thereof, wherein the condition is selected from the group consisting of insulin resistance, glucose intolerance, type 2 diabetes, and obesity.

11. A pharmaceutical composition, comprising:
a therapeutically effective amount of a compound of claim 1, or a pharmaceutically acceptable salt thereof, in combination with one or more pharmaceutically acceptable carriers.

\* \* \* \* \*